(12) United States Patent
Kasibhatla et al.

(10) Patent No.: US 7,592,143 B2
(45) Date of Patent: Sep. 22, 2009

(54) METHODS OF TREATING DISEASES RESPONSIVE TO INDUCTION OF APOPTOSIS AND SCREENING ASSAYS

(75) Inventors: Shailaja Kasibhatla, San Diego, CA (US); Sui Xiong Cai, San Diego, CA (US); Ben Tseng, San Diego, CA (US); Katayoun Alavi Jessen, San Diego, CA (US); Nicole Marion English, San Diego, CA (US); Serguei Maliartchouk, San Diego, CA (US); Songchun Jiang, San Diego, CA (US); Nilantha Sudath Sirisoma, San Diego, CA (US); Han-Zhong Zhang, San Diego, CA (US); Jared Kuemmerle, Del Mar, CA (US)

(73) Assignee: Cytovia, Inc., Tarrytown, NY (US)

( * ) Notice: Subject to any disclaimer, the term of this patent is extended or adjusted under 35 U.S.C. 154(b) by 390 days.

(21) Appl. No.: 10/826,909

(22) Filed: Apr. 19, 2004

(65) Prior Publication Data

US 2005/0004026 A1 Jan. 6, 2005

Related U.S. Application Data

(60) Provisional application No. 60/463,649, filed on Apr. 18, 2003, provisional application No. 60/463,662, filed on Apr. 18, 2003, provisional application No. 60/484,749, filed on Jul. 7, 2003, provisional application No. 60/484,750, filed on Jul. 7, 2003, provisional application No. 60/532,665, filed on Dec. 29, 2003.

(51) Int. Cl.
*G01N 33/53* (2006.01)
(52) U.S. Cl. .................................. 435/7.1; 530/350
(58) Field of Classification Search .............. 530/387.1, 530/350; 435/7.1
See application file for complete search history.

(56) References Cited

U.S. PATENT DOCUMENTS

| | | | |
|---|---|---|---|
| 4,434,156 A | 2/1984 | Trowbridge | |
| 4,545,985 A | 10/1985 | Pastan et al. | |
| 4,956,453 A | 9/1990 | Bjorn et al. | |
| 4,980,281 A | 12/1990 | Housey | |
| 5,000,935 A * | 3/1991 | Faulk | |
| 5,141,736 A | 8/1992 | Iwasa et al. | |
| 5,208,021 A | 5/1993 | Johnson et al. | |
| 5,352,447 A | 10/1994 | Johnson et al. | |
| 5,648,469 A | 7/1997 | Trowbridge et al. | |
| 5,667,781 A | 9/1997 | Trowbridge et al. | |
| 5,691,157 A | 11/1997 | Gong et al. | |
| 5,702,890 A | 12/1997 | Housman | |
| 5,728,383 A | 3/1998 | Johnson et al. | |
| 5,762,932 A | 6/1998 | Kemp | |
| 5,776,458 A | 7/1998 | Angelucci et al. | |
| 5,792,458 A | 8/1998 | Johnson et al. | |
| 5,798,097 A | 8/1998 | McKenzie et al. | |
| 5,827,516 A | 10/1998 | Urban et al. | |
| 6,132,981 A | 10/2000 | Gong et al. | |
| 6,171,807 B1 | 1/2001 | Novitsky et al. | |
| 6,197,294 B1 | 3/2001 | Tao et al. | |
| 6,245,888 B1 | 6/2001 | Staddon | |
| 6,265,229 B1 | 7/2001 | Fodstad et al. | |
| 6,290,929 B1 | 9/2001 | Camden | |
| 6,294,330 B1 | 9/2001 | Michnick et al. | |
| 6,333,031 B1 | 12/2001 | Olsson et al. | |
| 6,384,049 B1 | 5/2002 | Camden | |
| 6,399,054 B1 | 6/2002 | Casorati et al. | |
| 6,458,939 B1 * | 10/2002 | Shyjan | |
| 6,462,041 B1 | 10/2002 | Cai et al. | |
| 6,846,637 B1 | 1/2005 | Chiodi | |
| 2001/0044457 A1 | 11/2001 | Camden | |
| 2001/0047021 A1 | 11/2001 | Camden | |
| 2002/0019415 A1 | 2/2002 | Camden | |
| 2002/0025313 A1 | 2/2002 | Micklus et al. | |
| 2002/0048550 A1 | 4/2002 | Vallera et al. | |
| 2002/0103165 A1 | 8/2002 | Bot et al. | |

(Continued)

FOREIGN PATENT DOCUMENTS

| | | |
|---|---|---|
| CA | 2 396 005 A1 | 8/2000 |
| WO | WO 01/34591 A2 | 5/2001 |
| WO | WO 02/092083 A1 | 11/2002 |
| WO | WO 02/097043 A2 | 12/2002 |
| WO | WO 2004009622 A2 * | 1/2004 |

OTHER PUBLICATIONS

Hinoda et al Cancer Science, 95(8):621-625, 2004.*
Ng et al PNAS, 99(16):10706-10711, Aug. 6, 2002.*
Vaughan et al In. J Radiation Oncology Biol. Phys. 8:1943-1946, 1982.*
Kasibhatla et al (b) Clinical Cancer Research, 9:6164S #B107, Dec. 1, 2003.*
Xu et al Molecular Cancer Therapeutics 1:337-346, Mar. 2002.*
Cai et al Current Medicinal Chemistry, 13:2627-2644, 2006.*

(Continued)

*Primary Examiner*—Stephen L Rawlings
*Assistant Examiner*—Brad Dufy
(74) *Attorney, Agent, or Firm*—Sterne, Kessler, Goldstein & Fox P.L.L.C.

(57) ABSTRACT

The present invention relates to screening methods useful for drug discovery of apoptosis inducing compounds. In particular, the screening methodology relates to using Apoptosis Inducing Proteins (AIPs) as a target for the discovery of apoptosis activators useful as anticancer agents. The screening methods of the present invention can employ homogenous or heterogeneous binding assays using purified or partially purified AIPs; or whole cell assays using cells with altered levels of one or more AIPs. The invention also contemplates use of gambogic acid or GA-related compounds which bind AIPs and can accordingly be used to raise antibodies useful for drug discovery. Alternatively, labeled GA is used for competitive binding assays for drug discovery. Such assays afford high throughput screening of chemical libraries for apoptosis activators.

9 Claims, 4 Drawing Sheets

U.S. PATENT DOCUMENTS

| | | |
|---|---|---|
| 2002/0136732 A1 | 9/2002 | Houston |
| 2002/0160013 A1 | 10/2002 | Olsson et al. |
| 2002/0197262 A1 | 12/2002 | Hasan et al. |
| 2003/0021792 A1 | 1/2003 | Roben et al. |
| 2003/0035808 A1 | 2/2003 | Srivastava |
| 2003/0040498 A1 | 2/2003 | Ansardi et al. |
| 2003/0044408 A1 | 3/2003 | Levy et al. |
| 2003/0072812 A1 | 4/2003 | Sirbasku |

OTHER PUBLICATIONS

Johnson et al. (Mol. Biol. Cell. Dec. 20, 2006; electronically published ahead of print; see Pubmed ID. No. 17182845); pp. 1-43.*

Abstract of Bridge, J.A., et al., "Fusion of the *ALK* gene to the clathrin heavy chain gene, *CLTC*, in inflammatory myofibroblastic tumor," *Am. J. Pathol.* 159:411-415, The American Society for Investigative Pathology (2001).

Abstract of Geminard, C., etal., "Reticulocyte maturation: mitoptosis and exosome realease," *Biocell 26*:205-215, Instituto de Histologla y Embriologia (Aug. 2002).

Abstract of Hayashida-Hibino, S., et al., "The effect of TGF-beta1 on differential gene expression profiles in human corneal epithelium studied by cDNA expression array," *Invest. Ophthalmol. Vis. Sci* 42:1691-1697, The Association for Research in Vision and Ophthalmology (2001).

Abstract of Kalivendi, S.V., et al., "1-Methyl-4-phenylpyridinium (MPP+)-induced apoptosis and mitochondrial oxidant generation: role of transferrin-receptor-dependent Iron and hydrogen peroxide," *Biochem. J.* 371:151-164, American Chemical Society (Apr. 1, 2003).

Abstract of Kedra, D., et al., "Characterization of a second human clathrin heavy chain polypeptide gene (CLH-22) from chromosome 22q11," *Hum. Mol. Genet.* 5:625-631, Oxford University Press (1996).

Abstract of Lesnikov, V., et al., "Pro-apoptotic effects of transferrin and transferrin-derived glycans on hematopoietic cells and lymphocytes," *Exp. Hematol.* 29:477-489, International Society for Experimental Hematology and Elsevier Science, Inc. (2001).

Abstract of Matsushima, T., et al., "Receptor binding cancer antigen expressed on SiSo cells, a novel regulator of apoptosis of erythroid progenitor cells," *Blood* 98:313-321, American Society of Hematology (2001).

Abstract of Prescott, JL and Tindall, D.J., "Clathrin gene expression is androgen regulated in the prostate," *Endocrinology* 139:2111-2119, The Endocrine Society (1998).

Abstract of Pushkareva, M.Y., et al.,"Increased cell-surface receptor expression on U-937 cells Induced by 1-O-octadecyl-2-O-methyl-sn-glycero-3-phosphocholine," *Cancer Immunol. Immunother.* 48:569-578, Springer-Verlag GmbH (2000).

Abstract of Szekeres, T., et al., "Benzamide riboside, a recent inhibitor of inosine 5'- monophosphate dehydrogenase induces transferrin receptors in cancer cells," *Curr. Med. Chem.* 9:759-764, Bentham Science Publishers Ltd. (Apr. 2002).

Abstract of Tampo, Y., et al., "Oxidative stress-Induced iron signaling is responsible for peroxide-dependent oxidation of dichlorodihydrofluorescein in endothelial cells: role of transferrin receptor-dependent iron uptake in apoptosis," *Circ. Res.* 92:56-63, Lippincott Williams & Wilkins (Jan. 2003).

Abstract of Thompson, K., et al., "Mouse brains deficient in H-ferritin have normal iron concentration but a protein profile of iron deficiency and increased evidence of oxidative stress," *J. Neurosci. Res.* 71:46-63, John Wiley & Sons, Inc. (Jan. 2003).

Abstract of Touriol, C., et al., "Further demonstration of the diversity of chromosomal changes Involving 2p23 in ALK-positive lymphoma: 2 cases expressing ALK kinase fused to CLTCL (clathrin chain polypeptide-Iike)," *Blood* 95:3204-3207. American Society of Hematology (2000).

Abstract of Vaughan, A.T., et al., "The in vivo fate of a 211At labelled monoclonal antibody with known specificity In a murine system," *Int. J. Radiat. Oncol. Biol. Phys.* 8:1943-1946, Elsevier Inc.(1982).

Abstract of Yen, C.F., et al., "Regulation of low-density lipoprotein receptors and assessment of their functional role in Burkitt's lymphoma cells," *Biochim. Biophys. Acta.* 1257:47-57, Elsevier B.V. (1995).

Trowbridge, I.S., et al., "Structure-Function Analysis of the Human Transferrin Receptor: Effects of Anti-Receptor Monoclonal Antibodies on Tumor Growth," *Curr. Stud. Hematol. Blood Trans.* 58:139-147, Karger (1991).

Zhang et al., "Discovery, characterization and SAR of gambogic acid as a potent apoptosis inducer by a HTS assay," *Bioorganic & Medicinal Chemistry*, 12:309-317, Elsevier Science, The Netherlands (Jan. 2004).

Kasibhatla et al., "A role for transferrin receptor in triggering apoptosis when targeted with gambogic acid," *Proc Natl Acad Sci U S A*, 102:12095-12100, The National Academy of Sciences, Washington D.C. (Aug., 2005).

Jessen et al., "The discovery and mechanism of action of novel tumor-selective and apoptosis-inducing 3,5-diaryl-1,2,4-oxadiazole series using a chemical genetics approach," *Molecular Cancer Therapeutics*, 4:761-771, American Association for Cancer Research, Inc., Philadelphia, PA (May, 2005).

* cited by examiner

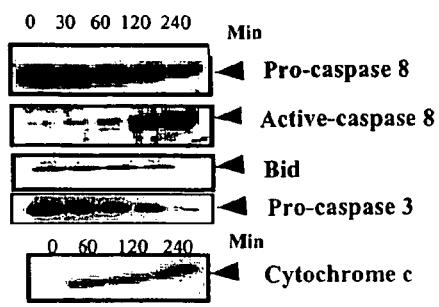
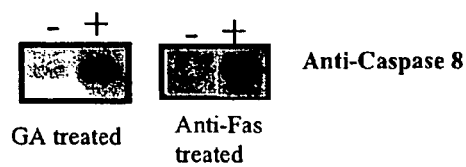
Fig. 4A
Fig. 4B
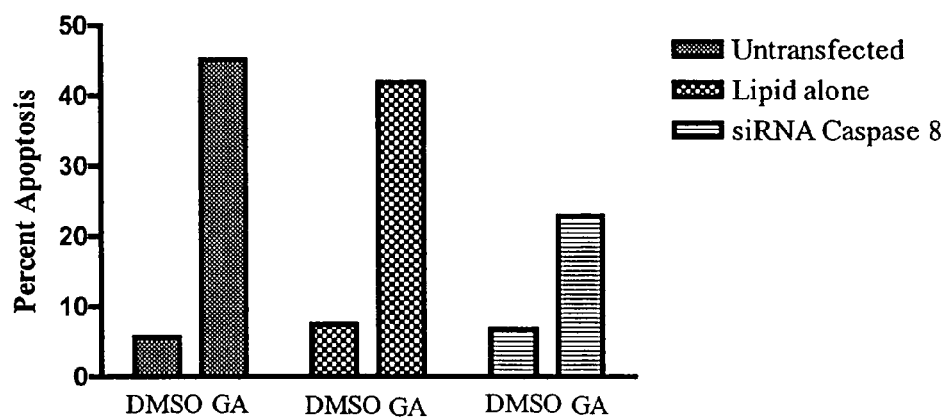
Fig. 4C

SEQUENCE LISTING

<160> NUMBER OF SEQ ID NOS: 49

<210> SEQ ID NO 1
<211> LENGTH: 760
<212> TYPE: PRT

<213> ORGANISM: Homo sapiens

<400> SEQUENCE: 1

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400
```

His Tyr Val Val Gly Ala Gln Arg Asp Ala Trp Gly Pro Gly Ala
            405                 410                 415

Ala Lys Ser Gly Val Gly Thr Ala Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
            485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
            725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 2
<211> LENGTH: 760
<212> TYPE: PRT
<213> ORGANISM: Homo sapiens

<400> SEQUENCE: 2

Met Met Asp Gln Ala Arg Ser Ala Phe Ser Asn Leu Phe Gly Gly Glu
1               5                   10                  15

-continued

```
Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
            115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
            195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
    275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430
```

```
Phe Ser Asp Met Val Leu Lys Asp Gly Phe Gln Pro Ser Arg Ser Ile
            435                 440                 445
Ile Phe Ala Ser Trp Ser Ala Gly Asp Phe Gly Ser Val Gly Ala Thr
        450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
Ser Ala Ser Pro Leu Leu Tyr Thr Leu Ile Glu Lys Thr Met Gln Asn
            500                 505                 510
Val Lys His Pro Val Thr Gly Gln Phe Leu Tyr Gln Asp Ser Asn Trp
        515                 520                 525
Ala Ser Lys Val Glu Lys Leu Thr Leu Asp Asn Ala Ala Phe Pro Phe
    530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
            580                 585                 590
Val Ala Gly Gln Phe Val Ile Lys Leu Thr His Asp Val Glu Leu Asn
        595                 600                 605
Leu Asp Tyr Glu Arg Tyr Asn Ser Gln Leu Leu Ser Phe Val Arg Asp
    610                 615                 620
Leu Asn Gln Tyr Arg Ala Asp Ile Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Gly Asn Ala Glu Lys Thr Asp Arg Phe Val Met Lys
            660                 665                 670
Lys Leu Asn Asp Arg Val Met Arg Val Glu Tyr His Phe Leu Ser Pro
        675                 680                 685
Tyr Val Ser Pro Lys Glu Ser Pro Phe Arg His Val Phe Trp Gly Ser
    690                 695                 700
Gly Ser His Thr Leu Pro Ala Leu Leu Glu Asn Leu Lys Leu Arg Lys
705                 710                 715                 720
Gln Asn Asn Gly Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
            740                 745                 750
Val Trp Asp Ile Asp Asn Glu Phe
        755                 760

<210> SEQ ID NO 3
<211> LENGTH: 760
<212> TYPE: PRT
<213> ORGANISM: Homo sapiens

<400> SEQUENCE: 3

Met Met Asp Gln Ala Arg Ser Ala Phe Ser Asn Leu Phe Gly Gly Glu
1               5                   10                  15
Pro Leu Ser Tyr Thr Arg Phe Ser Leu Ala Arg Gln Val Asp Gly Asp
            20                  25                  30
Asn Ser His Val Glu Met Lys Leu Ala Val Asp Glu Glu Glu Asn Ala
        35                  40                  45
```

```
Asp Asn Asn Thr Lys Ala Asn Val Thr Lys Pro Lys Arg Cys Ser Gly
         50                  55                  60
Ser Ile Cys Tyr Gly Thr Ile Ala Val Ile Val Phe Phe Leu Ile Gly
 65                  70                  75                  80
Phe Met Ile Gly Tyr Leu Gly Tyr Cys Lys Gly Val Glu Pro Lys Thr
                 85                  90                  95
Glu Cys Glu Arg Leu Ala Gly Thr Glu Ser Pro Val Arg Glu Glu Pro
             100                 105                 110
Gly Glu Asp Phe Pro Ala Ala Arg Arg Leu Tyr Trp Asp Asp Leu Lys
         115                 120                 125
Arg Lys Leu Ser Glu Lys Leu Asp Ser Thr Asp Phe Thr Gly Thr Ile
 130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                165                 170                 175
Lys Leu Ser Lys Val Trp Arg Asp Gln His Phe Val Lys Ile Gln Val
            180                 185                 190
Lys Asp Ser Ala Gln Asn Ser Val Ile Val Asp Lys Asn Gly Arg
        195                 200                 205
Leu Val Tyr Leu Val Glu Asn Pro Gly Gly Tyr Val Ala Tyr Ser Lys
    210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
            260                 265                 270
Ser Leu Asn Ala Ile Gly Val Leu Ile Tyr Met Asp Gln Thr Lys Phe
        275                 280                 285
Pro Ile Val Asn Ala Glu Leu Ser Phe Phe Gly His Ala His Leu Gly
    290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
            340                 345                 350
Cys Pro Ser Asp Trp Lys Thr Asp Ser Thr Cys Arg Met Val Thr Ser
        355                 360                 365
Glu Ser Lys Asn Val Lys Leu Thr Val Ser Asn Val Leu Lys Glu Ile
    370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
            420                 425                 430
Phe Ser Asp Met Val Leu Lys Asp Gly Phe Gln Pro Ser Arg Ser Ile
        435                 440                 445
Ile Phe Ala Ser Trp Ser Ala Gly Asp Phe Gly Ser Val Gly Ala Thr
    450                 455                 460
```

-continued

| | | | | | | | | | | | | | | |
|---|---|---|---|---|---|---|---|---|---|---|---|---|---|---|
|Glu|Trp|Leu|Glu|Gly|Tyr|Leu|Ser|Ser|Leu|His|Leu|Lys|Ala|Phe|Thr|
|465| | | |470| | | |475| | | |480|

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
    675                 680                 685

Tyr Val Ser Pro Lys Glu Ser Pro Phe Arg His Val Phe Trp Gly Ser
690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
    755                 760

<210> SEQ ID NO 4
<211> LENGTH: 760
<212> TYPE: PRT
<213> ORGANISM: Homo sapiens

<400> SEQUENCE: 4

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

```
Phe Met Ile Gly Tyr Leu Gly Tyr Cys Lys Gly Val Glu Pro Lys Thr
                85                  90                  95
Glu Cys Glu Arg Leu Ala Gly Thr Glu Ser Pro Val Arg Glu Glu Pro
            100                 105                 110
Gly Glu Asp Phe Pro Ala Ala Arg Leu Tyr Trp Asp Asp Leu Lys
        115                 120                 125
Arg Lys Leu Ser Glu Lys Leu Asp Ser Thr Asp Phe Thr Ser Thr Ile
    130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                165                 170                 175
Lys Leu Ser Lys Val Trp Arg Asp Gln His Phe Val Lys Ile Gln Val
            180                 185                 190
Lys Asp Ser Ala Gln Asn Ser Val Ile Ile Val Asp Lys Asn Gly Arg
        195                 200                 205
Leu Val Tyr Leu Val Glu Asn Pro Gly Gly Tyr Val Ala Tyr Ser Lys
    210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                245                 250                 255
Val Arg Ala Gly Lys Ile Thr Phe Ala Glu Lys Val Ala Asn Ala Glu
            260                 265                 270
Ser Leu Asn Ala Ile Gly Val Leu Ile Tyr Met Asp Gln Thr Lys Phe
        275                 280                 285
Pro Ile Val Asn Ala Glu Leu Ser Phe Phe Gly His Ala His Leu Gly
    290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                325                 330                 335
Ile Ser Arg Ala Ala Ala Glu Lys Leu Phe Gly Asn Met Glu Gly Asp
            340                 345                 350
Cys Pro Ser Asp Trp Lys Thr Asp Ser Thr Cys Arg Met Val Thr Ser
        355                 360                 365
Glu Ser Lys Asn Val Lys Leu Thr Val Ser Asn Val Leu Lys Glu Ile
    370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                405                 410                 415
Ala Lys Ser Gly Val Gly Thr Ala Leu Leu Leu Lys Leu Ala Gln Met
            420                 425                 430
Phe Ser Asp Met Val Leu Lys Asp Gly Phe Gln Pro Ser Arg Ser Ile
        435                 440                 445
Ile Phe Ala Ser Trp Ser Ala Gly Asp Phe Gly Ser Val Gly Ala Thr
    450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                485                 490                 495
```

```
Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 5
<211> LENGTH: 760
<212> TYPE: PRT
<213> ORGANISM: Homo sapiens

<400> SEQUENCE: 5

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110
```

```
Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525
```

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
    675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 6
<211> LENGTH: 760
<212> TYPE: PRT
<213> ORGANISM: Homo sapiens

<400> SEQUENCE: 6

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Glu Asn Ala
            35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

-continued

```
Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
                260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
        290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
                340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
        370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560
```

```
Thr Asp Tyr Pro Tyr Leu Gly Thr Thr Met Asp Thr Tyr Lys Glu Leu
            565                 570                 575
Ile Glu Arg Ile Pro Glu Leu Asn Lys Val Ala Arg Ala Ala Ala Glu
            580                 585                 590
Val Ala Gly Gln Phe Val Ile Lys Leu Thr His Asp Val Glu Leu Asn
            595                 600                 605
Leu Asp Tyr Glu Arg Tyr Asn Ser Gln Leu Leu Ser Phe Val Arg Asp
            610                 615                 620
Leu Asn Gln Tyr Arg Ala Asp Ile Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Gly Asn Ala Glu Lys Thr Asp Arg Phe Val Met Lys
                660                 665                 670
Lys Leu Asn Asp Arg Val Met Arg Val Glu Tyr His Phe Leu Ser Pro
            675                 680                 685
Tyr Val Ser Pro Lys Glu Ser Pro Phe Arg His Val Phe Trp Gly Ser
            690                 695                 700
Gly Ser His Thr Leu Pro Ala Leu Leu Glu Asn Leu Lys Leu Arg Lys
705                 710                 715                 720
Gln Asn Asn Gly Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
                740                 745                 750
Val Trp Asp Ile Asp Asn Glu Phe
            755                 760

<210> SEQ ID NO 7
<211> LENGTH: 63
<212> TYPE: PRT
<213> ORGANISM: Cavia Sp.

<400> SEQUENCE: 7

Lys Ile Thr Phe Ala Glu Lys Val Ala Asn Ala Glu Ser Leu Asn Ala
1               5                   10                  15
Leu Gly Val Leu Ile Tyr Leu Asp Trp Thr Lys Phe Pro Ile Pro Lys
            20                  25                  30
Ala Asp Leu Pro Val Phe Gly His Val His Leu Gly Thr Gly Asp Pro
        35                  40                  45
Tyr Thr Pro Gly Phe Pro Ser Phe Asn His Thr Gln Phe Pro Pro
    50                  55                  60

<210> SEQ ID NO 8
<211> LENGTH: 760
<212> TYPE: PRT
<213> ORGANISM: Homo sapiens

<400> SEQUENCE: 8

Met Met Asp Gln Ala Arg Ser Ala Phe Ser Asn Leu Phe Gly Gly Glu
1               5                   10                  15
Pro Leu Ser Tyr Thr Arg Phe Ser Leu Ala Arg Gln Val Asp Gly Asp
            20                  25                  30
Asn Ser His Val Glu Met Lys Leu Ala Val Asp Glu Glu Asn Ala
        35                  40                  45
Asp Asn Asn Thr Lys Ala Asn Val Thr Lys Pro Lys Arg Cys Ser Gly
    50                  55                  60
```

-continued

```
Ser Ile Cys Tyr Gly Thr Ile Ala Val Ile Val Phe Phe Leu Ile Gly
 65                  70                  75                  80

Phe Met Ile Gly Tyr Leu Gly Tyr Cys Lys Gly Val Glu Pro Lys Thr
                 85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
```

```
                485                 490                 495
Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
            565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
            645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
            725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 9
<211> LENGTH: 760
<212> TYPE: PRT
<213> ORGANISM: Homo sapiens

<400> SEQUENCE: 9

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
            35                  40                  45

Asp Asn Asn Thr Lys Ala Asn Val Thr Lys Pro Lys Arg Cys Ser Gly
        50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
            85                  90                  95
```

-continued

```
Glu Cys Glu Arg Leu Ala Gly Thr Glu Ser Pro Val Arg Glu Glu Pro
            100                 105                 110

Gly Glu Asp Phe Pro Ala Ala Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
```

-continued

```
                515                 520                 525
Ala Ser Lys Val Glu Lys Leu Thr Leu Asp Asn Ala Ala Phe Pro Phe
        530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
                580                 585                 590
Val Ala Gly Gln Phe Val Ile Lys Leu Thr His Asp Val Glu Leu Asn
            595                 600                 605
Leu Asp Tyr Glu Arg Tyr Asn Ser Gln Leu Leu Ser Phe Val Arg Asp
        610                 615                 620
Leu Asn Gln Tyr Arg Ala Asp Ile Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Gly Asn Ala Glu Lys Thr Asp Arg Phe Val Met Lys
                660                 665                 670
Lys Leu Asn Asp Arg Val Met Arg Val Glu Tyr His Phe Leu Ser Pro
        675                 680                 685
Tyr Val Ser Pro Lys Glu Ser Pro Phe Arg His Val Phe Trp Gly Ser
    690                 695                 700
Gly Ser His Thr Leu Pro Ala Leu Leu Glu Asn Leu Lys Leu Arg Lys
705                 710                 715                 720
Gln Asn Asn Gly Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
            740                 745                 750
Val Trp Asp Ile Asp Asn Glu Phe
        755                 760

<210> SEQ ID NO 10
<211> LENGTH: 760
<212> TYPE: PRT
<213> ORGANISM: Homo sapiens

<400> SEQUENCE: 10

Met Met Asp Gln Ala Arg Ser Ala Phe Ser Asn Leu Phe Gly Gly Glu
1               5                   10                  15
Pro Leu Ser Tyr Thr Arg Phe Ser Leu Ala Arg Gln Val Asp Gly Asp
                20                  25                  30
Asn Ser His Val Glu Met Lys Leu Ala Val Asp Glu Glu Asn Ala
            35                  40                  45
Asp Asn Asn Thr Lys Ala Asn Val Thr Lys Pro Lys Arg Cys Ser Gly
        50                  55                  60
Ser Ile Cys Tyr Gly Thr Ile Ala Val Ile Val Phe Phe Leu Ile Gly
65                  70                  75                  80
Phe Met Ile Gly Tyr Leu Gly Tyr Cys Lys Gly Val Glu Pro Lys Thr
                85                  90                  95
Glu Cys Glu Arg Leu Ala Gly Thr Glu Ser Pro Val Arg Glu Glu Pro
                100                 105                 110
Gly Glu Asp Phe Pro Ala Ala Arg Arg Leu Tyr Trp Asp Asp Leu Lys
            115                 120                 125
```

-continued

```
Arg Lys Leu Ser Glu Lys Leu Asp Ser Thr Asp Phe Thr Ser Thr Ile
    130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                    165                 170                 175
Lys Leu Ser Lys Val Trp Arg Asp Gln His Phe Val Lys Ile Gln Val
                180                 185                 190
Lys Asp Ser Ala Gln Asn Ser Val Ile Ile Val Asp Lys Asn Gly Arg
            195                 200                 205
Leu Val Tyr Leu Val Glu Asn Pro Gly Gly Tyr Val Ala Tyr Ser Lys
    210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                    245                 250                 255
Val Arg Ala Gly Lys Ile Thr Phe Ala Glu Lys Val Ala Asn Ala Glu
                260                 265                 270
Ser Leu Asn Ala Ile Gly Val Leu Ile Tyr Met Asp Gln Thr Lys Phe
            275                 280                 285
Pro Ile Val Asn Ala Glu Leu Ser Phe Phe Gly His Ala His Leu Gly
    290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                    325                 330                 335
Ile Ser Arg Ala Ala Ala Glu Lys Leu Phe Gly Asn Met Glu Gly Asp
                340                 345                 350
Cys Pro Ser Asp Trp Lys Thr Asp Ser Thr Cys Arg Met Val Thr Ser
            355                 360                 365
Glu Ser Lys Asn Val Lys Leu Thr Val Ser Asn Val Leu Lys Glu Ile
    370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                    405                 410                 415
Ala Lys Ser Gly Val Gly Thr Ala Leu Leu Leu Lys Leu Ala Gln Met
                420                 425                 430
Phe Ser Asp Met Val Leu Lys Asp Gly Phe Gln Pro Ser Arg Ser Ile
            435                 440                 445
Ile Phe Ala Ser Trp Ser Ala Gly Asp Phe Gly Ser Val Gly Ala Thr
    450                 455                 460
Glu Trp Leu Glu Gly Tyr Leu Ser Ser Leu His Leu Lys Ala Phe Thr
465                 470                 475                 480
Tyr Ile Asn Leu Asp Lys Ala Val Leu Gly Thr Ser Asn Phe Lys Val
                    485                 490                 495
Ser Ala Ser Pro Leu Leu Tyr Thr Leu Ile Glu Lys Thr Met Gln Asn
                500                 505                 510
Val Lys His Pro Val Thr Gly Gln Phe Leu Tyr Gln Asp Ser Asn Trp
            515                 520                 525
Ala Ser Lys Val Glu Lys Leu Thr Leu Asp Asn Ala Ala Phe Pro Phe
    530                 535                 540
Leu Ala Tyr Ser Gly Ile Pro Ala Val Ser Phe Cys Phe Cys Glu Asp
```

-continued

```
               545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
                580                 585                 590

Val Ala Gly Gln Phe Val Ile Lys Leu Thr His Asp Val Glu Leu Asn
            595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
                660                 665                 670

Lys Leu Asn Asp Arg Val Met Arg Val Glu Tyr His Phe Leu Ser Pro
            675                 680                 685

Tyr Val Ser Pro Lys Glu Ser Pro Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
                740                 745                 750

Val Trp Asp Ile Asp Asn Glu Phe
            755                 760

<210> SEQ ID NO 11
<211> LENGTH: 640
<212> TYPE: PRT
<213> ORGANISM: Homo sapiens

<400> SEQUENCE: 11

Arg Leu Tyr Trp Asp Asp Leu Lys Arg Lys Leu Ser Glu Lys Leu Asp
1               5                   10                  15

Ser Thr Asp Phe Thr Ser Thr Ile Lys Leu Leu Asn Glu Asn Ser Tyr
                20                  25                  30

Val Pro Arg Glu Ala Gly Ser Gln Lys Asp Glu Asn Leu Ala Leu Tyr
            35                  40                  45

Val Glu Asn Gln Phe Arg Glu Phe Lys Leu Ser Lys Val Trp Arg Asp
        50                  55                  60

Gln His Phe Val Lys Ile Gln Val Lys Asp Ser Ala Gln Asn Ser Val
65                  70                  75                  80

Ile Ile Val Asp Lys Asn Gly Arg Leu Val Tyr Leu Val Glu Asn Pro
                85                  90                  95

Gly Gly Tyr Val Ala Tyr Ser Lys Ala Ala Thr Val Thr Gly Lys Leu
            100                 105                 110

Val His Ala Asn Phe Gly Thr Lys Lys Asp Phe Glu Asp Leu Tyr Thr
        115                 120                 125

Pro Val Asn Gly Ser Ile Val Ile Val Arg Ala Gly Lys Ile Thr Phe
    130                 135                 140

Ala Glu Lys Val Ala Asn Ala Glu Ser Leu Asn Ala Ile Gly Val Leu
145                 150                 155                 160
```

-continued

```
Ile Tyr Met Asp Gln Thr Lys Phe Pro Ile Val Asn Ala Glu Leu Ser
                165                 170                 175
Phe Phe Gly His Ala His Leu Gly Thr Gly Asp Pro Tyr Thr Pro Gly
            180                 185                 190
Phe Pro Ser Phe Asn His Thr Gln Phe Pro Ser Arg Ser Ser Gly
        195                 200                 205
Leu Pro Asn Ile Pro Val Gln Thr Ile Ser Arg Ala Ala Glu Lys
    210                 215                 220
Leu Phe Gly Asn Met Glu Gly Asp Cys Pro Ser Asp Trp Lys Thr Asp
225                 230                 235                 240
Ser Thr Cys Arg Met Val Thr Ser Glu Ser Lys Asn Val Lys Leu Thr
                245                 250                 255
Val Ser Asn Val Leu Lys Glu Ile Lys Ile Leu Asn Ile Phe Gly Val
            260                 265                 270
Ile Lys Gly Phe Val Glu Pro Asp His Tyr Val Val Gly Ala Gln
        275                 280                 285
Arg Asp Ala Trp Gly Pro Gly Ala Ala Lys Ser Gly Val Gly Thr Ala
    290                 295                 300
Leu Leu Leu Lys Leu Ala Gln Met Phe Ser Asp Met Val Leu Lys Asp
305                 310                 315                 320
Gly Phe Gln Pro Ser Arg Ser Ile Ile Phe Ala Ser Trp Ser Ala Gly
                325                 330                 335
Asp Phe Gly Ser Val Gly Ala Thr Glu Trp Leu Glu Gly Tyr Leu Ser
            340                 345                 350
Ser Leu His Leu Lys Ala Phe Thr Tyr Ile Asn Leu Asp Lys Ala Val
        355                 360                 365
Leu Gly Thr Ser Asn Phe Lys Val Ser Ala Ser Pro Leu Leu Tyr Thr
    370                 375                 380
Leu Ile Glu Lys Thr Met Gln Asn Val Lys His Pro Val Thr Gly Gln
385                 390                 395                 400
Phe Leu Tyr Gln Asp Ser Asn Trp Ala Ser Lys Val Glu Lys Leu Thr
                405                 410                 415
Leu Asp Asn Ala Ala Phe Pro Phe Leu Ala Tyr Ser Gly Ile Pro Ala
            420                 425                 430
Val Ser Phe Cys Phe Cys Glu Asp Thr Asp Tyr Pro Tyr Leu Gly Thr
        435                 440                 445
Thr Met Asp Thr Tyr Lys Glu Leu Ile Glu Arg Ile Pro Glu Leu Asn
    450                 455                 460
Lys Val Ala Arg Ala Ala Ala Glu Val Ala Gly Gln Phe Val Ile Lys
465                 470                 475                 480
Leu Thr His Asp Val Glu Leu Asn Leu Asp Tyr Glu Arg Tyr Asn Ser
                485                 490                 495
Gln Leu Leu Ser Phe Val Arg Asp Leu Asn Gln Tyr Arg Ala Asp Ile
            500                 505                 510
Lys Glu Met Gly Leu Ser Leu Gln Trp Leu Tyr Ser Ala Arg Gly Asp
        515                 520                 525
Phe Phe Arg Ala Thr Ser Arg Leu Thr Thr Asp Phe Gly Asn Ala Glu
    530                 535                 540
Lys Thr Asp Arg Phe Val Met Lys Lys Leu Asn Asp Arg Val Met Arg
545                 550                 555                 560
Val Glu Tyr His Phe Leu Ser Pro Tyr Val Ser Pro Lys Glu Ser Pro
                565                 570                 575
Phe Arg His Val Phe Trp Gly Ser Gly Ser His Thr Leu Pro Ala Leu
```

```
                        580                 585                 590
Leu Glu Asn Leu Lys Leu Arg Lys Gln Asn Asn Gly Ala Phe Asn Glu
            595                 600                 605

Thr Leu Phe Arg Asn Gln Leu Ala Leu Ala Thr Trp Thr Ile Gln Gly
        610                 615                 620

Ala Ala Asn Ala Leu Ser Gly Asp Val Trp Asp Ile Asp Asn Glu Phe
625                 630                 635                 640

<210> SEQ ID NO 12
<211> LENGTH: 640
<212> TYPE: PRT
<213> ORGANISM: Homo sapiens

<400> SEQUENCE: 12

Arg Leu Tyr Trp Asp Asp Leu Lys Arg Lys Leu Ser Glu Lys Leu Asp
1               5                   10                  15

Ser Thr Asp Phe Thr Ser Thr Ile Lys Leu Leu Asn Glu Asn Ser Tyr
            20                  25                  30

Val Pro Arg Glu Ala Gly Ser Gln Lys Asp Glu Asn Leu Ala Leu Tyr
        35                  40                  45

Val Glu Asn Gln Phe Arg Glu Phe Lys Leu Ser Lys Val Trp Arg Asp
50                  55                  60

Gln His Phe Val Lys Ile Gln Val Lys Asp Ser Ala Gln Asn Ser Val
65                  70                  75                  80

Ile Ile Val Asp Lys Asn Gly Arg Leu Val Tyr Leu Val Glu Asn Pro
                85                  90                  95

Gly Gly Tyr Val Ala Tyr Ser Lys Ala Ala Thr Val Thr Gly Lys Leu
            100                 105                 110

Val His Ala Asn Phe Gly Thr Lys Lys Asp Phe Glu Asp Leu Tyr Thr
        115                 120                 125

Pro Val Asn Gly Ser Ile Val Ile Val Arg Ala Gly Lys Ile Thr Phe
130                 135                 140

Ala Glu Lys Val Ala Asn Ala Glu Ser Leu Asn Ala Ile Gly Val Leu
145                 150                 155                 160

Ile Tyr Met Asp Gln Thr Lys Phe Pro Ile Val Asn Ala Glu Leu Ser
                165                 170                 175

Phe Phe Gly His Ala His Leu Gly Thr Gly Asp Pro Tyr Thr Pro Gly
            180                 185                 190

Phe Pro Ser Phe Asn His Thr Gln Phe Pro Pro Ser Arg Ser Ser Gly
        195                 200                 205

Leu Pro Asn Ile Pro Val Gln Thr Ile Ser Arg Ala Ala Ala Glu Lys
210                 215                 220

Leu Phe Gly Asn Met Glu Gly Asp Cys Pro Ser Asp Trp Lys Thr Asp
225                 230                 235                 240

Ser Thr Cys Arg Met Val Thr Ser Glu Ser Lys Asn Val Lys Leu Thr
                245                 250                 255

Val Ser Asn Val Leu Lys Glu Ile Lys Ile Leu Asn Ile Phe Gly Val
            260                 265                 270

Ile Lys Gly Phe Val Glu Pro Asp His Tyr Val Val Gly Ala Gln
        275                 280                 285

Arg Asp Ala Trp Gly Pro Gly Ala Ala Lys Ser Gly Val Gly Thr Ala
        290                 295                 300

Leu Leu Leu Lys Leu Ala Gln Met Phe Ser Asp Met Val Leu Lys Asp
305                 310                 315                 320
```

```
Gly Phe Gln Pro Ser Arg Ser Ile Ile Phe Ala Ser Trp Ser Ala Gly
                325                 330                 335

Asp Phe Gly Ser Val Gly Ala Thr Glu Trp Leu Glu Gly Tyr Leu Ser
            340                 345                 350

Ser Leu His Leu Lys Ala Phe Thr Tyr Ile Asn Leu Asp Lys Ala Val
        355                 360                 365

Leu Gly Thr Ser Asn Phe Lys Val Ser Ala Ser Pro Leu Leu Tyr Thr
    370                 375                 380

Leu Ile Glu Lys Thr Met Gln Asn Val Lys His Pro Val Thr Gly Gln
385                 390                 395                 400

Phe Leu Tyr Gln Asp Ser Asn Trp Ala Ser Lys Val Glu Lys Leu Thr
                405                 410                 415

Leu Asp Asn Ala Ala Phe Pro Phe Leu Ala Tyr Ser Gly Ile Pro Ala
            420                 425                 430

Val Ser Phe Cys Phe Cys Glu Asp Thr Asp Tyr Pro Tyr Leu Gly Thr
        435                 440                 445

Thr Met Asp Thr Tyr Lys Glu Leu Ile Glu Arg Ile Pro Glu Leu Asn
    450                 455                 460

Lys Val Ala Arg Ala Ala Ala Glu Val Ala Gly Gln Phe Val Ile Lys
465                 470                 475                 480

Leu Thr His Asp Val Glu Leu Asn Leu Asp Tyr Glu Arg Tyr Asn Ser
                485                 490                 495

Gln Leu Leu Ser Phe Val Arg Asp Leu Asn Gln Tyr Arg Ala Asp Ile
            500                 505                 510

Lys Glu Met Gly Leu Ser Leu Gln Trp Leu Tyr Ser Ala Arg Gly Asp
        515                 520                 525

Phe Phe Arg Ala Thr Ser Arg Leu Thr Thr Asp Phe Gly Asn Ala Glu
    530                 535                 540

Lys Thr Asp Arg Phe Val Met Lys Lys Leu Asn Asp Arg Val Met Arg
545                 550                 555                 560

Val Glu Tyr His Phe Leu Ser Pro Tyr Val Ser Pro Lys Glu Ser Pro
                565                 570                 575

Phe Arg His Val Phe Trp Gly Ser Gly Ser His Thr Leu Pro Ala Leu
            580                 585                 590

Leu Glu Asn Leu Lys Leu Arg Lys Gln Asn Asn Gly Ala Phe Asn Glu
        595                 600                 605

Thr Leu Phe Arg Asn Gln Leu Ala Leu Ala Thr Trp Thr Ile Gln Gly
    610                 615                 620

Ala Ala Asn Ala Leu Ser Gly Asp Val Trp Asp Ile Asp Asn Glu Phe
625                 630                 635                 640

<210> SEQ ID NO 13
<211> LENGTH: 640
<212> TYPE: PRT
<213> ORGANISM: Homo sapiens

<400> SEQUENCE: 13

Arg Leu Tyr Trp Asp Asp Leu Lys Arg Lys Leu Ser Glu Lys Leu Asp
1               5                   10                  15

Ser Thr Asp Phe Thr Ser Thr Ile Lys Leu Leu Asn Glu Asn Ser Tyr
            20                  25                  30

Val Pro Arg Glu Ala Gly Ser Gln Lys Asp Glu Asn Leu Ala Leu Tyr
        35                  40                  45

Val Glu Asn Gln Phe Arg Glu Phe Lys Leu Ser Lys Val Trp Arg Asp
    50                  55                  60
```

```
Gln His Phe Val Lys Ile Gln Val Lys Asp Ser Ala Gln Asn Ser Val
65                  70                  75                  80

Ile Ile Val Asp Lys Asn Gly Arg Leu Val Tyr Leu Val Glu Asn Pro
                85                  90                  95

Gly Gly Tyr Val Ala Tyr Ser Lys Ala Ala Thr Val Thr Gly Lys Leu
                100                 105                 110

Val His Ala Asn Phe Gly Thr Lys Lys Asp Phe Glu Asp Leu Tyr Thr
                115                 120                 125

Pro Val Asn Gly Ser Ile Val Ile Val Arg Ala Gly Lys Ile Thr Phe
                130                 135                 140

Ala Glu Lys Val Ala Asn Ala Glu Ser Leu Asn Ala Ile Gly Val Leu
145                 150                 155                 160

Ile Tyr Met Asp Gln Thr Lys Phe Pro Ile Val Asn Ala Glu Leu Ser
                165                 170                 175

Phe Phe Gly His Ala His Leu Gly Thr Gly Asp Pro Tyr Thr Pro Gly
                180                 185                 190

Phe Pro Ser Phe Asn His Thr Gln Phe Pro Pro Ser Arg Ser Ser Gly
                195                 200                 205

Leu Pro Asn Ile Pro Val Gln Thr Ile Ser Arg Ala Ala Ala Glu Lys
                210                 215                 220

Leu Phe Gly Asn Met Glu Gly Asp Cys Pro Ser Asp Trp Lys Thr Asp
225                 230                 235                 240

Ser Thr Cys Arg Met Val Thr Ser Glu Ser Lys Asn Val Lys Leu Thr
                245                 250                 255

Val Ser Asn Val Leu Lys Glu Ile Lys Ile Leu Asn Ile Phe Gly Val
                260                 265                 270

Ile Lys Gly Phe Val Glu Pro Asp His Tyr Val Val Gly Ala Gln
                275                 280                 285

Arg Asp Ala Trp Gly Pro Gly Ala Ala Lys Ser Gly Val Gly Thr Ala
290                 295                 300

Leu Leu Leu Lys Leu Ala Gln Met Phe Ser Asp Met Val Leu Lys Asp
305                 310                 315                 320

Gly Phe Gln Pro Ser Arg Ser Ile Ile Phe Ala Ser Trp Ser Ala Gly
                325                 330                 335

Asp Phe Gly Ser Val Gly Ala Thr Glu Trp Leu Glu Gly Tyr Leu Ser
                340                 345                 350

Ser Leu His Leu Lys Ala Phe Thr Tyr Ile Asn Leu Asp Lys Ala Val
                355                 360                 365

Leu Gly Thr Ser Asn Phe Lys Val Ser Ala Ser Pro Leu Leu Tyr Thr
                370                 375                 380

Leu Ile Glu Lys Thr Met Gln Asn Val Lys His Pro Val Thr Gly Gln
385                 390                 395                 400

Phe Leu Tyr Gln Asp Ser Asn Trp Ala Ser Lys Val Glu Lys Leu Thr
                405                 410                 415

Leu Asp Asn Ala Ala Phe Pro Phe Leu Ala Tyr Ser Gly Ile Pro Ala
                420                 425                 430

Val Ser Phe Cys Phe Cys Glu Asp Thr Asp Tyr Pro Tyr Leu Gly Thr
                435                 440                 445

Thr Met Asp Thr Tyr Lys Glu Leu Ile Glu Arg Ile Pro Glu Leu Asn
                450                 455                 460

Lys Val Ala Arg Ala Ala Ala Glu Val Ala Gly Gln Phe Val Ile Lys
465                 470                 475                 480
```

```
Leu Thr His Asp Val Glu Leu Asn Leu Asp Tyr Glu Arg Tyr Asn Ser
                485                 490                 495

Gln Leu Leu Ser Phe Val Arg Asp Leu Asn Gln Tyr Arg Ala Asp Ile
            500                 505                 510

Lys Glu Met Gly Leu Ser Leu Gln Trp Leu Tyr Ser Ala Arg Gly Asp
        515                 520                 525

Phe Phe Arg Ala Thr Ser Arg Leu Thr Thr Asp Phe Gly Asn Ala Glu
    530                 535                 540

Lys Thr Asp Arg Phe Val Met Lys Lys Leu Asn Asp Arg Val Met Arg
545                 550                 555                 560

Val Glu Tyr His Phe Leu Ser Pro Tyr Val Ser Pro Lys Glu Ser Pro
                565                 570                 575

Phe Arg His Val Phe Trp Gly Ser Gly Ser His Thr Leu Pro Ala Leu
            580                 585                 590

Leu Glu Asn Leu Lys Leu Arg Lys Gln Asn Asn Gly Ala Phe Asn Glu
        595                 600                 605

Thr Leu Phe Arg Asn Gln Leu Ala Leu Ala Thr Trp Thr Ile Gln Gly
    610                 615                 620

Ala Ala Asn Ala Leu Ser Gly Asp Val Trp Asp Ile Asp Asn Glu Phe
625                 630                 635                 640

<210> SEQ ID NO 14
<211> LENGTH: 639
<212> TYPE: PRT
<213> ORGANISM: Homo sapiens

<400> SEQUENCE: 14

Leu Tyr Trp Asp Asp Leu Lys Arg Lys Leu Ser Glu Lys Leu Asp Ser
1               5                   10                  15

Thr Asp Phe Thr Ser Thr Ile Lys Leu Leu Asn Glu Asn Ser Tyr Val
            20                  25                  30

Pro Arg Glu Ala Gly Ser Gln Lys Asp Glu Asn Leu Ala Leu Tyr Val
        35                  40                  45

Glu Asn Glu Phe Arg Glu Phe Lys Leu Ser Lys Val Trp Arg Asp Gln
    50                  55                  60

His Phe Val Lys Ile Gln Val Lys Asp Ser Ala Gln Asn Ser Val Ile
65                  70                  75                  80

Ile Val Asp Lys Asn Gly Arg Leu Val Tyr Leu Val Glu Asn Pro Gly
                85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
        115                 120                 125

Val Asn Gly Ser Ile Val Ile Val Arg Ala Gly Lys Ile Thr Phe Ala
    130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175

Phe Gly His Ala His Leu Gly Thr Gly Asp Pro Tyr Thr Pro Gly Phe
            180                 185                 190

Pro Ser Phe Asn His Thr Gln Phe Pro Pro Ser Arg Ser Ser Gly Leu
        195                 200                 205

Pro Asn Ile Pro Val Gln Thr Ile Ser Arg Ala Ala Ala Glu Lys Leu
    210                 215                 220
```

```
Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
            245                 250                 255

Ser Asn Val Leu Lys Glu Ile Lys Ile Leu Asn Ile Phe Gly Val Ile
                260                 265                 270

Lys Gly Phe Val Glu Pro Asp His Tyr Val Val Gly Ala Gln Arg
            275                 280                 285

Asp Ala Trp Gly Pro Gly Ala Ala Lys Ser Gly Val Gly Thr Ala Leu
        290                 295                 300

Leu Leu Lys Leu Ala Gln Met Phe Ser Asp Met Val Leu Lys Asp Gly
305                 310                 315                 320

Phe Gln Pro Ser Arg Ser Ile Ile Phe Ala Ser Trp Ser Ala Gly Asp
                325                 330                 335

Phe Gly Ser Val Gly Ala Thr Glu Trp Leu Glu Gly Tyr Leu Ser Ser
            340                 345                 350

Leu His Leu Lys Ala Phe Thr Tyr Ile Asn Leu Asp Lys Ala Val Leu
        355                 360                 365

Gly Thr Ser Asn Phe Lys Val Ser Ala Ser Pro Leu Leu Tyr Thr Leu
370                 375                 380

Ile Glu Lys Thr Met Gln Asn Val Lys His Pro Val Thr Gly Gln Phe
385                 390                 395                 400

Leu Tyr Gln Asp Ser Asn Trp Ala Ser Lys Val Glu Lys Leu Thr Leu
                405                 410                 415

Asp Asn Ala Ala Phe Pro Phe Leu Ala Tyr Ser Gly Ile Pro Ala Val
            420                 425                 430

Ser Phe Cys Phe Cys Glu Asp Thr Asp Tyr Pro Tyr Leu Gly Thr Thr
        435                 440                 445

Met Asp Thr Tyr Lys Glu Leu Ile Glu Arg Ile Pro Glu Leu Asn Lys
450                 455                 460

Val Ala Arg Ala Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495

Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
        515                 520                 525

Phe Arg Ala Thr Ser Arg Leu Thr Thr Asp Phe Gly Asn Ala Glu Lys
530                 535                 540

Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
            580                 585                 590

Glu Asn Leu Lys Leu Arg Lys Gln Asn Asn Gly Ala Phe Asn Glu Thr
        595                 600                 605

Leu Phe Arg Asn Gln Leu Ala Leu Ala Thr Trp Thr Ile Gln Gly Ala
610                 615                 620

Ala Asn Ala Leu Ser Gly Asp Val Trp Asp Ile Asp Asn Glu Phe
625                 630                 635
```

<210> SEQ ID NO 15
<211> LENGTH: 639
<212> TYPE: PRT
<213> ORGANISM: Homo sapiens

<400> SEQUENCE: 15

| | | | | | | | | | | | | | | |
|---|---|---|---|---|---|---|---|---|---|---|---|---|---|---|
| Leu | Tyr | Trp | Asp | Asp | Leu | Lys | Arg | Lys | Leu | Ser | Glu | Lys | Leu | Asp | Ser |
| 1 | | | | 5 | | | | | 10 | | | | | 15 | |

Thr Asp Phe Thr Ser Thr Ile Lys Leu Leu Asn Glu Asn Ser Tyr Val
              20                  25                  30

Pro Arg Glu Ala Gly Ser Gln Lys Asp Glu Asn Leu Ala Leu Tyr Val
          35                  40                  45

Glu Asn Glu Phe Arg Glu Phe Lys Leu Ser Lys Val Trp Arg Asp Gln
 50                  55                  60

His Phe Val Lys Ile Gln Val Lys Asp Ser Ala Gln Asn Ser Val Ile
 65                  70                  75                  80

Ile Val Asp Lys Asn Gly Arg Leu Val Tyr Leu Val Glu Asn Pro Gly
                 85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
        115                 120                 125

Val Asn Gly Ser Ile Val Ile Val Arg Ala Gly Lys Ile Thr Phe Ala
130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175

Phe Gly His Ala His Leu Gly Thr Gly Asp Pro Tyr Thr Pro Gly Phe
            180                 185                 190

Pro Ser Phe Asn His Thr Gln Phe Pro Pro Ser Arg Ser Ser Gly Leu
        195                 200                 205

Pro Asn Ile Pro Val Gln Thr Ile Ser Arg Ala Ala Ala Glu Lys Leu
210                 215                 220

Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
                245                 250                 255

Ser Asn Val Leu Lys Glu Ile Lys Ile Leu Asn Ile Phe Gly Val Ile
            260                 265                 270

Lys Gly Phe Val Glu Pro Asp His Tyr Val Val Val Gly Ala Gln Arg
        275                 280                 285

Asp Ala Trp Gly Pro Gly Ala Ala Lys Ser Gly Val Gly Thr Ala Leu
290                 295                 300

Leu Leu Lys Leu Ala Gln Met Phe Ser Asp Met Val Leu Lys Asp Gly
305                 310                 315                 320

Phe Gln Pro Ser Arg Ser Ile Ile Phe Ala Ser Trp Ser Ala Gly Asp
                325                 330                 335

Phe Gly Ser Val Gly Ala Thr Glu Trp Leu Glu Gly Tyr Leu Ser Ser
            340                 345                 350

Leu His Leu Lys Ala Phe Thr Tyr Ile Asn Leu Asp Lys Ala Val Leu
        355                 360                 365

Gly Thr Ser Asn Phe Lys Val Ser Ala Ser Pro Leu Leu Tyr Thr Leu
370                 375                 380

```
Ile Glu Lys Thr Met Gln Asn Val Lys His Pro Val Thr Gly Gln Phe
385                 390                 395                 400

Leu Tyr Gln Asp Ser Asn Trp Ala Ser Lys Val Glu Lys Leu Thr Leu
            405                 410                 415

Asp Asn Ala Ala Phe Pro Phe Leu Ala Tyr Ser Gly Ile Pro Ala Val
        420                 425                 430

Ser Phe Cys Phe Cys Glu Asp Thr Asp Tyr Pro Tyr Leu Gly Thr Thr
    435                 440                 445

Met Asp Thr Tyr Lys Glu Leu Ile Glu Arg Ile Pro Glu Leu Asn Lys
450                 455                 460

Val Ala Arg Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495

Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
        515                 520                 525

Phe Arg Ala Thr Ser Arg Leu Thr Thr Asp Phe Gly Asn Ala Glu Lys
    530                 535                 540

Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
            580                 585                 590

Glu Asn Leu Lys Leu Arg Lys Gln Asn Asn Gly Ala Phe Asn Glu Thr
        595                 600                 605

Leu Phe Arg Asn Gln Leu Ala Leu Ala Thr Trp Thr Ile Gln Gly Ala
    610                 615                 620

Ala Asn Ala Leu Ser Gly Asp Val Trp Asp Ile Asp Asn Glu Phe
625                 630                 635

<210> SEQ ID NO 16
<211> LENGTH: 639
<212> TYPE: PRT
<213> ORGANISM: Homo sapiens

<400> SEQUENCE: 16

Leu Tyr Trp Asp Asp Leu Lys Arg Lys Leu Ser Glu Lys Leu Asp Ser
1               5                   10                  15

Thr Asp Phe Thr Ser Thr Ile Lys Leu Leu Asn Glu Asn Ser Tyr Val
            20                  25                  30

Pro Arg Glu Ala Gly Ser Gln Lys Asp Glu Asn Leu Ala Leu Tyr Val
        35                  40                  45

Glu Asn Glu Phe Arg Glu Phe Lys Leu Ser Lys Val Trp Arg Asp Gln
50                  55                  60

His Phe Val Lys Ile Gln Val Lys Asp Ser Ala Gln Asn Ser Val Ile
65                  70                  75                  80

Ile Val Asp Lys Asn Gly Arg Leu Val Tyr Leu Val Glu Asn Pro Gly
                85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
```

-continued

```
            115                 120                 125
Val Asn Gly Ser Ile Val Ile Val Arg Ala Gly Lys Ile Thr Phe Ala
    130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175

Phe Gly His Ala His Leu Gly Thr Gly Asp Pro Tyr Thr Pro Gly Phe
            180                 185                 190

Pro Ser Phe Asn His Thr Gln Phe Pro Pro Ser Arg Ser Ser Gly Leu
        195                 200                 205

Pro Asn Ile Pro Val Gln Thr Ile Ser Arg Ala Ala Glu Lys Leu
    210                 215                 220

Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
                245                 250                 255

Ser Asn Val Leu Lys Glu Ile Lys Ile Leu Asn Ile Phe Gly Val Ile
            260                 265                 270

Lys Gly Phe Val Glu Pro Asp His Tyr Val Val Gly Ala Gln Arg
        275                 280                 285

Asp Ala Trp Gly Pro Gly Ala Ala Lys Ser Gly Val Gly Thr Ala Leu
    290                 295                 300

Leu Leu Lys Leu Ala Gln Met Phe Ser Asp Met Val Leu Lys Asp Gly
305                 310                 315                 320

Phe Gln Pro Ser Arg Ser Ile Ile Phe Ala Ser Trp Ser Ala Gly Asp
                325                 330                 335

Phe Gly Ser Val Gly Ala Thr Glu Trp Leu Glu Gly Tyr Leu Ser Ser
            340                 345                 350

Leu His Leu Lys Ala Phe Thr Tyr Ile Asn Leu Asp Lys Ala Val Leu
        355                 360                 365

Gly Thr Ser Asn Phe Lys Val Ser Ala Ser Pro Leu Leu Tyr Thr Leu
    370                 375                 380

Ile Glu Lys Thr Met Gln Asn Val Lys His Pro Val Thr Gly Gln Phe
385                 390                 395                 400

Leu Tyr Gln Asp Ser Asn Trp Ala Ser Lys Val Glu Lys Leu Thr Leu
                405                 410                 415

Asp Asn Ala Ala Phe Pro Phe Leu Ala Tyr Ser Gly Ile Pro Ala Val
            420                 425                 430

Ser Phe Cys Phe Cys Glu Asp Thr Asp Tyr Pro Tyr Leu Gly Thr Thr
        435                 440                 445

Met Asp Thr Tyr Lys Glu Leu Ile Glu Arg Ile Pro Glu Leu Asn Lys
    450                 455                 460

Val Ala Arg Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495

Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
        515                 520                 525

Phe Arg Ala Thr Ser Arg Leu Thr Thr Asp Phe Gly Asn Ala Glu Lys
    530                 535                 540
```

```
Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
                580                 585                 590

Glu Asn Leu Lys Leu Arg Lys Gln Asn Gly Ala Phe Asn Glu Thr
            595                 600                 605

Leu Phe Arg Asn Gln Leu Ala Leu Ala Thr Trp Thr Ile Gln Gly Ala
    610                 615                 620

Ala Asn Ala Leu Ser Gly Asp Val Trp Asp Ile Asp Asn Glu Phe
625                 630                 635
```

<210> SEQ ID NO 17
<211> LENGTH: 639
<212> TYPE: PRT
<213> ORGANISM: Homo sapiens

<400> SEQUENCE: 17

```
Leu Tyr Trp Asp Asp Leu Lys Arg Lys Leu Ser Glu Lys Leu Asp Ser
1               5                   10                  15

Thr Asp Phe Thr Ser Thr Ile Lys Leu Leu Asn Glu Asn Ser Tyr Val
            20                  25                  30

Pro Arg Glu Ala Gly Ser Gln Lys Asp Glu Asn Leu Ala Leu Tyr Val
        35                  40                  45

Glu Asn Glu Phe Arg Glu Phe Lys Leu Ser Lys Val Trp Arg Asp Gln
50                  55                  60

His Phe Val Lys Ile Gln Val Lys Asp Ser Ala Gln Asn Ser Val Ile
65                  70                  75                  80

Ile Val Asp Lys Asn Gly Arg Leu Val Tyr Leu Val Glu Asn Pro Gly
                85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
        115                 120                 125

Val Asn Gly Ser Ile Val Ile Val Arg Ala Gly Lys Ile Thr Phe Ala
    130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175

Phe Gly His Ala His Leu Gly Thr Gly Asp Pro Tyr Thr Pro Gly Phe
            180                 185                 190

Pro Ser Phe Asn His Thr Gln Phe Pro Pro Ser Arg Ser Ser Gly Leu
        195                 200                 205

Pro Asn Ile Pro Val Gln Thr Ile Ser Arg Ala Ala Ala Glu Lys Leu
    210                 215                 220

Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
                245                 250                 255

Ser Asn Val Leu Lys Glu Ile Lys Ile Leu Asn Ile Phe Gly Val Ile
            260                 265                 270

Lys Gly Phe Val Glu Pro Asp His Tyr Val Val Val Gly Ala Gln Arg
```

```
                       275                 280                 285
Asp Ala Trp Gly Pro Gly Ala Lys Ser Gly Val Gly Thr Ala Leu
        290                 295                 300
Leu Leu Lys Leu Ala Gln Met Phe Ser Asp Met Val Leu Lys Asp Gly
305                 310                 315                 320
Phe Gln Pro Ser Arg Ser Ile Ile Phe Ala Ser Trp Ser Ala Gly Asp
                325                 330                 335
Phe Gly Ser Val Gly Ala Thr Glu Trp Leu Glu Gly Tyr Leu Ser Ser
            340                 345                 350
Leu His Leu Lys Ala Phe Thr Tyr Ile Asn Leu Asp Lys Ala Val Leu
        355                 360                 365
Gly Thr Ser Asn Phe Lys Val Ser Ala Ser Pro Leu Leu Tyr Thr Leu
370                 375                 380
Ile Glu Lys Thr Met Gln Asn Val Lys His Pro Val Thr Gly Gln Phe
385                 390                 395                 400
Leu Tyr Gln Asp Ser Asn Trp Ala Ser Lys Val Glu Lys Leu Thr Leu
                405                 410                 415
Asp Asn Ala Ala Phe Pro Phe Leu Ala Tyr Ser Gly Ile Pro Ala Val
            420                 425                 430
Ser Phe Cys Phe Cys Glu Asp Thr Asp Tyr Pro Tyr Leu Gly Thr Thr
        435                 440                 445
Met Asp Thr Tyr Lys Glu Leu Ile Glu Arg Ile Pro Glu Leu Asn Lys
    450                 455                 460
Val Ala Arg Ala Ala Ala Glu Val Ala Gly Gln Phe Val Ile Lys Leu
465                 470                 475                 480
Thr His Asp Val Glu Leu Asn Leu Asp Tyr Glu Glu Tyr Asn Ser Gln
                485                 490                 495
Leu Leu Ser Phe Val Arg Asp Leu Asn Gln Tyr Arg Ala Asp Ile Lys
            500                 505                 510
Glu Met Gly Leu Ser Leu Gln Trp Leu Tyr Ser Ala Arg Gly Asp Phe
        515                 520                 525
Phe Arg Ala Thr Ser Arg Leu Thr Thr Asp Phe Gly Asn Ala Glu Lys
530                 535                 540
Thr Asp Arg Phe Val Met Lys Lys Leu Asn Asp Arg Val Met Arg Val
545                 550                 555                 560
Glu Tyr His Phe Leu Ser Pro Tyr Val Ser Pro Lys Glu Ser Pro Phe
                565                 570                 575
Arg His Val Phe Trp Gly Ser Gly Ser His Thr Leu Pro Ala Leu Leu
            580                 585                 590
Glu Asn Leu Lys Leu Arg Lys Gln Asn Asn Gly Ala Phe Asn Glu Thr
        595                 600                 605
Leu Phe Arg Asn Gln Leu Ala Leu Ala Thr Trp Thr Ile Gln Gly Ala
    610                 615                 620
Ala Asn Ala Leu Ser Gly Asp Val Trp Asp Ile Asp Asn Glu Phe
625                 630                 635

<210> SEQ ID NO 18
<211> LENGTH: 639
<212> TYPE: PRT
<213> ORGANISM: Homo sapiens

<400> SEQUENCE: 18

Leu Tyr Trp Asp Asp Leu Lys Arg Lys Leu Ser Glu Lys Leu Asp Ser
1               5                   10                  15
```

```
Thr Asp Phe Thr Ser Thr Ile Lys Leu Leu Asn Glu Asn Ser Tyr Val
            20                  25                  30
Pro Arg Glu Ala Gly Ser Gln Lys Asp Glu Asn Leu Ala Leu Tyr Val
            35                  40                  45
Glu Asn Glu Phe Arg Glu Phe Lys Leu Ser Lys Val Trp Arg Asp Gln
 50                  55                  60
His Phe Val Lys Ile Gln Val Lys Asp Ser Ala Gln Asn Ser Val Ile
 65                  70                  75                  80
Ile Val Asp Lys Asn Gly Arg Leu Val Tyr Leu Val Glu Asn Pro Gly
            85                  90                  95
Gly Tyr Val Ala Tyr Ser Lys Ala Ala Thr Val Thr Gly Lys Leu Val
            100                 105                 110
His Ala Asn Phe Gly Thr Lys Lys Asp Phe Glu Asp Leu Tyr Thr Pro
            115                 120                 125
Val Asn Gly Ser Ile Val Ile Val Arg Ala Gly Lys Ile Thr Phe Ala
 130                 135                 140
Glu Lys Val Ala Asn Ala Glu Ser Leu Asn Ala Ile Gly Val Leu Ile
 145                 150                 155                 160
Tyr Met Asp Gln Thr Lys Phe Pro Ile Val Asn Ala Glu Leu Ser Phe
            165                 170                 175
Phe Gly His Ala His Leu Gly Thr Gly Asp Pro Tyr Thr Pro Gly Phe
            180                 185                 190
Pro Ser Phe Asn His Thr Gln Phe Pro Pro Ser Arg Ser Ser Gly Leu
            195                 200                 205
Pro Asn Ile Pro Val Gln Thr Ile Ser Arg Ala Ala Ala Glu Lys Leu
 210                 215                 220
Phe Gly Asn Met Glu Gly Asp Cys Pro Ser Asp Trp Lys Thr Asp Ser
 225                 230                 235                 240
Thr Cys Arg Met Val Thr Ser Glu Ser Lys Asn Val Lys Leu Thr Val
            245                 250                 255
Ser Asn Val Leu Lys Glu Ile Lys Ile Leu Asn Ile Phe Gly Val Ile
            260                 265                 270
Lys Gly Phe Val Glu Pro Asp His Tyr Val Val Gly Ala Gln Arg
            275                 280                 285
Asp Ala Trp Gly Pro Gly Ala Ala Lys Ser Gly Val Gly Thr Ala Leu
 290                 295                 300
Leu Leu Lys Leu Ala Gln Met Phe Ser Asp Met Val Leu Lys Asp Gly
 305                 310                 315                 320
Phe Gln Pro Ser Arg Ser Ile Ile Phe Ala Ser Trp Ser Ala Gly Asp
            325                 330                 335
Phe Gly Ser Val Gly Ala Thr Glu Trp Leu Glu Gly Tyr Leu Ser Ser
            340                 345                 350
Leu His Leu Lys Ala Phe Thr Tyr Ile Asn Leu Asp Lys Ala Val Leu
            355                 360                 365
Gly Thr Ser Asn Phe Lys Val Ser Ala Ser Pro Leu Leu Tyr Thr Leu
            370                 375                 380
Ile Glu Lys Thr Met Gln Asn Val Lys His Pro Val Thr Gly Gln Phe
 385                 390                 395                 400
Leu Tyr Gln Asp Ser Asn Trp Ala Ser Lys Val Glu Lys Leu Thr Leu
            405                 410                 415
Asp Asn Ala Ala Phe Pro Phe Leu Ala Tyr Ser Gly Ile Pro Ala Val
            420                 425                 430
Ser Phe Cys Phe Cys Glu Asp Thr Asp Tyr Pro Tyr Leu Gly Thr Thr
```

```
                    435                 440                 445
Met Asp Thr Tyr Lys Glu Leu Ile Glu Arg Ile Pro Glu Leu Asn Lys
            450                 455                 460

Val Ala Arg Ala Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495

Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
        515                 520                 525

Phe Arg Ala Thr Ser Arg Leu Thr Thr Asp Phe Gly Asn Ala Glu Lys
530                 535                 540

Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
            580                 585                 590

Glu Asn Leu Lys Leu Arg Lys Gln Asn Asn Gly Ala Phe Asn Glu Thr
        595                 600                 605

Leu Phe Arg Asn Gln Leu Ala Leu Ala Thr Trp Thr Ile Gln Gly Ala
        610                 615                 620

Ala Asn Ala Leu Ser Gly Asp Val Trp Asp Ile Asp Asn Glu Phe
625                 630                 635

<210> SEQ ID NO 19
<211> LENGTH: 639
<212> TYPE: PRT
<213> ORGANISM: Homo sapiens

<400> SEQUENCE: 19

Leu Tyr Trp Asp Asp Leu Lys Arg Lys Leu Ser Glu Lys Leu Asp Ser
1               5                   10                  15

Thr Asp Phe Thr Ser Thr Ile Lys Leu Leu Asn Glu Asn Ser Tyr Val
            20                  25                  30

Pro Arg Glu Ala Gly Ser Gln Lys Asp Glu Asn Leu Ala Leu Tyr Val
        35                  40                  45

Glu Asn Glu Phe Arg Glu Phe Lys Leu Ser Lys Val Trp Arg Asp Gln
50                  55                  60

His Phe Val Lys Ile Gln Val Lys Asp Ser Ala Gln Asn Ser Val Ile
65                  70                  75                  80

Ile Val Asp Lys Asn Gly Arg Leu Val Tyr Leu Val Glu Asn Pro Gly
                85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
        115                 120                 125

Val Asn Gly Ser Ile Val Ile Val Arg Ala Gly Lys Ile Thr Phe Ala
    130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175
```

```
Phe Gly His Ala His Leu Gly Thr Gly Asp Pro Tyr Thr Pro Gly Phe
            180                 185                 190

Pro Ser Phe Asn His Thr Gln Phe Pro Ser Arg Ser Ser Gly Leu
        195                 200                 205

Pro Asn Ile Pro Val Gln Thr Ile Ser Arg Ala Ala Glu Lys Leu
    210                 215                 220

Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
                245                 250                 255

Ser Asn Val Leu Lys Glu Ile Lys Ile Leu Asn Ile Phe Gly Val Ile
                260                 265                 270

Lys Gly Phe Val Glu Pro Asp His Tyr Val Val Gly Ala Gln Arg
            275                 280                 285

Asp Ala Trp Gly Pro Gly Ala Ala Lys Ser Gly Val Gly Thr Ala Leu
    290                 295                 300

Leu Leu Lys Leu Ala Gln Met Phe Ser Asp Met Val Leu Lys Asp Gly
305                 310                 315                 320

Phe Gln Pro Ser Arg Ser Ile Ile Phe Ala Ser Trp Ser Ala Gly Asp
                325                 330                 335

Phe Gly Ser Val Gly Ala Thr Glu Trp Leu Glu Gly Tyr Leu Ser Ser
                340                 345                 350

Leu His Leu Lys Ala Phe Thr Tyr Ile Asn Leu Asp Lys Ala Val Leu
            355                 360                 365

Gly Thr Ser Asn Phe Lys Val Ser Ala Ser Pro Leu Leu Tyr Thr Leu
    370                 375                 380

Ile Glu Lys Thr Met Gln Asn Val Lys His Pro Val Thr Gly Gln Phe
385                 390                 395                 400

Leu Tyr Gln Asp Ser Asn Trp Ala Ser Lys Val Glu Lys Leu Thr Leu
                405                 410                 415

Asp Asn Ala Ala Phe Pro Phe Leu Ala Tyr Ser Gly Ile Pro Ala Val
            420                 425                 430

Ser Phe Cys Phe Cys Glu Asp Thr Asp Tyr Pro Tyr Leu Gly Thr Thr
                435                 440                 445

Met Asp Thr Tyr Lys Glu Leu Ile Glu Arg Ile Pro Glu Leu Asn Lys
    450                 455                 460

Val Ala Arg Ala Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495

Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
            515                 520                 525

Phe Arg Ala Thr Ser Arg Leu Thr Thr Asp Phe Gly Asn Ala Glu Lys
    530                 535                 540

Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
            580                 585                 590

Glu Asn Leu Lys Leu Arg Lys Gln Asn Asn Gly Ala Phe Asn Glu Thr
```

-continued

```
                    595                 600                 605
Leu Phe Arg Asn Gln Leu Ala Leu Ala Thr Trp Thr Ile Gln Gly Ala
    610                 615                 620

Ala Asn Ala Leu Ser Gly Asp Val Trp Asp Ile Asp Asn Glu Phe
625                 630                 635

<210> SEQ ID NO 20
<211> LENGTH: 639
<212> TYPE: PRT
<213> ORGANISM: Homo sapiens

<400> SEQUENCE: 20

Leu Tyr Trp Asp Asp Leu Lys Arg Lys Leu Ser Glu Lys Leu Asp Ser
1               5                   10                  15

Thr Asp Phe Thr Ser Thr Ile Lys Leu Leu Asn Glu Asn Ser Tyr Val
                20                  25                  30

Pro Arg Glu Ala Gly Ser Gln Lys Asp Glu Asn Leu Ala Leu Tyr Val
            35                  40                  45

Glu Asn Glu Phe Arg Glu Phe Lys Leu Ser Lys Val Trp Arg Asp Gln
50                  55                  60

His Phe Val Lys Ile Gln Val Lys Asp Ser Ala Gln Asn Ser Val Ile
65                  70                  75                  80

Ile Val Asp Lys Asn Gly Arg Leu Val Tyr Leu Val Glu Asn Pro Gly
                85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
        115                 120                 125

Val Asn Gly Ser Ile Val Ile Val Arg Ala Gly Lys Ile Thr Phe Ala
130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175

Phe Gly His Ala His Leu Gly Thr Gly Asp Pro Tyr Thr Pro Gly Phe
            180                 185                 190

Pro Ser Phe Asn His Thr Gln Phe Pro Pro Ser Arg Ser Ser Gly Leu
        195                 200                 205

Pro Asn Ile Pro Val Gln Thr Ile Ser Arg Ala Ala Ala Glu Lys Leu
    210                 215                 220

Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
                245                 250                 255

Ser Asn Val Leu Lys Glu Ile Lys Ile Leu Asn Ile Phe Gly Val Ile
            260                 265                 270

Lys Gly Phe Val Glu Pro Asp His Tyr Val Val Gly Ala Gln Arg
        275                 280                 285

Asp Ala Trp Gly Pro Gly Ala Ala Lys Ser Gly Val Gly Thr Ala Leu
    290                 295                 300

Leu Leu Lys Leu Ala Gln Met Phe Ser Asp Met Val Leu Lys Asp Gly
305                 310                 315                 320

Phe Gln Pro Ser Arg Ser Ile Ile Phe Ala Ser Trp Ser Ala Gly Asp
                325                 330                 335
```

-continued

Phe Gly Ser Val Gly Ala Thr Glu Trp Leu Glu Gly Tyr Leu Ser Ser
                340                 345                 350

Leu His Leu Lys Ala Phe Thr Tyr Ile Asn Leu Asp Lys Ala Val Leu
            355                 360                 365

Gly Thr Ser Asn Phe Lys Val Ser Ala Ser Pro Leu Leu Tyr Thr Leu
        370                 375                 380

Ile Glu Lys Thr Met Gln Asn Val Lys His Pro Val Thr Gly Gln Phe
385                 390                 395                 400

Leu Tyr Gln Asp Ser Asn Trp Ala Ser Lys Val Glu Lys Leu Thr Leu
                405                 410                 415

Asp Asn Ala Ala Phe Pro Phe Leu Ala Tyr Ser Gly Ile Pro Ala Val
            420                 425                 430

Ser Phe Cys Phe Cys Glu Asp Thr Asp Tyr Pro Tyr Leu Gly Thr Thr
        435                 440                 445

Met Asp Thr Tyr Lys Glu Leu Ile Glu Arg Ile Pro Glu Leu Asn Lys
    450                 455                 460

Val Ala Arg Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495

Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
        515                 520                 525

Phe Arg Ala Thr Ser Arg Leu Thr Thr Asp Phe Gly Asn Ala Glu Lys
    530                 535                 540

Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
            580                 585                 590

Glu Asn Leu Lys Leu Arg Lys Gln Asn Asn Gly Ala Phe Asn Glu Thr
        595                 600                 605

Leu Phe Arg Asn Gln Leu Ala Leu Ala Thr Trp Thr Ile Gln Gly Ala
    610                 615                 620

Ala Asn Ala Leu Ser Gly Asp Val Trp Asp Ile Asp Asn Glu Phe
625                 630                 635

<210> SEQ ID NO 21
<211> LENGTH: 639
<212> TYPE: PRT
<213> ORGANISM: Homo sapiens

<400> SEQUENCE: 21

Leu Tyr Trp Asp Asp Leu Lys Arg Lys Leu Ser Glu Lys Leu Asp Ser
1               5                   10                  15

Thr Asp Phe Thr Ser Thr Ile Lys Leu Leu Asn Glu Asn Ser Tyr Val
            20                  25                  30

Pro Arg Glu Ala Gly Ser Gln Lys Asp Glu Asn Leu Ala Leu Tyr Val
        35                  40                  45

Glu Asn Glu Phe Arg Glu Phe Lys Leu Ser Lys Val Trp Arg Asp Gln
    50                  55                  60

His Phe Val Lys Ile Gln Val Lys Asp Ser Ala Gln Asn Ser Val Ile
65                  70                  75                  80

```
Ile Val Asp Lys Asn Gly Arg Leu Val Tyr Leu Val Glu Asn Pro Gly
                85                  90                  95

Gly Tyr Val Ala Tyr Ser Lys Ala Ala Thr Val Thr Gly Lys Leu Val
            100                 105                 110

His Ala Asn Phe Gly Thr Lys Lys Asp Phe Glu Asp Leu Tyr Thr Pro
            115                 120                 125

Val Asn Gly Ser Ile Val Ile Val Arg Ala Gly Lys Ile Thr Phe Ala
        130                 135                 140

Glu Lys Val Ala Asn Ala Glu Ser Leu Asn Ala Ile Gly Val Leu Ile
145                 150                 155                 160

Tyr Met Asp Gln Thr Lys Phe Pro Ile Val Asn Ala Glu Leu Ser Phe
                165                 170                 175

Phe Gly His Ala His Leu Gly Thr Gly Asp Pro Tyr Thr Pro Gly Phe
            180                 185                 190

Pro Ser Phe Asn His Thr Gln Phe Pro Pro Ser Arg Ser Ser Gly Leu
        195                 200                 205

Pro Asn Ile Pro Val Gln Thr Ile Ser Arg Ala Ala Ala Glu Lys Leu
        210                 215                 220

Phe Gly Asn Met Glu Gly Asp Cys Pro Ser Asp Trp Lys Thr Asp Ser
225                 230                 235                 240

Thr Cys Arg Met Val Thr Ser Glu Ser Lys Asn Val Lys Leu Thr Val
                245                 250                 255

Ser Asn Val Leu Lys Glu Ile Lys Ile Leu Asn Ile Phe Gly Val Ile
            260                 265                 270

Lys Gly Phe Val Glu Pro Asp His Tyr Val Val Gly Ala Gln Arg
        275                 280                 285

Asp Ala Trp Gly Pro Gly Ala Ala Lys Ser Gly Val Gly Thr Ala Leu
        290                 295                 300

Leu Leu Lys Leu Ala Gln Met Phe Ser Asp Met Val Leu Lys Asp Gly
305                 310                 315                 320

Phe Gln Pro Ser Arg Ser Ile Ile Phe Ala Ser Trp Ser Ala Gly Asp
                325                 330                 335

Phe Gly Ser Val Gly Ala Thr Glu Trp Leu Glu Gly Tyr Leu Ser Ser
            340                 345                 350

Leu His Leu Lys Ala Phe Thr Tyr Ile Asn Leu Asp Lys Ala Val Leu
        355                 360                 365

Gly Thr Ser Asn Phe Lys Val Ser Ala Ser Pro Leu Leu Tyr Thr Leu
    370                 375                 380

Ile Glu Lys Thr Met Gln Asn Val Lys His Pro Val Thr Gly Gln Phe
385                 390                 395                 400

Leu Tyr Gln Asp Ser Asn Trp Ala Ser Lys Val Glu Lys Leu Thr Leu
                405                 410                 415

Asp Asn Ala Ala Phe Pro Phe Leu Ala Tyr Ser Gly Ile Pro Ala Val
            420                 425                 430

Ser Phe Cys Phe Cys Glu Asp Thr Asp Tyr Pro Tyr Leu Gly Thr Thr
        435                 440                 445

Met Asp Thr Tyr Lys Glu Leu Ile Glu Arg Ile Pro Glu Leu Asn Lys
    450                 455                 460

Val Ala Arg Ala Ala Ala Glu Val Ala Gly Gln Phe Val Ile Lys Leu
465                 470                 475                 480

Thr His Asp Val Glu Leu Asn Leu Asp Tyr Glu Glu Tyr Asn Ser Gln
                485                 490                 495
```

```
Leu Leu Ser Phe Val Arg Asp Leu Asn Gln Tyr Arg Ala Asp Ile Lys
            500                 505                 510

Glu Met Gly Leu Ser Leu Gln Trp Leu Tyr Ser Ala Arg Gly Asp Phe
        515                 520                 525

Phe Arg Ala Thr Ser Arg Leu Thr Thr Asp Phe Gly Asn Ala Glu Lys
    530                 535                 540

Thr Asp Arg Phe Val Met Lys Lys Leu Asn Asp Arg Val Met Arg Val
545                 550                 555                 560

Glu Tyr His Phe Leu Ser Pro Tyr Val Ser Pro Lys Glu Ser Pro Phe
                565                 570                 575

Arg His Val Phe Trp Gly Ser Gly Ser His Thr Leu Pro Ala Leu Leu
            580                 585                 590

Glu Asn Leu Lys Leu Arg Lys Gln Asn Asn Gly Ala Phe Asn Glu Thr
        595                 600                 605

Leu Phe Arg Asn Gln Leu Ala Leu Ala Thr Trp Thr Ile Gln Gly Ala
    610                 615                 620

Ala Asn Ala Leu Ser Gly Asp Val Trp Asp Ile Asp Asn Glu Phe
625                 630                 635
```

<210> SEQ ID NO 22
<211> LENGTH: 63
<212> TYPE: PRT
<213> ORGANISM: Cavia porcellus

<400> SEQUENCE: 22

```
Lys Ile Thr Phe Ala Glu Lys Val Ala Asn Ala Glu Ser Leu Asn Ala
1               5                   10                  15

Leu Gly Val Leu Ile Tyr Leu Asp Trp Thr Lys Phe Pro Ile Pro Lys
            20                  25                  30

Ala Asp Leu Pro Val Phe Gly His Val His Leu Gly Thr Gly Asp Pro
        35                  40                  45

Tyr Thr Pro Gly Phe Pro Ser Phe Asn His Thr Gln Phe Pro Pro
    50                  55                  60
```

<210> SEQ ID NO 23
<211> LENGTH: 17
<212> TYPE: PRT
<213> ORGANISM: Homo sapiens

<400> SEQUENCE: 23

```
Arg Val Glu Tyr His Phe Leu Ser Pro Tyr Val Ser Pro Lys Glu Ser
1               5                   10                  15

Pro
```

<210> SEQ ID NO 24
<211> LENGTH: 15
<212> TYPE: PRT
<213> ORGANISM: Homo sapiens

<400> SEQUENCE: 24

```
Glu Ser Pro Phe Arg His Val Phe Trp Gly Ser Gly Ser His Thr
1               5                   10                  15
```

<210> SEQ ID NO 25
<211> LENGTH: 23
<212> TYPE: PRT
<213> ORGANISM: Homo sapiens
<220> FEATURE:
<221> NAME/KEY: misc_feature
<222> LOCATION: (13)..(13)

```
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 25

Leu Ala Gly Lys Glu Ser Pro Val Val Glu Glu Pro Xaa Glu Asp Phe
1               5                   10                  15

Pro Ala Ala Xaa Arg Leu Thr
            20

<210> SEQ ID NO 26
<211> LENGTH: 15
<212> TYPE: PRT
<213> ORGANISM: Homo sapiens

<400> SEQUENCE: 26

Phe Pro Ile Val Asn Ala Glu Leu Ser Phe Phe Gly His Ala His
1               5                   10                  15

<210> SEQ ID NO 27
<211> LENGTH: 2283
<212> TYPE: DNA
<213> ORGANISM: Homo sapiens

<400> SEQUENCE: 27 atggatggatc aagctagatc agcattctct aacttgtttg gtggagaacc attgtcatat        60
acccggttca gcctggctcg gcaagtagat ggcgataaca gtcatgtgga gatgaaactt       120
gctgtagatg aagaagaaaa tgctgacaat aacacaaagg ccaatgtcac aaaaccaaaa       180
aggtgtagtg aagtatctg ctatgggact attgctgtga tcgtcttttt cttgattgga        240
tttatgattg gctacttggg ctattgtaaa ggggtagaac caaaaactga gtgtgagaga       300
ctggcaggaa ccgagtctcc agtgagggag gagccaggag aggacttccc tgcagcacgt       360
cgcttatatt gggatgacct gaagagaaag ttgtcggaga aactggacag cacagacttc       420
accggcacca tcaagctgct gaatgaaaat tcatatgtcc ctcgtgaggc tggatctcaa       480
aaagatgaaa atcttgcgtt gtatgttgaa atcaatttc gtgaatttaa actcagcaaa       540
gtctggcgtg atcaacattt tgttaagatt caggtcaaag acagcgctca aaactcggtg       600
atcatagttg ataagaacgg tagacttgtt tacctggtgg agaatcctgg gggttatgtg       660
gcgtatagta aggctgcaac agttactggt aaactggtcc atgctaattt tggtactaaa       720
aaagattttg aggatttata cactcctgtg aatggatcta tagtgattgt cagagcaggg       780
aaaatcacct ttgcagaaaa ggttgcaaat gctgaaagct taaatgcaat tggtgtgttg       840
atatacatgg accagactaa atttcccatt gttaacgcag aactttcatt ctttggacat       900
gctcatctgg ggacaggtga cccttacaca cctggattcc cttccttcaa tcacactcag       960
tttccaccat ctcggtcatc aggattgcct aatatacctg tccagacaat ctccagagct      1020
gctgcagaaa agctgtttgg gaatatgaa ggagactgtc cctctgactg gaaaacagac      1080
tctacatgta ggatggtaac ctcagaaagc aagaatgtga agctcactgt gagcaatgtg      1140
ctgaaagaga taaaaattct taacatcttt ggagttatta aaggctttgt agaaccagat      1200
cactatgttt tagttggggc ccagagagat gcatggggcc ctggagctgc aaaatccggt      1260
gtaggcacag ctctcctatt gaaacttgcc cagatgttct cagatatggt cttaaaagat      1320
gggtttcagc ccagcagaag cattatcttt gccagttgga gtgctggaga ctttggatcg      1380
```

```
gttggtgcca ctgaatggct agagggatac ctttcgtccc tgcatttaaa ggctttcact   1440
tatattaatc tggataaagc ggttcttggt accagcaact tcaaggtttc tgccagccca   1500
ctgttgtata cgcttattga gaaaacaatg caaaatgtga agcatccggt tactgggcaa   1560
tttctatatc aggacagcaa ctgggccagc aaagttgaga aactcacttt agacaatgct   1620
gctttcccct tccttgcata ttctggaatc ccagcagttt ctttctgttt ttgcgaggac   1680
acagattatc cttatttggg taccaccatg acacctata aggaactgat tgagaggatt    1740
cctgagttga caaagtggc acgagcagct gcagaggtcg ctggtcagtt cgtgattaaa    1800
ctaacccatg atgttgaatt gaacctggac tatgagaggt acaacagcca actgctttca   1860
tttgtgaggg atctgaacca atacagagca gacataaagg aaatgggcct gagtttacag   1920
tggctgtatt ctgctcgtgg agacttcttc cgtgctactt ccagactaac aacagatttc   1980
gggaatgctg agaaaacaga cagatttgtc atgaagaaac tcaatgatcg tgtcatgaga   2040
gtggagtatc acttcctctc tccctacgta tctccaaaag agtctccttt ccgacatgtc   2100
ttctggggct ccggctctca cacgctgcca gctttactgg agaacttgaa actgcgtaaa   2160
caaaataacg gtgcttttaa tgaaacgctg ttcagaaacc agttggctct agctacttgg   2220
actattcagg gagctgcaaa tgccctctct ggtgacgttt gggacattga caatgagttt   2280
taa                                                                2283

<210> SEQ ID NO 28
<211> LENGTH: 2283
<212> TYPE: DNA
<213> ORGANISM: Homo sapiens

<400> SEQUENCE: 28
atgatggatc aagctagatc agcattctct aacttgtttg gtggagaacc attgtcatat    60
acccggttca gcctggctcg gcaagtagat ggcgataaca gtcatgtgga gatgaaactt   120
gctgtagatg aagaagaaaa tgctgacaat aacacaaagg ccaatgtcac aaaaccaaaa   180
aggtgtagtg gaagtatctg ctatgggact attgctgtga tcgtcttttt ccttgattgga  240 tttatgattg gctacttggg ctattgtaaa ggggtagaac caaaaactga gtgtgagaga   300
ctggcaggaa ccgagtctcc agtgagggag gagccaggag aggacttccc tgcagcacgt   360
cgcttatatt gggatgacct gaagagaaag ttgtcggaga aactggacag cacagacttc   420
accggcacca tcaagctgct gaatgaaaat tcatatgtcc ctcgtgaggc tggatctcaa   480
aaagatgaaa atcttgcgtt gtatgttgaa atcaatttc gtgaatttaa actcagcaaa   540
gtctggcgtg atcaacattt tgttaagatt caggtcaaag acagcgctca aaactcggtg   600
atcatagttg ataagaacgg tagacttgtt tacctggtgg agaatcctgg gggttatgtg   660
gcgtatagta aggctgcaac agttactggt aaactggtcc atgctaattt tggtactaaa   720
aaagattttg aggattata cactcctgtg aatggatcta tagtgattgt cagagcaggg   780
aaaatcacct ttgcagaaaa ggttgcaaat gctgaaagct aaatgcaat tggtgtgttg    840 atatacatgg accagactaa atttcccatt gttaacgcag aactttcatt ctttggacat   900
gctcatctgg ggacaggtga cccttacaca cctggattcc cttccttcaa tcacactcag   960
tttccaccat ctcggtcatc aggattgcct aatatacctg tccagacaat ctccagagct   1020
gctgcagaaa agctgtttgg aatatggaa ggagactgtc cctctgactg gaaaacagac    1080 tctcacatgta ggatggtaac ctcagaaaagc aagaatgtga agctcactgt gagcaatgtg  1140
ctgaaagaga taaaaattct taacatcttt ggagttatta aaggctttgt agaaccagat   1200
```

-continued

| | |
|---|---|
| cactatgttg tagttggggc ccagagagat gcatggggcc ctggagctgc aaaatccggt | 1260 |
| gtaggcacag ctctcctatt gaaacttgcc cagatgttct cagatatggt cttaaaagat | 1320 |
| gggtttcagc ccagcagaag cattatcttt gccagttgga gtgctggaga ctttggatcg | 1380 |
| gttggtgcca ctgaatggct agagggatac ctttcgtccc tgcatttaaa ggctttcact | 1440 |
| tatattaatc tggataaagc ggttcttggt accagcaact tcaaggtttc tgccagccca | 1500 |
| ctgttgtata cgcttattga gaaacaatg caaaatgtga agcatccggt tactgggcaa | 1560 |
| tttctatatc aggacagcaa ctgggccagc aaagttgaga aactcacttt agacaatgct | 1620 |
| gctttcccctt tccttgcata ttctggaatc ccagcagttt ctttctgttt ttgcgaggac | 1680 |
| acagattatc cttatttggg taccaccatg gacacctata aggaactgat tgagaggatt | 1740 |
| cctgagttga caaagtggc acgagcagct gcagaggtcg ctggtcagtt cgtgattaaa | 1800 |
| ctaacccatg atgttgaatt gaacctggac tatgagaggt acaacagcca actgctttca | 1860 |
| tttgtgaggg atctgaacca atacagagca gacataaagg aaatgggcct gagtttacag | 1920 |
| tggctgtatt ctgctcgtgg agacttcttc cgtgctactt ccagactaac aacagatttc | 1980 |
| gggaatgctg agaaaacaga cagatttgtc atgaagaaac tcaatgatcg tgtcatgaga | 2040 |
| gtggagtatc acttcctctc tccctacgta tctccaaaag agtctccttt ccgacatgtc | 2100 |
| ttctggggct ccggctctca cacgctgcca gctttactgg agaacttgaa actgcgtaaa | 2160 |
| caaaataacg gtgcttttaa tgaaacgctg ttcagaaacc agttggctct agctacttgg | 2220 |
| actattcagg gagctgcaaa tgccctctct ggtgacgttt gggacattga caatgagttt | 2280 |
| taa | 2283 |

<210> SEQ ID NO 29
<211> LENGTH: 2283
<212> TYPE: DNA
<213> ORGANISM: Homo sapiens

<400> SEQUENCE: 29

| | |
|---|---|
| atgatggatc aagctagatc agcattctct aacttgtttg gtggagaacc attgtcatat | 60 |
| acccggttca gcctggctcg gcaagtagat ggcgataaca gtcatgtgga gatgaaactt | 120 |
| gctgtagatg aagaagaaaa tgctgacaat aacacaaagg ccaatgtcac aaaaccaaaa | 180 |
| aggtgtagtg aagtatctg ctatgggact attgctgtga tcgtcttttt cttgattgga | 240 |
| tttatgattg gctacttggg ctattgtaaa ggggtagaac caaaaactga gtgtgagaga | 300 |
| ctggcaggaa ccgagtctcc agtgagggag gagccaggag aggacttccc tgcagcacgt | 360 |
| cgcttatatt gggatgacct gaagagaaag ttgtcggaga aactggacag cacagacttc | 420 |
| accggcacca tcaagctgct gaatgaaaat tcatatgtcc ctcgtgaggc tggatctcaa | 480 |
| aaagatgaaa tcttgcgtt gtatgttgaa atcaatttc gtgaatttaa actcagcaaa | 540 |
| gtctggcgtg atcaacattt tgttaagatt caggtcaaag acagcgctca aaactcggtg | 600 |
| atcatagttg ataagaacgg tagacttgtt tacctggtgg agaatcctgg gggttatgtg | 660 |
| gcgtatagta aggctgcaac agttactggt aaactggtcc atgctaattt tggtactaaa | 720 |
| aaagattttg aggatttata cactcctgtg aatggatcta tagtgattgt cagagcaggg | 780 |
| aaaatcacct ttgcagaaaa ggttgcaaat gctgaaagct taaatgcaat tggtgtgttg | 840 |
| atatacatgg accagactaa atttcccatt gttaacgcag aactttcatt ctttggacat | 900 |
| gctcatctgg ggacaggtga cccttacaca cctggattcc cttccttcaa tcacactcag | 960 |

```
tttccaccat ctcggtcatc aggattgcct aatatacctg tccagacaat ctccagagct    1020
gctgcagaaa agctgtttgg gaatatggaa ggagactgtc cctctgactg gaaaacagac    1080
tctacatgta ggatggtaac ctcagaaagc aagaatgtga agctcactgt gagcaatgtg    1140
ctgaaagaga taaaaattct taacatcttt ggagttatta aaggctttgt agaaccagat    1200
cactatgttg tagttggggc ccagagagat gcatgggccc tggagctgca aaatccggt     1260 gtaggcacag ctctcctatt gaaacttgcc cagatgttct cagatatggt cttaaaagat    1320
gggtttcagc ccagcagaag cattatcttt gccagttgga gtgctggaga ctttggatcg    1380
gttggtgcca ctgaatggct agagggatac ctttcgtccc tgcatttaaa ggctttcact    1440
tatattaatc tggataaagc ggttcttggt accagcaact tcaaggtttc tgccagccca    1500
ctgttgtata cgcttattga gaaaacaatg caaaatgtga agcatccggt tactgggcaa    1560
tttctatatc aggacagcaa ctgggccagc aaagttgaga aactcacttt agacaatgct    1620 gctttcccctt tccttgcata ttctggaatc ccagcagttt cttctgtttt ttgcgaggac    1680
acagattatc cttatttggg taccaccatg gacacctata aggaactgat tgagaggatt    1740
cctgagttga acaaagtggc acgagcagct gcagaggtcg ctggtcagtt cgtgattaaa    1800
ctaacccatg atgttgaatt gaacctggac tatgagaggt acaacagcca actgctttca    1860
tttgtgaggg atctgaacca atacagagca gacataaagg aaatgggcct gagtttacag    1920
tggctgtatt ctgctcgtgg agacttcttc cgtgctactt ccagactaac aacagatttc    1980
gggaatgctg agaaaacaga cagatttgtc atgaagaaac tcaatgatcg tgtcatgaga    2040
gtggagtatc acttcctctc tccctacgta tctccaaaag agtctccttt ccgacatgtc    2100
ttctggggct ccggctctca cacgctgcca gctttactgg agaacttgaa actgcgtaaa    2160
caaaataacg gtgcttttaa tgaaacgctg ttcagaaacc agttggctct agctacttgg    2220
actattcagg gagctgcaaa tgccctctct ggtgacgttt gggacattga caatgagttt    2280
taa                                                                  2283

<210> SEQ ID NO 30
<211> LENGTH: 2283
<212> TYPE: DNA
<213> ORGANISM: Homo sapiens

<400> SEQUENCE: 30
atgatggatc aagctagatc agcattctct aacttgtttg gtggagaaacc attgtcatat      60 acccggttca gcctggctcg gcaagtagat ggcgataaca gtcatgtgga gatgaaactt     120
gctgtagatg aagaagaaaa tgctgacaat aacacaaagg ccaatgtcac aaaaccaaaa     180
aggtgtagtg gaagtatctg ctatgggact attgctgtga tcgtcttttt cttgattgga     240
tttatgattg gctacttggg ctattgtaaa ggggtagaac caaaaactga gtgtgagaga     300
ctggcaggaa ccgagtctcc agtgagggag gagccaggaa aggacttccc tgcagcacgt     360
cgcttatatt gggatgacct gaagagaaag ttgtcggaga aactggacag cacagacttc     420
accagcacca tcaagctgct gaatgaaaat tcatatgtcc ctcgtgaggc tggatctcaa     480
aaagatgaaa atcttgcgtt gtatgttgaa atcaatttc gtgaatttaa actcagcaaa     540
gtctggcgtg atcaacattt tgttaagatt caggtcaaag acagcgctca aaactcggtg     600
atcatagttg ataagaacgg tagacttgtt tacctggtgg agaatcctgg gggttatgtg     660
gcgtatagta aggctgcaac agttactggt aaactggtcc atgctaattt tggtactaaa     720
aaagattttg aggatttata cactcctgtg aatggatcta tagtgattgt cagagcaggg     780
```

-continued

```
aaaatcacct tgcagaaaa ggttgcaaat gctgaaagct taaatgcaat tggtgtgttg      840
atatacatgg accagactaa atttcccatt gttaacgcag aactttcatt ctttggacat      900
gctcatctgg ggacaggtga cccttacaca cctggattcc cttccttcaa tcacactcag      960
tttccaccat ctcggtcatc aggattgcct aatatacctg tccagacaat ctccagagct     1020
gctgcagaaa agctgtttgg gaatatgaaa ggagactgtc cctctgactg gaaaacagac     1080
tctacatgta ggatggtaac ctcagaaagc aagaatgtga agctcactgt gagcaatgtg     1140
ctgaaagaga taaaaattct taacatcttt ggagttatta aaggctttgt agaaccagat     1200
cactatgttg tagttggggc ccagagagat gcatgggggcc ctggagctgc aaaatccggt     1260
gtaggcacag ctctcctatt gaaacttgcc cagatgttct cagatatggt cttaaaagat     1320
gggtttcagc ccagcagaag cattatcttt gccagttgga gtgctggaga ctttggatcg     1380
gttggtgcca ctgaatggct agagggatac ctttcgtccc tgcatttaaa ggctttcact     1440
tatattaatc tggataaagc ggttcttggt accagcaact tcaaggtttc tgccagccca     1500
ctgttgtata cgcttattga gaaaacaatg caaaatgtga agcatccggt tactgggcaa     1560
tttctatatc aggacagcaa ctgggccagc aaagttgaga aactcacttt agacaatgct     1620
gctttccctt tccttgcata ttctggaatc ccagcagttt cttctgtttt ttgcgaggac     1680
acagattatc cttatttggg taccaccatg gacacctata aggaactgat tgagaggatt     1740
cctgagttga caaagtggc acgagcagct gcagaggtcg ctggtcagtt cgtgattaaa     1800
ctaacccatg atgttgaatt gaacctggac tatgagaggt acaacagcca actgctttca     1860
tttgtgaggg atctgaacca atacagagca gacataaagg aaatgggcct gagtttacag     1920
tggctgtatt ctgctcgtgg agacttcttc cgtgctactt ccagactaac aacagatttc     1980
gggaatgctg agaaaacaga cagatttgtc atgaagaaac tcaatgatcg tgtcatgaga     2040
gtggagtatc acttcctctc tccctacgta tctccaaaag agtctccttt ccgacatgtc     2100
ttctggggct ccggctctca cacgctgcca gctttactgg agaacttgaa actgcgtaaa     2160
caaaataacg gtgcttttaa tgaaacgctg ttcagaaacc agttggctct agctacttgg     2220
actattcagg gagctgcaaa tgccctctct ggtgacgttt gggacattga caatgagttt     2280
taa                                                                   2283
```

<210> SEQ ID NO 31
<211> LENGTH: 2283
<212> TYPE: DNA
<213> ORGANISM: Homo sapiens

<400> SEQUENCE: 31

```
atgatggatc aagctagatc agcattctct aacttgtttg gtggagaacc attgtcatat       60
acccggttca gcctggctcg gcaagtagat ggcgataaca gtcatgtgga gatgaaactt      120
gctgtagatg aagaagaaaa tgctgacaat aacacaaagg ccaatgtcac aaaaccaaaa      180
aggtgtagtg aagtatctg ctatgggact attgctgtga tcgtcttttt cttgattgga      240
tttatgattg gctacttggg ctattgtaaa ggggtagaac caaaaactga gtgtgagaga      300
ctggcaggaa ccgagtctcc agtgagggag gagccaggag aggacttccc tgcagcacgt      360
cgcttatatt gggatgacct gaagagaaag ttgtcggaga aactggacag cacagacttc      420
accagcacca tcaagctgct gaatgaaaat tcatatgtcc ctcgtgaggc tggatctcaa      480
aaagatgaaa atcttgcgtt gtatgttgaa atcaatttc gtgaatttaa actcagcaaa      540
```

-continued

```
gtctggcgtg atcaacattt tgttaagatt caggtcaaag acagcgctca aaactcggtg      600
atcatagttg ataagaacgg tagacttgtt tacctggtgg agaatcctgg gggttatgtg      660
gcgtatagta aggctgcaac agttactggt aaactggtcc atgctaattt tggtactaaa      720
aaagattttg aggatttata cactcctgtg aatggatcta tagtgattgt cagagcaggg      780
aaaatcacct ttgcagaaaa ggttgcaaat gctgaaagct aaatgcaat tggtgtgttg       840 atatacatgg accagactaa atttcccatt gttaacgcag aactttcatt ctttggacat      900
gctcatctgg ggacaggtga cccttacaca cctggattcc cttccttcaa tcacactcag      960
tttccaccat ctcggtcatc aggattgcct aatatacctg tccagacaat ctccagagct     1020
gctgcagaaa agctgtttgg gaatatggaa ggagactgtc cctctgactg gaaaacagac     1080
tctacatgta ggatggtaac ctcagaaagc aagaatgtga agctcactgt gagcaatgtg     1140
ctgaaagaga taaaaattct taacatcttt ggagttatta aaggctttgt agaaccagat     1200
cactatgttg tagttgggc ccagagagat gcatggggcc ctggagctgc aaaatccggt      1260
gtaggcacag ctctcctatt gaaacttgcc cagatgttct cagatatggt cttaaaagat     1320
gggtttcagc ccagcagaag cattatcttt gccagttgga gtgctggaga ctttggatcg     1380
gttggtgcca ctgaatggct agagggatac ctttcgtccc tgcatttaaa ggctttcact     1440
tatattaatc tggataaagc ggttcttggt accagcaact tcaaggtttc tgccagccca     1500
ctgttgtata cgcttattga gaaaacaatg caaaatgtga agcatccggt tactgggcaa     1560
tttctatatc aggacagcaa ctgggccagc aaagttgaga aactcacttt agacaatgct     1620
gctttccctt tccttgcata ttctggaatc ccagcagttt ctttctgttt ttgcgaggac     1680
acagattatc cttatttggg taccaccatg gacacctata aggaactgat tgagaggatt     1740
cctgagttga acaaagtggc acgagcagct gcagaggtcg ctggtcagtt cgtgattaaa     1800
ctaacccatg atgttgaatt gaacctggac tatgagaggt acaacagcca actgctttca     1860
tttgtgaggg atctgaacca atacagagca gacataaagg aaatgggcct gagtttacag     1920
tggctgtatt ctgctcgtgg agacttcttc cgtgctactt ccagactaac aacagatttc     1980
gggaatgctg agaaaacaga cagatttgtc atgaagaaac tcaatgatcg tgtcatgaga     2040
gtggagtatc acttcctctc tccctacgta tctccaaaag agtctccttt ccgacatgtc     2100
ttctggggct ccggctctca cacgctgcca gctttactgg agaacttgaa actgcgtaaa     2160
caaaataacg gtgcttttaa tgaaacgctg ttcagaaacc agttggctct agctacttgg     2220
actattcagg gagctgcaaa tgccctctct ggtgacgttt gggacattga caatgagttt     2280
taa                                                                   2283
```

<210> SEQ ID NO 32
<211> LENGTH: 2283
<212> TYPE: DNA
<213> ORGANISM: Homo sapiens

<400> SEQUENCE: 32

```
atgatggatc aagctagatc agcattctct aacttgtttg gtggagaacc attgtcatat       60
acccggttca gcctggctcg gcaagtagat ggcgataaca gtcatgtgga gatgaaactt      120
gctgtagatg aagaagaaaa tgctgacaat aacacaaagg ccaatgtcac aaaaccaaaa      180
aggtgtagtg gaagtatctg ctatgggact attgctgtga tcgtcttttt cttgattgga      240
tttatgattg ctacttggg ctattgtaaa gggtagaac caaaaactga gtgtgagaga        300
ctggcaggaa ccgagtctcc agtgagggag gagccaggag aggacttccc tgcagcacgt      360
```

```
cgcttatatt gggatgacct gaagagaaag ttgtcggaga aactggacag cacagacttc      420
accagcacca tcaagctgct gaatgaaaat tcatatgtcc ctcgtgaggc tggatctcaa      480
aaagatgaaa tcttgcgtt gtatgttgaa atcaatttc gtgaatttaa actcagcaaa       540
gtctggcgtg atcaacattt tgttaagatt caggtcaaag acagcgctca aaactcggtg      600
atcatagttg ataagaacgg tagacttgtt tacctggtgg agaatcctgg ggttatgtg      660 gcgtatagta aggctgcaac agttactggt aaactggtcc atgctaattt tggtactaaa     720
aaagattttg aggatttata cactcctgtg aatggatcta tagtgattgt cagagcaggg    780
aaaatcacgt ttgcagaaaa ggttgcaaat gctgaaagct taaatgcaat tggtgtgttg     840
atatacatgg accagactaa atttcccatt gttaacgcag aactttcatt ctttggacat     900
gctcatctgg ggacaggtga cccttacaca cctggattcc cttccttcaa tcacactcag    960
tttccaccat ctcggtcatc aggattgcct aatatacctg tccagacaat ctccagagct     1020
gctgcagaaa agctgtttgg gaatatggaa ggagactgtc cctctgactg gaaaacagac    1080
tctacatgta ggatggtaac ctcagaaagc aagaatgtga agctcactgt gagcaatgtg    1140
ctgaaagaga taaaaattct taacatcttt ggagttatta aaggctttgt agaaccagat     1200
cactatgttg tagttggggc ccagagagat gcatggggcc ctggagctgc aaaatccggt     1260
gtaggcacag ctctcctatt gaaacttgcc cagatgttct cagatatggt cttaaaagat    1320
gggtttcagc ccagcagaag cattatcttt gccagttgga gtgctggaga ctttggatcg    1380
gttggtgcca ctgaatggct agagggatac ctttcgtccc tgcatttaaa ggctttcact    1440
tatattaatc tggataaagc ggttcttggt accagcaact tcaaggtttc tgccagccca    1500
ctgttgtata cgcttattga gaaaacaatg caaaatgtga agcatccggt tactgggcaa    1560
tttctatatc aggacagcaa ctgggccagc aaagttgaga aactcacttt agacaatgct    1620
gctttccctt tccttgcata ttctggaatc ccagcagttt ctttctgttt ttgcgaggac    1680
acagattatc cttatttggg taccaccatg gacacctata aggaactgat tgagaggatt    1740
cctgagttga acaaagtggc acgagcagct gcagaggtcg ctggtcagtt cgtgattaaa    1800
ctaacccatg atgttgaatt gaacctggac tatgagaggt acaacagcca actgctttca    1860
tttgtgaggg atctgaacca atacagagca gacataaagg aaatgggcct gagtttacag    1920
tggctgtatt ctgctcgtgg agacttcttc cgtgctactt ccagactaac aacagatttc    1980
gggaatgctg agaaaacaga cagatttgtc atgaagaaac tcaatgatcg tgtcatgaga    2040
gtggagtatc acttcctctc tccctacgta tctccaaaag agtctccttt ccgacatgtc    2100
ttctggggct ccggctctca cacgctgcca gctttactgg agaacttgaa actgcgtaaa    2160
caaaataacg gtgcttttaa tgaaacgctg ttcagaaacc agttggctct agctacttgg    2220
actattcagg gagctgcaaa tgccctctct ggtgacgttt gggacattga caatgagttt    2280
taa                                                                    2283
```

<210> SEQ ID NO 33
<211> LENGTH: 189
<212> TYPE: DNA
<213> ORGANISM: Cavia sp.

<400> SEQUENCE: 33

```
aaaatcactt ttgcagaaaa ggttgcaaat gctgaaagct taaatgcact tggtgtcttg    60
atatacctgg actggactaa gtttcccatc cctaaggcag accttccagt cttcggtcat    120
```
gttcatctag gaacaggtga cccttataca cctgggttcc cttctttcaa tcatactcaa    180
ttcccaccg    189

<210> SEQ ID NO 34
<211> LENGTH: 1675
<212> TYPE: PRT
<213> ORGANISM: Homo sapiens

<400> SEQUENCE: 34

Met Ala Gln Ile Leu Pro Ile Arg Phe Gln Glu His Leu Gln Leu Gln
1               5                   10                  15

Asn Leu Gly Ile Asn Pro Ala Asn Ile Gly Phe Ser Thr Leu Thr Met
                20                  25                  30

Glu Ser Asp Lys Phe Ile Cys Ile Arg Glu Lys Val Gly Gln Ala
            35                  40                  45

Gln Val Val Ile Ile Asp Met Asn Asp Pro Ser Asn Pro Ile Arg Arg
        50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe

-continued

```
            355                 360                 365
Asn Ala Leu Phe Ala Gln Gly Asn Tyr Ser Glu Ala Ala Lys Val Ala
        370                 375                 380
Ala Asn Ala Pro Lys Gly Ile Leu Arg Thr Pro Asp Thr Ile Arg Arg
385                 390                 395                 400
Phe Gln Ser Val Pro Ala Gln Pro Gly Gln Thr Ser Pro Leu Leu Gln
                405                 410                 415
Tyr Phe Gly Ile Leu Leu Asp Gln Gly Gln Leu Asn Lys Tyr Glu Ser
                420                 425                 430
Leu Glu Leu Cys Arg Pro Val Leu Gln Gln Gly Arg Lys Gln Leu Leu
                435                 440                 445
Glu Lys Trp Leu Lys Glu Asp Lys Leu Glu Cys Ser Glu Glu Leu Gly
            450                 455                 460
Asp Leu Val Lys Ser Val Asp Pro Thr Leu Ala Leu Ser Val Tyr Leu
465                 470                 475                 480
Arg Ala Asn Val Pro Asn Lys Val Ile Gln Cys Phe Ala Glu Thr Gly
                485                 490                 495
Gln Val Gln Lys Ile Val Leu Tyr Ala Lys Lys Val Gly Tyr Thr Pro
            500                 505                 510
Asp Trp Ile Phe Leu Leu Arg Asn Val Met Arg Ile Ser Pro Asp Gln
            515                 520                 525
Gly Gln Gln Phe Ala Gln Met Leu Val Gln Asp Glu Glu Pro Leu Ala
            530                 535                 540
Asp Ile Thr Gln Ile Val Asp Val Phe Met Glu Tyr Asn Leu Ile Gln
545                 550                 555                 560
Gln Cys Thr Ala Phe Leu Leu Asp Ala Leu Lys Asn Asn Arg Pro Ser
                565                 570                 575
Glu Gly Pro Leu Gln Thr Arg Leu Leu Glu Met Asn Leu Met His Ala
            580                 585                 590
Pro Gln Val Ala Asp Ala Ile Leu Gly Asn Gln Met Phe Thr His Tyr
            595                 600                 605
Asp Arg Ala His Ile Ala Gln Leu Cys Glu Lys Ala Gly Leu Leu Gln
            610                 615                 620
Arg Ala Leu Glu His Phe Thr Asp Leu Tyr Asp Ile Lys Arg Ala Val
625                 630                 635                 640
Val His Thr His Leu Leu Asn Pro Glu Trp Leu Val Asn Tyr Phe Gly
                645                 650                 655
Ser Leu Ser Val Glu Asp Ser Leu Glu Cys Leu Arg Ala Met Leu Ser
                660                 665                 670
Ala Asn Ile Arg Gln Asn Leu Gln Ile Cys Val Gln Val Ala Ser Lys
                675                 680                 685
Tyr His Glu Gln Leu Ser Thr Gln Ser Leu Ile Glu Leu Phe Glu Ser
            690                 695                 700
Phe Lys Ser Phe Glu Gly Leu Phe Tyr Phe Leu Gly Ser Ile Val Asn
705                 710                 715                 720
Phe Ser Gln Asp Pro Asp Val His Phe Lys Tyr Ile Gln Ala Ala Cys
                725                 730                 735
Lys Thr Gly Gln Ile Lys Glu Val Glu Arg Ile Cys Arg Glu Ser Asn
                740                 745                 750
Cys Tyr Asp Pro Glu Arg Val Lys Asn Phe Leu Lys Glu Ala Lys Leu
                755                 760                 765
Thr Asp Gln Leu Pro Leu Ile Ile Val Cys Asp Arg Phe Asp Phe Val
            770                 775                 780
```

-continued

```
His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Ile
                805                 810                 815

Gly Gly Leu Leu Asp Val Asp Cys Ser Glu Asp Val Ile Lys Asn Leu
                820                 825                 830

Ile Leu Val Val Arg Gly Gln Phe Ser Thr Asp Glu Leu Val Ala Glu
                835                 840                 845

Val Glu Lys Arg Asn Arg Leu Lys Leu Leu Pro Trp Leu Glu Ala
850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Pro Glu Arg Phe Leu Arg Glu
                885                 890                 895

Asn Pro Tyr Tyr Asp Ser Arg Val Val Gly Lys Tyr Cys Glu Lys Arg
                900                 905                 910

Asp Pro His Leu Ala Cys Val Ala Tyr Glu Arg Gly Gln Cys Asp Leu
                915                 920                 925

Glu Leu Ile Asn Val Cys Asn Glu Asn Ser Leu Phe Lys Ser Leu Ser
                930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
                980                 985                 990

Lys Ala Phe Met Thr Ala Asp Leu Pro Asn Glu Leu Ile Glu Leu Leu
                995                 1000                1005

Glu Lys Ile Val Leu Asp Asn Ser Val Phe Ser Glu His Arg Asn
    1010                1015                1020

Leu Gln Asn Leu Leu Ile Leu Thr Ala Ile Lys Ala Asp Arg Thr
    1025                1030                1035

Arg Val Met Glu Tyr Ile Asn Arg Leu Asp Asn Tyr Asp Ala Pro
    1040                1045                1050

Asp Ile Ala Asn Ile Ala Ile Ser Asn Glu Leu Phe Glu Glu Ala
    1055                1060                1065

Phe Ala Ile Phe Arg Lys Phe Asp Val Asn Thr Ser Ala Val Gln
    1070                1075                1080

Val Leu Ile Glu His Ile Gly Asn Leu Asp Arg Ala Tyr Glu Phe
    1085                1090                1095

Ala Glu Arg Cys Asn Glu Pro Ala Val Trp Ser Gln Leu Ala Lys
    1100                1105                1110

Ala Gln Leu Gln Lys Gly Met Val Lys Glu Ala Ile Asp Ser Tyr
    1115                1120                1125

Ile Lys Ala Asp Asp Pro Ser Ser Tyr Met Glu Val Val Gln Ala
    1130                1135                1140

Ala Asn Thr Ser Gly Asn Trp Glu Glu Leu Val Lys Tyr Leu Gln
    1145                1150                1155

Met Ala Arg Lys Lys Ala Arg Glu Ser Tyr Val Glu Thr Glu Leu
    1160                1165                1170

Ile Phe Ala Leu Ala Lys Thr Asn Arg Leu Ala Glu Leu Glu Glu
    1175                1180                1185
```

-continued

Phe Ile Asn Gly Pro Asn Asn Ala His Ile Gln Gln Val Gly Asp
1190             1195                 1200

Arg Cys Tyr Asp Glu Lys Met Tyr Asp Ala Ala Lys Leu Leu Tyr
1205             1210                 1215

Asn Asn Val Ser Asn Phe Gly Arg Leu Ala Ser Thr Leu Val His
1220             1225                 1230

Leu Gly Glu Tyr Gln Ala Ala Val Asp Gly Ala Arg Lys Ala Asn
1235             1240                 1245

Ser Thr Arg Thr Trp Lys Glu Val Cys Phe Ala Cys Val Asp Gly
1250             1255                 1260

Lys Glu Phe Arg Leu Ala Gln Met Cys Gly Leu His Ile Val Val
1265             1270                 1275

His Ala Asp Glu Leu Glu Leu Ile Asn Tyr Tyr Gln Asp Arg
1280             1285                 1290

Gly Tyr Phe Glu Glu Leu Ile Thr Met Leu Glu Ala Ala Leu Gly
1295             1300                 1305

Leu Glu Arg Ala His Met Gly Met Phe Thr Glu Leu Ala Ile Leu
1310             1315                 1320

Tyr Ser Lys Phe Lys Pro Gln Lys Met Arg Glu His Leu Glu Leu
1325             1330                 1335

Phe Trp Ser Arg Val Asn Ile Pro Lys Val Leu Arg Ala Ala Glu
1340             1345                 1350

Gln Ala His Leu Trp Ala Glu Leu Val Phe Leu Tyr Asp Lys Tyr
1355             1360                 1365

Glu Glu Tyr Asp Asn Ala Ile Ile Thr Met Met Asn His Pro Thr
1370             1375                 1380

Asp Ala Trp Lys Glu Gly Gln Phe Lys Asp Ile Ile Thr Lys Val
1385             1390                 1395

Ala Asn Val Glu Leu Tyr Tyr Arg Ala Ile Gln Phe Tyr Leu Glu
1400             1405                 1410

Phe Lys Pro Leu Leu Leu Asn Asp Leu Leu Met Val Leu Ser Pro
1415             1420                 1425

Arg Leu Asp His Thr Arg Ala Val Asn Tyr Phe Ser Lys Val Lys
1430             1435                 1440

Gln Leu Pro Leu Val Lys Pro Tyr Leu Arg Ser Val Gln Asn His
1445             1450                 1455

Asn Asn Lys Ser Val Asn Glu Ser Leu Asn Asn Leu Phe Ile Thr
1460             1465                 1470

Glu Glu Asp Tyr Gln Ala Leu Arg Thr Ser Ile Asp Ala Tyr Asp
1475             1480                 1485

Asn Phe Asp Asn Ile Ser Leu Ala Gln Arg Leu Glu Lys His Glu
1490             1495                 1500

Leu Ile Glu Phe Arg Arg Ile Ala Ala Tyr Leu Phe Lys Gly Asn
1505             1510                 1515

Asn Arg Trp Lys Gln Ser Val Glu Leu Cys Lys Lys Asp Ser Leu
1520             1525                 1530

Tyr Lys Asp Ala Met Gln Tyr Ala Ser Glu Ser Lys Asp Thr Glu
1535             1540                 1545

Leu Ala Glu Glu Leu Leu Gln Trp Phe Leu Gln Glu Glu Lys Arg
1550             1555                 1560

Glu Cys Phe Gly Ala Cys Leu Phe Thr Cys Tyr Asp Leu Leu Arg
1565             1570                 1575

Pro Asp Val Val Leu Glu Thr Ala Trp Arg His Asn Ile Met Asp

-continued

```
                  1580                  1585                  1590
Phe Ala Met Pro Tyr Phe Ile Gln Val Met Lys Glu Tyr Leu Thr
   1595                  1600                  1605
Lys Val Asp Lys Leu Asp Ala Ser Glu Ser Leu Arg Lys Glu Glu
   1610                  1615                  1620
Glu Gln Ala Thr Glu Thr Gln Pro Ile Val Tyr Gly Gln Pro Gln
   1625                  1630                  1635
Leu Met Leu Thr Ala Gly Pro Ser Val Ala Val Pro Pro Gln Ala
   1640                  1645                  1650
Pro Phe Gly Tyr Gly Tyr Thr Ala Pro Pro Tyr Gly Gln Pro Gln
   1655                  1660                  1665
Pro Gly Phe Gly Tyr Ser Met
   1670                  1675

<210> SEQ ID NO 35
<211> LENGTH: 5028
<212> TYPE: DNA
<213> ORGANISM: Homo sapiens

<400> SEQUENCE: 35
atggcccaga ttctgccaat tcgttttcag gagcatctcc agctccagaa cctgggtatc      60
aacccagcaa acattggctt cagtaccctg actatggagt ctgacaaatt catctgcatt     120
agagaaaaag taggagagca ggcccaggtg gtaatcattg atatgaatga cccaagtaat     180
ccaattcgaa gaccaatttc agcagacagc gccatcatga tccagctag caaagtaatt     240 gcactgaaag ctgggaaaac tcttcagatt tttaacattg aaatgaaaag taaaatgaag     300
gctcatacca tgactgatga tgtcaccttt tggaaatgga tctcttttga tacggttgct     360
cttgttacgg ataatgcagt ttatcactgg agtatggaag gagagtctca gccagtgaaa     420
atgtttgatc gccattctag ccttgcaggg tgccagatta tcaattaccg tacagatgca     480
aaacaaaagt ggttacttct gactggtata tctgcacagc aaaatcgtgt ggtgggagct     540
atgcagctat attctgtaga taggaaagtg tctcagccca ttgaaggaca tgcagctagc     600
tttgcacagt ttaagatgga aggaaatgca gaagaatcaa cgttattttg ttttgcagtt     660
cggggccaag ctggagggaa gttacatatt attgaagttg gcacaccacc tacagggaac     720
cagccctttc caagaaggc agtggatgtc ttctttcctc cagaagcaca aaatgatttt     780
cctgttgcaa tgcagatcag tgaaaagcat gatgtggtgt tcttgataac caagtatggt     840
tatatccacc tctatgatct tgagactggt acctgcatct acatgaatag aatcagtgga     900
gaaacaattt ttgttactgc acctcatgaa gccacagctg aataattgg agtaaacaga     960 aagggacaag ttctgtcagt gtgtgtggaa gaagaaaaca taattcctta catcaccaat    1020
gttctacaaa atcctgattt ggctctgaga atggctgtac gtaataactt agccggtgct    1080
gaagaactct tgcccggaa atttaatgct cttttttgccc agggaaatta ctcggaggca    1140 gcaaggtgg ctgctaatgc accaagggaa attcttcgta ctccagacac tatccgtcgg    1200
ttccagagtg tcccagccca gccaggtcaa acttctcctc tacttcagta ctttggtatc    1260 ctttttggacc agggacagct caacaaatac gaatccttag gctttgtag gcctgtactt    1320 cagcaagggc gaaacagct tttggagaaa tggttaaaag aagataagct ggaatgttct    1380
gaagaactgg gtgatcttgt gaaatctgtg gaccctacat ggcacttag tgtgtaccta    1440 agggctaacg tcccaaataa agtcattcag tgctttgcag aaacaggtca agtccaaaag    1500
attgttttat atgctaaaaa agttggatac actccagatt ggatatttct gctgagaaat    1560
```

```
gtaatgcgaa tcagtccaga tcagggacag cagtttgccc aaatgttagt tcaagatgaa    1620
gagcctcttg ctgacatcac acagattgta gatgtcttta tggaatacaa tctaattcag    1680
cagtgtactg cattcttgct tgatgctctg aagaataatc gcccatctga aggtccttta    1740
cagacgcggt tacttgagat gaaccttatg catgcgcctc aagttgcaga tgctattcta    1800
ggcaatcaga tgttcacaca ttatgaccgg gctcatattg ctcaactgtg tgaaaaggct    1860
ggcctactgc agcgtgcatt agaacatttc actgatttat atgatataaa acgtgcagtg    1920
gttcacaccc atcttcttaa ccctgagtgg ttagtcaact actttggttc cttatcagta    1980
gaagactccc tagaatgtct cagagccatg ctgtctgcca acatccgtca gaatctgcag    2040
atttgtgttc aggtggcttc taaatatcat gaacaactgt caactcagtc tctgattgaa    2100
ctttttgaat ctttcaagag ttttgaaggt ctctttttatt ttctgggatc cattgttaac    2160
tttagccagg acccagatgt gcactttaaa tatattcagg cagcttgcaa gactgggcaa    2220
atcaaagaag tagaaagaat ctgtagagaa agcaactgct acgatcctga gcgagtcaag    2280
aattttctta aggaagcaaa actaacagat cagctaccac ttatcattgt gtgtgatcga    2340
tttgactttg tccatgattt ggtgctctat ttatatagaa ataatcttca aaagtatata    2400
gagatatatg tacagaaggt gaatccaagt cgacttcctg tagttattgg aggattactt    2460
gatgttgact gttctgaaga tgtcataaaa aacttgattc ttgttgtaag aggtcaattc    2520
tctactgatg agcttgttgc tgaggttgaa aaaagaaaca gattgaaact gcttctgcct    2580
tggctagagg ccagaattca tgagggctgt gaggagcctg ctactcacaa tgccttagcc    2640
aaaatctaca tagacagtaa taacaacccg gagagatttc ttcgtgaaaa tccctactat    2700
gacagtcgcg ttgttggaaa gtattgtgag aagagagatc cacatctggc ctgtgttgct    2760
tatgaacgtg gccaatgtga tctggaactt attaatgttt gcaatgagaa ttccctcttc    2820
aaaagtcttt ctcgctacct ggtacgtcga aaggatccag aattgtgggg cagcgtgctg    2880
ctggaaagca atccttacag gagacctcta attgaccagg ttgtacaaac agctttgtct    2940
gagactcagg accctgaaga agtgtcagta actgtaaagg cttctcatgac tgcagacctt    3000 cctaatgaac tcattgaact gctggagaaa attgtccttg ataactctgt attcagtgaa    3060
cacaggaatc tgcaaaacct ccttatcctc actgcaatta aggctgaccg tacacgtgtt    3120
atggagtata ttaaccgcct ggataattat gatgccccag atattgccaa tatcgccatc    3180
agcaatgagc tgtttgaaga agcatttgcc attttccgga aatttgatgt caatacttca    3240
gcagttcagg tcttaattga gcatattgga aacttggatc gggcatatga gtttgctgaa    3300
cgttgcaatg aacctgcggt ctggagtcaa cttgcaaaag cccagttgca gaaaggaatg    3360
gtgaaagaag ccattgattc ttatatcaaa gcagatgatc cttcctccta catggaagtt    3420
gttcaggctg ccaatactag tggaaactgg gaagaactgg tgaagtactt gcagatggcc    3480
cgtaagaagg ctcgagagtc ctatgtggag acagaactga tattcgcact ggctaaaaca    3540
aaccgccttg cagagttaga agaatttatc aatggaccaa ataatgctca tatccaacaa    3600
gttggtgacc gttgttatga tgaaaaaatg tatgatgctg ctaagttgtt gtacaataat    3660
gtttccaatt ttggacgttt ggcatctacc ctggttcacc tgggtgaata tcaggcagct    3720
gttgatgggg ctaggaaagc taacagtact cgaacatgga aagaggtctg cttcgcctgt    3780
gtagatggga aagaattccg tcttgctcag atgtgtggac ttcatattgt tgtacatgca    3840
gatgaattag aagaacttat caactactat caggatcgtg gctattttga agagctgatc    3900
```

```
accatgttgg aagcagcact gggacttgag cgagctcaca tgggaatgtt tactgaatta    3960
gctattctat actctaaatt taagcctcag aaaatgaggg agcacctgga gctgttctgg    4020
tctagagtga atattcccaa ggtgctaaga gctgcagaac aagctcatct ttgggcagaa    4080
ctggtgtttt tgtatgacaa gtatgaagaa tatgataatg ccataattac catgatgaat    4140
catccaactg atgcctggaa agaagggcaa ttcaaagata tcattaccaa ggttgccaat    4200
gtggaactat actacagagc aatacagttc tacttagaat tcaagcctct gttgttaaat    4260
gatttgctga tggtgctgtc tccacggttg gatcacactc gtgcagtcaa ttatttcagc    4320
aaggttaaac agctaccact ggtgaaaccg tatttgcgtt cagttcagaa ccataacaac    4380
aaatctgtga atgaatcatt gaacaatctt tttattacag aagaagatta tcaggctctg    4440
cgaacatcaa tagatgctta tgacaacttt gacaatatct cgcttgctca gcgtttggaa    4500
aaacatgaac tcattgagtt caggagaatt gctgcttatc tcttcaaagg caacaatcgc    4560
tggaaacaga gtgtagagct gtgcaagaaa gacagccttt acaaggatgc aatgcagtat    4620
gcttctgaat ctaaagatac tgaattggct gaagaactcc tgcagtggtt tttgcaggaa    4680
gaaaaaagag agtgctttgg agcttgtctg tttacctgtt acgatctttt aaggccagat    4740
gtcgtcctag aaactgcatg gaggcacaat atcatggatt ttgccatgcc ctatttcatc    4800
caggtcatga aggagtactt gacaaaggtg gataaattag atgcttcaga atcactgaga    4860
aaagaagaag aacaagctac agagacacaa cccattgttt atggtcagcc ccagttgatg    4920
ctgacagcag gacccagtgt tgccgtccct ccccaggcac cttttggtta tggttatacc    4980
gcaccaccgt atggacagcc acagcctggc tttgggtaca gcatgtga                 5028
```

<210> SEQ ID NO 36
<211> LENGTH: 1657
<212> TYPE: PRT
<213> ORGANISM: Homo sapiens

<400> SEQUENCE: 36

```
Met Ser Ala Ala Asp Glu Val Asp Gly Leu Gly Val Ala Arg Pro His
1               5                   10                  15

Tyr Gly Ser Val Leu Asp Asn Glu Arg Leu Thr Ala Glu Glu Met Asp
            20                  25                  30

Glu Arg Arg Arg Gln Asn Val Ala Tyr Glu Tyr Leu Cys His Leu Glu
        35                  40                  45

Glu Ala Lys Arg Trp Met Glu Ala Cys Leu Gly Glu Asp Leu Pro Pro
    50                  55                  60

Thr Thr Glu Leu Glu Glu Gly Leu Arg Asn Gly Val Tyr Leu Ala Lys
65                  70                  75                  80

Leu Gly Asn Phe Phe Ser Pro Lys Val Val Ser Leu Lys Lys Ile Tyr
                85                  90                  95

Asp Arg Glu Gln Thr Arg Tyr Lys Ala Thr Gly Leu His Phe Arg His
            100                 105                 110

Thr Asp Asn Val Ile Gln Trp Leu Asn Ala Met Asp Glu Ile Gly Leu
        115                 120                 125

Pro Lys Ile Phe Tyr Pro Glu Thr Thr Asp Ile Tyr Asp Arg Lys Asn
    130                 135                 140

Met Pro Arg Cys Ile Tyr Cys Ile His Ala Leu Ser Leu Tyr Leu Phe
145                 150                 155                 160

Lys Leu Gly Leu Ala Pro Gln Ile Gln Asp Leu Tyr Gly Lys Val Asp
                165                 170                 175
```

```
Phe Thr Glu Glu Glu Ile Asn Asn Met Lys Thr Glu Leu Glu Lys Tyr
            180                 185                 190

Gly Ile Gln Met Pro Ala Phe Ser Lys Ile Gly Ile Leu Ala Asn
            195                 200                 205

Glu Leu Ser Val Asp Glu Ala Ala Leu His Ala Val Ile Ala Ile
            210                 215                 220

Asn Glu Ala Ile Asp Arg Arg Ile Pro Ala Asp Thr Phe Ala Ala Leu
225                 230                 235                 240

Lys Asn Pro Asn Ala Met Leu Val Asn Leu Glu Glu Pro Leu Ala Ser
                245                 250                 255

Thr Tyr Gln Asp Ile Leu Tyr Gln Ala Lys Gln Asp Lys Met Thr Asn
            260                 265                 270

Ala Lys Asn Arg Thr Glu Asn Ser Glu Arg Glu Arg Asp Val Tyr Glu
            275                 280                 285

Glu Leu Leu Thr Gln Ala Glu Ile Gln Gly Asn Ile Asn Lys Val Asn
            290                 295                 300

Thr Phe Ser Ala Leu Ala Asn Ile Asp Leu Ala Leu Glu Gln Gly Asp
305                 310                 315                 320

Ala Leu Ala Leu Phe Arg Ala Leu Gln Ser Pro Ala Leu Gly Leu Arg
                325                 330                 335

Gly Leu Gln Gln Gln Asn Ser Asp Trp Tyr Leu Lys Gln Leu Leu Ser
            340                 345                 350

Asp Lys Gln Gln Lys Arg Gln Ser Gly Gln Thr Asp Pro Leu Gln Lys
            355                 360                 365

Glu Glu Leu Gln Ser Gly Val Asp Ala Ala Asn Ser Ala Ala Gln Gln
            370                 375                 380

Tyr Gln Arg Arg Leu Ala Ala Val Ala Leu Ile Asn Ala Ala Ile Gln
385                 390                 395                 400

Lys Gly Val Ala Glu Lys Thr Val Leu Glu Leu Met Asn Pro Glu Ala
                405                 410                 415

Gln Leu Pro Gln Val Tyr Pro Phe Ala Ala Asp Leu Tyr Gln Lys Glu
            420                 425                 430

Leu Ala Thr Leu Gln Arg Gln Ser Pro Glu His Asn Leu Thr His Pro
            435                 440                 445

Glu Leu Ser Val Ala Val Glu Met Leu Ser Ser Val Ala Leu Ile Asn
            450                 455                 460

Arg Ala Leu Glu Ser Gly Asp Val Asn Thr Val Trp Lys Gln Leu Ser
465                 470                 475                 480

Ser Ser Val Thr Gly Leu Thr Asn Ile Glu Glu Asn Cys Gln Arg
                485                 490                 495

Tyr Leu Asp Glu Leu Met Lys Leu Lys Ala Gln Ala His Ala Glu Asn
            500                 505                 510

Asn Glu Phe Ile Thr Trp Asn Asp Ile Gln Ala Cys Val Asp His Val
            515                 520                 525

Asn Leu Val Val Gln Glu Glu His Glu Arg Ile Leu Ala Ile Gly Leu
            530                 535                 540

Ile Asn Glu Ala Leu Asp Glu Gly Asp Ala Gln Lys Thr Leu Gln Ala
545                 550                 555                 560

Leu Gln Ile Pro Ala Ala Lys Leu Glu Gly Val Leu Ala Glu Val Ala
                565                 570                 575

Gln His Tyr Gln Asp Thr Leu Ile Arg Ala Lys Arg Glu Lys Ala Gln
            580                 585                 590

Glu Ile Gln Asp Glu Ser Ala Val Leu Trp Leu Asp Glu Ile Gln Gly
```

-continued

```
                595                 600                 605
Gly Ile Trp Gln Ser Asn Lys Asp Thr Gln Glu Ala Gln Lys Phe Ala
    610                 615                 620

Leu Gly Ile Phe Ala Ile Asn Glu Ala Val Glu Ser Gly Asp Val Gly
625                 630                 635                 640

Lys Thr Leu Ser Ala Leu Arg Ser Pro Asp Val Gly Leu Tyr Gly Val
                645                 650                 655

Ile Pro Glu Cys Gly Glu Thr Tyr His Ser Asp Leu Ala Glu Ala Lys
                660                 665                 670

Lys Lys Lys Leu Ala Val Gly Asp Asn Asn Ser Lys Trp Val Lys His
                675                 680                 685

Trp Val Lys Gly Gly Tyr Tyr Tyr His Asn Leu Glu Thr Gln Glu
    690                 695                 700

Gly Gly Trp Asp Glu Pro Pro Asn Phe Val Gln Asn Ser Met Gln Leu
705                 710                 715                 720

Ser Arg Glu Glu Ile Gln Ser Ser Ile Ser Gly Val Thr Ala Ala Tyr
                725                 730                 735

Asn Arg Glu Gln Leu Trp Leu Ala Asn Glu Gly Leu Ile Thr Arg Leu
                740                 745                 750

Gln Ala Arg Cys Arg Gly Tyr Leu Val Arg Gln Glu Phe Arg Ser Arg
                755                 760                 765

Met Asn Phe Leu Lys Lys Gln Ile Pro Ala Ile Thr Cys Ile Gln Ser
770                 775                 780

Gln Trp Arg Gly Tyr Lys Gln Lys Ala Tyr Gln Asp Arg Leu Ala
785                 790                 795                 800

Tyr Leu Arg Ser His Lys Asp Glu Val Val Lys Ile Gln Ser Leu Ala
                805                 810                 815

Arg Met His Gln Ala Arg Lys Arg Tyr Arg Asp Arg Leu Gln Tyr Phe
                820                 825                 830

Arg Asp His Ile Asn Asp Ile Lys Ile Gln Ala Phe Ile Arg Ala
                835                 840                 845

Asn Lys Ala Arg Asp Asp Tyr Lys Thr Leu Ile Asn Ala Glu Asp Pro
850                 855                 860

Pro Met Val Val Arg Lys Phe Val His Leu Leu Asp Gln Ser Asp
865                 870                 875                 880

Gln Asp Phe Gln Glu Glu Leu Asp Leu Met Lys Met Arg Glu Glu Val
                885                 890                 895

Ile Thr Leu Ile Arg Ser Asn Gln Gln Leu Glu Asn Asp Leu Asn Leu
                900                 905                 910

Met Asp Ile Lys Ile Gly Leu Leu Val Lys Asn Lys Ile Thr Leu Gln
                915                 920                 925

Asp Val Val Ser His Ser Lys Lys Leu Thr Lys Lys Asn Lys Glu Gln
                930                 935                 940

Leu Ser Asp Met Met Met Ile Asn Lys Gln Lys Gly Gly Leu Lys Ala
945                 950                 955                 960

Leu Ser Lys Glu Lys Arg Glu Lys Leu Glu Ala Tyr Gln His Leu Phe
                965                 970                 975

Tyr Leu Leu Gln Thr Asn Pro Thr Tyr Leu Ala Lys Leu Ile Phe Gln
                980                 985                 990

Met Pro Gln Asn Lys Ser Thr Lys Phe Met Asp Ser Val Ile Phe Thr
                995                 1000                1005

Leu Tyr Asn Tyr Ala Ser Asn Gln Arg Glu Glu Tyr Leu Leu Leu
    1010                1015                1020
```

```
-continued

Arg Leu Phe Lys Thr Ala Leu Gln Glu Glu Ile Lys Ser Lys Val
    1025                1030                1035

Asp Gln Ile Gln Glu Ile Val Thr Gly Asn Pro Thr Val Ile Lys
    1040                1045                1050

Met Val Val Ser Phe Asn Arg Gly Ala Arg Gly Gln Asn Ala Leu
    1055                1060                1065

Arg Gln Ile Leu Ala Pro Val Val Lys Glu Ile Met Asp Asp Lys
    1070                1075                1080

Ser Leu Asn Ile Lys Thr Asp Pro Val Asp Ile Tyr Lys Ser Trp
    1085                1090                1095

Val Asn Gln Met Glu Ser Gln Thr Gly Glu Ala Ser Lys Leu Pro
    1100                1105                1110

Tyr Asp Val Thr Pro Glu Gln Ala Leu Ala His Glu Glu Val Lys
    1115                1120                1125

Thr Arg Leu Asp Ser Ser Ile Arg Asn Met Arg Ala Val Thr Asp
    1130                1135                1140

Lys Phe Leu Ser Ala Ile Val Ser Ser Val Asp Lys Ile Pro Tyr
    1145                1150                1155

Gly Met Arg Phe Ile Ala Lys Val Leu Lys Asp Ser Leu His Glu
    1160                1165                1170

Lys Phe Pro Asp Ala Gly Glu Asp Glu Leu Leu Lys Ile Ile Gly
    1175                1180                1185

Asn Leu Leu Tyr Tyr Arg Tyr Met Asn Pro Ala Ile Val Ala Pro
    1190                1195                1200

Asp Ala Phe Asp Ile Ile Asp Leu Ser Ala Gly Gly Gln Leu Thr
    1205                1210                1215

Thr Asp Gln Arg Arg Asn Leu Gly Ser Ile Ala Lys Met Leu Gln
    1220                1225                1230

His Ala Ala Ser Asn Lys Met Phe Leu Gly Asp Asn Ala His Leu
    1235                1240                1245

Ser Ile Ile Asn Glu Tyr Leu Ser Gln Ser Tyr Gln Lys Phe Arg
    1250                1255                1260

Arg Phe Phe Gln Thr Ala Cys Asp Val Pro Glu Leu Gln Asp Lys
    1265                1270                1275

Phe Asn Val Asp Glu Tyr Ser Asp Leu Val Thr Leu Thr Lys Pro
    1280                1285                1290

Val Ile Tyr Ile Ser Ile Gly Glu Ile Ile Asn Thr His Thr Leu
    1295                1300                1305

Leu Leu Asp His Gln Asp Ala Ile Ala Pro Glu His Asn Asp Pro
    1310                1315                1320

Ile His Glu Leu Leu Asp Asp Leu Gly Glu Val Pro Thr Ile Glu
    1325                1330                1335

Ser Leu Ile Gly Glu Ser Ser Gly Asn Leu Asn Asp Pro Asn Lys
    1340                1345                1350

Glu Ala Leu Ala Lys Thr Glu Val Ser Leu Thr Leu Thr Asn Lys
    1355                1360                1365

Phe Asp Val Pro Gly Asp Glu Asn Ala Glu Met Asp Ala Arg Thr
    1370                1375                1380

Ile Leu Leu Asn Thr Lys Arg Leu Ile Val Asp Val Ile Arg Phe
    1385                1390                1395

Gln Pro Gly Glu Thr Leu Thr Glu Ile Leu Glu Thr Pro Ala Thr
    1400                1405                1410
```

| | | | | | | | | | | |
|---|---|---|---|---|---|---|---|---|---|---|
| Ser | Glu | Gln | Glu | Ala | Glu | His | Gln | Arg | Ala | Met | Gln | Arg | Arg | Ala |
| | 1415 | | | | 1420 | | | | 1425 | |

Ser Glu Gln Glu Ala Glu His Gln Arg Ala Met Gln Arg Arg Ala
    1415                1420                1425

Ile Arg Asp Ala Lys Thr Pro Asp Lys Met Lys Lys Ser Lys Ser
    1430                1435                1440

Val Lys Glu Asp Ser Asn Leu Thr Leu Gln Glu Lys Lys Glu Lys
    1445                1450                1455

Ile Gln Thr Gly Leu Lys Lys Leu Thr Glu Leu Gly Thr Val Asp
    1460                1465                1470

Pro Lys Asn Lys Tyr Gln Glu Leu Ile Asn Asp Ile Ala Arg Asp
    1475                1480                1485

Ile Arg Asn Gln Arg Arg Tyr Arg Gln Arg Lys Ala Glu Leu
    1490                1495                1500

Val Lys Leu Gln Gln Thr Tyr Ala Ala Leu Asn Ser Lys Ala Thr
    1505                1510                1515

Phe Tyr Gly Glu Gln Val Asp Tyr Tyr Lys Ser Tyr Ile Lys Thr
    1520                1525                1530

Cys Leu Asp Asn Leu Ala Ser Lys Gly Lys Val Ser Lys Lys Pro
    1535                1540                1545

Arg Glu Met Lys Gly Lys Lys Ser Lys Lys Ile Ser Leu Lys Tyr
    1550                1555                1560

Thr Ala Ala Arg Leu His Glu Lys Gly Val Leu Leu Glu Ile Glu
    1565                1570                1575

Asp Leu Gln Val Asn Gln Phe Lys Asn Val Ile Phe Glu Ile Ser
    1580                1585                1590

Pro Thr Glu Glu Val Gly Asp Phe Glu Val Lys Ala Lys Phe Met
    1595                1600                1605

Gly Val Gln Met Glu Thr Phe Met Leu His Tyr Gln Asp Leu Leu
    1610                1615                1620

Gln Leu Gln Tyr Glu Gly Val Ala Val Met Lys Leu Phe Asp Arg
    1625                1630                1635

Ala Lys Val Asn Val Asn Leu Leu Ile Phe Leu Leu Asn Lys Lys
    1640                1645                1650

Phe Tyr Gly Lys
    1655

<210> SEQ ID NO 37
<211> LENGTH: 4974
<212> TYPE: DNA
<213> ORGANISM: Homo sapiens

<400> SEQUENCE: 37

```
atgtccgccg cagacgaggt tgacgggctg ggcgtggccc ggccgcacta tggctctgtc      60
ctggataatg aaagacttac tgcagaggag atggatgaaa ggagacgtca gaacgtggct     120
tatgagtacc tttgtcattt ggaagaagcg aagaggtgga tggaagcatg cctaggggaa     180
gatctgcctc ccaccacaga actggaggag gggcttagga atggggtcta ccttgccaaa     240
ctggggaact tcttctctcc caaagtagtg tccctgaaaa aaatctatga tcgagaacag     300
accagataca aggcgactgg cctccacttt agacacactg ataatgtgat tcagtggttg     360
aatgccatgg atgagattgg attgcctaag attttttacc cagaaactac agatatctat     420
gatcgaaaga acatgccaag atgtatctac tgtatccatg cactcagttt gtacctgttc     480
aagctaggcc tggcccctca gattcaagac ctatatggaa aggttgactt cacagaagaa     540
gaaatcaaca acatgaagac tgagttggag aagtatggca tccagatgcc tgcctttagc     600
```

-continued

```
aagattgggg gcatcttggc taatgaactg tcagtggatg aagccgcatt acatgctgct    660
gttattgcta ttaatgaagc tattgaccgt agaattccag ccgacacatt tgcagctttg    720
aaaaatccga atgccatgct tgtaaatctt gaagagccct tggcatccac ttaccaggat    780
atactttacc aggctaagca ggacaaaatg acaaatgcta aaacaggac agaaaactca     840 gagagagaaa gagatgttta tgaggagctg ctcacgcaag ctgaaattca aggcaatata    900
aacaaagtca atacattttc tgcattagca aatatcgacc tggctttaga acaaggagat    960
gcactggcct tgttcagggc tctgcagtca ccagccctgg ggcttcgagg actgcagcaa    1020
cagaatagcg actggtactt gaagcagctc ctgagtgata acagcagaa gagacagagt    1080 ggtcagactg accccctgca aaggaggag ctgcagtctg gagtggatgc tgcaaacagt     1140
gctgcccagc aatatcagag aagattgca gcagtagcac tgattaatgc tgcaatccag     1200
aagggtgttg ctgagaagac tgttttggaa ctgatgaatc ccgaagccca gctgccccag    1260
gtgtatccat ttgccgccga tctctatcag aaggagctgg ctaccctgca cgacaaagt    1320 cctgaacata atctcaccca cccagagctc tctgtcgcag tggagatgtt gtcatcggtg    1380
gccctgatca acagggcatt ggaatcagga gatgtgaata cagtgtggaa gcaattgagc    1440
agttcagtta ctggtcttac caatattgag gaagaaaact gtcagaggta tctcgatgag    1500
ttgatgaaac tgaaggctca ggcacatgca gagaataatg aattcattac atggaatgat    1560
atccaagctt gcgtggacca tgtgaacctg gtggtgcaag aggaacatga gaggattta     1620 gccattggtt taattaatga agccctggat gaaggtgatg cccaaaagac tctgcaggcc    1680
ctacagattc ctgcagctaa acttgaggga gtccttgcag aagtggccca gcattaccaa    1740
gacacgctga ttagagcgaa gagagagaaa gcccaggaaa tccaggatga gtcagctgtg    1800
ttatggttgg atgaaattca aggtggaatc tggcagtcca acaaagacac ccaagaagca    1860
cagaagtttg ccttaggaat ctttgccatt aatgaggcag tagaaagtgg tgatgttggc    1920
aaaacactga gtgcccttcg ctcccctgat gttggcttgt atggagtcat ccctgagtgt    1980
ggtgaaactt accacagtga tcttgctgaa gccaagaaga aaaaactggc agtaggagat    2040
aataacagca agtgggtgaa gcactgggta aaaggtggat attattatta ccacaatctg    2100
gagacccagg aaggaggatg ggatgaacct ccaaattttg tgcaaaattc tatgcagctt    2160
tctcgggagg agatccagag ttctatctct ggggtgactg ccgcatataa ccgagaacag    2220
ctgtggctgg ccaatgaagg cctgatcacc aggctgcagg ctcgctgccg tggatactta    2280
gttcgacagg aattccgatc caggatgaat ttcctgaaga acaaatccc tgccatcacc     2340 tgcattcagt cacagtggag aggatacaag cagaagaagg catatcaaga tcggttagct    2400
tacctgcgct cccacaaaga tgaagttgta aagattcagt ccctggcaag gatgcaccaa    2460
gctcgaaagc gctatcgaga tcgcctgcag tacttccggg accatataaa tgacattatc    2520
aaaatccagg cttttattcg ggcaaacaaa gctcggatg actacaagac tctcatcaat     2580
gctgaggatc ctcctatggt tgtggtccga aaatttgtcc acctgctgga ccaaagtgac    2640
caggattttc aggaggagct tgaccttatg aagatgcggg aagaggttat caccctcatt    2700
cgttctaacc agcagctgga gaatgacctc aatctcatgg atatcaaaat tggactgcta    2760
gtgaaaaata agattacgtt gcaggatgtg gtttcccaca gtaaaaaact taccaaaaaa    2820
aataaggaac agttgtctga tatgatgatg ataaataaac agaagggagg tctcaaggct    2880
ttgagcaagg agaagagaga gaagttggaa gcttaccagc acctgttta tttattgcaa     2940 accaatccca cctatctggc caagctcatt tttcagatgc cccagaacaa gtccaccaag    3000
```

```
ttcatggact ctgtaatctt cacactctac aactacgcgt ccaaccagcg agaggagtac    3060
ctgctcctgc ggctctttaa gacagcactc caagaggaaa tcaagtcgaa ggtagatcag    3120
attcaagaga ttgtgacagg aaatcctacg gttattaaaa tggttgtaag tttcaaccgt    3180
ggtgcccgtg gccagaatgc cctgagacag atcttggccc cagtcgtgaa ggaaattatg    3240
gatgacaaat ctctcaacat caaaactgac cctgtggata tttacaaatc ttgggttaat    3300
cagatggagt ctcagacagg agaggcaagc aaactgccct atgatgtgac ccctgagcag    3360
gcgctagctc atgaagaagt gaagacacgg ctagacagct ccatcaggaa catgcgggct    3420
gtgacagaca gtttctctc agccattgtc agctctgtgg acaaaatccc ttatgggatg    3480
cgcttcattg ccaaagtgct gaaggactcg ttgcatgaga agttccctga tgctggtgag    3540
gatgagctgc tgaagattat tggtaacttg ctttattatc gatacatgaa tccagccatt    3600
gttgctcctg atgcctttga catcattgac ctgtcagcag gaggccagct taccacagac    3660
caacgccgaa atctgggctc cattgcaaaa atgcttcagc atgctgcttc caataagatg    3720
tttctgggag ataatgccca cttaagcatc attaatgaat atctttccca gtcctaccag    3780
aaattcagac ggttttttcca aactgcttgt gatgtcccag agcttcagga taaatttaat    3840
gtggatgagt actctgattt agtaaccctc accaaaccag taatctacat ttccattggt    3900
gaaatcatca cacccacac tctcctgttg gatcaccagg atgccattgc tccggagcac    3960
aatgatccaa tccacgaact gctggacgac ctcggcgagg tgcccaccat cgagtccctg    4020 atagggggaaa gctctggcaa tttaaatgac ccaaataagg aggcactggc taagacggaa    4080
gtgtctctca ccctgaccaa caagttcgac gtgcctggag atgagaatgc agaaatggat    4140
gctcgaacca tcttactgaa tacaaaacgt ttaattgtgg atgtcatccg gttccagcca    4200
ggagagacct tgactgaaat cctagaaaca ccagccacca gtgaacagga agcagaacat    4260
cagagagcca tgcagagacg tgctatccgt gatgccaaaa cacctgacaa gatgaaaaag    4320
tcaaaatctg taaggaaga cagcaacctc actcttcaag agaagaaaga gaagatccag    4380
acaggtttaa agaagctaac agagcttgga accgtggacc caaagaacaa ataccaggaa    4440
ctgatcaacg acattgccag ggatattcgg aatcagcgga ggtaccgaca gaggagaaag    4500
gccgaactag tgaaactgca acagacatac gctgctctga actctaaggc caccttttat    4560
ggggagcagg tggattacta taaaagctat atcaaaacct gcttggataa cttagccagc    4620
aagggcaaag tctccaaaaa gcctagggaa atgaaaggaa agaaaagcaa aaagatttct    4680
ctgaaatata cagcagcaag actacatgaa aaaggagttc ttctggaaat tgaggacctg    4740
caagtgaatc agtttaaaaa tgttatattt gaaatcagtc caacagaaga agttggagac    4800
ttcgaagtga agccaaatt catgggagtt caaatggaga cttttatgtt acattatcag    4860
gacctgctgc agctacagta tgaaggagtt gcagtcatga aattatttga tagagctaaa    4920
gtaaatgtca acctcctgat cttccttctc aacaaaaagt tctacgggaa gtaa          4974

<210> SEQ ID NO 38
<211> LENGTH: 724
<212> TYPE: PRT
<213> ORGANISM: Homo sapiens

<400> SEQUENCE: 38

Met Pro Glu Glu Val His His Gly Glu Glu Glu Val Glu Thr Phe Ala
1               5                   10                  15

Phe Gln Ala Glu Ile Ala Gln Leu Met Ser Leu Ile Ile Asn Thr Phe
```

-continued

```
                 20                  25                  30
Tyr Ser Asn Lys Glu Ile Phe Leu Arg Glu Leu Ile Ser Asn Ala Ser
             35                  40                  45
Asp Ala Leu Asp Lys Ile Arg Tyr Glu Ser Leu Thr Asp Pro Ser Lys
 50                  55                  60
Leu Asp Ser Gly Lys Glu Leu Lys Ile Asp Ile Ile Pro Asn Pro Gln
65                  70                  75                  80
Glu Arg Thr Leu Thr Leu Val Asp Thr Gly Ile Gly Met Thr Lys Ala
                 85                  90                  95
Asp Leu Ile Asn Asn Leu Gly Thr Ile Ala Lys Ser Gly Thr Lys Ala
            100                 105                 110
Phe Met Glu Ala Leu Gln Ala Gly Ala Asp Ile Ser Met Ile Gly Gln
            115                 120                 125
Phe Gly Val Gly Phe Tyr Ser Ala Tyr Leu Val Ala Glu Lys Val Val
            130                 135                 140
Val Ile Thr Lys His Asn Asp Asp Glu Gln Tyr Ala Trp Glu Ser Ser
145                 150                 155                 160
Ala Gly Gly Ser Phe Thr Val Arg Ala Asp His Gly Glu Pro Ile Gly
                165                 170                 175
Arg Gly Thr Lys Val Ile Leu His Leu Lys Glu Asp Gln Thr Glu Tyr
            180                 185                 190
Leu Glu Glu Arg Arg Val Lys Glu Val Val Lys Lys His Ser Gln Phe
            195                 200                 205
Ile Gly Tyr Pro Ile Thr Leu Tyr Leu Glu Lys Glu Arg Glu Lys Glu
            210                 215                 220
Ile Ser Asp Asp Glu Ala Glu Glu Lys Gly Glu Lys Glu Glu
225                 230                 235                 240
Asp Lys Asp Asp Glu Glu Lys Pro Lys Ile Glu Asp Val Gly Ser Asp
                245                 250                 255
Glu Glu Asp Asp Ser Gly Lys Asp Lys Lys Lys Thr Lys Lys Ile
            260                 265                 270
Lys Glu Lys Tyr Ile Asp Gln Glu Glu Leu Asn Lys Thr Lys Pro Ile
            275                 280                 285
Trp Thr Arg Asn Pro Asp Asp Ile Thr Gln Glu Glu Tyr Gly Glu Phe
            290                 295                 300
Tyr Lys Ser Leu Thr Asn Asp Trp Glu Asp His Leu Ala Val Lys His
305                 310                 315                 320
Phe Ser Val Glu Gly Gln Leu Glu Phe Arg Ala Leu Leu Phe Ile Pro
                325                 330                 335
Arg Arg Ala Pro Phe Asp Leu Phe Glu Asn Lys Lys Lys Lys Asn Asn
            340                 345                 350
Ile Lys Leu Tyr Val Arg Arg Val Phe Ile Met Asp Ser Cys Asp Glu
            355                 360                 365
Leu Ile Pro Glu Tyr Leu Asn Phe Ile Arg Gly Val Val Asp Ser Glu
            370                 375                 380
Asp Leu Pro Leu Asn Ile Ser Arg Glu Met Leu Gln Gln Ser Lys Ile
385                 390                 395                 400
Leu Lys Val Ile Arg Lys Asn Ile Val Lys Lys Cys Leu Glu Leu Phe
                405                 410                 415
Ser Glu Leu Ala Glu Asp Lys Glu Asn Tyr Lys Lys Phe Tyr Glu Ala
            420                 425                 430
Phe Ser Lys Asn Leu Lys Leu Gly Ile His Glu Asp Ser Thr Asn Arg
            435                 440                 445
```

```
Arg Arg Leu Ser Glu Leu Leu Arg Tyr His Thr Ser Gln Ser Gly Asp
    450                 455                 460
Glu Met Thr Ser Leu Ser Glu Tyr Val Ser Arg Met Lys Glu Thr Gln
465                 470                 475                 480
Lys Ser Ile Tyr Tyr Ile Thr Gly Glu Ser Lys Glu Gln Val Ala Asn
            485                 490                 495
Ser Ala Phe Val Glu Arg Val Arg Lys Arg Gly Phe Glu Val Val Tyr
        500                 505                 510
Met Thr Glu Pro Ile Asp Glu Tyr Cys Val Gln Gln Leu Lys Glu Phe
    515                 520                 525
Asp Gly Lys Ser Leu Val Ser Val Thr Lys Glu Gly Leu Glu Leu Pro
530                 535                 540
Glu Asp Glu Glu Glu Lys Lys Lys Met Glu Glu Ser Lys Ala Lys Phe
545                 550                 555                 560
Glu Asn Leu Cys Lys Leu Met Lys Glu Ile Leu Asp Lys Lys Val Glu
            565                 570                 575
Lys Val Thr Ile Ser Asn Arg Leu Val Ser Ser Pro Cys Cys Ile Val
        580                 585                 590
Thr Ser Thr Tyr Gly Trp Thr Ala Asn Met Glu Arg Ile Met Lys Ala
    595                 600                 605
Gln Ala Leu Arg Asp Asn Ser Thr Met Gly Tyr Met Met Ala Lys Lys
610                 615                 620
His Leu Glu Ile Asn Pro Asp His Pro Ile Val Glu Thr Leu Arg Gln
625                 630                 635                 640
Lys Ala Glu Ala Asp Lys Asn Asp Lys Ala Val Lys Asp Leu Val Val
            645                 650                 655
Leu Leu Phe Glu Thr Ala Leu Leu Ser Ser Gly Phe Ser Leu Glu Asp
        660                 665                 670
Pro Gln Thr His Ser Asn Arg Ile Tyr Arg Met Ile Lys Leu Gly Leu
    675                 680                 685
Gly Ile Asp Glu Asp Glu Val Ala Ala Glu Glu Pro Asn Ala Ala Val
690                 695                 700
Pro Asp Glu Ile Pro Pro Leu Glu Gly Asp Glu Asp Ala Ser Arg Met
705                 710                 715                 720
Glu Glu Val Asp

<210> SEQ ID NO 39
<211> LENGTH: 2175
<212> TYPE: DNA
<213> ORGANISM: Homo sapiens

<400> SEQUENCE: 39
atgcctgagg aagtgcacca tggagaggag gaggtggaga cttttgcctt tcaggcagaa      60
attgcccaac tcatgtccct catcatcaat accttctatt ccaacaagga gattttcctt     120
cgggagttga tctctaatgc ttctgatgcc ttggacaaga ttcgctatga gagcctgaca     180
gacccttcga gttggacag tggtaaagag ctgaaaattg acatcatccc caaccctcag     240
gaacgtaccc tgactttggt agacacaggc attggcatga ccaaagctga tctcataaat     300
aatttgggaa ccattgccaa gtctggtact aaagcattca tggaggctct tcaggctggt     360
gcagacatct ccatgattgg cagtttggt gttggctttt attctgccta cttggtggca     420
gagaaagtgg ttgtgatcac aaagcacaac gatgatgaac agtatgcttg ggagtcttct     480
gctggaggtt ccttcactgt gcgtgctgac catggtgagc ccattggcag gggtaccaaa     540
```

-continued

```
gtgatcctcc atcttaaaga agatcagaca gagtacctag aagagaggcg ggtcaaagaa    600
gtagtgaaga agcattctca gttcataggc tatcccatca ccctttattt ggagaaggaa    660
cgagagaagg aaattagtga tgatgaggca gaggaagaga aaggtgagaa agaagaggaa    720
gataaagatg atgaagaaaa acccaagatc gaagatgtgg gttcagatga ggaggatgac    780
agcggtaagg ataagaagaa gaaaactaag aagatcaaag agaaatacat tgatcaggaa    840
gaactaaaca agaccaagcc tatttggacc agaaaccctg atgacatcac ccaagaggag    900
tatggagaat tctacaagag cctcactaat gactgggaag accacttggc agtcaagcac    960
ttttctgtag aaggtcagtt ggaattcagg gcattgctat ttattcctcg tcgggctccc   1020
tttgaccttt ttgagaacaa gaagaaaaag aacaacatca aactctatgt ccgccgtgtg   1080
ttcatcatgg acagctgtga tgagttgata ccagagtatc tcaattttat ccgtggtgtg   1140
gttgactctg aggatctgcc cctgaacatc tcccgagaaa tgctccagca gagcaaaatc   1200
ttgaaagtca ttcgcaaaaa cattgttaag aagtgccttg agctcttctc tgagctggca   1260
gaagacaagg agaattacaa gaaattctat gaggcattct ctaaaaatct caagcttgga   1320
atccacgaag actccactaa ccgccgccgc ctgtctgagc tgctgcgcta tcatacctcc   1380
cagtctggag atgagatgac atctctgtca gagtatgttt ctcgcatgaa ggagacacag   1440
aagtccatct attacatcac tggtgagagc aaagagcagg tggccaactc agcttttgtg   1500
gagcgagtgc ggaaacgggg cttcgaggtg gtatatatga ccgagcccat tgacgagtac   1560
tgtgtgcagc agctcaagga atttgatggg aagagcctgg tctcagttac caaggagggt   1620
ctggagctgc ctgaggatga ggaggagaag aagaagatgg aagagagcaa ggcaaagttt   1680
gagaacctct gcaagctcat gaaagaaatc ttagataaga aggttgagaa ggtgacaatc   1740
tccaatagac ttgtgtcttc accttgctgc attgtgacca gcacctacgg ctggacagcc   1800
aatatggagc ggatcatgaa agcccaggca cttcgggaca actccaccat gggctatatg   1860
atggccaaaa agcacctgga gatcaaccct gaccacccca ttgtggagac gctgcggcag   1920
aaggctgagg ccgacaagaa tgataaggca gttaaggacc tggtggtgct gctgtttgaa   1980
accgccctgc tatcttctgg cttttccctt gaggatcccc agacccactc caaccgcatc   2040
tatcgcatga tcaagctagg tctaggtatt gatgaagatg aagtggcagc agaggaaccc   2100
aatgctgcag ttcctgatga gatccccccct ctcgagggcg atgaggatgc gtctcgcatg   2160
gaagaagtcg attag                                                    2175
```

<210> SEQ ID NO 40
<211> LENGTH: 21
<212> TYPE: DNA
<213> ORGANISM: Artificial
<220> FEATURE:
<223> OTHER INFORMATION: Target sequence for caspase 8

<400> SEQUENCE: 40

```
aaggaaagtt ggacatcctg a                                              21
```

<210> SEQ ID NO 41
<211> LENGTH: 4
<212> TYPE: PRT
<213> ORGANISM: Artificial
<220> FEATURE:
<223> OTHER INFORMATION: Synthetic Peptide

<400> SEQUENCE: 41

```
Asp Glu Val Asp
1
```

<210> SEQ ID NO 42
<211> LENGTH: 7
<212> TYPE: PRT
<213> ORGANISM: Artificial
<220> FEATURE:
<223> OTHER INFORMATION: Synthetic Peptide

<400> SEQUENCE: 42

```
Asp Glu Val Asp Ala Pro Lys
1               5
```

<210> SEQ ID NO 43
<211> LENGTH: 8
<212> TYPE: PRT
<213> ORGANISM: Artificial
<220> FEATURE:
<223> OTHER INFORMATION: Synthetic Peptide

<400> SEQUENCE: 43

```
Val Asp Gln Met Asp Gly Trp Lys
1               5
```

<210> SEQ ID NO 44
<211> LENGTH: 7
<212> TYPE: PRT
<213> ORGANISM: Artificial
<220> FEATURE:
<223> OTHER INFORMATION: Synthetic Peptide

<400> SEQUENCE: 44

```
Asp Glu Val Asp Ala Arg Lys
1               5
```

<210> SEQ ID NO 45
<211> LENGTH: 5
<212> TYPE: PRT
<213> ORGANISM: Artificial
<220> FEATURE:
<223> OTHER INFORMATION: Synthetic Peptide

<400> SEQUENCE: 45

```
Val Asp Val Ala Asp
1               5
```

<210> SEQ ID NO 46
<211> LENGTH: 8
<212> TYPE: PRT
<213> ORGANISM: Artificial
<220> FEATURE:
<223> OTHER INFORMATION: Synthetic Peptide

<400> SEQUENCE: 46

```
Val Asp Val Ala Asp Gly Trp Lys
1               5
```

<210> SEQ ID NO 47
<211> LENGTH: 8
<212> TYPE: PRT
<213> ORGANISM: Artificial
<220> FEATURE:
<223> OTHER INFORMATION: Synthetic Peptide

<400> SEQUENCE: 47

```
Val Asp Gln Val Asp Gly Trp Lys
```

```
<210> SEQ ID NO 48
<211> LENGTH: 4
<212> TYPE: PRT
<213> ORGANISM: Artificial
<220> FEATURE:
<223> OTHER INFORMATION: Synthetic Peptide

<400> SEQUENCE: 48

Val Glu Ile Asp
1

<210> SEQ ID NO 49
<211> LENGTH: 7
<212> TYPE: PRT
<213> ORGANISM: Artificial
<220> FEATURE:
<223> OTHER INFORMATION: Synthetic Peptide

<400> SEQUENCE: 49

Val Gln Val Asp Gly Trp Lys
1               5
```

METHODS OF TREATING DISEASES RESPONSIVE TO INDUCTION OF APOPTOSIS AND SCREENING ASSAYS

RELATED APPLICATIONS

The present application claims the benefit under 35 U.S.C. §119(e) of the following U.S. provisional applications which are wholly incorporated by reference: U.S. 60/463,649, filed Apr. 18, 2003; U.S. 60/463,662, filed Apr. 18, 2003; U.S. 60/484,749, filed Jul. 7, 2003; U.S. 60/484,750, filed Jul. 7, 2003; and U.S. 60/532,665, filed Dec. 29, 2003.

BACKGROUND OF THE INVENTION

1. Field of the Invention

The present invention relates to a method of treating, preventing or ameliorating a disease responsive to induction of the caspase cascade in an animal, comprising administering to the animal a compound which binds specifically to one or more Apoptosis Inducing Proteins (AIPs). AIPs include Transferrin Receptor Related Apoptosis Inducing Proteins (TRRAIPs), Clathrin Heavy Chain Related Apoptosis Inducing Proteins (CHCRAIPs), IQ motif containing GTPase Activating Protein Related Apoptosis Inducing Proteins (IQ-GAPRAIPs), and Heat Shock Protein Related Apoptosis Inducing Proteins (HSPRAIPs). The present invention also relates to methods for identifying such AIP binding compounds. The invention also relates to the use of biochemical and cell based screening assays to identify Alp binding compounds that may be administered to animals for treating, preventing or ameliorating a disease responsive to induction of the caspase cascade.

2. Related Art

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms have heretofore not been clear. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

SUMMARY OF THE INVENTION

As described in U.S. Pat. No. 6,462,041, gambogic acid is a potent and highly efficacious activator of the caspase cascade and activator of apoptosis. The present invention relates to the discovery that apoptosis is induced upon the binding of gambogic acid to an AIP. Such binding is a starting point for initiating the caspase cascade and apoptosis. The binding of gambogic acid to an AIP results in fast induction of apoptosis in cells, typically within 15 minutes to 10 hours.

Generally, the present invention relates to compounds which bind specifically to an AIP and induce fast activation of the caspase cascade and apoptosis; pharmaceutical formulations of these compounds; methods of treating, preventing or ameliorating a disease responsive to induction of the caspase cascade in an animal, comprising administering to the animal such compounds; methods for identifying such AIP binding compounds; and use of homogenous, heterogenous, protein and/or cell based screening assays to identify AIP binding compounds that may be administered to animals for treating, preventing or ameliorating a disease responsive to induction of the caspase cascade.

Non-limiting examples of TRRAIP binding compounds include 1-allyl-1,3,3a,4,5,12a-hexahydro-7,13-dioxo-1,5-methano-furo[3,4-d]xanthene, 1-allyl-1,3,3a,4,4a, 11a-hexahydro-10,12-dioxo-1,4a-methano-furo[3,4-b]xanthene, 1-(3-methyl-2-butenyl)-3,3-dimethyl-1,3,3a,4,5,12a-hexahydro-7,13-dioxo-1,5-methano-faro[3,4-d]xanthene, 1-(3-methyl-2-butenyl)-3,3-dimethyl-1,3,3a,4,4a,11a-hexahydro-10,12-dioxo-1,4a-methano-furo[3,4-b]xanthene, 1-(3-methyl-2-butenyl)-3,3-dimethyl-1,3,3a,4,5,10a-hexahydro-7,11-dioxo-9-phenyl-1,5-methano-furo[3,4-i]chromene, and 1-(3-methyl-2-butenyl)-3,3-dimethyl-1,3,3a,4,4a,9a-hexahydro-8,10-dioxo-6-phenyl-1,4a-methano-furo[3,4-g]chromene.

A first embodiment of the invention relates to a method of treating, preventing or ameliorating a disease responsive to induction of the caspase cascade in an animal, comprising administering to the animal a compound which binds specifically to an AIP, wherein the compound induces activation of the caspase cascade in the animal and the disease is treated, prevented or ameliorated; with the proviso that the compound is not gambogic acid (GA) or a GA-related compound.

In this embodiment, the AIP may be a Transferrin Receptor Related Apoptosis Inducing Protein (TRRAIP), a Clathrin Heavy Chain Related Apoptosis Inducing Protein (CHCRAIP), an IQ motif containing GTPase Activating Protein Related Apoptosis Inducing Protein (IQGAPRAIP), or a Heat Shock Protein Related Apoptosis Inducing Protein (HSPRAIP).

In this embodiment, the disease may be a hyperproliferative disease. The hyperproliferative disease may be a cancer. The cancer may be Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis flngoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical hyperplasia, renal cell carcinomas, endometrial carcinomas, polycythemia vera, essential thrombocytosis, adrenal cortex carcinomas, skin cancer, or prostatic carcinomas. Alternatively, the disease may be an inflammatory disease. The compound may be identified by determining whether the compound binds specifically to an AIP. The AIP may be a transferrin receptor protein, a clathrate heavy chain protein, an IQ motif containing GTPase activating protein, or a heat shock protein.

The invention also relates to the discovery that AIPs are useful for screening for other apoptotic inducing agents. Such screening can employ one or more AIPs, one or more nucleotides which encode AIPs, or one or more nucleotides which hybridize to the nucleotides which encode AIPs, and combinations thereof.

In another embodiment, the invention pertains to a method of identifying potentially therapeutic anticancer compounds comprising: (a) contacting an AIP with one or more test compounds; and (b) monitoring whether the one or more test compounds binds to the AIP; wherein compounds which bind the AIP are potentially therapeutic anticancer compounds. The AIP may be a transferrin receptor protein, a clathrate heavy chain protein, an IQ motif containing GTPase activating protein, or a heat shock protein.

In this embodiment, the AIP may be a Transferrin Receptor Related Apoptosis Inducing Protein (TRRAIP), a Clathrin Heavy Chain Related Apoptosis Inducing Protein (CHCRAIP), an IQ motif containing GTPase Activating Protein Related Apoptosis Inducing Protein (IQGAPRAIP), or a Heat Shock Protein Related Apoptosis Inducing Protein (HSPRAIP).

The invention also pertains to the use of partially or fully purified Alps which may be used in homogenous or heterogenous binding assays to screen a large number or library of compounds and compositions for their potential ability to induce apoptosis. Those compositions capable of binding to an AIP are potentially useful for inducing apoptosis in vivo. AlPs can be synthesized or isolated from cells which over express these polypeptides. Accordingly, the invention also relates to nucleotides that encode for AIPs; vectors comprising these nucleotides; and cells comprising these vectors.

In another embodiment of the invention, determining whether the compound binds specifically to an AIP may comprise a competitive or noncompetitive homogeneous assay. The homogeneous assay may be a fluorescence polarization assay or a radioassay. Alternatively, determining whether the compound binds specifically to an AIP may comprise a competitive heterogeneous assay. The heterogeneous assay may be a fluorescence assay, a radioassay or an assay comprising avidin and biotin. The AIP may comprise a detectable label. The label on the AIP may be selected from the group consisting of a fluorescent label and a radiolabel. Alternatively, the gambogic acid or a gambogic acid-related compound may comprise a detectable label. The label on the gambogic acid or a gambogic acid-related compound may be selected from the group consisting of a fluorescent label and a radiolabel.

The invention also pertains to cells with altered levels of expression of one or more AIPs which may be used in cell-based screening assays to screen a large number or library of compounds and compositions for their ability to induce apoptosis. Such screening assays may be performed with intact cells and afford the identification of potentially therapeutic antineoplastic compositions. In one embodiment, cells have altered levels of expression of one or more AIPs by use of antisense nucleotides or RNA interference. In another embodiment, cells have reduced levels of expression of one or more AIPs by modifying or knocking out the genes in cellular genomic or mitochondrial DNA encoding the AIP(s). In another embodiment, vectors are introduced into the cells thereby elevating levels of expression of one or more AIPs. In another embodiment, cellular genomic or mitochondrial DNA is modified thereby elevating levels of expression of one or more AIPs. In a further embodiment, an AIP binding compound is determined in cell-based screening by i) introducing a compound to a cell having an altered level of expression of one or more AIPs; and ii) monitoring the extent to which the compound induces apoptosis by measuring observable changes in reporter compounds' response to the caspase cascade. Hence, in another embodiment of the invention, the AIP may be present in cells in vitro.

The invention also relates to the use of gambogic acid (or a GA-related compound) for raising antibodies which can be used to screen chemical libraries for other compositions that bind one or more AIPs, or that activate apoptosis. Accordingly, in another embodiment, the invention pertains to a method of identifying potentially therapeutic anticancer compounds comprising: (a) contacting an antibody to gambogic acid (GA) or a GA-related compound; and (b) determining whether the compound binds to the antibody; wherein compounds which bind the antibody are potentially therapeutic anticancer compounds.

In another embodiment, the invention pertains to a method of prognosing the efficacy of an anti-cancer AIP binding composition in a cancer patient comprising: (a) taking a fluid or tissue sample from an individual manifesting a cancer; (b) quantifying the total mRNA encoding one or more AIPs; (c) calculating a ratio comprising the quantity of the mRNA to the average quantity of the mRNA in a population not manifesting the cancer; wherein a ratio greater than 1 indicates that the anti-cancer AIP binding composition is efficacious.

In another embodiment, the invention pertains to a method of prognosing the efficacy of an anti-cancer AIP binding composition in a cancer patient comprising: (a) taking a fluid or tissue sample from an individual manifesting a cancer; (b) quantifying the one or more AIPs present in the sample; (c) calculating a ratio comprising the quantity of the one or more AIPs to the average quantity of the one or more AIPs in a population not manifesting the cancer; wherein a ratio greater than 1 indicates that the anti-cancer AIP binding composition is efficacious.

The invention also relates to the use of the structures of AIPs to design compositions that bind these polypeptides, or to design compositions that activate apoptosis.

Apoptosis may be induced by the compounds of the present invention within 15 minutes to 10 hours of introduction to the cell, or administration to an animal. Apoptosis may also be induced by such compounds within 0.5, 0.75, 1, 2, 3, 4, 5, 6, 7, 8, or 9 hours. These compounds preferably have a molecular weight ranging from 200 Daltons (g/mole) to 20,000 Daltons (g/mole). The compounds may also have a molecular weight ranging from 500 Daltons to 10,000 Daltons.

The invention also relates to a complex, comprising: i) an AIP; and ii) an AIP binding compound; with the proviso that the AIP binding compound is not GA or a GA-related compound.

The invention also relates to a detectably labeled gambogic acid or gambogic acid related compound comprising i) gambogic acid or a gambogic acid related compound; ii) optionally a linker; and iii) a label; wherein said gambogic acid or said gambogic acid related compound is covalently linked to said label optionally via said linker. The linker may be N,N-(1,2-aminoethyl); N,N-(2-{2-[2-(2-aminoethoxy)-ethoxy]-ethoxy}-aminoethyl); N,N-(2-[2-(2-aminoethoxy)-ethoxy]-aminoethyl); N,N-[2-(2-{2-[2-(2-aminoethoxy)-ethoxy]-ethylcarbamoyl}-ethyldisulfanyl)-aminoethyl]; N,N-(amidoacetamido); N-[(5-{2-[2-(2-aminoethoxy)-ethoxy]-ethylcarbamoyl}-pentyl)-carboxamide]; N-({5-[2-(2-aminoethyldisulfanyl)-ethylcarbamoyl]-pentyl})-carboxamide; N,N-[(5-aminopentyl)-thioureidyl]; or N-({2-[2-(2-aminoethoxy)-ethoxy]-ethyl}-carboxamide). The detectable label may be biotin, a fluorescent label, or a radiolabel.

The invention also relates to a composition comprising i) gambogic acid or a gambogic acid related compound; ii) optionally a linker; and iii) a solid phase; wherein said gambogic acid or said gambogic acid related compound is covalently linked to said solid phase optionally via said linker. The solid phase may be amino-agarose or N-hydroxysuccinimidylcarboxylagarose. The composition may be prepared by bonding N-hydroxysuccinimidylgambogate to said solid phase.

BRIEF DESCRIPTION OF THE DRAWINGS

FIG. 1A. GA binds transferrin receptor in vitro. 96-well plates were coated with soluble human transferrin receptor (shTR) (SEQ ID NO. 1) at 375 ng/well and blocked with Bovine Serum Albumin (BSA). Wells were incubated with increasing concentrations of biotin-GA in binding/washing buffer for 20 min at 30° C. Eu-streptavidin was used for the detection. Amounts of bound Eu-Streptavidin were quantified by measuring time-delayed fluorescence. Confirmed in three independent experiments.

FIG. 1B. IC$_{50}$ of active and inactive GA derivatives. In competition experiments, biotin-GA at 3.16 µM was premixed with increasing amounts of GA or the inactive-GA as competitor. Amounts of bound Eu-Streptavidin were quantified by measuring time-delayed fluorescence. Confirmed in three independent experiments.

FIG. 1C. GA bound to transferrin receptor (SEQ ID NO. 1) in vitro can be displaced by active GA derivatives. shTR-coated wells were incubated with biotin-GA as described, washed and incubated with GA or binding/washing buffer as a wash off control. Separate control wells were probed with biotinylated holo-transferrin (bio-Trn) to control for TR retention and possible denaturation over long incubation times. Independently confirmed in three experiments.

FIG. 1D. Binding of Biotin-GA and tritium-GA to transferrin receptor (SEQ ID NO. 1) is not inhibited by either apo-transferrin or holo-transferrin. Binding of Biotin-GA and tritium-GA to Jurkat cells (hatched) or in-vitro TfR-binding (solid) in the presence of 1 µM GA, 50 µg/ml of apo-transferrin or 50 μg/ml of holo-transferrin is shown in this graph. Confirmed in three independent experiments.

FIG. 2A. GA interferes with receptor internalization as monitored by soluble transferrin internalization. T47D cells were treated with DMSO or 2 μM GA for 10 min (panels A and C respectively) and DMSO or 2 μM GA for 30 min (panels B and D, respectively) and further treated with FITC conjugated anti-transferrin receptor for 30 mins at 37° C. The cells were then fixed with methanol at −20° C. for 5 min, washed with PBS and mounted with Vectashield mounting medium. Representative of three independently confirmed experiments.

FIG. 2B. GA interferes with transferrin receptor (SEQ ID NO. 1) internalization as indicated by cell surface transferrin receptor expression. Jurkat cells were treated with holo-transferrin (50 μg/ml) or GA (5 μM) alone for 5 min or pretreat for 5 min with holo-transferrin followed by 5 min GA (5 μM) treatment. Cells were then stained with FITC-conjugated anti-transferrin receptor antibody for 30 minutes at 4° C. After washing, cells were analyzed on a Becton Dickinson FACS Calibur. Data is shown as mean flourescence units (mfu). Confirmed in three independent experiments.

FIG. 3A. Realtime PCR showing the down-regulation of the TfR (SEQ ID NO. 1) at the mRNA level. 293T cells were transfected for 48 h as untransfected, lipid alone, cph (50 nM), and TfR siRNA (50 nM). TfR mRNA levels were normalized to cyclophilin, a housekeeping gene. Cyclophilin downregulation was normalized to GAPD. Confirmed in three independent experiments.

FIG. 3B. Western blot representing the down-regulation of transferrin receptor (SEQ ID NO. 1) in siRNA transfected cells. Whole cell lysates of 293 T cells post transfection were subjected to SDS-PAGE and immunoblotted onto PVDF. Anti-TfR antibody was used to detect the levels of transferrin receptor representing the duplicate samples in the upper panel. Equal loading was confirmed by western blotting of actin (lower panel).

FIG. 3C. Down regulation of TfR (SEQ ID NO. 1) protects cells from GA-induced apoptosis. 293T cells were plated onto glass cover slips in a 24 well plate and transfected with TfR siRNA (50 nM) for 48 h. Post-transfection, cells were treated with DMSO or 1 μM GA for 5 h. Cells were fixed with 3% para-formaldehyde, stained with DAPI at 0.1 ug/ml and mounted with Vectashield mounting medium. Quantification of death, post TfR down regulation and GA treatment, was assessed by determining the mean number of cells with fragmented nuclei in 3 representative 20× fields. Independently confirmed in three experiments.

FIGS. 4A-4C Signaling pathway of GA-induced apoptosis.

FIG. 4A. Western blots representing the apoptosis inducers. Jurkat cells at $5 \times 10^6$/ml were treated with DMSO or GA (5 μM) for the times indicated. Lysates were subject to SDS PAGE analysis then blotted onto PVDF membrane. Membranes were probed with anti-caspase 3, anti-caspase 8, Bid, or Cytochrome c antibodies and detected using enhanced chemiluminescence (ECL).

FIGS. 4B. Jurkat cells cultured at $5 \times 10^6$/ml were treated with FK19 (Fluoromethyl Ketone), biotinylated caspase inhibitor (10 μM) for 30 min followed by treatment with DMSO or GA (5 μM) for 1 hr. Lysates were mixed with 100 μl of streptavidin-agarose beads for 2 hr or overnight at 4° C. Samples were subject to SDS-PAGE analysis and blotted onto PVDF membrane. Membranes were probed with anti-caspase 8 and detected by ECL.

FIG. 4C. Downregulation of caspase 8 decreases caspase activation. 293 T cells were transfected with caspase 8 siRNA (50 nM) for 48 h. Controls used were untransfected and lipid alone. Post-transfection, cells were treated with 2 μM GA for 5 h. Cell viability was measured by PI staining using flow cytometry.

DETAILED DESCRIPTION OF THE INVENTION

I. Definitions

Figure 1A:
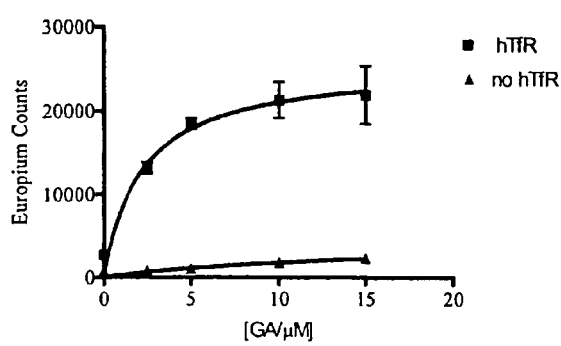
FIGS. 1A-1D Gambogic acid (GA) binding to transferrin receptor (TR) (SEQ ID NO. 1).
Figure 1B:
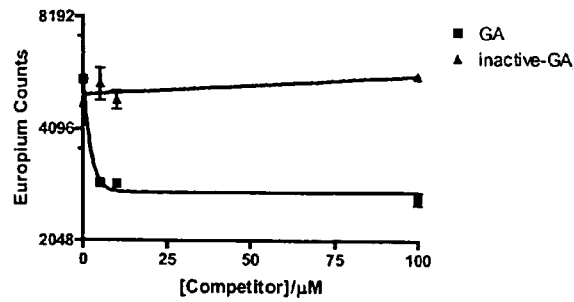
Figure 1C:
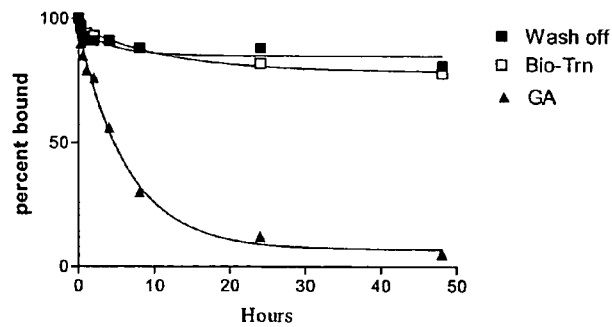
Figure 1D:
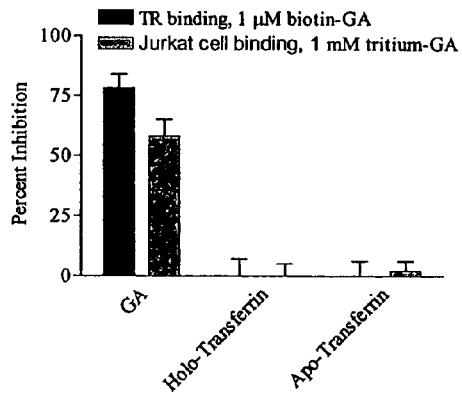
Figure 2A:
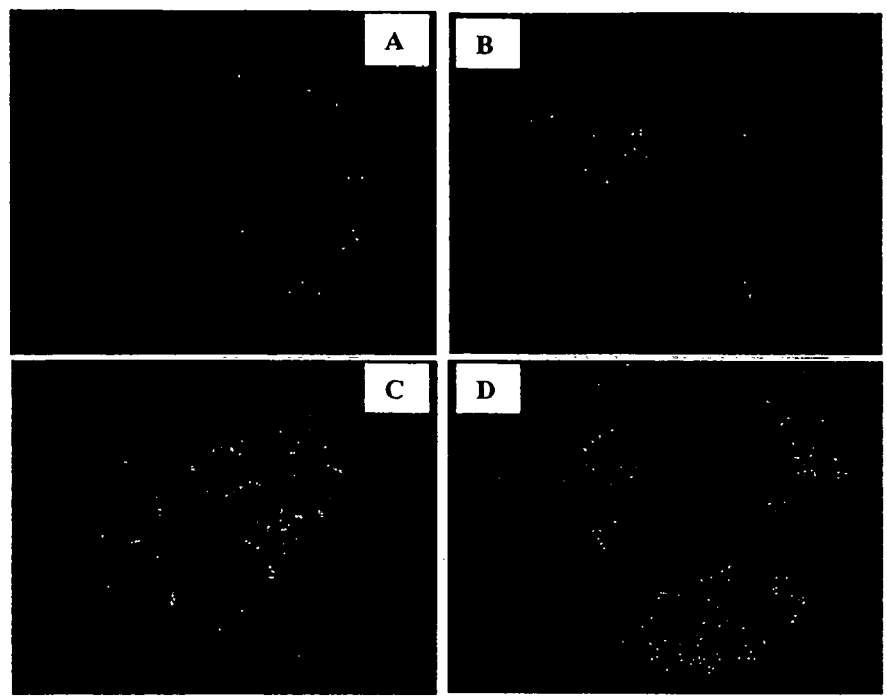
FIGS. 2A and 2B. Gambogic acid (GA) interferes with transferrin receptor (SEQ ID NO. 1) internalization.
Figure 2B:
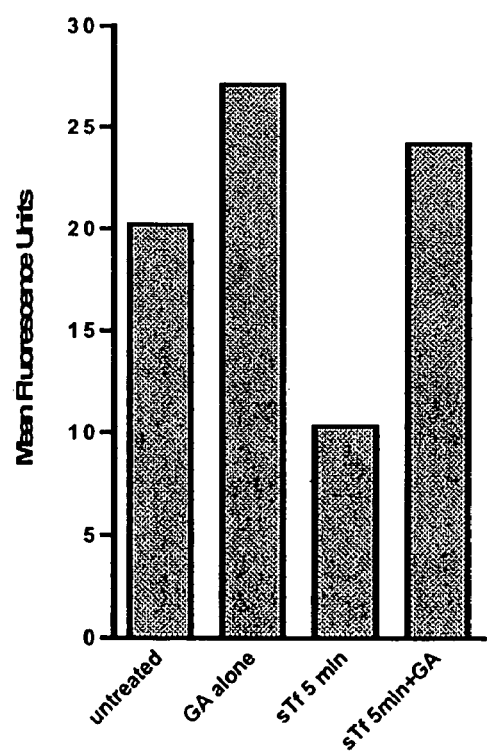
Figure 3A:
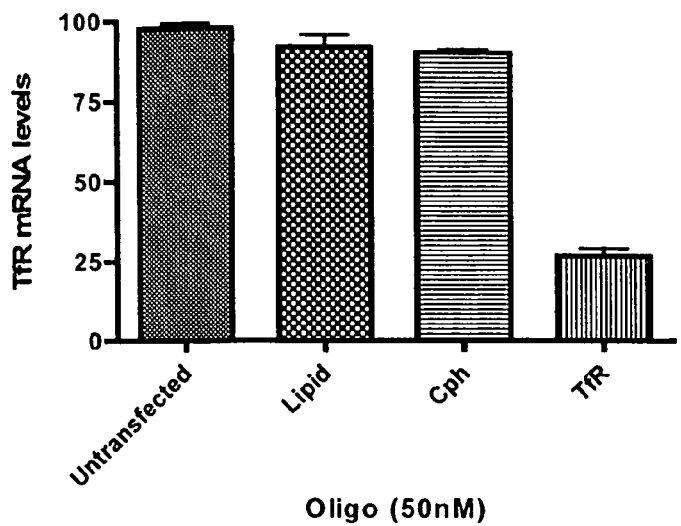
FIGS. 3A-3C. Down-regulation of the transferrin receptor (SEQ ID NO. 1) using siRNA technology leads to a decrease in apoptosis with gambogic acid treatment.
Figure 3B:
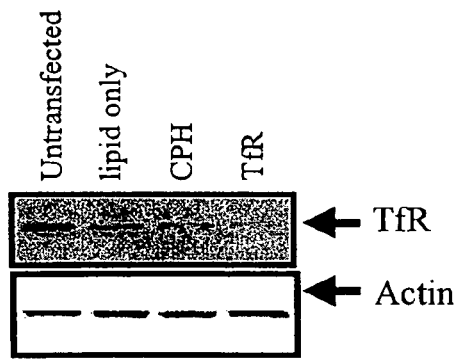
Figure 3C:
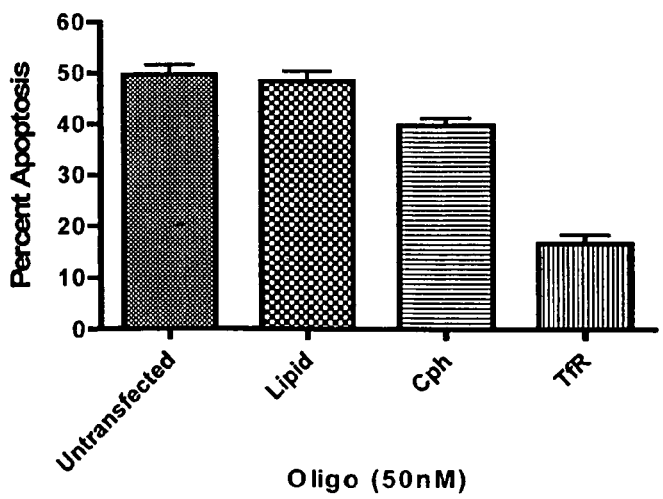

Unless defined otherwise, all technical and scientific terms used herein have the same meaning as is commonly understood by one of ordinary skill in the art to which this invention belongs.

As used herein, apoptosis is a highly conserved, genetically programmed form of cellular suicide characterized by distinct morphological changes such as cytoskeletal disruption, cell shrinkage, membrane blebbing, nuclear condensation, fragmentation of DNA, and loss of mitochondrial function.

As used herein, a caspase is a cysteine protease of the interleukin-1β/CED-3 family. As used herein, the caspase cascade is a sequential activation of at least two caspases, or the activation of caspase activity that behaves as if it involves the sequential activation of at least two caspases.

As used herein, "Apoptosis Inducing Proteins" and "AIPs" are used interchangeably and refer to Transferrin Receptor Related Apoptosis Inducing Proteins (TRRAIPs), Clathrin Heavy Chain Related Apoptosis Inducing Proteins (CHCRAIPs), IQ motif containing GTPase Activating Protein Related Apoptosis Inducing Proteins (IQGAPRAIPs), and Heat Shock Protein Related Apoptosis Inducing Proteins (HSPRAIPs). As used herein, an "AIP binding compound" is used to refer to TRRAIP binding compounds, CHCRAIP binding compounds, IQGAPRAIP binding compounds and HSPRAIP binding compounds.

As used herein, "Transferrin Receptor Related Apoptosis Inducing Proteins" and "TRRAIPs" are used interchangeably and refer to SEQ ID NO: 1 or 4, their mutants, homologs, derivatives and fragments which affect apoptosis upon binding gambogic acid (GA) or GA-related compounds such as those described herein or in U.S. Pat. No. 6,462,041. Methods for determining whether a given TRRAIP binds to GA or GA-related compounds can be determined by the assays described herein. As used herein, the term "TRRAIP binding compound" refers to a compound which binds specifically to a TRRAIP, induces activation of the caspase cascade, and can be administered in the method of treating, preventing or ameliorating a disease responsive to induction of the caspase cascade in an animal, such as a hyperproliferative disease. As used herein, the term "test compound" refers to a compound that can be tested for its ability to bind an AIP or a TRRAIP. Test compounds identified as capable of binding TRRAIP are TRRAIP binding compounds.

As used herein, "TR" and "TfR" both refer to transferrin receptor.

As used herein, "Clathrin Heavy Chain Related Apoptosis Inducing Proteins" and "CHCRAIPs" are used interchangeably and refer to SEQ ID NO:34, its mutants, homologs, derivatives and fragments which affect apoptosis upon binding gambogic acid (GA) or GA-related compounds such as those described herein or in U.S. Pat. No. 6,462,041. Methods for determining whether a given CHCRAIP binds to GA or GA-related compounds can be determined by the assays described herein. As used herein, the term "CHCRAIP binding compound" refers to a compound which binds specifically to an CHCRAIP, induces activation of the caspase cascade, and can be administered in the method of treating, preventing or ameliorating a disease responsive to induction of the caspase cascade in an animal, such as a hyperproliferative disease. As used herein, the term "test compound" refers to a compound that can be tested for its ability to bind an AIP or a CHCRAIP. Test compounds identified as capable of binding CHCRAIP are CHCRAIP binding compounds.

As used herein, "IQ motif containing GTPase Activating Protein Related Apoptosis Inducing Proteins" and "IQGAPRAIPs" are used interchangeably and refer to SEQ ID NO: 36, its mutants, homologs, derivatives and fragments which affect apoptosis upon binding gambogic acid (GA) or GA-related compounds such as those described herein or in U.S. Pat. No. 6,462,041. Methods for determining whether a given IQGAPRAIP binds to GA or GA-related compounds can be determined by the assays described herein. As used herein, the term "IQGAPRAIP binding compound" refers to a compound which binds specifically to an IQGAPRAIP, induces activation of the caspase cascade, and can be administered in the method of treating, preventing or ameliorating a disease responsive to induction of the caspase cascade in an animal, such as a hyperproliferative disease. As used herein, the term "test compound" refers to a compound that can be tested for its ability to bind an AIP or an IQGAPRAIP. Test compounds identified as capable of binding IQGAPRAIP are IQGAPRAIP binding compounds.

As used herein, "Heat Shock Protein Related Apoptosis Inducing Proteins" and "HSPRAIPs" are used interchangeably and refer to SEQ ID NO: 38, its mutants, homologs, derivatives and fragments which affect apoptosis upon binding gambogic acid (GA) or GA-related compounds such as those described herein or in U.S. Pat. No. 6,462,041. Methods for determining whether a given HSPRAIP binds to GA or GA-related compounds can be determined by the assays described herein. As used herein, the term "HSPRAIP binding compound" refers to a compound which binds specifically to a HSPRAIP, induces activation of the caspase cascade, and can be administered in the method of treating, preventing or ameliorating a disease responsive to induction of the caspase cascade in an animal, such as a hyperproliferative disease. As used herein, the term "test compound" refers to a compound that can be tested for its ability to bind an AIP or an HSPRAIP. Test compounds identified as capable of binding HSPRAIP are HSPRAIP binding compounds.

The test compounds may be pure substances or mixtures of substances such as in combinatorial libraries. The test compounds may be any natural product, synthesized organic or inorganic molecule, or biological macromolecules. Preferably, the test compounds are preselected to have <500 MW, $\leq 5$ H-bond donors, $\leq 10$ H-bond acceptors, and logP<5. Computer programs may be used to diversify the compound library. The test compounds may be at least 85% pure.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, may be a mixture of stereoisomers. In such instances, further purification might increase the specific activity of the compound.

As used herein, a disease which is "responsive to induction of the caspase cascade" is a disease which may be treated with an AIP binding compound. Non-limiting examples of such diseases include hyperproliferative and inflammatory diseases. As used herein, hyperproliferative diseases include any disease characterized by inappropriate cell proliferation. Such hyperproliferative diseases include skin diseases such as psoriasis, as well as cancer. Non limiting examples of inflammatory diseases include autoimmune diseases such as rheumatoid arthritis, multiple sclerosis, insulin-dependent diabetes mellitus, lupus and muscular dystrophy.

As used herein, a cell which expresses a cancer phenotype includes cells which are characteristic of cancer. Such cells may have come from animals manifesting a cancer, from animal bone, tissue or fluid manifesting a cancer, or from cancer cell lines well known in the art.

As used herein, cancer is a group of diseases characterized by the uncontrolled growth and spread of abnormal cells or one in which compounds that activate the caspase cascade have therapeutic use. Such diseases include, but are not limited to, Hodgkin's disease, non-Hodgkin's lymphomas, acute and chronic lymphocytic leukemias, multiple myeloma, neuroblastoma, breast carcinomas, ovarian carcinomas, lung carcinomas, Wilms' tumor, cervical carcinomas, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, neuroblastoma, rhabdomyosarcoma, Kaposi's sarcoma, genitourinary carcinomas, thyroid carcinomas, esophageal carcinomas, malignant hypercalcemia, cervical carcinomas, cervical hyperplasia, renal cell carcinomas, endometrial carcinomas, polycythemia vera, essential thrombocytosis, adrenal cortex carcinomas, skin cancer, and prostatic carcinomas.

As used herein an effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

As used herein, treatment means any manner in which the symptoms of a condition, disorder or disease are ameliorated or otherwise beneficially altered.

As used herein, amelioration of the symptoms of a particular disorder by administration of a particular pharmaceutical composition refers to any lessening, whether permanent or temporary, lasting or transient, that can be attributed to or associated with administration of the composition.

As used herein, $EC_{50}$ refers to a dosage, concentration or amount of a particular compound that elicits a dose-dependent response at 50% of maximal expression of a particular response that is induced, provoked or potentiated by the particular compound.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady, *Medicinal Chemistry: A Biochemical Approach*, Oxford University Press, New York, pages 388-392 (1985)). For example, succinylsulfathiazole is a prodrug of 4-amino-N-(2-thiazoyl)benzenesulfonamide(sulfathiazole) that exhibits altered transport characteristics.

Examples of prodrugs of the compounds of the invention include the simple esters of carboxylic acid containing compounds (e.g. those obtained by condensation with a $C_{1-4}$ alcohol according to methods known in the art); esters of hydroxy containing compounds (e.g. those obtained by condensation with a $C_{1-4}$ carboxylic acid, $C_{3-6}$ dioic acid or anhydride thereof (e.g. succinic and fumaric anhydrides according to methods known in the art); imines of amino containing compounds (e.g. those obtained by condensation with a $C_{1-4}$ aldehyde or ketone according to methods known in the art); and acetals and ketals of alcohol containing compounds (e.g. those obtained by condensation with chloromethyl methyl ether or chloromethyl ethyl ether according to methods known in the art).

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions, and mixtures.

Gambogic acid and GA-related compounds as used herein include those compounds represented by Formulae I-III:

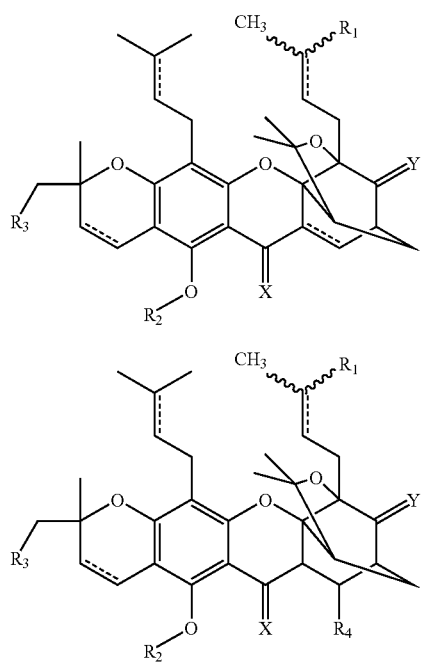

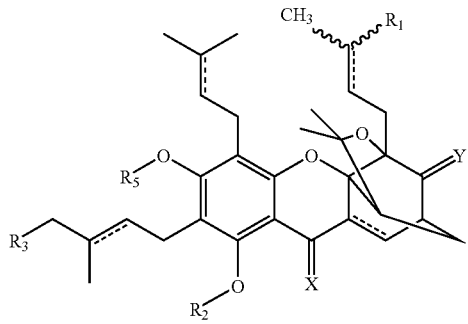

or pharmaceutically acceptable salts or prodrugs thereof, wherein:

the dotted lines are single bonds, double bonds or an epoxy group;

X together with the attached carbon is a methylene, carbonyl, hydroxymethinyl, alkoxymethinyl, aninomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is hydrogen, optionally substituted lower alkyl, optionally substituted aryl, optionally substituted lower aralkyl group or N-succinimidyl; $R_b$, and $R_c$ are independently hydrogen, optionally substituted heteroalkyl, optionally substituted lower alkyl, optionally substituted aryl, optionally substituted heteroaryl or optionally substituted lower aralkyl groups; or $R_b$, and $R_c$ may be taken together with the attached N to form an optionally substituted, saturated or partially saturated 5-7 membered heterocyclo group, including piperidine, morpholine and piperazine;

$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is hydrogen, halogen, hydroxy, optionally substituted alkyl, cycloalkyl, alkoxy, alkylthio or amino; and $R_5$ is hydrogen, optionally substituted alkyl or acyl ($R_aCO$), carbamyl ($R_bR_cNCO$) or sulfonyl ($R_dSO_2$), where $R_a$, $R_b$, $R_c$ and $R_d$ are defined above.

Gambogic acid and GA-related compounds as used herein also include such compounds having the above ring structure described in U.S. Pat. No. 6,462,041. Gambogic acid and GA-related compounds as used herein also include the following:

Methyl gambogate;
9,10-Dihydrogambogic acid;
9,10-Dihydrogambogyl(4-methylpiperazine);
9,10-Dihydrogambogyl(2-dimethylaminoethylamine);
Gambogyl diethylamine;
Gambogyl dimethylamine;
Gambogyl amine;
Gambogyl hydroxyamine;
Gambogyl piperidine;
6-Methoxy-gambogic acid;

6-(2-dimethylaminoethoxy)-gambogic acid;
6-(2-piperidinylethoxy)-gambogic acid;
6-(2-morpholinylethoxy)-gambogic acid;
6-Methoxy-gambogyl piperidine;
Gambogyl morpholine;
Gambogyl(2-dimethylaminoethylamine);
10-Morpholinyl-gambogyl morpholine;
10-Morpholinyl-gambogyl piperidine;
10-(4-methylpiperazinyl)-gambogyl piperidine;
10-(4-methylpiperazinyl)-gambogyl morpholine;
10-Piperidinyl-gambogyl piperidine;
10-(4-methylpiperazinyl)-gambogyl (4-methylpiperazine);
Gambogyl(4-methylpiperazine);
Methyl-6-Methoxy-gambogate;
Gambogenic acid;
Gambogenin;
10-Methoxy-gambogic acid;
10-Butylthio-gambogic acid;
10-(4-Methylpiperazinyl)-gambogic acid;
10-Pyrrolidinyl-gambogic acid;
Methyl-10-Morpholinyl-gambogate;
10-Piperidinyl-gambogic acid;
10-Morpholinyl-gambogic acid;
N-(2-Gambogylamidoethyl)biotinamide;
Gambogyl(2-morpholinylethylamine);
9,10-Epoxygambogic acid;
Gambogyl(4-(2-pyridyl)piperazine);
10-(4-(2-Pyridyl)piperazinyl)gambogyl (4-(2-pyridyl) piperazine);
6-Acetylgambogic acid;
10-(4-(2-Pyridyl)piperazinyl)gambogic acid;
N-Hydroxysuccinimidyl gambogate;
8-(Gambogylamido)octanoic acid;
6-(Gambogylamido)hexanoic acid;
12-(Gambogylamido)dodecanoic acid;
N-Hydroxysuccinimidyl-8-(gambogylamido)octanoate;
N-Hydroxysuccinimidyl-6-(gambogylamido)hexanoate;
N-Hydroxysuccinimidyl-12-(gambogylamido)dodecanoate;
10-Methoxy-gambogyl piperidine;
Gambogyl(4-(2-pyrimidyl)piperazine);
Gambogyl(bis(2-pyridylmethyl)amine);
Gambogyl(N-(3-pyridyl)-N-(2-hydroxybenzyl)amine);
Gambogyl(4-benzylpiperazine);
Gambogyl(4-(3,4-methylenedioxybenzyl)piperazine);
Gambogyl(N-methyl-5-(methylamino)-3-oxapentylamine);
Gambogyl(N-methyl-8-(methylamino)-3,6-dioxaoctylamine);
Gambogyl(N-ethyl-2-(ethylamino)ethylamine);
Gambogyl(4-isopropylpiperazine);
Gambogyl(4-cyclopentylpiperazine);
Gambogyl(N-(2-oxo-2-ethoxyethyl)-(2-pyridyl)methylamine);
Gambogyl(2,5-dimethylpiperazine);
Gambogyl(3,5-dimethylpiperazine);
Gambogyl(4-(4-acetylphenyl)piperazine);
Gambogyl(4-ethoxycarbonylpiperazine);
Gambogyl(4-(2-oxo-2-pyrrolidylethyl)piperazine);
Gambogyl(4-(2-hydroxyethyl)piperazine);
Gambogyl(N-methyl-2-(methylamino)ethylamine);
Gambogyl(N-methyl-2-(benzylamino)ethylamine);
Gambogyl(N-methyl-(6-methyl-2-pyridyl)methylamine);
Gambogyl(N-ethyl-2-(2-pyridyl)ethylamine);
Gambogyl(N-methyl-(2-pyridyl)methylamine);
Gambogyl(N-methyl-4-(3-pyridyl)butylamine);
Gambogyl(bis(3-pyridylmethyl)amine);
Gambogyl(2,4-dimethyl-2-imidazoline);
Gambogyl(4-methyl-homopiperazine);
Gambogyl(4-(5-hydroxy-3-oxapentyl)piperazine);
Gambogyl(3-dimethylaminopyrrolidine);
Gambogyl((2-furanyl)methylamine);
Gambogyl(2-hydroxy-1-methyl-2-phenylethylamine);
Gambogyl(3,4,5-trimethoxybenzylamine);
Gambogyl(2-(2-methoxyphenyl)ethylamine);
Gambogyl(2-methoxybenzylamine);
Gambogyl(3,4-methylenedioxybenzylamine);
Gambogyl(2-(2,5-dimethoxyphenyl)ethylamine);
Gambogyl(2-(3-methoxyphenyl)ethylamine);
Gambogyl(3-(piperidinyl)propylamine);
Gambogyl(2-(piperidinyl)ethylamine);
Gambogyl(3,4-dimethoxybenzylamine);
Gambogyl((2-tetrahydrofuranyl)methylamine);
Gambogyl((N-ethyl-2-pyrrolidinyl)methylamine);
Gambogyl(2-diethylaminoethylamine);
Gambogyl(2,2-dimethyl-3-dimethylaminopropylamine);
Gambogyl((N-ethoxycarbonyl-4-piperidinyl)amine);
Gambogyl(2-carbamylpyrrolidine);
Gambogyl(3-(homopiperidinyl)propylamine);
Gambogyl((N-benzyl-4-piperidinyl)amine);
Gambogyl(2-(4-methoxyphenyl)ethylamine);
Gambogyl(4-oxa-hex-5-enylamine);
Gambogyl(6-hydroxyhexylamine);
Gambogyl(2-(3,5-dimethoxyphenyl)ethylamine);
9,10-Dihydro-12-hydroxygambogic acid;
Gambogyl-4-morpholine;
10-Cyclohexyl-gambogic acid;
10-Methyl-gambogic acid;
Gambogyl(2-(4-morpholinyl)ethylamine);
Isogambogic acid;
Morellinol;
Morellic acid;
Desoxymorellin;
Isomorellinol;
Isomorellin;
Morellin-dimethylacetal;
Isomoreollin B;
The derivative of Isomoreollin B wherein $R_4$ of Formula II above is ethoxy (instead of methoxy, as in Isomoreollin B);
Moreollic acid(9,10-dihydro-10-methoxy-morellic acid);
Isogambogenin;
Desoxygambogenin;
Gambogenin dimethylacetal;
Gambogellic acid;
Hanburin;
Gambogin;
Morellin;
Moreollin;
Desoxyisomorellin;
Dihydroisomorellin;
Ethoxydihydroisomorellin;
Isomorellic acid;
Neo-gambogic acid;
Forbesione;
Gaudichaudiones A-H;
Gaudichaudic Acids A-E;
Methyl gambogate ester;
9,10-Dihydro-10-morpholinyl-gambogyl morpholine;
9,10-Dihydro-10-morpholinyl-gambogyl piperidine;
9,10-Dihydro-10-(4-methylpiperazinyl)-gambogyl piperidine;
9,10-Dihydro-10-(4-methylpiperazinyl)-gambogyl morpholine;

9,10-Dihydro-10-piperidinyl-gambogyl piperidine;
9,10-Dihydro-10-(4-methylpiperazinyl)-gambogyl (4-methylpiperazine);
10-Cyclohexyl-9,10-dihydrogambogic acid;
9,10-Dihydro-10-methyl gambogic acid;
9,10-Dihydro-10-methoxy-gambogic acid;
10-Butylthio-9,10-dihydrogambogic acid;
9,10-Dihydro-10-(4-methylpiperazinyl)-gambogic acid;
9,10-Dihydro-10-pyrrolidinyl-gambogic acid;
Methyl-9,10-dihyrdro-10-morpholinyl-gambogate;
9,10-Dihydro-10-piperidinyl-gambogic acid;
9,10-Dihydro-10-morpholinyl-gambogic acid;
N-(2-Gambogylamido-ethyl)biotinamide;
Gambogyl(2-(4-morpholinyl)ethylamine);
9,10-Dihydro-10-(4-(2-pyridyl)piperazinyl)gambogyl (4-(2-pyridyl)piperazine);
9,10-Dihydro-10-(4-(2-pyridyl)piperazinyl)gambogic acid;
9,10-Dihydro-10-methoxy-gambogyl piperidine;
9,10-Dihydrogambogyl (dimethylamino)ethylamine;
Gambogyl(3,5-dimethoxybenzylamine); and
Gambogyl(2-carbamyl-2-(4-hydroxyphenyl)ethylamine).

Gambogic acid (GA) and GA-related compounds also include those compounds represented by Formulae IV and V:

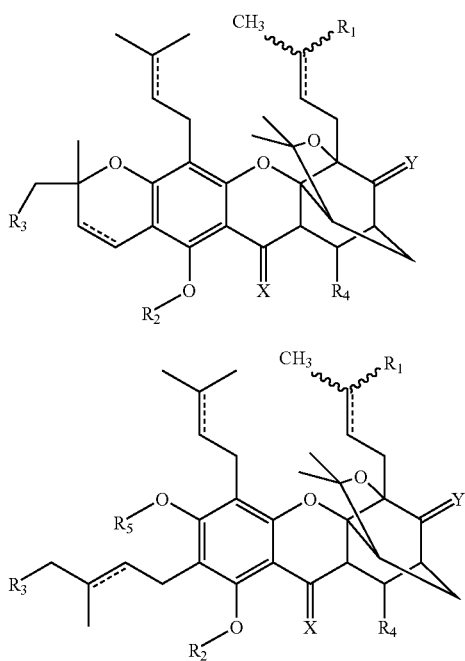

(IV)

(V)

or pharmaceutically acceptable salts or prodrugs thereof, wherein:

the dotted lines are single bonds, double bonds or an epoxy group;

X together with the attached carbon is a methylene, carbonyl, hydroxymethinyl, alkoxymethinyl, aminomethinyl, an oxime, a hydrazone, an arylhydrazone or semicarbazone;

Y together with the attached carbon is a methylene, carbonyl, hydroxymethinyl, alkoxymethinyl, aminomethinyl, an oxime, a hydrazone, an arylhydrazone or semicarbazone;

$R_1$ is formyl, methylenehydroxy, carboxy, acyl ($R_aCO$), optionally substituted alkoxycarbonyl ($R_aOCO$), optionally substituted alkylthiocarbonyl, optionally substituted aminocarbonyl (carbamyl, $R_bR_cNCO$) or hydroxyaminocarbonyl, where $R_a$ is hydrogen, optionally substituted lower alkyl, optionally substituted aryl, or optionally substituted lower aralkyl group; $R_b$ and $R_c$ are independently hydrogen, optionally substituted lower alkyl, optionally substituted aryl, or optionally substituted lower aralkyl groups; or $R_b$ and $R_c$ may be taken together with the attached N to form a heterocycle, including piperidine, morpholine and piperazine;

$R_2$ is hydrogen, optionally substituted alkyl, acyl ($R_aCO$), carbamyl ($R_bR_cNCO$) or sulfonyl ($R_dSO_2$), where $R_a$, $R_b$ and $R_c$ are defined above; $R_d$ is hydrogen, optionally substituted lower alkyl, optionally substituted aryl, or optionally substituted lower aralkyl groups;

$R_3$ is hydrogen or prenyl;

$R_4$ is hydrogen, halogen, hydroxy, optionally substituted alkyl, cycloalkyl, alkoxy, arylalkoxy, aryloxy, heteroaryloxy, alkylthio, arylalkylthio, arylthio, heteroarylthio, or amino; and $R_5$ is hydrogen, optionally substituted alkyl or acyl ($R_aCO$), carbamyl ($R_bR_cNCO$) or sulfonyl ($R_dSO_2$), where $R_a$, $R_b$, $R_c$ and $R_d$ are defined above.

GA and GA-related compounds also include, without limitation:

9,10-Dihydro-10-morpholinyl-gambogyl(N-methylpiperazine);
9,10-Dihydro-10-piperidinyl-gambogyl(N-methylpiperazine);
9,10-Dihydro-10-[2-(morpholinyl)ethylamino]-gambogyl (N-methyl-piperazine);
9,10-Dihydro-10-[4-(2-pyridyl)piperazinyl]-gambogyl (N-methyl-piperazine);
9,10-Dihydro-10-[2-(morpholinyl)ethoxy]-gambogyl(N-methyl-piperazine);
9,10-Dihydro-10-(2-dimethylaminoethoxy)-gambogyl (N-methyl-piperazine);
9,10-Dihydro-10-ethoxy-gambogyl piperidine;
9,10-Dihydro-10-morpholinyl-gambogyl(dimethylamine);
Ethyl 9,10-dihydro-10-morpholinyl-gambogate;
Methyl 9,10-dihydro-10-benzyloxy-gambogate;
Methyl 9,10-dihydro-10-(4-acetylpiperazinyl)-gambogate;
Methyl 9,10-dihydro-10-(piperidinyl)-gambogate;
9,10-Dihydro-10-[4-(2-pyridyl)piperazinyl]-gambogyl (diethylamine);
9,10-Dihydro-10-[4-(2-pyridyl)piperazinyl]-gambogyl (methylamine);
9,10-Dihydro-10-(morpholinyl)-gambogyl(diethylamine);
Methyl-9,10-dihydro-10-ethoxy-gambogate;
9,10-Dihydro-10-ethoxy-gambogic acid;
9,10-Dihydro-10-ethoxy-gambogyl(diethylamine);
Ethyl 9,10-dihydro-10-ethoxy-gambogate;
Methyl 9,10-dihydro-10-(4-methylpiperazinyl)-gambogate;
Ethyl 9,10-dihydro-10-(piperidinyl)-gambogate;
Ethyl 9,10-dihydro-10-(4-methylpiperazinyl)-gambogate; and
Ethyl 9,10-dihydro-10-(4-acetylpiperazinyl)-gambogate.

The positions in gambogic acid and GA-related compounds described herein are numbered according to Asano, J., et al., *Phytochemistry* 41:815-820 (1996), and Lin, L.-J., et al., *Magn. Reson. Chem.* 31:340-347 (1993). The tricyclic ring (shown as part of the ring on the far right of formulae I-V above) is essential for the TfR binding activity of GA. The α,β unsaturated ketone (found in the two rings furthest to the right of formulae I-V above) is also essential for the TfR binding activity of GA.

As used herein in the context of polypeptides, "mutants" include TRRAIPs given by SEQ ID NO: 1 or 4 having one or more amino acid substitutions. Mutants include naturally occurring or artificially generated TRRAIPs. Naturally occurring mutants include TRRAIPs which are encoded by allelic variation in the TRRAIP gene. As used herein in the context of polypeptides, "mutants" also include CHCRAIPs given by SEQ ID NO: 34 having one or more amino acid substitutions. Mutants include naturally occurring or artificially generated CHCRAIPs. Naturally occurring mutants include CHCRAIPs which are encoded by allelic variation in the CHCRAIP gene. As used herein in the context of polypeptides, "mutants" also include IQGAPRAIPs given by SEQ ID NO: 36 having one or more amino acid substitutions. Mutants include naturally occurring or artificially generated IQGAPRAIPs. Naturally occurring mutants include IQGAPRAIPs which are encoded by allelic variation in the IQGAPRAIP gene. As used herein in the context of polypeptides, "mutants" also include HSPRAIPs given by SEQ ID NO: 38 having one or more amino acid substitutions. Mutants include naturally occurring or artificially generated HSPRAIPs. Naturally occurring mutants include HSPRAIPs which are encoded by allelic variation in the HSPRAIP gene.

As used herein in the context of polypeptides, "homologs" include TRRAIP sequences that are 70% or more homologous to SEQ ID NO: 1 or 4, as measured by the percent identity of the homolog's primary amino acid sequence to that of SEQ ID NO: 1 or 4. For example, a homolog that is only 700 amino acids long is 60 amino acids shorter than SEQ ID NO: 1.

However, if 650 amino acids of this homolog have an identical sequential arrangement with respect to SEQ ID NO: 1, then the homolog is about 93% identical ((650/700)× 100%) to SEQ ID NO: 1. Preferably, homologs are 90%, 91%, 92%, 93%, 94%, 95%, 96%, 97%, 98%, 99% or more homologous to SEQ ID NO: 1 or 4.

As used herein in the context of polypeptides, "homologs" also include CHCRAIP sequences that are 70% or more homologous to SEQ ID NO: 34, as measured by the percent identity of the homolog's primary amino acid sequence to that of SEQ ID NO: 34. For example, a homolog that is only 1000 amino acids long is 675 amino acids shorter than SEQ ID NO: 34.

However, if 900 amino acids of this homolog have an identical sequential arrangement with respect to SEQ ID NO: 34, then the homolog is 90% identical ((900/1000)×100%) to SEQ ID NO: 34. Preferably, homologs are 90%, 91%, 92%, 93%, 94%, 95%, 96%, 97%, 98%, 99% or more homologous to SEQ ID NO: 34.

As used herein in the context of polypeptides, "homologs" also include IQGAPRAIP sequences that are 70% or more homologous to SEQ ID NO: 36, as measured by the percent identity of the homolog's primary amino acid sequence to that of SEQ ID NO: 36. For example, a homolog that is only 1000 amino acids long is 657 amino acids shorter than SEQ ID NO: 36. However, if 900 amino acids of this homolog have an identical sequential arrangement with respect to SEQ ID NO: 36, then the homolog is 90% identical ((900/1000) x 100%) to SEQ ID NO: 36. Preferably, homologs are 90%, 91%, 92%, 93%, 94%, 95%, 96%, 97%, 98%, 99% or more homologous to SEQ ID NO: 36.

As used herein in the context of polypeptides, "homologs" also include HSPRAIP sequences that are 70% or more homologous to SEQ ID NO: 38, as measured by the percent identity of the homolog's primary amino acid sequence to that of SEQ ID NO: 38. For example, a homolog that is only 600 amino acids long is 124 amino acids shorter than SEQ ID NO: 38. However, if 540 amino acids of this homolog have an identical sequential arrangement with respect to SEQ ID NO: 38, then the homolog is 90% identical ((540/600)×100%) to SEQ ID NO:38. Preferably, homologs are 90%, 91%, 92%, 93%, 94%, 95%, 96%, 97%, 98%, 99% or more homologous to SEQ ID NO: 38.

As used herein in the context of polypeptides, "derivatives" refer to TRRAIPs, CHCRAIPs, IQGAPRAIPs and HSPRAIPs that are respectively derivatized or modified forms of SEQ ID NO: 1 or 4, 34, 36 or 38. Such derivatives may include, for example, post-expression modifications, amidated carboxyl groups, glycosylated amino acid residues, and formylated and acetylated amino groups. Such derivatives may also include TRRAIP, CHCRAIP, IQGAPRATP or HSPRAIP having a leader or secretory sequence, such as a pre-, pro- or prepro-protein sequence; or TRRAIP, CHCRAIP, IQGAPRAIP or HSPRAIP fused to amino acids or other proteins, such as those which provide additional functionalities.

As used herein in the context of polypeptides, "fragments" refer to any oligopeptide or polypeptide which is less than the full length of SEQ ID NO: 1, 4, 34, 36 or 38. Fragments may be 70% or more identical to SEQ ID NO: 1, 4, 34, 36 or 38. Preferably, fragments are 90%, 91%, 92%, 93%, 94%, 95%, 96%, 97%, 98%, 99% or more identical to SEQ ID NO: 1, 4, 34, 36 or 38. Fragments may be 20, 25, 30, 40, 50, 60, 70, 80, 90, 100, 120, 140, 160, 180, 200, 300, 400, 500, 600, 700 or more contiguous amino acids of SEQ ID NO: 1, 4 or 38. Fragments may also be 20, 25, 30, 40, 50, 60, 70, 80, 90, 100, 120, 140, 160, 180, 200, 300, 400, 500, 600, 700, 800, 900, 1000, 1100, 1200, 1300, 1400, 1500, 1600 or more contiguous amino acids of SEQ ID NO: 34 or 36.

Fragments which are 20 amino acids long (referred to as "20-mers") include amino acids 1-20, 2-21, 3-22, 4-23, 5-24, 6-25, 7-26, 8-27, 9-28, 10-29, 11-30, 12-31, 13-32, 14-33, 15-34, 16-35, 17-36, 18-37, 19-38, 20-39, 21-40, 22-41, 23-42, 24-43, 25-44, 26-45, 27-46, 28-47, 29-48, 30-49, 31-50, 32-51, 33-52, 34-53, 35-54, 36-55, 37-56, 38-57, 39-58, 40-59, 41-60, 42-61, 43-62, 44-63, 45-64, 46-65, 47-66, 48-67, 49-68, 50-69, 51-70, 52-71, 53-72, 54-73, 55-74, 56-75, 57-76, 58-77, 59-78, 60-79, 61-80, 62-81, 63-82, 64-83, 65-84, 66-85, 67-86, 68-87, 69-88, 70-89, 71-90, 72-91, 73-92, 74-93, 75-94, 76-95, 77-96, 78-97, 79-98, 80-99, 81-100, 82-101, 83-102, 84-103, 85-104, 86-105, 87-106, 88-107, 89-108, 90-109, 91-110, 92-111, 93-112, 94-113, 95-114, 96-115, 97-116, 98-117, 99-118, 100-119, 101-120, 102-121, 103-122, 104-123, 105-124, 106-125, 107-126, 108-127, 109-128, 110-129, 111-130, 112-131, 113-132, 114-133, 115-134, 116-135, 117-136, 118-137, 119-138, 120-139, 121-140, 122-141, 123-142, 124-143, 125-144, 126-145, 127-146, 128-147, 129-148, 130-149, 131-150, 132-151, 133-152, 134-153, 135-154, 136-155, 137-156, 138-157, 139-158, 140-159, 141-160, 142-161, 143-162, 144-163, 145-164, 146-165, 147-166, 148-167, 149-168, 150-169, 151-170, 152-171, 153-172, 154-173, 155-174, 156-175, 157-176, 158-177, 159-178, 160-179, 161-180, 162-181, 163-182, 164-183, 165-184, 166-185, 167-186, 168-187, 169-188, 170-189, 171-190, 172-191, 173-192, 174-193, 175-194, 176-195, 177-196, 178-197, 179-198, 180-199, 181-200, 182-201, 183-202, 184-203, 185-204, 186-205, 187-206, 188-207, 189-208, 190-209, 191-210, 192-211, 193-212, 194-213, 195-214, 196-215, 197-216, 198-217, 199-218, 200-219, 201-220, 202-221, 203-222, 204-223, 205-224, 206-225, 207-226, 208-227, 209-228, 210-229, 211-230, 212-231, 213-232, 214-233, 215-234, 216-235, 217-236, 218-237, 219-238, 220-239, 221-240, 222-241, 223-242, 224-243, 225-244, 226-245, 227-246, 228-247, 229-248, 230-249, 231-250, 232-251, 233-252, 234-253, 235-254, 236-255, 237-256, 238-257, 239-258, 240-259, 241-260, 242-261, 243-262, 244-263, 245-264, 246-265, 247-266, 248-267, 249-268, 250-269, 251-270, 252-271, 253-272, 254-273, 255-274, 256-275, 257-276, 258-277, 259-278, 260-279, 261-280, 262-281, 263-282, 264-283, 265-284, 266-285, 267-286, 268-287, 269-288, 270-289, 271-290, 272-291, 273-292, 274-293, 275-294, 276-295, 277-296, 278-297, 279-298, 280-299, 281-300, 282-301, 283-302, 284-303, 285-304, 286-305, 287-306, 288-307, 289-308, 290-309, 291-310, 292-311, 293-312, 294-313, 295-314, 296-315, 297-316, 298-317, 299-318, 300-319, 301-320, 302-321, 303-322, 304-323, 305-324, 306-325, 307-326, 308-327, 309-328, 310-329, 311-330, 312-331, 313-332, 314-333, 315-334, 316-335, 317-336, 318-337, 319-338, 320-339, 321-340, 322-341, 323-342, 324-343, 325-344, 326-345, 327-346, 328-347, 329-348, 330-349, 331-350, 332-351, 333-352, 334-353, 335-354, 336-355, 337-356, 338-357, 339-358, 340-359, 341-360, 342-361, 343-362, 344-363, 345-364, 346-365, 347-366, 348-367, 349-368, 350-369, 351-370, 352-371, 353-372, 354-373, 355-374, 356-375, 357-376, 358-377, 359-378, 360-379, 361-380, 362-381, 363-382, 364-383, 365-384, 366-385, 367-386, 368-387, 369-388, 370-389, 371-390, 372-391, 373-392, 374-393, 375-394, 376-395, 377-396, 378-397, 379-398, 380-399, 381-400, 382-401, 383-402, 384-403, 385-404, 386-405, 387-406, 388-407, 389-408, 390-409, 391-410, 392-411, 393-412, 394-413, 395-414, 396-415, 397-416, 398-417, 399-418, 400-419, 401-420, 402-421, 403-422, 404-423, 405-424, 406-425, 407-426, 408-427, 409-428, 410-429, 411-430, 412-431, 413-432, 414-433, 415-434, 416-435, 417-436, 418-437, 419-438, 420-439, 421-440, 422-441, 423-442, 424-443, 425-444, 426-445, 427-446, 428-447, 429-448, 430-449, 431-450, 432-451, 433-452, 434-453, 435-454, 436-455, 437-456, 438-457, 439-458, 440-459, 441-460, 442-461, 443-462, 444-463, 445-464, 446-465, 447-466, 448-467, 449-468, 450-469, 451-470, 452-471, 453-472, 454-473, 455-474, 456-475, 457-476, 458-477, 459-478, 460-479, 461-480, 462-481, 463-482, 464-483, 465-484, 466-485, 467-486, 468-487, 469-488, 470-489, 471-490, 472-491, 473-492, 474-493, 475-494, 476-495, 477-496, 478-497, 479-498, 480-499, 481-500, 482-501, 483-502, 484-503, 485-504, 486-505, 487-506, 488-507, 489-508, 490-509, 491-510, 492-511, 493-512, 494-513, 495-514, 496-515, 497-516, 498-517, 499-518, 500-519, 501-520, 502-521, 503-522, 504-523, 505-524, 506-525, 507-526, 508-527, 509-528, 510-529, 511-530, 512-531, 513-532, 514-533, 515-534, 516-535, 517-536, 518-537, 519-538, 520-539, 521-540, 522-541, 523-542, 524-543, 525-544, 526-545, 527-546, 528-547, 529-548, 530-549, 531-550, 532-551, 533-552, 534-553, 535-554, 536-555, 537-556, 538-557, 539-558, 540-559, 541-560, 542-561, 543-562, 544-563, 545-564, 546-565, 547-566, 548-567, 549-568, 550-569, 551-570, 552-571, 553-572, 554-573, 555-574, 556-575, 557-576, 558-577, 559-578, 560-579, 561-580, 562-581, 563-582, 564-583, 565-584, 566-585, 567-586, 568-587, 569-588, 570-589, 571-590, 572-591, 573-592, 574-593, 575-594, 576-595, 577-596, 578-597, 579-598, 580-599, 581-600, 582-601, 583-602, 584-603, 585-604, 586-605, 587-606, 588-607, 589-608, 590-609, 591-610, 592-611, 593-612, 594-613, 595-614, 596-615, 597-616, 598-617, 599-618, 600-619, 601-620, 602-621, 603-622, 604-623, 605-624, 606-625, 607-626, 608-627, 609-628, 610-629, 611-630, 612-631, 613-632, 614-633, 615-634, 616-635, 617-636, 618-637, 619-638, 620-639, 621-640, 622-641, 623-642, 624-643, 625-644, 626-645, 627-646, 628-647, 629-648, 630-649, 631-650, 632-651, 633-652, 634-653, 635-654, 636-655, 637-656, 638-657, 639-658, 640-659, 641-660, 642-661, 643-662, 644-663, 645-664, 646-665, 647-666, 648-667, 649-668, 650-669, 651-670, 652-671, 653-672, 654-673, 655-674, 656-675, 657-676, 658-677, 659-678, 660-679, 661-680, 662-681, 663-682, 664-683, 665-684, 666-685, 667-686, 668-687, 669-688, 670-689, 671-690, 672-691, 673-692, 674-693, 675-694, 676-695, 677-696, 678-697, 679-698, 680-699, 681-700, 682-701, 683-702, 684-703, 685-704, 686-705, 687-706, 688-707, 689-708, 690-709, 691-710, 692-711, 693-712, 694-713, 695-714, 696-715, 697-716, 698-717, 699-718, 700-719, 701-720, 702-721, 703-722, 704-723, 705-724, 706-725, 707-726, 708-727, 709-728, 710-729, 711-730, 712-731, 713-732, 714-733, 715-734, 716-735, 717-736, 718-737, 719-738, 720-739, 721-740, 722-741, 723-742, 724-743, 725-744, 726-745, 727-746, 728-747, 729-748, 730-749, 731-750, 732-751, 733-752, 734-753, 735-754, 736-755, 737-756, 738-757, 739-758, 740-759, 741-760, 742-761, 743-762, 744-763, 745-764, 746-765, 747-766, 748-767, 749-768, 750-769, 751-770, 752-771, 753-772, 754-773, 755-774, 756-775, 757-776, 758-777, 759-778, 760-779, 761-780, 762-781, 763-782, 764-783, 765-784, 766-785, 767-786, 768-787, 769-788, 770-789, 771-790, 772-791, 773-792, 774-793, 775-794, 776-795, 777-796, 778-797, 779-798, 780-799, 781-800, 782-801, 783-802, 784-803, 785-804, 786-805, 787-806, 788-807, 789-808, 790-809, 791-810, 792-811, 793-812, 794-813, 795-814, 796-815, 797-816, 798-817, 799-818, 800-819, 801-820, 802-821, 803-822, 804-823, 805-824, 806-825, 807-826, 808-827, 809-828, 810-829, 811-830, 812-831, 813-832, 814-833, 815-834, 816-835, 817-836, 818-837, 819-838, 820-839, 821-840, 822-841, 823-842, 824-843, 825-844, 826-845, 827-846, 828-847, 829-848, 830-849, 831-850, 832-851, 833-852, 834-853, 835-854, 836-855, 837-856, 838-857, 839-858, 840-859, 841-860, 842-861, 843-862, 844-863, 845-864, 846-865, 847-866, 848-867, 849-868, 850-869, 851-870, 852-871, 853-872, 854-873, 855-874, 856-875, 857-876, 858-877, 859-878, 860-879, 861-880, 862-881, 863-882, 864-883, 865-884, 866-885, 867-886, 868-887, 869-888, 870-889, 871-890, 872-891, 873-892, 874-893, 875-894, 876-895, 877-896, 878-897, 879-898, 880-899, 881-900, 882-901, 883-902, 884-903, 885-904, 886-905, 887-906, 888-907, 889-908, 890-909, 891-910, 892-911, 893-912, 894-913, 895-914, 896-915, 897-916, 898-917, 899-918, 900-919, 901-920, 902-921, 903-922, 904-923, 905-924, 906-925, 907-926, 908-927, 909-928, 910-929, 911-930, 912-931, 913-932, 914-933, 915-934, 916-935, 917-936, 918-937, 919-938, 920-939, 921-940, 922-941, 923-942, 924-943, 925-944, 926-945, 927-946, 928-947, 929-948, 930-949, 931-950, 932-951, 933-952, 934-953, 935-954, 936-955, 937-956, 938-957, 939-958, 940-959, 941-960, 942-961, 943-962, 944-963, 945-964, 946-965, 947-966, 948-967, 949-968, 950-969, 951-970, 952-971, 953-972, 954-973, 955-974, 956-975, 957-976, 958-977, 959-978, 960-979, 961-980, 962-981, 963-982, 964-983, 965-984, 966-985, 967-986, 968-987, 969-988, 970-989, 971-990, 972-991, 973-992, 974-993, 975-994, 976-995, 977-996, 978-997, 979-998, 980-999, 981-1000, 982-1001, 983-1002, 984-1003, 985-1004, 986-1005, 987-1006, 988-1007, 989-1008, 990-1009, 991-1010, 992-1011, 993-1012, 994-1013, 995-1014, 996-1015, 997-1016, 998-1017, 999-1018, 1000-1019, 1001-1020, 1002-1021, 1003-1022, 1004-1023, 1005-1024, 1006-1025, 1007-1026, 1008-

1027, 1009-1028, 1010-1029, 1011-1030, 1012-1031, 1013-1032, 1014-1033, 1015-1034, 1016-1035, 1017-1036, 1018-1037, 1019-1038, 1020-1039, 1021-1040, 1022-1041, 1023-1042, 1024-1043, 1025-1044, 1026-1045, 1027-1046, 1028-1047, 1029-1048, 1030-1049, 1031-1050, 1032-1051, 1033-1052, 1034-1053, 1035-1054, 1036-1055, 1037-1056, 1038-1057, 1039-1058, 1040-1059, 1041-1060, 1042-1061, 1043-1062, 1044-1063, 1045-1064, 1046-1065, 1047-1066, 1048-1067, 1049-1068, 1050-1069, 1051-1070, 1052-1071, 1053-1072, 1054-1073, 1055-1074, 1056-1075, 1057-1076, 1158-1077, 1059-1078, 1060-1079, 1061-1080, 1062-1081, 1063-1082, 1064-1083, 1065-1084, 1066-1085, 1067-1086, 1068-1087, 1069-1088, 1070-1089, 1071-1090, 1072-1091, 1073-1092, 1074-1093, 1075-1094, 1076-1095, 1077-1096, 1078-1097, 1079-1098, 1080-1099, 1081-1100, 1082-1101, 1083-1102, 1084-1103, 1085-1104, 1086-1105, 1087-1106, 1088-1107, 1089-1108, 1090-1109, 1091-1110, 1092-1111, 1093-1112, 1094-1113, 1095-1114, 1096-1115, 1097-1116, 1098-1117, 1099-1118, 1100-1119, 1101-1120, 1102-1121, 1103-1122, 1104-1123, 1105-1124, 1106-1125, 1107-1126, 1108-1127,1109-1128, 1110-1129,1111-1130, 1112-1131,1113-1132, 1114-1133,1115-1134, 1116-1135,1117-1136, 1118-1137,1119-1138, 1120-1139, 1121-1140, 1122-1141, 1123-1142, 1124-1143, 1125-1144, 1126-1145, 1127-1146, 1128-1147, 1129-1148, 1130-1149, 1131-1150, 1132-1151, 1133-1152, 1134-1153, 1135-1154, 1136-1155, 1137-1156, 1138-1157, 1139-1158, 1140-1159, 1141-1160, 1142-1161, 1143-1162, 1144-1163, 1145-1164, 1146-1165, 1147-1166, 1148-1167, 1149-1168, 1150-1169, 1151-1170, 1152-1171, 1153-1172, 1154-1173, 1155-1174, 1156-1175, 1157-1176, 1158-1177, 1159-1178, 1160-1179, 1161-1180, 1162-1181, 1163-1182, 1164-1183, 1165-1184, 1166-1185, 1167-1186, 1168-1187, 1169-1188, 1170-1189, 1171-1190, 1172-1191, 1173-1192, 1174-1193, 1175-1194, 1176-1195, 1177-1196, 1178-1197, 1179-1198, 1180-1199, 1181-1200, 1182-1201, 1183-1202, 1184-1203, 1185-1204, 1186-1205, 1187-1206, 1188-1207, 1189-1208, 1190-1209, 1191-1210, 1192-1211, 1193-1212, 1194-1213, 1195-1214, 1196-1215, 1197-1216, 1198-1217, 1199-1218, 1200-1219, 1201-1220, 1202-1221, 1203-1222, 1204-1223, 1205-1224, 1206-1225, 1207-1226, 1208-1227, 1209-1228, 1210-1229, 1211-1230, 1212-1231, 1213-1232, 1214-1233, 1215-1234, 1216-1235, 1217-1236, 1218-1237, 1219-1238, 1220-1239, 1221-1240, 1222-1241, 1223-1242, 1224-1243, 1225-1244, 1226-1245, 1227-1246, 1228-1247, 1229-1248, 1230-1249, 1231-1250, 1232-1251, 1233-1252, 1234-1253, 1235-1254, 1236-1255, 1237-1256, 1238-1257, 1239-1258, 1240-1259, 1241-1260, 1242-1261, 1243-1262, 1244-1263, 1245-1264, 1246-1265, 1247-1266, 1248-1267, 1249-1268, 1250-1269, 1251-1270, 1252-1271, 1253-1272, 1254-1273, 1255-1274, 1256-1275, 1257-1276, 1258-1277, 1259-1278, 1260-1279, 1261-1280, 1262-1281, 1263-1282, 1264-1283, 1265-1284, 1266-1285, 1267-1286, 1268-1287, 1269-1288, 1270-1289, 1271-1290, 1272-1291, 1273-1292, 1274-1293, 1275-1294, 1276-1295, 1277-1296, 1278-1297, 1279-1298, 1280-1299, 1281-1300, 1282-1301, 1283-1302, 1284-1303, 1285-1304, 1286-1305, 1287-1306, 1288-1307, 1289-1308, 1290-1309, 1291-1310, 1292-1311, 1293-1312, 1294-1313, 1295-1314, 1296-1315, 1297-1316, 1298-1317, 1299-1318, 1300-1319, 1301-1320, 1302-1321, 1303-1322, 1304-1323, 1305-1324, 1306-1325, 1307-1326, 1308-1327, 1309-1328, 1310-1329, 1311-1330, 1312-1331, 1313-1332, 1314-1333, 1315-1334, 1316-1335, 1317-1336, 1318-1337, 1319-1338, 1320-1339, 1321-1340, 1322-1341, 1323-1342, 1324-1343, 1325-1344, 1326-1345, 1327-1346, 1328-1347, 1329-1348, 1330-1349, 1331-1350, 1332-1351, 1333-1352, 1334-1353, 1335-1354, 1336-1355, 1337-1356, 1338-1357, 1339-1358, 1340-1359, 1341-1360, 1342-1361, 1343-1362, 1344-1363, 1345-1364, 1346-1365, 1347-1366, 1348-1367, 1349-1368, 1350-1369, 1351-1370, 1352-1371, 1353-1372, 1354-1373, 1355-1374, 1356-1375, 1357-1376, 1358-1377, 1359-1378, 1360-1379, 1361-1380, 1362-1381, 1363-1382, 1364-1383, 1365-1384, 1366-1385, 1367-1386, 1368-1387, 1369-1388, 1370-1389, 1371-1390, 1372-1391, 1373-1392, 1374-1393, 1375-1394, 1376-1395, 1377-1396, 1378-1397, 1379-1398, 1380-1399, 1381-1400, 1382-1401, 1383-1402, 1384-1403, 1385-1404, 1386-1405, 1387-1406, 1388-1407, 1389-1408, 1390-1409, 1391-1410, 1392-1411, 1393-1412, 1394-1413, 1395-1414, 1396-1415, 1397-1416, 1398-1417, 1399-1418, 1400-1419, 1401-1420, 1402-1421, 1403-1422, 1404-1423, 1405-1424, 1406-1425, 1407-1426, 1408-1427, 1409-1428, 1410-1429, 1411-1430, 1412-1431, 1413-1432, 1414-1433, 1415-1434, 1416-1435, 1417-1436, 1418-1437, 1419-1438, 1420-1439, 1421-1440, 1422-1441, 1423-1442, 1424-1443, 1425-1444, 1426-1445, 1427-1446, 1428-1447, 1429-1448, 1430-1449, 1431-1450, 1432-1451, 1433-1452, 1434-1453, 1435-1454, 1436-1455, 1437-1456, 1438-1457, 1439-1458, 1440-1459, 1441-1460, 1442-1461, 1443-1462, 1444-1463, 1445-1464, 1446-1465, 1447-1466, 1448-1467, 1449-1468, 1450-1469, 1451-1470, 1452-1471, 1453-1472, 1454-1473, 1455-1474, 1456-1475, 1457-1476, 1458-1477, 1459-1478, 1460-1479, 1461-1480, 1462-1481, 1463-1482, 1464-1483, 1465-1484, 1466-1485, 1467-1486, 1468-1487, 1469-1488, 1470-1489, 1471-1490, 1472-1491, 1473-1492, 1474-1493, 1475-1494, 1476-1495, 1477-1496, 1478-1497, 1479-1498, 1480-1499, 1481-1500, 1482-1501, 1483-1502, 1484-1503, 1485-1504, 1486-1505, 1487-1506, 1488-1507, 1489-1508, 1490-1509, 1491-1510, 1492-1511, 1493-1512, 1494-1513, 1495-1514, 1496-1515, 1497-1516, 1498-1517, 1499-1518, 1500-1519, 1501-1520, 1502-1521, 1503-1522, 1504-1523, 1505-1524, 1506-1525, 1507-1526, 1508-1527, 1509-1528, 1510-1529, 151-1530, 1512-1531, 1513-1532, 1514-1533, 1515-1534, 1516-1535, 1517-1536, 1518-1537, 1519-1538, 1520-1539, 1521-1540, 1522-1541, 1523-1542, 1524-1543, 1525-1544, 1526-1545, 1527-1546, 1528-1547, 1529-1548, 1530-1549, 1531-1550, 1532-1551, 1533-1552, 1534-1553, 1535-1554, 1536-1555, 1537-1556, 1538-1557, 1539-1558, 1540-1559, 1541-1560, 1542-1561, 1543-1562, 1544-1563, 1545-1564, 1546-1565, 1547-1566, 1548-1567, 1549-1568, 1550-1569, 1551-1570, 1552-1571, 1553-1572, 1554-1573, 1555-1574, 1556-1575, 1557-1576, 1558-1577, 1559-1578, 1560-1579, 1561-1580, 1562-1581, 1563-1582, 1564-1583, 1565-1584, 1566-1585, 1567-1586, 1568-1587, 1569-1588, 1570-1589, 1571-1590, 1572-1591, 1573-1592, 1574-1593, 1575-1594, 1576-1595, 1577-1596, 1578-1597, 1579-1598, 1580-1599, 1581-1600, 1582-1601, 1583-1602, 1584-1603, 1585-1604, 1586-1605, 1587-1606, 1588-1607, 1589-1608, 1590-1609, 1591-1610, 1592-1611, 1593-1612, 1594-1613, 1595-1614, 1596-1615, 1597-1616, 1598-1617, 1599-1618, 1600-1619, 1601-1620, 1602-1621, 1603-1622, 1604-1623, 1605-1624, 1606-1625, 1607-1626, 1608-1627, 1609-1628, 1610-1629, 1611-1630, 1612-1631, 1613-1632, 1614-1633, 1615-1634, 1616-1635, 1617-1636, 1618-1637, 1619-1638, 1620-1639, 1621-1640, 1622-1641, 1623-1642, 1624-1643, 1625-1644, 1626-1645, 1627-1646, 1628-1647, 1629-1648, 1630-1649, 1631-1650, 1632-1651, 1633-1652, 1634-1653, 1635-1654, 1636-1655, 1637-1656, 1638-1657, 1639-1658, 1640-1659, 1641-1660, 1642-1661, 1643-1662, 1644-1663, 1645-1664, 1646-1665, 1647-1666, 1648-1667, 1649-1668, 1650-1669, 1651-1670, 1652-1671, 1653-1672, 1654-1673, 1655-1674, 1656-1675 of one of the corresponding SEQ ID NOs: 1, 4, 34, 36 or 38. Fragments also include any combination of two or more overlapping or adjacent 20-mers in any one of SEQ ID NOs: 1, 4, 34, 36 or 38 of the above list of 20-mers. For example, a combination of amino acids 643-662 of SEQ ID NO: 1 and amino acids 655-674 of SEQ ID NO: 1 provides a fragment that is 32 amino acids long (a 32-mer) composed of amino acids 643-674 of SEQ ID NO: 1.

As used herein, "nucleotides" and "polynucleotides" are used interchangeably and refer to single or double stranded polynucleic acid molecules composed of DNA or RNA. The term "nucleotides" includes any polynucleic acid molecule that encodes for SEQ ID NOs: 1, 4, 34, 36 or 38, their mutants, homologs, derivatives and fragments which affect apoptosis upon binding gambogic acid (GA) or GA-related compounds such as those described herein or in U.S. Pat. No. 6,462,041. The term "nucleotides" also includes any polynucleic acid molecule which hybridize to a nucleotide which encodes for any one of SEQ ID NOs: 1, 4, 34, 36 or 38, their mutants, homologs, derivatives and fragments which affect apoptosis upon binding gambogic acid (GA) or GA-related compounds such as those described herein or in U.S. Pat. No. 6,462,041. Nucleotides encoding for TRRAIPs, CHCRAIPs, IQGAPRAIPs or HSPRAIPs include the respective coding sequence for the TRRAIP, CHCRAIP, IQGAPRAIP or HSPRAIP polypeptides and optionally additional sequences.

The term "nucleotides" also includes variants. "Variants" refer to one of several alternate forms of a gene occupying a given locus on a chromosome of an organism. Genes II, Lewin, B., ed., John Wiley & Sons, New York (1985). "Variants" also includes non-naturally occurring variants produced using art-known mutagenesis techniques. Variants include those produced by nucleotide substitutions, deletions or additions which may involve one or more nucleotides. The variants may be altered in regions coding for TRRAIP, CHCRAIP, IQGAPRAIP or HSPRAIP, and/or other regions. Alterations in the coding regions may produce conservative or non-conservative amino acid substitutions, deletions or additions. Silent substitutions, additions and deletions which do not alter the properties and activities of the TRRAIP, CHCRAIP, IQGAPRAIP or HSPRAIP, or portions thereof, and conservative substitutions may also be used.

The term "nucleotides" also includes splice variants. "Splice variants" refer to a transcribed RNA in which one or more DNA introns are removed. Hence, the skilled artisan will recognize that any of the nucleotides described herein may have a splice variant. AIPs also include polypeptides encoded by these splice variants.

Nucleotides encoding for AIPs may include, but are not limited to, those encoding the amino acid sequence of the AIPs described herein by themselves. Nucleotides encoding for AIPs also include those encoding an AIP and additional nucleotide sequences. "Additional nucleotide sequences" may include, but are not limited to i) nucleic acid sequences which encode an amino acid leader or secretory sequence, such as a pre-, pro- or prepro-protein sequence; ii) non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; and iii) an additional coding sequence which codes for additional amino acids, such as those which provide additional functionalities. Thus, the nucleotide sequence encoding the AIP may be fused to a marker sequence, such as a sequence encoding a peptide which facilitates purification of the fused polypeptide. In other embodiments of this aspect of the invention, the marker amino acid sequence is a hexa-histidine peptide, such as the tag provided in a pQE vector (Qiagen, Inc.), among others, many of which are commercially available. As described in Gentz et al, Proc. Natl. Acad. Sci. USA 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al, Cell 37:767-778 (1984).

Nucleotides which encode for an AIP may also comprise polynucleotides which hybridize under stringent hybridization conditions to a portion of the polynucleotides described herein, as described in U.S. Pat. No. 6,027,916. By a polynucleotide which hybridizes to a "portion" of a polynucleotide is intended a polynucleotide (either DNA or RNA) hybridizing to at least about 15, 20, 30, 40, 50, 60 or 70 nucleotides (nt) of the reference polynucleotide. These are useful as diagnostic probes and primers.

Nucleotides are at least 90%, 91%, 92%, 93%, 94%, 95%, 96%, 97%, 98%, 99% or more identical to the sequences described herein. By a polynucleotide having a nucleotide sequence at least, for example, 95% "identical" to a reference nucleotide sequence encoding an AIP, is intended that the nucleotide sequence of the polynucleotide is identical to the reference sequence except that the polynucleotide sequence may include up to five point mutations per each 100 nucleotides of the reference nucleotide sequence encoding the AIP. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 91%, 92%, 93%, 94%, 95%, 96%, 97%, 98%, 99% or more identical to a nucleotide sequences described herein can be determined conventionally using known computer programs such as the Bestfit program. Wisconsin Sequence Analysis Package, Version 8 for Unix, Genetics Computer Group, University Research Park, 575 Science Drive, Madison, Wis. 53711. Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

Of course, due to the degeneracy of the genetic code, one of ordinary skill in the art will immediately recognize that a large number of the nucleic acid molecules having a sequence at least 90%, 91%, 92%, 93%, 94%, 95%, 96%, 97%, 98%, 99% or more identical to the nucleic acid sequences described herein will encode an AIP. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode AIPs. This is because the skilled artisan is fully aware of amino acid substitutions that are either less likely or not likely to significantly effect protein function For example, replacing one aliphatic amino acid with a second aliphatic amino acid is not likely to alter AIP function. Guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

As used herein, a cell which "up regulates" an AIP is a cell with an elevated level of AIP as compared to normal cells or cells which down regulate AIP. The manner by which a cell up regulates AIP is described below and includes, for example, an altered AIP gene or AIP promoter, or a transfection vector that encodes AIP. As used herein, a cell which "down regulates" AIP is a cell with a reduced level of AIP as compared to normal cells or as compared to cells which up regulate AIP. The manner by which a cell down regulates AIP is described below and includes, for example, an altered AIP gene or AIP promoter, antisense mRNA, or RNAi. As used. herein, a "normal" cell neither up regulates or down regulates AIP. Hence, a normal cell does not have an altered AIP gene or AIP promoter, a transfection vector encoding AIP, antisense mRNA or RNAi. Elevated levels of AIP include increased levels of functional AIP. Reduced levels of AIP includes reduced levels of expressed or reduced levels of functional Alp. Normal cells have less functional AIP than cells which up regulate AIP; and more functional AIP than cells which down regulate AIP.

As used herein, a subinducing amount of a substance is an amount that is sufficient to produce a measurable change in caspase cascade activity when used in the method of the present invention and which produces a greater measurable change in caspase cascade activity when used in synergistic combination with an AIP binding compound in the method of the present invention.

"Label" is used herein to refer to any atom or molecule that is detectable and can be attached to a protein or test compound of interest. Examples of labels include, but are not limited to, radiolabels, fluorescent labels, phosphorescent labels, chemiluminescent labels and magnetic labels. Any label known in the art can be used in the present invention. As used herein, "homogenous assays" refer to assays in which all components are mixed together in the same phase. One example of a homogenous assay is where the components mixed together are all in solution. In contrast, "heterogenous assays" refer to assays in which a first component is attached to a solid phase such as a bead or other solid substrate and one or more additional components are in solution.

As used herein, the term "fluorophore" or "fluorescent group" means any conventional chemical compound, which when excited by light of suitable wavelength, will emit fluorescence with high quantum yield. See, for example, J. R. Lakowicz in "Principles of Fluorescence Spectroscopy," Plenum Press, 1983. Numerous known fluorophores of a wide variety of structures and characteristics are suitable for use in the practice of this invention. In choosing a fluorophore for fluorescence polarization assays, it is preferred that the lifetime of the fluorophore's exited state be long enough, relative to the rate of motion of the labeled test compound, to permit measurable loss of polarization following emission. Typical fluorescing compounds, which are suitable for use in the present invention, include, for example, rhodamine, substituted rhodamine, fluorescein, fluorescein isothiocyanate, naphthofluorescein, dichlorotriazinylamine fluorescein, dansyl chloride, phycoerythrin, and umbelliferone. Other suitable fluorescent groups for use in the present invention include, but are not limited to, those described in U.S. Pat. Nos. 4,255,329, 4,668,640 and 5,315,015.

As used herein, the term "reporter molecule" is synonymous with the term "reporter compound" and the two terms are used interchangeably. A reporter molecule is a fluorogenic, chromogenic or chemiluminescent substrate that produces a signal such as fluorescence, light absorption within the ultraviolet, visible or infrared spectrum, or light emission, under the influence of the caspase cascade.

The reporter molecule may be composed of at least two covalently linked parts. One part is an amino acid sequence which may be recognized by any of the intracellular proteases or peptidases that are produced as a result of caspase cascade activation. This sequence is bonded to an aromatic or conjugated moiety that undergoes a detectable physical change upon its release from all or part of the amino acid sequence. Such moieties include a fluorogenic moiety that fluoresces more strongly after the reporter molecule is hydrolyzed by one of the proteases, a chromogenic moiety that changes its light absorption characteristics after the reporter molecule is hydrolyzed by one of the proteases, or a chemiluminescent moiety that produces light emission after the reporter molecule is hydrolyzed by one of the proteases. Alternatively, the aromatic or conjugated moiety may be linked to a plurality of aminoacid sequences.

One type of such a reporter molecule is given by Formula VI:

$$x\text{-}y\text{-}z \qquad (VI)$$

or biologically acceptable salts or pro-reporter molecules (such as methyl ester form of carboxyl-containing amino acid residues) thereof, wherein x and z is the same or different and is a peptide or amino acid or acyl group or other structure such that compounds of Formula VI are substrates for a caspase or other enzyme involved in the intracellular apoptosis cascade; and wherein the scissile bond is only one or both of the x-y and y-z bonds in Formula VI when x is the same as z, or wherein the scissile bond is only one of the x-y or y-z bond in Formula VI when x is not the same as z. y is a fluorogenic or fluorescent moiety. See U.S. Pat. No. 6,342,611.

Particular reporter compounds are represented by Formula VII:

$$R_1\text{-}(AA)_n\text{-}Asp\text{-}y\text{-}Asp\text{-}(AA)_n\text{-}R_1 \qquad (VII)$$

or biologically acceptable salts or pro-reporter molecules (such as methyl ester form of carboxyl-containing amino acid residues) thereof, wherein $R_1$ is an N-terminal protecting group such as t-butyloxycarbonyl, acetyl, and benzyloxycarbonyl; each AA independently is a residue of any natural or non-natural α-amino acid or β-amino acid, or derivatives of an α-amino acid or β-amino acid; each n is independently 0-5; and y is a fluorogenic or fluorescent moiety. y may be a Rhodamine including Rhodamine 110, Rhodamine 116 and Rhodamine 19.

Other particular reporter compounds are represented by Formula VIII:

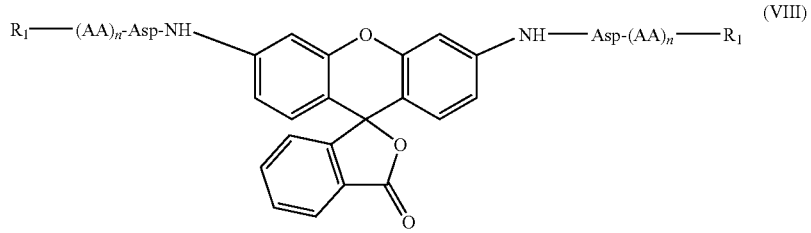

or biologically acceptable salts or pro-reporter molecules (such as methyl ester form of carboxyl-containing amino acid residues) thereof, wherein $R_1$, AA, n are as defined previously in Formula VII. $R_1$ may be t-butyloxycarbonyl, acetyl and benzyloxycarbonyl. Values of n are 1-3.

Another group of compounds falling within the scope of Formula VI include compounds wherein x is not the same as z. Particular compounds of this group include those wherein x is a peptide or other structure which makes the compound a substrate for a caspase or other enzyme related to apoptosis, and the x-y bond in Formula VI is the only bond which is scissile under biological conditions. z is a blocking group and the y-z bond in Formula VI is not a scissile bond under biological conditions.

Specifically, the fluorogenic or fluorescent reporter compounds that may be used in this invention are of Formula IX:

$$R_1\text{-}(AA)_n\text{-}Asp\text{-}y\text{-}R_6 \quad (IX)$$

or biologically acceptable salts or pro-reporter molecules (such as methyl ester form of carboxyl-containing amino acid residues) thereof, wherein: $R_1$, AA, n and y are as defined previously in Formula VII; and $R_6$ is a blocking group which is not an amino acid or a derivative of an amino acid.

Particular $R_6$ blocking groups include, but are not limited to, an alkyloxycarbonyl group such as methoxycarbonyl, an arylalkyloxycarbonyl group such as benzyloxycarbonyl, a $C_{2-6}$ acyl (alkanoyl) group such as acetyl, a carbamyl group such as dimethylcarbamyl, and an alkyl, haloalkyl or aralkyl sulfonyl group such as methanesulfonyl. Particular y is a Rhodamine including Rhodamine 110, Rhodamine 116 and Rhodamine 19.

In other embodiments, the reporter compounds are represented by Formula X:

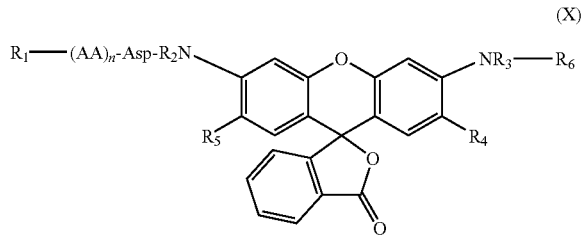

or biologically acceptable salts or pro-reporter molecules (such as methyl ester form of carboxyl-containing amino acid residues) thereof, wherein $R_1$, $R_6$, AA and n are as defined previously in Formula VII; $R_2$ and $R_3$ are the same or different and are independently hydrogen, alkyl or aryl; and $R_4$ and $R_5$ are the same or different and are independently hydrogen or alkyl.

$R_1$ may be t-butyloxycarbonyl, acetyl and benzyloxycarbonyl. Values of n may be 1-3. $R_2$ and $R_3$ may be hydrogen, methyl or ethyl. $R_4$ and $R_5$ may be hydrogen or methyl. $R_6$ blocking groups include, but are not limited to, an alkyloxycarbonyl group such as methoxycarbonyl, an arylalkyloxycarbonyl group such as benzyloxycarbonyl, an acyl group such as acetyl, a carbamyl group such as dimethylcarbamyl, and an alkyl, haloalkyl or aralkyl sulfonyl group such as methanesulfonyl.

Example of reporter molecules which are useful for the screening methods of the present invention include N-(Ac-DEVD)-N'-acetyl-Rhodamine 110 (SEQ ID NO.: 41), N-(Ac-DEVD)-N'-ethoxycarbonyl-Rhodamine 110 (SEQ ID NO.: 41), N-(Ac-DEVD)-N'-hexyloxycarbonyl-Rhodamine 110 (SEQ ID NO.: 41), N-(Ac-DEVD)-N'-octyloxycarbonyl-Rhodamine 110 (SEQ ID NO.: 41), N-(Ac-DEVD)-N'-decyloxycarbonyl-Rhodamine 110 (SEQ ID NO.: 41), N-(Ac-DEVD)-N'-dodecyloxycarbonyl-Rhodamine 110 (SEQ ID NO.: 41), N-(Ac-DEVD)-N'-2-butoxyethoxycarbonyl-Rhodamine 110 (SEQ ID NO.: 41), N-(Ac-DEVD)-N'-(ethylthio)carbonyl-Rhodamine 110 (SEQ ID NO.: 41), N-(Ac-DEVD)-N'-(hexylthio)carbonyl-Rhodamine 110 (SEQ ID NO.: 41), N-(Ac-DEVD)-N'-(octylthio)carbonyl-Rhodamine 110 (SEQ ID NO.: 41), N-(Ac-DEVD)-N'-(N-hexyl-N-methylcarbamyl)-Rhodamine 110 (SEQ ID NO.: 41), N-(Ac-DEVD)-N'-(2,3,4,5,6-pentafluorobenzoyl)-Rhodamine (SEQ ID NO.: 41), N-(Ac-DEVD)-N'-(2,3,4,5-tetrafluorobenzoyl)-Rhodamine (SEQ ID NO.: 41) and others disclosed in U.S. Pat. Nos. 6,342,611, 6,335,429 and 6,248,904. Since they are relatively small in size and lipophilic at the same time, many of these substrates can be used in the assays of the invention in the absence of a permeabilization enhancer.

Other useful reporter molecules include Ac-DEVD-pNA (SEQ ID NO.: 41), Ac-DEVD-AMC (SEQ ID NO.: 41), MCA-DEVDAPK(DNP)-OH (SEQ ID NO.: 42), Z-DEVD-AFC (SEQ ID NO.: 41), MCA-VDQMDGW[K-DNP]-NH$_2$ (SEQ ID NO.: 43), MCA-DEVDAR[K-DNP]-NH$_2$ (SEQ ID NO.: 44), Z-VDVAD-AFC (SEQ ID NO.: 45), MCA-VDVADGW[K-DNP]-NH$_2$ (SEQ ID NO.: 46), MCA-VDQVDGW[K-DNP]-NH$_2$ (SEQ ID NO.: 47), Ac-VEID-pNA (SEQ ID NO.: 48), Ac-VEID-AMC (SEQ ID NO.: 48), Z-VEID-AFC (SEQ ID NO.: 48) and MCA-VQVDGW[K-DNP]-NH$_2$ (SEQ ID NO.: 49), (CALBIOCHEM, California).

Other fluorogenic reporter molecules useful in the practice of the present invention are disclosed in the following U.S. Pat. Nos.: 4,336,186; 4,557,862; 4,640,893; 5,208,148; 5,227,487; 5,362,628; 5,443,986; 5,556,992; 5,587,490; 5,605,809; 5,698,411; 5,714,342; 5,733,719; 5,776,720, 5,849,513; 5,871,946; 5,897,992; 5,908,750; 5,976,822. Useful reporter molecules are also described in EP 0285179 B1; EP 623599 A1; WO 93/04192; WO 93/10461; WO 96/20721; WO 96/36729; WO 98/57664; Ganesh, S. et al., *Cytometry* 20:334-340 (1995); Haugland, R. and Johnson, I., *J. Fluorescence* 3:119-127 (1993); Haugland, R., *Biotechnic and Histochemistry* 70:243-251 (1995); Haugland, R., Molecular Probes Handbook of Fluorescent Probes and Research Chemicals, pp. 28 and 54, 6th Ed. (1996); Holskin, B., et al., *Anal. Biochem.* 226:148-155 (1995); Johnson, A., et al., *Anal. Chem.* 65:2352-2359 (1993); Klingel, S., et al., *Methods in Cell Biology* 41:449-459 (1994); Leytus, S., et al., *Biochem. J.* 215:253-260 (1983); Leytus, S., et al., *Biochem. J.* 209: 299-307 (1983); Matayoshi, E., et al., *Science* 247:954-958 (1990); Morliere, P., et al., *Biochem. Biophys. Res. Commun.* 146:107-113 (1987); O'Boyle, D., et al., *Virology* 236:338-347 (1997); Richards, A., et al., *J. Biol. Chem.* 265:7733-7736 (1990); Rothe, G., et al., *Biol. Chem. Hoppe-Seyler* 373:547-554 (1992); Stevens, J., et al., *Eur. J. Biochem.* 226:361-367 (1994); Tamburini, P., et al., *Anal. Biochem.* 186:363-368 (1990); Thornberry, N., et al., *J. Biol. Chem.* 272:17907-17911 (1997); Toth, M. and Marshall, G., *Int. J. Peptide Protein Res.* 36:544-550 (1990); Tyagi, S. and Carter, C., *Anal. Biochem.* 200:143-148 (1992); Weber, J. "Adenovirus Endopeptidase and Its Role in Virus Infection" in The Molecular Repertoir of Adenoviruses I, Doerfler, W. and Bohm, P. eds., pp. 227-235, Springer Press, New York (1995); Zhang, R., et al., *J. Virology* 71:6208-6213 (1997); Mangel, W., et al., *Biol. Chem. Hoppe-Seyler* 373:433-440 (1992);

Bonneau, P., et al., *Anal. Biochem.* 255:59-65 (1998); and DiIanni, C., et al., *J. Biol. Chem.* 268:25449-25454 (1993).

As used herein, the abbreviations for any protective groups, amino acids, and other compounds, are, unless indicated otherwise, in accord with their common usage, or recognized abbreviations.

II. Therapeutic Methods

One embodiment of the invention relates to compounds which bind one or more AIPs and induce activation of apoptosis. Another embodiment of the invention relates to pharmaceutical formulations of these compounds, and methods of administration of compositions comprising these compounds for preventing, treating or ameliorating a disease responsive to induction of the caspase cascade in an animal. Another embodiment of the invention pertains to a method of treating, preventing or ameliorating a disease in an animal comprising administering to the animal a composition comprising a compound which binds specifically to an AIP.

The present invention includes a therapeutic method useful to modulate in vivo apoptosis or in vivo neoplastic disease, comprising administering to a subject in need of such treatment an effective amount of one or more AIP binding compounds, or a pharmaceutically acceptable salt or prodrug of one or more AIP binding compound described herein, which functions as a caspase cascade activator and inducer of apoptosis.

The present invention also includes a therapeutic method comprising administering to an animal an effective amount of one or more AIP binding compounds, or a pharmaceutically acceptable salt or prodrug of one or more AIP binding compounds, wherein the therapeutic method is useful to treat cancer, which is a group of diseases characterized by the uncontrolled growth and spread of abnormal cells.

In practicing the therapeutic methods, effective amounts of compositions containing therapeutically effective concentrations of the AIP binding compounds formulated for oral, intravenous, local and topical application (for the treatment of neoplastic diseases and other diseases in which caspase cascade mediated physiological responses are implicated), are administered to an individual exhibiting the symptoms of one or more of these disorders. The amounts are effective to ameliorate or eliminate one or more symptoms of the disorder. An effective amount of an AIP binding compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

In another embodiment, a pharmaceutical composition comprising an AIP binding compound, or a pharmaceutically acceptable salt of an AIP binding compound described herein, which functions as a caspase cascade activator and inducer of apoptosis in combination with a pharmaceutically acceptable vehicle, is provided.

Another embodiment of the present invention is directed to a composition effective to inhibit neoplasia comprising an AIP binding compound, or a pharmaceutically acceptable salt or prodrug of an AIP binding compound described herein, which functions as a caspase cascade activator and inducer of apoptosis, in combination with at least one known cancer chemotherapeutic agent, or a pharmaceutically acceptable salt of the agent. Examples of known anti-cancer agents which can be used for combination therapy include, but are not limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; and antibodies, such as Herceptin® and Rituxan®. Other known anticancer agents, which can be used for combination therapy, include arsenic trioxide, gamcitabine, melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen and alanosine.

In practicing the methods of the present invention, the AIP binding compound of the invention may be administered together with the at least one known chemotherapeutic agent as part of a unitary pharmaceutical composition. Alternatively, the AIP binding compound of the invention may be administered apart from the at least one known cancer chemotherapeutic agent. In this embodiment, the AIP binding compound of the invention and the at least one known cancer chemotherapeutic agent are administered substantially simultaneously, i.e. the AIP binding compounds are administered at the same time or one after the other, so long as the AIP binding compounds reach therapeutic levels for a period of time in the blood.

It has been reported that alpha-1-adrenoceptor antagonists, such as doxazosin, terazosin, and tamsulosin can inhibit the growth of prostate cancer cell via induction of apoptosis (Kyprianou, N., et al., *Cancer Res* 60:4550-4555, (2000)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known alpha-i-adrenoceptor antagonists, or a pharmaceutically acceptable salt of the agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., *Cancer Res.* 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., *Cancer Res.* 62:313-322 (2002)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known sigma-2 receptor agonists, or a pharmaceutically acceptable salt of the agent. Examples of known sigma-2 receptor agonists, which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., *Int. J. Cancer* 97:746-750 (2002)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known HMG-CoA reductase inhibitor, or a pharmaceutically acceptable salt of the agent. Examples of known HMG-CoA reductase inhibitors, which can be used for combination therapy include, but are not limited to, lovastatin, simvastatin, pravastatin, fluvastatin, atorvastatin and cerivastatin.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., *Cancer Chemother. Pharmacol.* 43:145-150 (1999)). 4HPR also was reported to have good activity in combination with gamma-radiation on bladder cancer cell lines (Zou, C., et al., *Int. J. Oncol.* 13:1037-1041 (1998)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known retinoid and synthetic retinoid, or a pharmaceutically acceptable salt of the agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., *Leukemia* 16:433-443 (2002)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known proteasome inhibitor, or a pharmaceutically acceptable salt of the agent. Examples of known proteasome inhibitors, which can be used for combination therapy include, but are not limited to, lactacystin, MG-132, and PS-341.

It has been reported that tyrosine kinase inhibitors, such as STI571 (Imatinib mesilate, GLEEVEC®), have potent synergetic effect in combination with other anti-leukemic agents, such as etoposide (Liu, W. M., et al. *Br. J. Cancer* 86:1472-1478 (2002)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known tyrosine kinase inhibitor, or a pharmaceutically acceptable salt of the agent. Examples of known tyrosine kinase inhibitors, which can be used for combination therapy include, but are not limited to, GLEEVEC®, ZD1839 (IRESSA®), SH268, genistein, CEP2563, SU6668, SU11248, and EMD121974.

It has been reported that prenyl-protein transferase inhibitors, such as farnesyl protein transferase inhibitor RI 15777, possess preclinical antitumor activity against human breast cancer (Kelland, L. R., et. al., *Clin. Cancer Res.* 7:3544-3550 (2001)). Synergy of the protein farnesyltransferase inhibitor SCH66336 and cisplatin in human cancer cell lines also has been reported (Adjei, A. A., et al., *Clin. Cancer. Res.* 7:1438-1445 (2001)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of the agent. Examples of known prenyl-protein transferase inhibitors, which can be used for combination therapy include, but are not limited to, R115777, SCH66336, L-778,123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., *Clin. Cancer Res.* 7:4209-4219, (2001)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known cyclin-dependent kinase inhibitor, or a pharmaceutically acceptable salt of the agent. Examples of known cyclin-dependent kinase inhibitor, which can be used for combination therapy include, but are not limited to, flavopiridol, UCN-01, roscovitine and olomoucine.

It has been reported that in preclinical studies COX-2 inhibitors were found to block angiogenesis, suppress solid tumor metastases, and slow the growth of implanted gastrointestinal cancer cells (Blanke, C. D., *Oncology (Huntingt)* 16(No. 4 Suppl. 3):17-21 (2002)). Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known COX-2 inhibitors, or a pharmaceutically acceptable salt of the agent. Examples of known COX-2 inhibitors, which can be used for combination therapy include, but are not limited to, celecoxib, valecoxib, and rofecoxib.

It has been reported in clinical studies that regular administration of non-steroidal anti-inflammatory drugs (NSAIDs) reduces the risk of breast cancer. It has also been reported that in colon cancer cells, NSAIDs prevent interleukin-6 from activating STAT1; STAT1 prevents cellular suicide. Hence, NSAIDs are believed to make cells more conducive to apoptosis. Therefore, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with at least one known NSAID, or a pharmaceutically acceptable salt of the agent. Examples of known NSAIDs, which can be used for combination therapy include, but are not limited to, ibuprofen, aspirin and sulindac.

Another embodiment of the present invention is directed to compositions and methods effective to inhibit neoplasia comprising a bioconjugate of an AIP binding compound described herein, which functions as a caspase cascade activator and inducer of apoptosis, in bioconjugation with at least one known therapeutically useful antibody, such as Herceptin® or Rituxan®, growth factors, such as DGF, NGF; cytokines, such as IL-2, IL-4, or any molecule that binds to the cell surface. The antibodies and other molecules will deliver an AIP binding compound described herein to its targets and make it an effective anticancer agent. The bioconjugates could also enhance the anticancer effect of therapeutically useful antibodies, such as Herceptin® or Rituxan®.

Similarly, another embodiment of the present invention is directed to compositions and methods effective to inhibit neoplasia comprising an AIP binding compound, or a pharmaceutically acceptable salt or prodrug of an AIP binding compound described herein, which functions as a caspase cascade activator and inducer of apoptosis, in combination with radiation therapy. In this embodiment, the AIP binding compound of the invention may be administered at the same time as the radiation therapy is administered or at a different time.

Yet another embodiment of the present invention is directed to compositions and methods effective for post-surgical treatment of cancer, comprising an AIP binding compound, or a pharmaceutically acceptable salt or prodrug of an AIP binding compound described herein, which functions as a caspase cascade activator and inducer of apoptosis. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms maintaining immune homeostasis. This deletion of reactive cells has been shown to be regulated by a phenomenon known as apoptosis. Autoimmune diseases have been lately identified as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S., et al., *Cell Death Differ.* 6(1):13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly and generalized lymphadenopathy, hypergammaglobulinemia, and autoantibody formation. (Infante, A. J., et al., *J. Pediatr.* 133(5):629-633 (1998) and Vaishnaw, A. K., et al., *J. Clin. Invest.* 103(3):355-363 (1999)). It was reported that overexpression of Bcl-2, which is a member of the Bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., *Int. J. Mol. Med.* 1(2):475-483 (1998)). It is therefore, evident that many types of autoimmune disease are caused by defects of the apoptotic process and one treatment strategy would be to turn on apoptosis in the lymphocytes that are causing autoimmune disease (O'Reilly, L. A. & Strasser, A., *Inflamm. Res.* 48(1):5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., *J. Immunol.* 162(1):603-608 (1999)) reported that by direct injection of DNA expression vectors encoding FasL into the inflamed thyroid, the development of lymphocytic infiltration of the thyroid was inhibited and induction of the death of infiltrating T cells was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells, both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. (Zhou, T., et al, *Nat. Med.* 5(1):42-8 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of an AIP binding compound, or a pharmaceutically acceptable salt or prodrug of an AIP binding compound described herein, which functions as a caspase cascade activator and inducer of apoptosis, should be an effective treatment for autoimmune disease.

Psoriasis is a chronic skin disease, which is characterized by scaly red patches. Psoralen plus ultraviolet A (PLVA) is a widely used and effective treatment for psoriasis vulgaris and Coven, T. R., et al., *Photodermatol. Photoimmunol. Photomed.* 15(1):22-7 (1999), reported that lymphocytes treated with psoralen 8-MOP or TMP plus UVA displayed DNA degradation patterns typical of apoptotic cell death. Ozawa, M., et al., *J. Exp. Med.* 189(4):711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, M., et al., *Arch. Dermatol. Res.* 290(5):240-245 (1998), reported that low doses of methotrexate may induce apoptosis and this mode of action could explain the reduction in epidermal hyperplasia during treatment of psoriasis with methotrexate. Therefore, an effective amount of an AIP binding compound, or a pharmaceutically acceptable salt or prodrug of an AIP binding compound described herein, which functions as a caspase cascade activator and inducer of apoptosis, should be an effective treatment for psoriasis.

Synovial cell hyperplasia is a characteristic of patients with rheumatoid arthritis (RA). Excessive proliferation of RA synovial cells that, in addition, are defective in synovial cell death might be responsible for the synovial cell hyperplasia. Wakisaka, S., et al., *Clin. Exp. Immunol.* 114(1):119-28 (1998), found that, although RA synovial cells could die via apoptosis through Fas/FasL pathway, apoptosis of synovial cells was inhibited by proinflammatory cytokines present within the synovium, and suggested that inhibition of apoptosis by the proinflammatory cytokines may contribute to the outgrowth of synovial cells and lead to pannus formation and the destruction of joints in patients with RA. Therefore, an effective amount of an AIP binding compound, or a pharmaceutically acceptable salt or prodrug of an AIP binding compound described herein, which functions as a caspase cascade activator and inducer of apoptosis, should be an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61(4):375-80 (1997)). Boirivant, M., et al., *Gastroenterology* 116(3):557-65 (1999), reported that lamina propria T cells isolated from areas of inflammation in Crohn's disease, ulcerative colitis, and other inflammatory states manifest decreased CD2 pathway-induced apoptosis, and that studies of cells from inflamed Crohn's disease tissue, indicate that this defect is accompanied by elevated Bcl-2 levels. Therefore an effective amount of an AIP binding compound, or a pharmaceutically acceptable salt or prodrug of an AIP binding compound described herein, which functions as a caspase cascade activator and inducer of apoptosis, should be an effective treatment for inflammation.

Caspase cascade activators and inducers of apoptosis may also be a desirable therapy in the elimination of pathogens, such as HIV, Hepatitis C and other viral pathogens. The long lasting quiescence, followed by disease progression, may be explained by an anti-apoptotic mechanism of these pathogens leading to persistent cellular reservoirs of the virions. It has been reported that HIV-1infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis may serve as a beneficial host mechanism to limit the spread of HIV and new therapeutics using caspase/apoptosis activators may be useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers may be useful as therapeutics for HIV and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, may be useful as therapeutics for in-stent restenosis.

Compositions within the scope of this invention include all compositions wherein the AIP binding compounds of the present invention are contained in an amount which is effective to achieve its intended purpose. While individual needs vary, determination of optimal ranges of effective amounts of each component is within the skill of the art. Typically, the AIP binding compounds may be administered to mammals, e.g. humans, orally at a dose of 0.0025 to 100 mg/kg, or an equivalent amount of the pharmaceutically acceptable salt thereof, per day of the body weight of the mammal being treated for apoptosis-mediated disorders. The AIP binding compounds may be administered to mammals, e.g. humans, intravenously at a dose of 0.025 to 200 mg/kg, or an equivalent amount of the pharmaceutically acceptable salt thereof, per day of the body weight of the mammal being treated for apoptosis-mediated disorders. Preferably, approximately 0.01 to approximately 50 mg/kg is orally administered to treat or prevent such disorders. For intramuscular injection, the dose is generally approximately one-half of the oral dose. For example, a suitable intramuscular dose would be approximately 0.0025 to approximately 50 mg/kg, and most preferably, from approximately 0.01 to approximately 10 mg/kg. If a known cancer chemotherapeutic agent is also administered, it is administered in an amount which is effective to achieve its intended purpose. The amounts of such known cancer chemotherapeutic agents effective for cancer are well known to those of skill in the art.

The unit oral dose may comprise from approximately 0.01 to approximately 50 mg, preferably approximately 0.1 to approximately 10 mg of the AIP binding compound of the invention. The unit dose may be administered one or more times daily as one or more tablets, each containing from approximately 0.1 to approximately 10, conveniently approximately 0.25 to 50 mg of the AIP binding compound or its solvates.

In a topical formulation, the AIP binding compound may be present at a concentration of approximately 0.01 to 100 mg per gram of carrier.

In addition to administering the AIP binding compound as a raw chemical, the AIP binding compounds of the invention may be administered as part of a pharmaceutical preparation containing suitable pharmaceutically acceptable carriers comprising excipients and auxiliaries, which facilitate processing of the AIP binding compounds into preparations that can be used pharmaceutically. Preferably, the preparations, particularly those preparations, which can be administered orally and which can be used for the preferred type of administration, such as tablets, dragees, and capsules, and also preparations, which can be administered rectally, such as suppositories, as well as suitable solutions for administration by injection or orally, contain from approximately 0.01 to 99 percent, preferably from approximately 0.25 to 75 percent of active AIP binding compound(s), together with the excipient.

Also included within the scope of the present invention are the non-toxic pharmaceutically acceptable salts of the AIP binding compounds of the present invention. Acid addition salts are formed by mixing a solution of the particular apoptosis inducer of the present invention with a solution of a pharmaceutically acceptable non-toxic acid, such as hydrochloric acid, hydrobromic acid, fumaric acid, maleic acid, succinic acid, acetic acid, citric acid, lactic acid, tartaric acid, carbonic acid, phosphoric acid, sulfuric acid, oxalic acid, and the like. Basic salts are formed by mixing a solution of the particular apoptosis inducer of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the AIP binding compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use can be obtained by combining the active AIP binding compounds with solid excipients, optionally grinding the resultant mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g. *maize* starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g. silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active AIP binding compound doses.

Other pharmaceutical preparations, which can be used orally, include push-fit capsules made of gelatin, as well as soft, sealed capsules made of gelatin and a plasticizer, such as glycerol or sorbitol. The push-fit capsules can contain the active AIP binding compounds in the form of granules, which may be mixed with fillers, such as lactose, binders such as starches, and/or lubricants such as talc or magnesium stearate and, optionally, stabilizers. In soft capsules, the active AIP binding compounds are preferably dissolved or suspended in suitable liquids, such as fatty oils, or liquid paraffin. In addition, stabilizers may be added.

Possible pharmaceutical preparations, which can be used rectally include, e.g. suppositories, which consist of a combination of one or more of the active AIP binding compounds with a suppository base. Suitable suppository bases are, e.g. natural or synthetic triglycerides, or paraffin hydrocarbons. In addition, it is also possible to use gelatin rectal capsules, which consist of a combination of the active AIP binding compounds with a base. Possible base materials include, e.g. liquid triglycerides, polyethylene glycols, or paraffin hydrocarbons.

Suitable formulations for parenteral administration include aqueous solutions of the active AIP binding compounds in water-soluble form, e.g. water-soluble salts and alkaline solutions. In addition, suspensions of the active AIP binding compounds as appropriate oily injection suspensions may be administered. Suitable lipophilic solvents or vehicles include fatty oils, e.g. sesame oil; or synthetic fatty acid esters, e.g. ethyl oleate or triglycerides or polyethylene glycol-400 (the AIP binding compounds may be soluble in PEG-400). Aqueous injection suspensions may contain substances, which increase the viscosity of the suspension include, e.g. sodium carboxymethyl cellulose, sorbitol, and/or dextran. Optionally, the suspension may also contain stabilizers.

In accordance with one aspect of the present invention, AIP binding compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes approximately 40 parts water, approximately 20 parts beeswax, approximately 40 parts mineral oil, and approximately 1 part almond oil.

Ointments may be formulated by mixing a solution of the active ingredient in a vegetable oil, such as almond oil with warm soft paraffin and allowing the mixture to cool. A typical example of such an ointment is one which includes approximately 30% almond oil and approximately 70% white soft paraffin by weight.

Also included within the scope of the present invention are dosage forms of the AIP binding compounds, in which the oral pharmaceutical preparations comprise an enteric coating. The term "enteric coating" is used herein to refer to any coating over an oral pharmaceutical dosage form that inhibits dissolution of the active ingredient in acidic media, but dissolves rapidly in neutral to alkaline media and has good stability to long-term storage. Alternatively, the dosage form having an enteric coating may also comprise a water soluble separating layer between the enteric coating and the core.

The core of the enterically coated dosage form comprises an AIP binding compound. Optionally, the core also comprises pharmaceutical additives and/or excipients. The separating layer may be a water soluble inert AIP binding compound or polymer for film coating applications. The separating layer is applied over the core by any conventional coating technique known to one of ordinary skill in the art. Examples of separating layers include, but are not limited to sugars, polyethylene glycol, polyvinylpyrrolidone, polyvinyl alcohol, hydroxypropyl cellulose, polyvinyl acetal diethylaminoacetate and hydroxypropyl methylcellulose. The enteric coating is applied over the separating layer by any conventional coating technique. Examples of enteric coatings include, but are not limited to cellulose acetate phthalate, hydroxypropyl methylcellulose phthalate, polyvinyl acetate phthalate, carboxymethylethylcellulose, copolymers of methacrylic acid and methacrylic acid methyl esters, such as Eudragit®L 12,5 or Eudragit®L 100 (R hm Pharma), water based dispersions such as Aquateric® (FMC Corporation), Eudragit®L 100-55 (R hm Pharma) and Coating CE 5142 (BASF), and those containing water soluble plasticizers such as Citroflex® (Pfizer). The final dosage form is either an enteric coated tablet, capsule or pellet.

III. Polypeptide and Polynucleotide Sequences

This section lists non-limiting examples of AIPs and the corresponding nucleotides which encode these AIPs. The polypeptide and polynucleotide sequences described below in subsections A-H are wholly incorporated by reference herein, and are useful with the screening methods of the present invention.

A. Transferrin Receptor Related Apoptosis Inducing Proteins (TRRAIPs)

Non-limiting examples of TRRAIPs include Transferrin receptor (p90, CD71) [*Homo sapiens*] (SEQ ID NO: 1) (NCBI Accession No. XP_052730); Transferrin receptor [*Homo sapiens*] (SEQ ID NO: 2) (NCBI Accession No. AAF04564); Transferrin receptor (p90, CD71) [*Homo sapiens*] (SEQ ID NO: 3) (NCBI Accession No. AAH01188); Transferrin receptor (p90, CD 71) [*Homo sapiens*] (SEQ ID NO: 4) (NCBI Accession No. NP_003225); Put. transferrin receptor (aa 1-760) [*Homo sapiens*] (SEQ ID NO: 5) (NCBI Accession No. CAA25527); Transferrin receptor [*Homo sapiens*] (SEQ ID NO: 6) (NCBI Accession No. AAA61153); Transferrin receptor [*Cavia* (guinea pigs)] (SEQ ID NO: 7) (NCBI Accession No. AAB35972); Transferrin receptor protein 1 (TfR1) (TR) (TfR) (Trfr) (CD71 antigen) (T9) (p90) [*Homo sapiens*] (SEQ ID NO: 8) (NCBI Accession No. P02786); Transferrin receptor [*Homo sapiens*] (SEQ ID NO: 9) (NCBI Accession No. JXHU); Transferrin receptor [*Homo sapiens*] (SEQ ID NO: 10) (NCBI Accession No. 1011297A); Chain C, Hemochromatosis Protein Hfe Complexed With Transferrin Receptor [*Homo sapiens*] (SEQ ID NO: 11) (NCBI Accession No. IDE4_C); Chain F, Hemochromatosis Protein Hfe Complexed With Transferrin Receptor [*Homo sapiens*] (SEQ ID NO: 12) (NCBI Accession No. IDE4_F); Chain I, Hemochromatosis Protein Hfe Complexed With Transferrin Receptor [*Homo sapiens*] (SEQ ID NO: 13) (NCBI Accession No. 1DE4_I); Chain A, Crystal Structure Of The Ectodomain Of Human Transferrin Receptor [*Homo sapiens*] (SEQ ID NO: 14) (NCBI Accession No. 1CX8_A); Chain B, Crystal Structure Of The Ectodomain Of Human Transferrin Receptor [*Homo sapiens*] (SEQ ID NO: 15) (NCBI Accession No. 1CX8_B); Chain C, Crystal Structure Of The Ectodomain Of Human Transferrin Receptor [*Homo sapiens*] (SEQ ID NO: 16) (NCBI Accession No. 1CX8_C); Chain D, Crystal Structure Of The Ectodomain Of Human Transferrin Receptor [*Homo sapiens*] (SEQ ID NO: 17) (NCBI Accession No. 1CX8_D); Chain E, Crystal Structure Of The Ectodomain Of Human Transferrin Receptor [*Homo sapiens*] (SEQ ID NO: 18) (NCBI Accession No. 1CX8_E); Chain F, Crystal Structure Of The Ectodomain Of Human Transferrin Receptor [*Homo sapiens*] (SEQ ID NO: 19) (NCBI Accession No. 1CX8_F); Chain G, Crystal Structure Of The Ectodomain Of Human Transferrin Receptor [*Homo sapiens*] (SEQ ID NO: 20) (NCBI Accession No. 1CX8_G); Chain H, Crystal Structure Of The Ectodomain Of Human Transferrin Receptor [*Homo sapiens*] (SEQ ID NO: 21) (NCBI Accession No. 1CX8_H); Transferrin receptor—guinea pig (fragment) [*Cavia porcellus* (domestic guinea pig)] (SEQ ID NO: 22) (NCBI Accession No. S68317); Transferrin receptor [human, Peptide Partial, 17 aa] [*Homo sapiens*] (SEQ ID NO: 23) (NCBI Accession No. AAB22984); Transferrin receptor p95, TfR p95 (internal fragment) [human, prostatic-carcinoma cell line DU 145, Peptide Partial, 15 aa, segment 2 of 2] [Homo sapiens] (SEQ ID NO: 24) (NCBI Accession No. AAB34741); Transferrin receptor [human, K562 erythroleukemia cells, Peptide Partial, 23 aa] [Homo sapiens](SEQ ID NO: 25) (NCBI Accession No. AAB19499); Transferrin receptor p95, TfR p95 (internal fragment) [human, prostatic-carcinoma cell line DU 145, Peptide Partial, 15 aa, segment 1 of 2] [*Homo sapiens*] (SEQ ID NO: 26) (NCBI Accession No. AAB34739); and transferrin receptor 2, TFR2 [*Homo sapiens*] (NCBI Accession No. NP_003218).

B. Nucleotide Sequences Encoding for Transferrin Receptor Related Apoptosis Inducing Proteins (TRRAIPs)

Non-limiting examples of nucleotide sequences which encode for TRRAIPs include *Homo sapiens*transferrin receptor (p90, CD71) (TFRC), mRNA [*Homo sapiens*] (SEQ ID NO: 27) (NCBI Accession No. XM_052730); *Homo sapiens*transferrin receptor (TFRC) gene, complete cds [*Homo sapiens*] (SEQ ID NO. 28) (NCBI Accession No. AF187320); Homo sapiens, transferrin receptor (p90, CD71), clone MGC: 3151 IMAGE:3354176, mRNA, complete cds [*Homo sapiens*] (SEQ ID NO: 29) (NCBI Accession No. BC001188); *Homo sapiens*transferrin receptor (p90, CD71) (TFRC), mRNA [*Homo sapiens*] (SEQ ID NO. 30) (NCBI Accession No. NM_003234); Human mRNA for transferrin receptor [*Homo sapiens*] (SEQ ID NO. 31) (NCBI Accession No. X01060); Human transferrin receptor mRNA, complete cds. [Homo Sapiens] (SEQ ID NO. 32) (NCBI Accession No. M11507); Transferrin receptor [guinea pigs, liver, mRNA Partial, 189 nt] [*Cavia* (guinea pigs)] (SEQ ID NO. 33) (NCBI Accession No. S81327).

C. Clathrin Heavy Chain Related Apoptosis Inducing Proteins (CHCRAIPs)

Non-limiting examples of CHCRAIPs include Clathrin, heavy polypeptide-like 2 [*Homo sapiens*] (SEQ ID NO. 34) (NCBI Accession No. NP_004850); Clathrin, heavy polypeptide-like 1 isoform a [*Homo sapiens*] (NCBI Accession No. NP_001826); Clathrin, heavy polypeptide-like 1 isoform b [*Homo sapiens*] (NCBI Accession No. NP_009029); Muscle clathrin heavy chain [*Homo sapiens*] (NCBI Accession No. AAC50494); Clathrin heavy chain 2 [*Homo sapiens*] (NCBI Accession No. AAB40909); Clathrin heavy chain 2 [*Homo sapiens*] (NCBI Accession No. AAB40908); KIAA0034 [*Homo sapiens*] (NCBI Accession No. BAA04801); Clathrin heavy chain polypeptide [*Homo sapiens*] (NCBI Accession No. CAA64753); Clathrin heavy chain polypeptide [*Homo sapiens*] (NCBI Accession No. CAA64752); Clathrin heavy chain [*Homo sapiens*] (NCBI Accession No. CAA39363); Clathrin heavy chain [*Rattus novegicus*] (NCBI Accession No. AAA40874); Clathrin, heavy polypeptide (Hc) [*Rattus novegicus*] (NCBI Accession No. NP_062172); Clathrin heavy chain [*Bos taurus*] (NCBI Accession No. AAC48524); Clathrin, heavy polypeptide (Hc) [*Bos taurus*] (NCBI Accession No. NP_776448); Clathrin heavy-chain [*Gallus gallus*] (NCBI Accession No. CAD20886); Clathrin heavy-chain [*Gallus gallus*] (NCBI Accession No. CAD22061); Clathrin heavy-chain [*Gallus gallus*] (NCBI Accession No. CAD22060); Clathrin heavy-chain [*Gallus gallus*] (NCBI Accession No. CAD22059); Clathrin heavy-chain [*Gallus gallus*] (NCBI Accession No. CAD22058); Clathrin heavy-chain [*Gallus gallus*] (NCBI Accession No. CAD22057); RIKEN cDNA 3110065L21 [*Mus musculus*] (NCBI Accession No. XP_126363); RIKEN cDNA 3110065L21 [*Mus musculus*] (NCBI Accession No. XP_181312); mKLAA0034 protein [*Mus musculus*] (NCBI Accession No. BAC65475); Similar to RIKEN cDNA 3110065L21 gene [*Mus musculus*] (NCBI Accession No.

AAH31408); PRO2051 [*Homo sapiens*] (NCBI Accession No.AAG35490); Clathrin heavy chain 1 (CLH-17) [*Homo sapiens*] (NCBI Accession No. Q00610); CLATHRIN HEAVY CHAIN [*Bos taurus*] (NCBI Accession No. P49951); Clathrin heavy chain [*Rattus novegicus*] (NCBI Accession No. P11442); Clathrin heavy chain—rat [*Rattus novegicus*] (NCBI Accession No. LRRTH); Clathrin heavy chain 2—human [*Homo sapiens*] (NCBI Accession No. G02757); Chain B, Clathrin Heavy-Chain Terminal Domain And Linker [*Rattus novegicus*] (NCBI Accession No. 1BPO_B); Chain C, Clathrin Heavy-Chain Terminal Domain And Linker [*Rattus novegicus*] (NCBI Accession No. 1BPO_C); Chain B, Peptide-In-Groove Interactions Link Target Proteins To The B-Propeller Of Clathrin [*Rattus novegicus*] (NCBI Accession No. 1C9I_B); Chain B, Peptide-In-Groove Interactions Link Target Proteins To The B-Propeller Of Clathrin [*Rattus novegicus*] (NCBI Accession No. 1C9L_B); Clathrin heavy chain 2 (CLH-22) [*Homo sapiens*] (NCBI Accession No. P53675); Clathrin heavy chain—human [*Homo sapiens*] (NCBI Accession No. T09522); Chain A, Clathrin Heavy-Chain Terminal Domain And Linker [*Rattus novegicus*] (NCBI Accession No. 1BPO_A); Chain A, Clathrin Heavy Chain Proximal Leg Segment (Bovine) [*Bos taurus*] (NCBI Accession No.1B89_A); Chain A, Peptide-In-Groove Interactions Link Target Proteins To The B-Propeller Of Clathrin [*Rattus norvegicus*] (NCBI Accession No. 1C9I_A); Chain A, Peptide-In-Groove Interactions Link Target Proteins To The B-Propeller Of Clathrin [*Rattus norvegicus*] (NCBI Accession No. 1C9L_A); Clathrin heavy chain—human (fragment) [*Homo sapiens*] (NCBI Accession No. A40573).

D. Nucleotide Sequences Encoding for Clathrin Heavy Chain Related Apoptosis Inducing Proteins (CHCRAIPs)

Non-limiting examples of nucleotide sequences which encode for CHCRAIPs include Clathrin, heavy polypeptide (Hc) (CLTC) [*Homo sapiens*] (SEQ ID NO. 35) (NCBI Accession No. NM_004859); Clathrin, heavy polypeptide-like 1 (CLTCL1), transcript variant 1, [*Homo sapiens*] (NCBI Accession No. NM_001835); Clathrin, heavy polypeptide-like 1 (CLTCL1), transcript variant 2 [*Homo sapiens*] (NCBI Accession No. NM_007098); Human muscle specific clathrin heavy chain (CLTD), complete cds (NCBI Accession No. U41763); Human clathrin heavy chain 2 (CLTCL) mRNA, complete cds [*Homo sapiens*] (NCBI Accession No. U60803); Human clathrin heavy chain 2 (CLTCL) mRNA, longer alternatively spliced transcript, complete cds [*Homo sapiens*] (NCBI Accession No.U60802); *Homo sapiens*KIAA0034 mRNA, complete cds [*Homo sapiens*] (NCBI Accession No. D21260); *H.sapiens* mRNA for clathrin heavy chain [*Homo sapiens*] (NCBI Accession No. X95487); *H.sapiens* mRNA for clathrin heavy chain (alternatively spliced) [*Homo sapiens*] (NCBI Accession No. X95486); Human mRNA for clathrin heavy chain, partial [*Homo sapiens*] (NCBI Accession No. X55878) Rat clathrin heavy chain mRNA, complete cds [*Rattus novegicus*] (NCBI Accession No. J03583); *Rattus novegicus*clathrin, heavy polypeptide (Hc) (Cltc), mRNA [*Rattus novegicus*] (NCBI Accession No. NM_019299); *Bos taurus* clathrin heavy chain mRNA, complete cds [*Bos taurus*] (NCBI Accession No. U31757); *Bos taurus*clathrin, heavy polypeptide (Hc) (CLTC), mRNA [*Bos taurus*] (NCBI Accession No. NM_174023); *Gallus gallus* partial mRNA for clathrin heavy-chain (CHC gene) [*Gallus gallus*] (NCBI Accession No. AJ427965); *Gallus gallus* partial chc gene for clathrin heavy-chain, exons14-17 [*Gallus gallus*] (NCBI Accession No. AJ429076); *Gallus gallus* partial chc gene for clathrin heavy-chain, exons 12-13 [*Gallus gallus*] (NCBI Accession Nd. AJ429075); *Gallus gallus*partial chc gene for clathrin heavy-chain, exon 11 [*Gallus gallus*] (NCBI Accession No. AJ429074); *Gallus gallus* partial chc gene for clathrin heavy-chain, exons 4-10 [*Gallus gallus*] (NCBI Accession No. AJ429073); *Gallus gallus* partial chc gene for clathrin heavy-chain, exons 1-3 [*Gallus gallus*] (NCBI Accession No. AJ429072); *Mus musculus* clathrin, heavy polypeptide (Hc) (Cltc), mRNA [*Mus musculus*] (NCBI Accession No. XM_126363); *Mus musculus* clathrin, heavy polypeptide (Hc) (Cltc), mRNA [*Mus musculus*] (NCBI Accession No. XM_181312); *Mus musculus* mRNA for mKIAA0034 protein [*Mus musculus*] (NCBI Accession No. AK122193); *Mus musculus*, Similar to RIKEN cDNA 3110065L21 gene, clone IMAGE:4949242, mRNA, partial cds. (NCBI Accession No. BC031408); *Homo sapiens*clone FLB7715 PRO2051 mRNA, complete cds [*Homo sapiens*] (NCBI Accession No. AF 130062).

E. IQ Motif Containing GTPase Activating Protein Related Apoptosis Inducing Proteins (IQGAPRAIPs)

Non-limiting examples of IQGAPRAIPs include IQ motif containing GTPase activating protein 1 [*Homo sapiens*] (SEQ ID NO. 36) (NCBI Accession No. NP_003861); KIAA0051 [*Homo sapiens*] (NCBI Accession No. BAA06123); Ras GTPase-activating-like protein [*Homo sapiens*] (NCBI Accession No. AAA59187); IQ motif containing GTPase activating protein 1 [*Mus musculus*] (NCBI Accession No. NP_057930); IQ motif containing GTPase activating protein 1 [*Mus musculus*] (NCBI Accession No. AAF60344); IQ motif containing GTPase activating protein 1 [*Mus musculus*] (NCBI Accession No. AAH46385); Similar to IQ motif containing GTPase activating protein 1 [*Mus musculus*] (NCBI Accession No. AAH37685); Unnamed protein product [*Mus musculus*] (NCBI Accession No. BAC26538); Unnamed protein product [*Mus musculus*] (NCBI Accession No. BAC36765); Unnamed protein product [*Mus musculus*] (NCBI Accession No. BAC26450); Unnamed protein product [*Mus musculus*] (NCBI Accession No. BAB30486); Unnamed protein product [*Mus musculus*] (NCBI Accession No. BAC28488); IQGAP1 protein [*Homo sapiens*] (NCBI Accession No. AAL02166); Similar to chromobox homolog 3 [*Rattus novegicus*] (NCBI Accession No. XP_218836); Ras GTPase-activating-like protein IQGAP1 (P195) [*Homo sapiens*] (NCBI Accession No. P46940); Ras GTPase activating protein-related protein—human [*Homo sapiens*] (NCBI Accession No. A54854); Ras GTPase-activating-like protein IQGAP1 [*Mus musculus*] (NCBI Accession No. Q9JKF1); Sequence 1 from US Pat. No. 5639651 [Unknown] (NCBI Accession No. AAB74847); Sequence 3 from US Pat. No. 5639651 [Unknown] (NCBI Accession No. AAB74848); Sequence 22 from US Pat. No. 5639651 [Unknown] (NCBI Accession No. AAB74867); Sequence 17 from US Pat. No. 5639651 [Unknown] (NCBI Accession No. AAB74862); Sequence 20 from US Pat. No. 5639651 [Unknown] (NCBI Accession No. AAB74865); Sequence 18 from US Pat. No. 5639651 [Unknown] (NCBI Accession No. AAB74863); Sequence 19 from US Pat. No. 5639651 [Unknown] (NCBI Accession No. AAB74864); Sequence 21 from US Pat. No. 5639651 [Unknown] (NCBI Accession No. AAB74866); Sequence 13 from US Pat. No. 5639651 [Unknown] (NCBI Accession No. AAB74858); Sequence 12 from US Pat. No. 5639651 [Unknown] (NCBI Accession No. AAB74857); Sequence 15 from US Pat. No. 5639651 [Unknown] (NCBI Accession No. AAB74860); Sequence 14 from US Pat. No. 5639651 [Unknown] (NCBI Accession No. AA1B74859).

F. Nucleotide Sequences Encoding for IQ Motif Containg GTPase Activating Protein Related Apoptosis Inducing Proteins (IQGAPRAIPs)

Non-limiting examples of nucleotide sequences which encode for IQGAPRAIPs include Homo sapiens IQ motif containing GTPase activating protein 1(IQGAP1), mRNA [Homo sapiens] (SEQ ID NO. 37) (NCBI Accession No. NM_003870); Homo sapiensKIAA0051 mRNA, complete cds [Homo sapiens] (NCBI Accession No. D29640); Homo sapiensras GTPase-activating-like protein (IQGAP1) mRNA, complete cds [Homo sapiens] (NCBI Accession No. L33075); Mus musculus IQ motif containing GTPase activating protein 1(Iqgap1), mRNA [Mus musculus] (NCBI Accession No. NM_016721); Mus musculus IQ motif containing GTPase activating protein 1 (Iqgap1) mRNA, complete cds [Mus musculus] (NCBI Accession No. AF240630); Mus musculus, IQ motif containing GTPase activating protein 1, clone MGC:51367 IMAGE:3256630, mRNA, complete cds [Mus musculus] (NCBI Accession No. BC046385); Mus musculus, Similar to IQ motif containing GTPase activating protein 1, clone IMAGE:3673375, mRNA, partial cds [Mus musculus] (NCBI Accession No. BC037685); Mus musculus adult male testis cDNA, RIKEN full-length enriched library, clone: 4930417E17 product:IQ motif containing GTPase activating protein 1, full insert sequence [Mus musculus] (NCBI Accession No. AK029631); Mus musculus adult male pituitary gland cDNA, RIKEN full-length enriched library, clone: 5330436H04 product:IQ motif containing GTPase activating protein 1, full insert sequence [Mus musculus] (NCBI Accession No. AK077354); Mus musculus 0 day neonate head cDNA, RIKEN full-length enriched library, clone: 4833436C10 product:IQ motif containing GTPase activating protein 1, full insert sequence [Mus musculus] (NCBI Accession No. AK029434); Mus musculus adult male testis cDNA, RIKEN full-length enriched library, clone:4933424L13 product:IQ motif containing GTPase activating protein 1, full insert sequence [Mus musculus] (NCBI Accession No. AK016896); Mus musculus adult male epididymis cDNA, RIKEN full-length enriched library, clone:92301 16M15 product:IQ motif containing GTPase activating protein 1, full insert sequence (NCBI Accession No. AK033829); Homo sapiens IQGAP1 protein mRNA, partial cds [Homo sapiens] (NCBI Accession No. AF401205); Rattus novegicus similar to chromobox homolog 3, mRNA [Rattus novegicus] (NCBI Accession No. XM_188836).

G. Heat Shock Protein Related Apoptosis Inducing Proteins (HSPRAIPs)

Non-limiting examples of HSPRAIPs include Heat shock 90 kDa protein 1, beta; heat shock 90 kD protein 1, beta [Homo sapiens] (SEQ ID NO. 38) (NCBI Accession No. NP_031381); 90 kD heat shock protein [Homo sapiens] (NCBI Accession No. AAA36026); Unknown (protein for MGC:10493) [Homo sapiens] (NCBI Accession No. AAH04928); Unknown (protein for MGC:3483) [Homo sapiens] (NCBI Accession No. AAH12807); Unknown (protein for MGC:23206) [Homo sapiens] (NCBI Accession No. AAH14485); Unknown (protein for MGC:1138) [Homo sapiens] (NCBI Accession No. AAH16753); Similar to heat shock protein 84—mouse [Rattus norvegicus] (NCBI Accession No. XP_217339); 90 kDa heat shock protein [Homo sapiens] (NCBI Accession No. AAA36025); Heat shock protein 90 beta [Equus caballus] (NCBI Accession No. BAB20776); Hypothetical protein [Homo sapiens] (NCBI Accession No. CAB66478); Chaperone protein HSP90 beta [Homo sapiens] (NCBI Accession No. AAF82792); Heat shock 90 kD protein 1, beta [Homo sapiens] (NCBI Accession No. AAH09206); Hsp89-alpha-delta-N [Homo sapiens] (NCBI Accession No. AAC25497); Unknown (protein for MGC:30059) [Homo sapiens] (NCBI Accession No. AAH23006); 90 kDa heat-shock protein (AA 1-732) [Homo sapiens] (NCBI Accession No. CAA33259); heat shock 90 kDa protein 1, alpha; heat shock 90 kD protein 1, alpha [Homo sapiens] (NCBI Accession No. NP_005339); Heat shock protein [Homo sapiens] (NCBI Accession No. AAA63194); Unknown (protein for IMAGE:3446372) [Homo sapiens] (NCBI Accession No. AAH00987); Similar to heat shock 90 kD protein 1, alpha [Homo sapiens] (NCBI Accession No. AAH07989); Similar to heat shock protein 84 [Mus musculus] (NCBI Accession No. AAH44888); Unnamed protein product [Homo sapiens] (NCBI Accession No. BAB15121); Unnamed protein product [Homo sapiens] (NCBI Accession No. CAD62296); Similar to heat shock 90 kDa protein 1, alpha; heat shock 90 kD protein 1, alpha [Homo sapiens] (NCBI Accession No. XP_084514); Heat shock protein 90 beta [Bos taurus] (NCBI Accession No. CAC84136); Similar to heat shock protein 84—mouse [Rattus novegicus] (NCBI Accession No. XP_234134); Similar to Heat shock protein HSP 90-beta (HSP 84) (HSP 90) [Homo sapiens] (NCBI Accession No. XP_055551); Heat shock protein 90 alpha [Coturnix japonica] (NCBI Accession No. AAL83217); Heat shock protein 86 (AA 1-312) [Homo sapiens] (NCBI Accession No. CAA30255); Heat shock protein 86 [Homo sapiens] (NCBI Accession No. AAA36023); Unnamed protein product [Mus musculus] (NCBI Accession No. BAC40681); Similar to heat shock protein 86 [Rattus norvegicus] (NCBI Accession No. XP_216334); Heat shock protein 86 [Homo sapiens] (NCBI Accession No. AAA36024); Similar to heat shock protein 84—mouse [Mus musculus] (NCBI Accession No. XP_138010); ebiP7687 [Anopheles gambiae str. PEST] (NCBI Accession No. EAA04769); Similar to heat-shock protein hsp84 [Rattus novegicus] (NCBI Accession No. XP_215734); Similar to heat shock protein 84—mouse [Mus musculus] (NCBI Accession No. XP_111980); Heat shock protein 90 alpha [Cyprinus carpio] (NCBI Accession No. AAD50972); Stress protein HSP90-beta [Cyprinus carpio] (NCBI Accession No. AAD50973); HSP90; HSP84 [Mus sp.] (NCBI Accession No. AAB23704); Similar to heat-shock protein hsp84 [Rattus norvegicus] (NCBI Accession No. XP_227737); 90 kDa heat-shock protein [Scyliorhinus torazame] (NCBI Accession No. AAG22091); Similar to heat-shock protein hsp84 [Rattus novegicus] (NCBI Accession No. XP_227300); Similar to heat shock protein 86 [Rattus novegicus] (NCBI Accession No. XP_218659); Heat shock protein 90 [Homo sapiens] (NCBI Accession No. BAA13431); Similar to Heat shock protein HSP 90-beta (HSP 84) [Rattus norvegicus] ] (NCBI Accession No. XP_226259); Similar to hypothetical protein DKFZp761K0511.1—human [Rattus novegicus] (NCBI Accession No. XP_236446); Similar to Heat shock protein HSP 90-beta (HSP 84) [Mus musculus] ] (NCBI Accession No. XP_195404); Unnamed protein product [Homo sapiens] (NCBI Accession No. CAD66568); Heat shock protein 84 [Mus musculus] (NCBI Accession No. AAC36532); Heat shock protein beta [Homo sapiens] (NCBI Accession No. BAA22050); Heat shock protein 90 [Xenopus laevis] (NCBI Accession No. AAA96259); Heat shock protein 90 [Danio rerio] (NCBI Accession No. AAA97519); Similar to heat-shock protein hsp84 [Rattus novegicus] (NCBI Accession No. XP _217390); Similar to heat shock protein 86 [Rattus novegicus] [Homo sapiens] (NCBI Accession No. XP_060949); Heat shock protein 90 [Danio rerio] (NCBI Accession No. AAA97518); Heat shock protein 90 [Meloidogyne arenaria] (NCBI Accession No. AA014541); Similar to Heat shock protein HSP 90-beta (HSP 84) [Homo sapiens] (NCBI Accession No. XP_210549); Heat shock protein 90 [*Pratylenchus crenatus*] (NCBI Accession No. AA014543); hsp-90 [*Meloidogyne incognita*] (NCBI Accession No. AAN76188); Heat shock protein 90 [*Meloidogyne sasseri*] (NCBI Accession No. AA014542); hsp-90 [*Heterodera* sp. AAMS-2002] (NCBI Accession No. AAN76187); Heat shock protein 90 [*Pratylenchus teres*] (NCBI Accession No. AA014545); Heat shock protein 90 [*Bursaphelenchus xylophilus*] (NCBI Accession No. AA014540); Heat shock protein 90 [*Pratylenchus teres*] (NCBI Accession No. AA014544); Similar to Heat shock protein HSP 90-beta (HSP 84) [*Homo sapiens*] (NCBI Accession No. XP_210729); 90-kda heat shock protein beta HSP90 beta [*Homo sapiens*] (NCBI Accession No. AAD14062); Heat shock protein hsp-90 [*Heterodera glycines*] (NCBI Accession No. AAN76047); Heat shock protein hsp-90 [*Heterodera glycines*] (NCBI Accession No. AAN76049); Heat shock protein hsp-90 [*Heterodera glycines*] (NCBI Accession No. AAN76045); Heat shock protein hsp-90 [*Heterodera glycines*] (NCBI Accession No. AAN76186); Heat shock protein hsp-90 [*Heterodera glycines*] (NCBI Accession No. AAN76048); Heat shock protein hsp-90 [*Heterodera glycines*] (NCBI Accession No. AAN76185); Heat shock protein hsp-90 [*Heterodera glycines*] (NCBI Accession No. AAN76046); Heat shock protein [*Mus musculus*] (NCBI Accession No. AAA37867); Similar to Heat shock protein HSP 90-beta (HSP 84) (HSP 90) [*Mus musculus*] (NCBI Accession No. XP_285390); Heat shock protein 90 [*Gallus gallus*] (NCBI Accession No. CAA33132); Similar to Heat shock protein HSP 90-alpha (HSP 86) [*Rattus novegicus*] (NCBI Accession No. XP_216245); hsp82 heat shock protein [*Tetrahymena thermophila*] (NCBI Accession No. AAD41356); Heat shock protein 83-2 [*Leishmania infantum*] (NCBI Accession No. CAD30507); Similar to Heat shock protein HSP 90-beta (HSP 84) [*Rattus novegicus*] (NCBI Accession No. XP_224384); Heat shock protein HSP 90-beta (HSP 84) (HSP 90) [*Homo sapiens*] (NCBI Accession No. P08238); Heat shock protein 84—mouse [*Mus musculus*(house mouse)] (NCBI Accession No. HHMS84); Heat shock protein 90-beta [validated]—human [*Homo sapiens*] (NCBI Accession No. HHHU84); Heat shock protein 90 kD [*Homo sapiens*] (NCBI Accession No. 1307197A); Heat shock protein HSP 90-beta (HSP 84) [*Equus caballus* (horse)] (NCBI Accession No. Q9GKX8); Hypothetical protein DKFZp761K0511.1—human [*Homo sapiens*] (NCBI Accession No. T46243); Heat shock protein HSP 90-alpha (HSP 86) [*Homo sapiens*] (NCBI Accession No. P07900); Heat shock protein 90-alpha—human [*Homo sapiens*] (NCBI Accession No. HHHU86); 86K heat shock protein IV—human (fragment) [*Homo sapiens*] (NCBI Accession No. JQ0129); Human Hsp90 Geldanamycin-Binding Domain, 'closed' Conformation [*Homo sapiens*] (NCBI Accession No. 1YER); Human Hsp90 Geldanamycin-Binding Domain, 'open' Conformation [*Homo sapiens*] (NCBI Accession No. 1YES); Geldanamycin Bound To The Hsp90 Geldanamycin-Binding Domain [*Homo sapiens*] (NCBI Accession No. 1YET); Chain A, Hsp90 N-Terminal Domain Bound To Adp-Mg [*Homo sapiens*] (NCBI Accession No. 1BYQA); HSP90—mouse (fragment) [*Mus* sp.] (NCBI Accession No. 157523); Heat shock protein 90 beta—zebra fish [*Danio rerio*] (NCBI Accession No. JC2344); Heat shock protein 90 alpha—zebra fish [*Danio rerio*] (NCBI Accession No. JC2343); Heat shock protein 90—bovine (fragments) [*Bos taurus*] (NCBI Accession No. PC2185); Heat shock protein 84 homolog, brain-specific—rat (fragment) [*Rattus novegicus*] (NCBI Accession No. A61052); Ca2+/calmodulin-dependent protein kinase (EC 2.7.1.123) 111, eEF-2 specific—rabbit (fragments) [*Oryctolagus cuniculus*] (NCBI Accession No. A41163); hsp 84 homolog {internal fragment} [rats, A1 embryo fibroblast cell line, Peptide Partial, 24 aa, segment 2 of 3] [*Rattus* sp.] (NCBI Accession No. AAB47167); Heat shock protein, 90K—bovine (fragment) [*Bos taurus*] (NCBI Accession No. S13268); Heat shock 90K protein—bovine (fragments) [*Bos taurus*] (NCBI Accession No. A27683); Heat shock protein HSP 90-alpha [*Oryctolagus cuniculus*] (NCBI Accession No. P30946); Heat shock protein 90—rat (fragment) [*Rattus novegicus*] (NCBI Accession No. S71306); hsp 84 homolog {internal fragment} [rats, A1 embryo fibroblast cell line, Peptide Partial, 15 aa, segment 1 of 3] [*Rattus* sp.] (NCBI Accession No. AAB47165).

H. Nucleotide Sequences Encoding for Heat Shock Protein Related Apoptosis Inducing Proteins (HSPRAIPs)

Non-limiting examples of nucleotide sequences which encode for HSPRAIPs include *Homo sapiens*heat shock 90 kDa protein 1, beta (HSPCB), mRNA [*Homo sapiens*] (SEQ ID NO. 39) (NCBI Accession No. NM_007355); Human 90 kD heat shock protein gene, complete cds [*Homo sapiens*] (NCBI Accession No. J04988); *Homo sapiens*, clone MGC: 10493 IMAGE:3621040, mRNA, complete cds [*Homo sapiens*] (NCBI Accession No. BC004928); *Homo sapiens*, clone MGC:3483 IMAGE:3530042, mRNA, complete cds [*Homo sapiens*] (NCBI Accession No. BC012807); *Homo sapiens*, clone MGC:23206 IMAGE:4870198, mRNA, complete cds *Homo sapiens*] (NCBI Accession No. BC014485); *Homo sapiens*, clone MGC: 1138 IMAGE:2987963, mRNA, complete cds [*Homo sapiens*] (NCBI Accession. No. BC016753); *Rattus novegicus*similar to heat shock protein 84—mouse (LOC301252), mRNA [*Rattus novegicus*] (NCBI Accession No. XM_217339); Human 90-kDa heat-shock protein gene, cDNA, complete [*Homo sapiens*] (NCBI Accession No. M16660); *Equus caballus* Hsp90beta mRNA for heat shock protein 90 beta, partial cds [*Equus caballus*] (NCBI Accession No. AB043676); *Homo sapiens*mRNA; cDNA DKFZp761K0511 (from clone DKFZp761K0511); partial cds [*Homo sapiens*] (NCBI Accession No. AL136543); *Homo sapiens* isolate Liv chaperone protein HSP90 beta (HSP90BETA) mRNA, complete cds [*Homo sapiens*] (NCBI Accession No. AF275719); *Homo sapiens*, heat shock 90 kD protein 1, beta, clone MGC:16067 IMAGE:3615632, mRNA, complete cds. [*Homo sapiens*] (NCBI Accession No. BC009206); *Homo sapiens*Hsp89-alpha-delta-N mRNA, complete cds [*Homo sapiens*] (NCBI Accession No. AF028832); *Homo sapiens*, clone MGC:30059 IMAGE: 4404328, mRNA, complete cds [*Homo sapiens*] (NCBI Accession No. BC023006); Human mRNA for 90-kDa heat-shock protein [*Homo sapiens*] (NCBI Accession No. X15183); *Homo sapiens* heat shock 90 kDa protein 1, alpha (HSPCA), mRNA [*Homo sapiens*] (NCBI Accession No. NM_005348); *Homo sapiens* heat shock protein (HSP89-alpha) gene, complete cds [*Homo sapiens*] (NCBI Accession No. M27024); *Homo sapiens*, clone IMAGE:3446372, mRNA, partial cds [*Homo sapiens*] (NCBI Accession No. BC000987); *Homo sapiens*, Similar to heat shock 90 kD protein 1, alpha, clone IMAGE:3030617, mRNA, partial cds [*Homo sapiens*] (NCBI Accession No. BC007989); *Mus musculus*, similar to heat shock protein 84, clone IMAGE: 3588159, mRNA, partial cds [*Mus musculus*] (NCBI Accession No. BC044888); *Homo sapiens*cDNA: FLJ21717 fis, clone COL10322 [*Homo sapiens*] (NCBI Accession No. AK025370); Human full-length cDNA clone CSOCAP007YF18 of Thymus of *Homo sapiens*(human) [*Homo sapiens*] (NCBI Accession No. BX247955); *Homo sapiens*heat shock 90 kDa protein 1, alpha-like 3 (HSP- CAL3), mRNA [*Homo sapiens*] (NCBI Accession No. XM_084514); *Bos taurus* partial mRNA for heat shock protein 90 beta (hsp90 beta gene) [*Bos taurus* (cow)] (NCBI Accession No. AJ308989); *Rattus novegicus* similar to heat shock protein 84—mouse (LOC314117), mRNA [*Rattus novegicus*] (NCBI Accession No. XM_234134); *Homo sapiens* similar to Heat shock protein HSP 90-beta (HSP 84) (HSP 90) (LOC220763), mRNA [*Homo sapiens*] (NCBI Accession No. XM_055551); *Coturnix japonica*heat shock protein 90 alpha mRNA, partial cds [*Coturnix japonica*] (NCBI Accession No. AF473560); Human mRNA for heat shock protein hsp86 [*Homo sapiens*] (NCBI Accession No. X07270); Human heat shock protein 86 (HSP86) gene, exons 2-6 [*Homo sapiens*] (NCBI Accession No. M30626); *Mus musculus* 2 days neonate thymus thymic cells cDNA, RIKEN full-length enriched library, clone:E430034E15 product:heat shock protein, 86 kDa 1, full insert sequence [*Mus musculus* (house mouse)] (NCBI Accession No. AK088975); *Rattus novegicus* similar to heat shock protein 86 [*Rattus novegicus*] (LOC297852), mRNA (NCBI Accession No. XM_216334); Human heat shock protein 86 mRNA, 5'end [*Homo sapiens*] (NCBI Accession No. M30627); *Mus musculus*similar to heat shock protein 84—mouse (LOC207908), mRNA (NCBI Accession No. XM_138010); *Anopheles gambiae* str. PEST CRA_x9P1GAV591D, whole genome shotgun sequence [*Anopheles gambiae* str. PEST] (NCBI Accession No. AAAB01008807); *Rattus novegicus* similar to heat-shock protein hsp84 (LOC295614), mRNA [*Rattus novegicus*] (NCBI Accession No. XM_215734); *Mus musculus* similar to heat shock protein 84—mouse (LOC194839),mRNA [*Mus musculus*] (NCBI Accession No. XM_111980); *Cyprinus carpio* heat shock protein 90 alpha mRNA, partial cds [*Cyprinus carpio*] (NCBI Accession No. AF170295); *Cyprinus carpio* stress protein HSP90-beta mRNA, partial cds [*Cyprinus carpio*] (NCBI Accession No.AF170296); HSP90=heat shock protein [mice, heart, mRNA Partial, 806 nt] [*Mus* sp.] (NCBI Accession No. S46109); *Rattus novegicus* similar to heat-shock protein hsp84 (LOC310888), mRNA (NCBI Accession No. XM_227737); *Scyliorhinus torazame* 90 kDa heat-shock protein (hsp90) mRNA, partial cds [*Scyliorhinus torazame*] (NCBI Accession No. AF306643); *Rattus novegicus*similar to heat-shock protein hsp84 (LOC310531),mRNA [*Rattus novegicus*] (NCBI Accession No. XM_227300); *Rattus novegicus* similar to heat shock protein 86 [*Rattus novegicus*] (LOC308623), mRNA ] (NCBI Accession No. XM_218659); Human heart mRNA for heat shock protein 90, partial cds [*Homo sapiens*] (NCBI Accession No. D87666); *Rattus norvegicus* similar to Heat shock protein HSP 90-beta (HSP 84) (LOC291871), mRNA [*Rattus novegicus*] (NCBI Accession No. XM_226259); *Rattus novegicus* similar to hypothetical protein DKFZp761K0511.1—human (LOC315845), mRNA [*Rattus novegicus*] (NCBI Accession No. XM_236446); *Mus musculus* similar to Heat shock protein HSP 90-beta (HSP 84) (LOC270366), mRNA [*Mus musculus*] (NCBI Accession No. XM_195404); Human full-length cDNA 5-PRIME end of clone CSODN005YI08 of Adult brain of *Homo sapiens* (human) [*Homo sapiens*] (NCBI Accession No. BX248761); *Mus musculus* strain BALB/c heat shock protein 84 (hsp84) mRNA, partial cds [*Mus musculus*] (NCBI Accession No. U89426); *Homo sapiens* DNA for heat shock protein beta, partial cds [*Homo sapiens*] (NCBI Accession No. D17804); *Xenopus laevis* heat shock protein 90 (Hsp90) gene, partial cds [*Xenopus laevis*] (NCBI Accession No. U42697); *Danio rerio* heat shock protein 90 (hsp90) gene, partial cds [*Danio rerio*] (NCBI Accession No. L35587); *Rattus novegicus* similar to heat-shock protein hsp84 (LOC301375), mRNA [*Rattus novegicus*] (NCBI Accession No. XM_217390); *Homo sapiens* similar to heat shock protein 86 [*Rattus novegicus*] (LOC128364), mRNA [*Homo sapiens*] (NCBI Accession No. XM_060949); *Danio rerio* heat shock protein 90 (hsp90) gene, partial cds [*Danio rerio*] (NCBI Accession No. L35586); *Meloidogyne arenaria* heat shock protein 90 gene, partial cds [*Meloidogyne arenaria*] (NCBI Accession No.AF457580); *Homo sapiens* similar to Heat shock protein HSP 90-beta (HSP 84) (LOC285288), mRNA [*Homo sapiens*] (NCBI Accession No. XM_210549); *Pratylenchus crenatus* heat shock protein 90 gene, partial cds [*Pratylenchus crenatus*] (NCBI Accession No. AF457582); *Meloidogyne incognita* hsp-90 (hsp-90) gene, partial cds [*Meloidogyne incognita*] (NCBI Accession No. AF459026); *Meloidogyne sasseri* heat shock protein 90 gene, partial cds [*Meloidogyne incognita*] (NCBI Accession No. AF457581); *Heterodera* sp. AAMS-2002 hsp-90 (hsp-90) gene, partial cds [*Heterodera* sp. AAMS-2002] (NCBI Accession No. AF459025); *Pratylenchus teres* isolate RTB heat shock protein 90 gene, partial cds [*Pratylenchus teres*] (NCBI Accession No. AF457584); *Bursaphelenchus xylophilus* heat shock protein 90 gene, partial cds [*Bursaphelenchus xylophilus*] (NCBI Accession No. AF457579); *Pratylenchus teres* isolate JK heat shock protein 90 gene, partial cds [*Pratylenchus teres*] (NCBI Accession No. AF457583); *Homo sapiens* similar to Heat shock protein HSP 90-beta (HSP 84) (LOC286192), mRNA [*Homo sapiens*] (NCBI Accession No. XM_210729); D6S182=90-kda heat shock protein beta HSP90 beta [human, Genomic,346 nt, segment 2 of 2] [*Homo sapiens*] (NCBI Accession No. S70561); *Heterodera glycines* strain TN5 heat shock protein hsp-90 (hsp90)gene, partial cds [*Heterodera glycines*] (NCBI Accession No. AF449487); *Heterodera glycines* strain TN8 heat shock protein hsp-90 (hsp90) gene, partial cds [*Heterodera glycines*] (NCBI Accession No. AF449489): *Heterodera glycines* strain OP50 heat shock protein hsp-90 (hsp90) gene, partial cds [*Heterodera glycines*] (NCBI Accession No. AF449485); *Heterodera glycines* strain TN7 heat shock protein hsp-90 gene, partial cds [*Heterodera glycines*] (NCBI Accession No. AF457464); *Heterodera glycines* strain TN6 heat shock protein hsp-90 (hsp90) gene, partial cds [*Heterodera glycines*] (NCBI Accession No. AF449488); *Heterodera glycines* strain OP25 heat shock protein hsp-90 gene, partial cds [*Heterodera glycines*] (NCBI Accession No. AF457463); *Heterodera glycines* strain NL1-RHp heat shock protein hsp-90 (hsp90) gene, partial cds [*Heterodera glycines*] (NCBI Accession No. AF449486); Mouse heat shock protein (Hsp86) gene, partial cds [*Mus musculus*] (NCBI Accession No. M57673); *Mus musculus* similar to Heat shock protein HSP 90-beta (HSP 84) (HSP 90) (LOC329532), mRNA [*Mus musculus*] (NCBI Accession No. XM_285390); Chicken hsp90 gene for 90 kDa-heat shock protein 5'-end [*Gallus gallus*] (NCBI Accession No. X15028); *Rattus novegicus* similar to Heat shock protein HSP 90-alpha (HSP 86) (LOC297539), mRNA [*Rattus norvegicus*] (NCBI Accession No. XM_216245); *Tetrahymena thermophila* strain CU428.1 hsp82 heat shock protein (HSP82) mRNA, partial cds [*Tetrahymena thermophila*] (NCBI Accession No. AF151113); *Leishmania infantum* hsp83-1 gene for heat shock protein 83-1 and hsp83-2 gene for heat shock protein 83-2 [*Leishmania infantum*] (NCBI Accession No. X87770); *Rattus novegicus* similar to Heat shock protein HSP 90-beta (HSP 84) (LOC290386), mRNA [*Rattus novegicus*] (NCBI Accession No. XM_224384).

The skilled artisan recognizes the presence of human and statistical error in sequencing nucleotides. Nucleotide sequences determined by automation are typically at least about 90% identical, more typically at least about 95% to at least about 99.9% identical to the actual nucleotide sequence of the sequenced nucleotide molecule. The actual sequence can be more precisely determined by other approaches including manual nucleotide sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The skilled artisan also recognizes that nucleotides encoding AIPs may include splice variants of the nucleotides described herein. See, for example Evans, P. and Kemp, J., "Exon/intron structure of the human transferrin receptor gene," Gene, 199: 123-31 (1997).

IV. Expression Vectors and Transfected Cells

The present invention also relates to vectors which include the isolated nucleotide molecules of the present invention, host cells which are genetically engineered with the recombinant vectors, and the production of AIP by recombinant techniques. AIP may be extracted from cultures of the below described transfected cells and used for the homogenous and heterogenous assays described herein. Alternatively, AIP can be synthesized for these assays using peptide synthetic techniques known in the art. Also, the below described expression vectors and transfected cells are useful for whole cell assays described herein.

The polynucleotides may be joined to a vector containing a selectable marker for propagation in a host. Generally, a plasmid vector is introduced in a precipitate, such as a calcium phosphate precipitate, or in a complex with a charged cationic lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs may include a translation initiating at the beginning and a termination codon (UAA, UGA or UAG) appropriately positioned at the end of the polypeptide to be translated.

As indicated, the expression vectors may include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Vectors which may be used in bacteria include pQE70, pQE60 and pQE-9, available from Qiagen; pBS vectors, Phagescript vectors, Bluescript vectors, pNH8A, pNH 16a, pNH 18A, pNH46A, available from Stratagene; and ptrc99a, pKK223-3, pKK233-3, pDR540, pRIT5 available from Pharmacia. Eukaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of nucleotides into the host cell can be affected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986). Methods of formulating nucleotides with compositions (e.g., lipids) to facilitate introduction of the nucleotide into the cell are disclosed in, for example, U.S. Pat. Nos. 4,897,355, 4,394,448, 4,235,871, 4,231,877, 4,224,179, 4,753,788, 4,673,567, 4,247,411, 4,814,270, 5,279,833, and 5,753,613; and in published U.S. patent application 2002/0086849. Other methods for transfecting cells which are useful for the present invention include those described in U.S. Pat. Nos. 5,547,932; 5,981,273; 6,022,735; 6,077,663; 6,274,322; and Published International Application No. WO 00/43494.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. An example of a fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof.

AIPs can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, or hydroxylapatite chromatography. High performance liquid chromatography ("HPLC") can also be employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

V. Homogenous and Heterogenous Screening Assays

One aspect of the present invention relates to a method of identifying AIP binding compounds using homogenous or heterogenous binding assays. This may be accomplished by using non-competitive binding assays, or assays in which test compounds compete with gambogic acid or GA-related compounds such as those described in U.S. Pat. No. 6,462,041, or the compounds described in this application, such as the GA-biotin conjugates in Example 1-6, GA-fluorescein conjugates in Example 7-11, GA-agarose in Example 12-13, and radioactive labeled GA analog in Example 14. Any method known to one of ordinary skill in the art that detects binding between a test compound and a protein or antibody may be used in the present invention. These assays may be radioassays, fluorescence polarization assays or other fluorescence techniques, or biotin-avidin based assays. Test compounds capable of binding to AIPs are candidates for activators of apoptosis. Test compounds may be capable of binding to AIPs as strongly or more strongly than gambogic acid or GA-related compounds.

Another aspect of the present invention relates to a method of identifying AIP binding compounds using antibodies to GA or GA-related compounds. Such a method relates to detecting binding between i) an antibody to gambogic acid or GA-related compounds and ii) a test compound. Because gambogic acid or GA-related compounds bind AIPs, an antibody which is specific for gambogic acid or GA-related compounds is likely to be specific for other compositions having the physical characteristics that afford AIP specific binding. Hence, antibodies can be used to screen chemical libraries for other compositions that bind AIPs and that activate apoptosis. In such assays, the antibody may give rise to a detectable signal upon binding a test compound. For example, the antibodies may be labeled with a fluorophore. Antibodies bound to a test compound may also be detected using radiolabels.

Assays for use in the present invention are preferably high throughput screening methods, capable of screening large numbers of compounds in a rapid fashion. This includes, for example, screening methods that use microbeads or plates having multiple wells.

A. Competitive and Non-Competitive Homogenous Binding Assays

Any homogeneous assay well known in the art can be used in the present invention to determine binding between test compounds of interest and an AIP. For example, radioassays, fluorescence polarization assays and time-resolved fluorescence assays may all be used. Where the AIP is labeled, the assay may be a non-competitive binding assay in which the ability of test compounds to bind the AIP is determined. Where GA or GA-related compounds are labeled, such as those described in Example 1-14 of this application, the assay may be a competitive binding assay where the ability of a test compound to displace the AIP-bound GA or GA-related compound is determined.

A homogeneous binding assay used in the present invention, and which uses fluorescence to detect the test compound/AIP binding, may employ fluorescently labeled gambogic acid or GA-related compounds, or fluorescently labeled AIP. Any method known to one of ordinary skill in the art can be used to link the fluorophore to gambogic acid, GA-related compound or polypeptide of interest. See, e.g., Richard P. Haugland, Molecular Probes: Handbook of Fluorescent Probes and Research Chemicals 1992-1994 (5th edit, 1994, Molecular Probes, Inc.).

Fluorescence Polarization (FP), first described by Perrin, *J. Phys. Rad.* 1:390-401 (1926), is based upon the finding that the emission of light by a fluorophore can be depolarized by a number of factors, the most predominant being rotational diffusion, or, in other words, the rate at which a molecule tumbles in solution. "Polarization" is the measurement of the average angular displacement of the fluorophore that occurs between the absorption and subsequent emission of a photon. This angular displacement of the fluorophore is, in turn, dependent upon the rate and extent of rotational diffusion during the lifetime of the excited state, which is influenced by the viscosity of the solution and the size and shape of the diffusing fluorescent species. If viscosity and temperature are held constant, the polarization is directly related to the molecular volume or size of the fluorophore. In addition, the polarization value is a dimensionless number (being a ratio of vertical and horizontal fluorescent intensities) and is not affected by the intensity of the fluorophore.

In fluorescent assays, light from a monochromatic source passes through a vertical polarizing filter to excite fluorescent molecules in a sample tube. Only those molecules that are orientated in the vertically polarized plane absorb light, become excited, and subsequently emit light. The emission light intensity is measured both parallel and perpendicular to the exciting light. The fraction of the original incident, vertical light intensity that is emitted in the horizontal plane is a measure of the amount of rotation that the fluorescently labeled AIP has undergone during the excited state, and therefore is a measure of its relative size. See, "Introduction to Fluorescence Polarization," Pan Vera Corp., Madison, Wis., Jun. 17, 1996. Other publications describing the fluorescence polarization technique include G. Weber, *Adv. Protein Chem.* 8:415-459 (1953); W. B. Dandilker, et al., *Immunochemistry* 10:219-227 (1973); and M. E. Jolley, *J. Anal. Toxicol.* 5:236-240 (1981); "Chapter 4—Introduction to Fluorescence Polarization, "the FPM-1™ Operators Manual, pp. 9-10, Jolley Consulting and Research, Inc. Grayslake, Ill.; Lynch, B. A., et al., *Anal. Biochem.* 247:77-82 (1997); Wei, A. P. and Herron, J. N., *Anal. Chem.* 65:3372-3377 (1993); and Kauvar, L. M, et al., *Chem. Biol.* 2:107-118 (1995).

The apparatus used in fluorescence polarization techniques are well known in the art. Examples of an apparatus used in fluorescence polarization are given in U.S. Pat. No. 6,482,601 B1; U.S. Pat. No. 6,455,861; U.S. Pat. No. 5,943,129; U.S. Pat. No. 4,699,512 and U.S. Pat. No. 4,548,499. Other specific examples of instruments for use in the invention include, but are limited to, the Sentry-FPO fluorescence polarization instrument (Diachemix Corp., Milwaukee, Wis.); the BEACON® 2000 fluorescence polarization instrument (PanVera, Madison, Wis.); the POLARSCAN® portable fluorescence polarization system (Associates of Cape Cod, Inc., Falmouth, Mass.); the VICTORS series instruments (PerkinElmer, Inc., Wellesley, Mass.); and the AFFINTY® and SYMMETRY® fluorescence systems (CRi, Inc., Wobom, Mass.).

One embodiment of the invention relates to a non-competitive fluorescent assay. Such an assay employs an AIP covalently attached to a fluorophore. Free AIP has higher fluorescence intensity than AIP bound to a test compound. Confer Hwang, et al., *Biochemistry* 31:11536-11545 (1992). Once the test compound/AIP complex is formed, it rotates and tumbles more slowly and has less fluorescence intensity. Confer "Introduction to Fluorescence Polarization," Pan Vera Corp., Madison, Wis., Jun. 17, 1996; Perrin, *J. Phys. Rad.* 1:390-401 (1926). Hence, when the test compound and an AIP bind, the fluorescence intensity of the labeled AIP decreases proportional to binding.

In this embodiment, a solution of the labeled AIP is prepared and its fluorescence polarization is measured. The AIP and the test compound are mixed together and the solution is allowed to reach equilibrium over some time period. The fluorescence of any test compound/AIP complex which forms is then measured. The decrease in fluorescence intensity is proportional to binding. The test compound binding may be compared to a baseline fluorescence intensity value determined for gambogic acid or GA-related compounds bound to AIP. Test compounds that bind to AIP are considered candidates for activators of apoptosis. The skilled artisan will recognize that a variety of parameters such as temperature, time, concentration and pH can be varied to study the binding between the test compound and an AIP.

The baseline fluorescence polarization value is determined by preparing labeled AIP and measuring its fluorescence polarization. Gambogic acid or a GA-related compound is mixed with labeled AIP and allowed to equilibrate for a sufficient time to form a complex between gambogic acid (or a GA-related compound) and AIP. The fluorescence polarization of the solution comprising the complex is measured. The relative change in the fluorescence polarization is the baseline value against which all other test compounds will be measured. A variety of parameters such as temperature, time, concentration and pH can be varied to develop a range of values for the change in fluorescence polarization under a variety of conditions.

In determining whether a test compound binds to an AIP strongly enough to be considered a candidate for inducing apoptosis, the change in fluorescence polarization between unbound and bound test compound is compared with the change in fluorescence polarization between unbound and bound gambogic acid or GA-related compounds. Test compounds that bind as strongly as or more strongly than gambogic acid or GA-related compounds are candidates for activators of apoptosis.

Competitive homogenous fluorescence assays can also be used in the present invention to find new candidates for activating apoptosis. Competitive assays are well known in the art and any method can be used in the present invention. For example, U.S. Pat. No. 6,511,815 B1 describes an assay for quantitating competitive binding of test compounds to proteins utilizing fluorescence polarization.

In this embodiment of the invention, gambogic acid or a GA-related compound is first labeled with a fluorophore. The labeled gambogic acid or GA-related compound is mixed with an AIP in a buffered solution. The mixture is allowed to equilibrate and the fluorescence polarization of the gambogic acid/AIP (or GA-related compound/AIP) complex is measured. The test compound is then introduced into the mixture and allowed to equilibrate. Where a given test compound effectively competes for an Alp binding site, the labeled gambogic acid (or labeled GA-related compound) will be displace and become free, labeled gambogic acid (or free, labeled GA-related compound). Because the fluorophore (covalently attached to the GA or GA-related compound) is no longer associated with the bulky AIP, it gives rise to a more intense fluorescence polarization signal. Accordingly, in this embodiment, increases in fluorescent signals are proportional to the ability of a test compound to bind AIP.

In the above assays, several components of the mixture can affect the fluorescence intensity other than the labeled moiety. The polarity of the solvent and non-specific binding molecules can have significant affects on the intensity, which can be incorrectly interpreted. Therefore, an alternative assay for determining test compound/AIP binding for use in the present invention relies on time-resolved fluorescence techniques, which minimizes the above problems. The method of time-resolved fluorescence is described in detail in I. Hemmilä, et al., "High Throughput Screening. The Discovery of Bioactive Substances," Chapter 20, J. P. Devlin, ed., Marcel Dekker, Inc., New York (1997). The excited state lifetime of the test compound/AIP complex is longer than that for the impurities and other components that add background fluorescence. Therefore, the solution comprising the test compound/AIP complex mixture may be illuminated and after a short period of time on the order of nano to micro seconds, the solution fluorescence is measured.

In one embodiment of a time-resolved competitive fluorescence based homogeneous assay for use in the present invention, the fluorescent signal is generated when an AIP and GA (or GA-related compound) bind. In this embodiment, either the AIP or GA (or GA-related compound) is covalently bound to an energy donating Eu-cryptate having a long-lived fluorescent excited state. The other is attached to an energy-accepting protein, allophycocyanin, having a short fluorescent excited state. Energy transfer occurs between the Eu-cryptate and the allphycocyanin when they are less than 7 rum apart. During the assay, the Eu-cryptate is excited by a pulsed laser, and its fluorescent emission continually re-excites the allophycocyanin, whose fluorescence is measured by a time resolved fluorescence reader. Confer A. J.

Kolb, et al., "High Throughput Screening. The Discovery of Bioactive Substances," Chapter 19, J. P. Devlin, ed., Marcel Dekker, Inc., New York (1997).

In this embodiment of a time-resolved competitive fluorescence based homogeneous assay, the AIP and GA (or GA-related compound) attached to the Eu-cryptate or allophycocyanin are mixed together and allowed to equilibrate. Once equilibrated, the fluorescence intensity is measured. The test compound is then introduced into the mixture and allowed to equilibrate.

Where a given test compound effectively competes for an AIP binding site, the labeled gambogic acid (or labeled GA-related compound) will be displaced and the Eu-cryptate and allophycocyanin will no longer be less than 7 nm apart. Accordingly, the fluorescence intensity will decrease. Hence, in this embodiment, decreases in fluorescent signals is proportional to the ability of a test compound to bind an AIP.

Alternative homogeneous assays for use in the invention include those described in U.S. Pat. Nos. 6,492,128 B1; 6,406,913 B1; 6,326,459 B1; 5,928,862; 5,876,946; 5,612,221; 5,556,758.

The skilled artisan will recognize that radiolabels can also be used in homogenous competitive binding assays. In such assays, GA (or GA-related compound) is radiolabeled and allowed to equilibrate with an AIP in solution. Then, a test compound is introduced into the solution and allowed to equilibrate. The AIP (bound either to radiolabeled GA (or GA-related compound) or to the test compound) is then separated from unbound GA (or GA-related compound) and unbound test compound. Where a test compound is a poor AIP binder, most of the AIP will be bound to radiolabeled GA (or GA-related compound) and this can be detected by a scintillation counter, photoradiography, or other techniques well known in the art. If, however, the test compound is a strong AIP binder and displaces radiolabeled GA (or GA-related compound), then most of the AIP will not be bound to radiolabeled GA (or GA-related compound). Hence, ability of a test compound to bind an AIP is inversely proportional to the amount of radiolabel detected with the AIP.

B. Competitive Heterogenous Binding Assays

Detection of the test compound binding to ASP may also be accomplished using heterogeneous assays. Heterogeneous assays for use in the present invention may be based on radioassays, fluorescence-based assays and biotin-avidin based assays. In heterogenous assays, a first component is attached to a solid phase such as a bead or other solid substrate and one or more additional components are in solution. For example, an AIP may be bound to a bead or other solid substrate and labeled GA (or GA-related compound) is introduced as a solution. The label may be a radiolabel, chemiluminescent label, fluorescent label, chromogenic label, or other label well known in the art. After the mixture equilibrates and the GA/AIP complexes (or GA-related compound/

AIP complexes) form, a solution of test compound is introduced and allowed to equilibrate to form test compound/AIP complexes. The beads or solid components are separated from the solutions. This can be done, for example, using magnetic fields where the beads are magnetic. Alternatively, where an AIP is bound to a solid substrate, separation can occur simply by rinsing the solid substrate with water or a buffer to remove any solution containing unbound labeled GA (or labeled GA-related compound) or unbound test compound. The extent to which an AIP remains associated with the detectably labeled GA (or labeled GA-related compound) is measured. Such measurements can be performed while the AIP remains bound to the bead or solid substrate. Alternatively, such measurements can be made after the AIP has been removed from the bead or solid substrate. In such competitive binding assays, decreases in signal associated with the detectable label are proportionally related to increases in the ability of test compounds to bind the AIP by displacing GA (or GA-related compounds).

The skilled artisan recognizes that the GA or GA-related compound may also be the component bound to the beads or solid substrate. In such assays, labeled AIP is introduced as a solution and allowed to equilibrate forming the GA/AIP complexes (or GA-related compound/AIP complexes). The label may be a radiolabel, chemiluminescent label, fluorescent label, chromogenic label, or other label well known in the art. Then, a test compound is added as a solution. If a test compound displaces GA (or a GA-related compound), then the AIP will fall back into solution and not be bound to the bead or solid substrate through GA (or the GA-related compound). As described above, the beads or solid substrate are removed from the solution but the solution is retained to measure the extent of the detectable label. Here, increases in signal associated with the detectable label are proportional to the ability of a test compound to bind AIP.

Solid phase supports for use in the present invention include any insoluble support known in the art that is capable of binding an AIP or gambogic acid or GA-related compounds. This includes, for example, glass and natural and synthetic polymers such as agaroses, polystyrene, polypropylene, polyethylene, dextran, nylon, amylases, natural and modified celluloses, polyacrylamides, and magnetite. The support material may have virtually any possible structural configuration so long as the support-bound molecule is capable of binding to a test compound, GA (or GA-related compound) or to the AIP. Thus, the support configuration may be spherical, as in a bead, or cylindrical, as in the inside surface of a test tube, or the external surface of a rod, or hemishperical surface such as the well of a microtitre plate. Alternatively, the surface may be flat such as a sheet, test strip, etc. Those skilled in the art will note many other suitable carriers for binding gambogic acid (or GA-related compounds) or the AIP, or will be able to ascertain the same by use of routine experimentation.

An example of a heterogeneous assay for use in the present invention is the radioassay. A good description of a radioassay may be found in Laboratory Techniques and Biochemistry in Molecular Biology, by Work, T. S., et al., North Holland Publishing Company, NY (1978), with particular reference to the chapter entitled "An Introduction to Radioimmune Assay and Related Techniques" by Chard, T. Examples of other competitive radioassays are given in U.S. Pat. Nos. 3,937,799; 4,102,455; 4,333,918 and 6,071,705. Inherent in such assays is the need to separate the bead or substrate bound component from the solution component. Various ways of accomplishing the required separation have been developed, including those exemplified in U.S. Pat. Nos. 3,505,019; 3,555,143; 3,646,346; 3,720,760; and 3,793,445. The skilled artisan will recognize that separation can include filtering, centrifuging, washing, or draining the solid substrate to insure efficient separation of the substrate bound and solution phases.

The radioactive isotope or radiolabel can be detected by such means as the use of a gamma counter or a scintillation counter or by audioradiography. Isotopes which are particularly useful for the purpose of the present invention are: $^{3}$H, $^{123}$I, $^{125}$I, $^{131}$I, $^{35}$S, $^{31}$P, $^{14}$C, $^{111}$In, $^{97}$Ru, $^{67}$Cu, $^{67}$Ga, $^{68}$Ga, $^{72}$As, $^{89}$Zr and $^{201}$Tl. Those of ordinary skill in the art will know of other suitable labels, which may be employed in accordance with the present invention. The binding of these labeled AIP, GA or GA-related compounds can be accomplished using standard techniques commonly known to those of ordinary skill in the art. Typical techniques are described by Kennedy, J. H., et al. (Clin. Chim. Acta 70:1-31 (1976)), and Schurs, A. H. W. M., et al. (Clin. Chim. Acta 81:1-40 (1977)). In a particular embodiment, one or more hydrogen and/or carbon atoms of the AIP, gambogic acid or GA-related compounds are replaced by $^{3}$H and $^{14}$C, by methods well known in the art.

In one embodiment of the invention, the AIP is attached to a solid support. Radiolabeled gambogic acid or a GA-related compound is prepared. The bound AIP is admixed with the solution comprising radiolabeled gambogic acid or GA-related compound. The mixture is allowed to equilibrate for a time period. A test compound is added to the mixture and allowed to equilibrate for some time period. The test compound competes for the binding site of the AIP with the radiolabeled gambogic acid (or radiolabeled GA-related compound). The solid support that has bound AIP is removed from the mixture. The amount of radiolabel associated with the AIP is measured. Decreases in the amount of radiolabel are proportional to the ability of a test compound to displace GA (or the GA-related compound) and bind the AIP. Alternatively, the radiation of the solution comprising unbound and uncomplexed radiolabeled gambogic acid (or GA-related compound) can be measured. Using this assay, test compounds that bind to the AIP receptor as strongly or more strongly than gambogic acid or GA-related compounds can easily be discovered.

Alternative labels for use in the heterogeneous assays of the present invention include chemiluminescent labels, such as those described in U.S. Pat. No. 4,380,580; and enzyme substrate labels, such as those assays described in U.S. Pat. No. 4,492,751. For example, a fluorescent label may be used.

In these competitive fluorescence-based heterogeneous assays, a solution of fluorescently labeled gambogic acid or a GA-related compound is prepared. An AIP is attached to a solid support. The bound AIP is admixed with the solution comprising fluorescently labeled gambogic acid (or a fluorescently labeled GA-related compound). The mixture is allowed to equilibrate for a time period. A test compound is added to the mixture and the mixture is allowed to equilibrate for some time period. The test compound competes for the binding receptor of the AIP with fluorescently labeled gambogic acid (or a fluorescently labeled GA-related compound). The solid support that has bound the AIP is removed from the mixture. The amount of fluorescence associated with the AIP attributed to the fluorescent label is measured. Decreases in the amount of this fluorescence are proportional to the ability of a test compound to displace GA (or the GA-related compound) and bind the AIP. Alternatively, the fluorescence of the solution comprising unbound and uncomplexed fluorescently labeled gambogic acid (or GA-related compound) can be measured. Using this assay, test compounds that bind to AIP receptors as strongly or more strongly than gambogic acid or GA-related compounds can easily be discovered.

An alternative heterogeneous assay for use in the present invention is a biotin/avidin based assay. For examples of the various ways in which this assay can be performed in the present invention, see, e.g., Blake, R. C., et al. *Anal. Biochem.* 272:123-134 (1999); Cho, H. C., et al. *Anal. Sciences* 15:343-347 (1999); Choi, M. H., et al. *Bull. Korean Chem. Soc.* 22:417-420 (2001); U.S. Pat. No. 6,096,508; U.S. Pat. No. 4,863,876; and U.S. Pat. No. 4,228,237. In the present invention, avidin may be labeled with any label, preferably, avidin is fluorescently labeled or conjugated to an enzyme. Any detectably labeled enzyme can be used in the present invention. specific examples include, but are not limited to, horseradish peroxidase, alkaline phophatase, β-galactosidase and glucose oxidase.

One particular embodiment of the invention employs a competitive heterogeneous biotin-avidin assay. In this assay, the test compound competes with gambogic acid (or a GA-related compound) for the AIP binding sites. Here, biotinylated gambogic acid (or GA-related compound) is prepared. An AIP bound to solid support is admixed with the biotinylated gambogic acid (or GA-related compound) and incubated for some defined period of time. Gambogic acid or GA-related compound binds to AIP and forms a complex on the solid support. The solid support comprising biotinylated gambogic acid/AIP complexes (or GA-related compound/AIP complexes) is then admixed with a solution comprising the test compound. The mixture is allowed to incubate for some defined period of time. The test compound competes for AIP binding sites. The solid phase is then separated from any solutions containing unbound biotinylated GA (or biotinylated GA-related compound) or unbound test compound, and washed. The solid phase is then admixed with a composition comprising labeled avidin. The avidin binds only to the biotinylated gambogic acid (or biotinylated GA-related compound). The mixture is allowed to incubate for some defined period of time, and the amount of biotin-avidin complex is measured. The decrease in amount of biotin-avidin complex is directly related to the increase in test compound binding. Test compounds that bind AIPs are candidates as apoptosis inducers.

The skilled artisan recognizes that in all of the heterogenous competitive assays described above, the ability of a test compound to effectively compete with GA (or GA-related compound) to bind to the AIP can be ascertained by using base line values. For example, a given assay may be done with labeled GA (or GA-related compound). The amount of signal associated with that label found in the labeled GA (or GA-related compound) bound AIP component can be determined to give a base line value. Then, the test compound may be introduced and a second measurement of the signal attributable to the detectable label is taken which can be compared to the base line value. The extent to which the test compound decreases the base line value is a function of the ability of the test compound to bind AIP.

C. Assays Using Gambogic Acid or GA-Related Compound Specific Antibodies

In another aspect of the invention, new candidate drugs that induce apoptosis may be identified by assaying for binding between test compounds of interest and antibodies raised against gambogic acid or a GA-related compound.

Antibodies to gambogic acid and GA-related compounds may be generated and purified using conventional, well-known methods. Such methods are described for example, in Cohler & Milstein, Nature, 256, pp. 495-497 (1975); "Antibodies-A Laboratory Manual", E. Harlow & D. Lane, Cold-spring Harbor Laboratory, pp. 55-144 (1988); C. Williams & M. Chase, in "Methods in Immunology & Immunochemistry," Academic Press, New York, Vol. 1, Chap. 3, (1967); and S. Burchiel, in "Methods in Enzymology," Vol. 121, Chap. 57, pp. 596-615, Academic Press, New York (1986). In general, an immunogen comprising gambogic acid or a GA-related compound is administered to an animal in order to elicit an immune response against the immunogen. Polyclonal antibodies generated against the immunogen are obtained from the animal antisera and are then purified using well-known methods. Monoclonal antibodies against the immunogen can be obtained from hybridoma cells using well-known methods.

Suitable immunogens for raising polyclonal antibodies include, but are not limited to, bioconjugates of gambogic acid and GA-related compounds. Examples of bioconjugates include, but are not limited to, conjugates between gambogic acid and GA-related and any biological molecule, such as proteins, growth factors and cytokines. Examples include, but are not limited to proteins such as bovine hemoglobin; bovine serum albumin; growth factors such as DGF and NGF; and cytokines such as IL-2 and IL-4.

Bioconjugates are prepared by any method known to one of ordinary skill in the art. See for example, F. J. Burrows and P. E. Thorpe, "Eradication of large solid tumors in mice with an immunotoxin directed against tumor vasculature," *Proc. Natl. Acad. Sci. USA* 90:8996-9000 (1993); M. Adamczyk, et al., "Characterization of Protein-Hapten Conjugates. 2. Electrospray Mass Spectrometry of Bovine Serum Albumin-Hapten Conjugates," *Bioconjugate Chem.* 7:475-481 (1996); R. B. Greenwald, et al., "PEG Thiazolidiine-2-thione, a Novel Reagent for Facile Protein Modification: Conjugation of Bovine Hemoglobin," *Bioconjugate Chem.* 7:638-641 (1996); U.S. Pat. Nos. 6,482,601 and 6,462,041; Maragos, C. M., Bennett, G. A., Richard, J. L., *Food & Agricultural Immunology* 9:3-12 (1997) and Azcona-Olivera, J. I., Abouzied, M. M., Plattner, R. D., Norred, W. P., Pestka, J. J., *Appl. & Environ. Microbiol* 58:169-173 (1992). The above immunogens or bioconjugates are illustrative examples only, and any protein or polyamino acid may also be used as the carrier in a manner apparent to a person skilled in the art.

Sheep, goats and mice can be immunized with the above bioconjugates and antisera can be obtained by methods well known in the art. The antibodies may then be detectably labeled, e.g. with a radiolabel, fluorescence label, enzyme label, biotin, avidin or other label, as described above or according to methods well known in the art. Detection of binding between the test compounds of interest and the antibodies can be done by the homogenous or heterogenous methods as described above, or by any method known in the art.

VI. Cell-Based Assays

Another aspect of the present invention relates to a method of identifying AIP binding compounds using cells. Cells with altered (i.e., elevated or reduced) levels of AIP are useful for screening libraries of chemicals and compositions for AIP binding compounds that are apoptotic activating compounds which are potentially useful therapeutically as antineoplastic drugs. Such alteration can be afforded by a variety of techniques known in the art. Such techniques include antisense and RNAi methods, transfection of cells and alteration of the cellular genome.

Down regulated or reduced expression of an AIP can lead to cellular resistance to apoptosis. Such resistance is manifested, for example, in a cellular culture which is non-responsive to an apoptosis activating composition. Whereas an apoptosis activating composition normally activates the caspase cascade resulting in cell death, non-responsive cells continue to thrive in the presence of such compositions. In contrast, up regulated or elevated levels of an AIP may lead to cells which are more susceptible to apoptosis mediated by AIP binding compounds.

As described in greater detail below, cellular apoptosis can be monitored by following the growth rate of a cellular culture, microscopically examining cellular structure, or spectroscopically using reporter compounds. Cells with aberrant expression of an AIP can be mixed with test compounds. The affect of these test compounds is compared amongst cells with elevated, reduced or normal AIP levels to determine those compounds which bind AIP and activate apoptosis.

Another aspect of the invention relates to a complex, comprising: i) an AIP; and ii) an AIP binding compound; with the proviso that the AIP binding compound is not GA or a GA-related compound. In addition to the above described methods, the ability of a compound to bind an AIP may be determined by creating an FITC-tagged compound according to the examples described below. The AIP and bound FITC-tagged compound are isolated according to the examples described below.

A. Antisense Mediated Down Regulation of AIPs

The level of AIP expression can be down regulated through the use of antisense nucleotides. An antisense nucleotide is a nucleic acid molecule that interferes with the function of DNA and/or RNA. This may result in suppression of expression. Antisense oligonucleotides also include any natural or modified oligonucleotide or chemical entity that binds specifically to a pre-mRNA or mature mRNA which results in interference or inhibition with translation of the mature mRNA or prevents the synthesis of the polypeptide encoded by the mature mRNA.

Antisense RNA sequences have been described as naturally occurring biological inhibitors of gene expression in both prokaryotes (Mizuno, T., Chou, M-Y, and Inouye, M. (1984), Proc. Natl. Acad. Sci. USA 81, (1966-1970)) and eukaryotes (Heywood, S. M. Nucleic Acids Res. , 14, 6771-6772 (1986) and these sequences presumably function by hybridizing to complementary mRNA sequences, resulting in hybridization arrest of translation (Paterson, B. M., Roberts, B. E., and Kuff, E. L., (1977) Proc. Natl. Acad. Sci. USA, 74, 4370-4374. Antisense oligodeoxynucleotides are short synthetic nucleotide sequences formulated to be complementary to a specific gene or RNA message. Through the binding of these oligomers to a target DNA or mRNA sequence, transcription or translation of the gene can be selectively blocked and the disease process generated by that gene can be halted. The cytoplasmic location of mRNA provides a target considered to be readily accessible to antisense oligodeoxynucleotides entering the cell; hence much of the work in the field has focused on RNA as a target. Currently, the use of antisense oligodeoxynucleotides provides a useful tool for exploring regulation of gene expression in vitro and in tissue culture (Rothenberg, M., Johnson, G., Laughlin, C., Green, I., Craddock, J., Sarver, N., and Cohen, J. S.(1989) J. Natl. Cancer Inst., 81:1539-1544.

The concept behind antisense therapy relies on the ability of antisense oligonucleotides to be taken up by cells and form a stable heteroduplex with the target DNA or mRNA. The end result of antisense oligonucleotide hybridization is the down regulation of the targeted protein's synthesis. Down regulation of protein synthesis by antisense oligonucleotides has been postulated to result from two possible mechanisms: 1) "hybrid arrest," where direct blocking in pre-mRNA and/or mRNA of sequences important for processing or translation prevents full-length proteins from being synthesized; and 2) an RNase H mediated cleavage and subsequent degradation of the RNA portion of the RNA:DNA heteroduplex (Haeuptle, M. et al. (1986) Nuc. Acids Res. 14: 1427-1448; Minshull, J. and J. Hunt (1986) Nuc. Acids Res. 14: 6433-6451). Down regulation of a protein is functionally equivalent to a decrease in its activity. U.S. Pat. Nos. 5, 580,969; 5,585,479; and 5,596,090 describe antisense techniques which can be used in the down regulation of AIPs.

Antisense oligonucleotides include S-oligos (nucleoside phosphorothioates) which are isoelectronic analogs of an oligonucleotide (O-oligo) in which a nonbridging oxygen atom of the phosphate group is replaced by a sulfur atom. S-oligos may be prepared by treatment of the corresponding O-oligos with 3H-1,2-benzodithiol-3-one-1,1-dioxide which is a sulfur transfer reagent. See Iyer, R. P. et al., J. Org. Chem. 55:4693-4698 (1990); and Iyer, R. P. et al., J. Am. Chem. Soc. 112:1253-1254 (1990). Antisense oligonucleotides also include such derivatives as described in U.S. Pat. Nos. 6,031, 086, 5,929,226, 5,886,165, 5,693,773, 6,054,439, 5,919,772, 5,985,558, 5,595,096, 5,916,807, 5,885,970, 5,877,309, 5,681,944, 5,602,240, 5,596,091, 5,506,212, 5,521,302, 5,541,307, 5,510,476, 5,514,787, 5,543,507, 5,512,438, 5,510,239, 5,514,577, 5,519,134, 5,554,746, 5,276,019, 5,286,717, 5,264,423, as well as WO96/35706, WO96/32474, WO96/29337 (thiono triester modified antisense oligodeoxynucleotide phosphorothioates), WO94/17093 (oligonucleotide alkylphosphonates and alkylphosphothioates), WO94/08004 (oligonucleotide phosphothioates, methyl phosphates, phosphoramidates, dithioates, bridged phosphorothioates, bridge phosphoramidates, sulfones, sulfates, ketos, phosphate esters and phosphorobutylamines (van der Krol et al., Biotech. 6:958-976 (1988); Uhlmann et al., Chem. Rev. 90:542-585 (1990)), WO94/02499 (oligonucleotide alkylphosphonothioates and arylphosphonothioates), and WO92/20697 (3'-end capped oligonucleotides). Further, useful antisense oligonucleotides include derivatives such as S-oligonucleotides (phosphorothioate derivatives or S-oligos, see, Jack Cohen, Oligodeoxynucleotides, Antisense Inhibitors of Gene Expression, CRC Press (1989) which can be prepared, e.g., as described by Iyer et al. (J. Org. Chem. 55:4693-4698 (1990) and J. Am. Chem. Soc. 112:1253-1254 (1990)).

Antisense oligonucleotides may be coadministered with an agent which enhances the uptake of the antisense molecule by the cells. For example, the antisense oligonucleotide may be combined with a lipophilic cationic compound which may be in the form of liposomes. Methods of formulating antisense nucleotides with compositions to facilitate introduction of the antisense nucleotides into cells is disclosed, for example, in U.S. Pat. Nos. 4,897,355, 4,394,448, 4,235,871, 4,231,877, 4,224,179, 4,753,788, 4,673,567, 4,247,411, 4,814,270, 5,279,833, and 5,753,613; Published International Application Document WO 00/27795; and in published U.S. patent application 2002/0086849. Alternatively, the antisense oligonucleotide may be combined with a lipophilic carrier such as any one of a number of sterols including cholesterol, cholate and deoxycholic acid.

The antisense oligonucleotide may be conjugated to a peptide that is ingested by cells. Examples of useful peptides include peptide hormones, cell surface receptor ligands, antigens or antibodies, and peptide toxins. By choosing a peptide that is selectively taken up by the cells, specific delivery of the antisense agent may be effected. The antisense oligonucleotide may be covalently bound via the 5'H group by formation of an activated aminoalkyl derivative. The peptide of choice may then be covalently attached to the activated antisense oligonucleotide via an amino and sulfhydryl reactive hetero bifunctional reagent. The latter is bound to a cysteine residue present in the peptide. Upon exposure of cells to the antisense oligonucleotide bound to the peptide, the peptidyl antisense agent is endocytosed and the antisense oligonucleotide binds to the target AIP mRNA to inhibit translation. See PCT Application Publication No. PCT/US89/02363.

The antisense oligonucleotide may be at least a 15-mer that is complementary to a nucleotide molecule coding for an AIP as described herein. The antisense oligonucleotides of the present invention may be prepared according to any of the methods that are well known to those of ordinary skill in the art. The antisense oligonucleotides may be prepared by solid phase synthesis. See, Goodchild, J., Bioconjugate Chemistry, 1:165-167 (1990), for a review of the chemical synthesis of oligonucleotides. Alternatively, the antisense oligonucleotides can be obtained from a number of companies which specialize in the custom synthesis of oligonucleotides.

Methods within the scope of this invention include those wherein the antisense oligonucleotide is used in an amount which is effective to achieve inhibition of AIP expression in cells. Determination of effective amounts of each component is within the skill of the art.

B. RNA Interference (RNAi) Mediated Down Regulation of AIPs

Methods employing interfering RNA ("RNAi") use double stranded RNA that results in catalytic degradation of specific mRNAs, and can also be used to lower gene expression. See U.S. Pat. Nos. 6,458,382, 6,506,559 and 6,511,824. In this method, complementary sense and antisense RNAs derived from a portion of a gene of interest are synthesized in vitro using techniques well known in the art. The resulting sense and antisense RNAs are annealed in a buffer, and the double stranded RNA is introduced into the cell.

As described in U.S. Pat. No. 6,515,109, RNAi is the process of sequence-specific, post-transcriptional gene silencing in animals and plants, initiated by double-stranded RNA (dsRNA) that is homologous in sequence to the silenced gene. Methods relating to the use of RNAI to silence genes in C. elegans, Drosophila, plants, and mammals are known in the art (Fire A, et al., Nature 391:806-811 (1998); Fire, A., Trends Genet. 15:358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619, and Elbashir S M, et al., 2001 Nature 411:494-498). U.S. Pat. No. 6,511,824, also describes RNAi mediated loss-of-function phenotypes.

RNAi-mediated inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNAi-mediated inhibition in a cell line, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

RNAi mediated down regulation is affected by double stranded RNA sequences identical to a portion of the target. Accordingly, double strand RNA sequences comprise a first strand that encodes an AIP as described herein and a second strand complementary to the first strand. Alternatively, the double strand RNA comprises a first strand identical to the nucleotides described herein and a second strand complementary to the first strand. The skilled artisan recognizes that an RNA sequence is identical to a DNA sequence even though i) the ribose portion is not deoxyribose as in DNA, and ii) the nucleotide pyrimidine base thymine (usually found in DNA) is replaced by uracil. The double-stranded structure may also be formed by a single self-complementary RNA strand.

The double stranded RNA can have insertions, deletions, and single point mutations relative to the target sequence. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). In one embodiment there is more than 90% sequence identity, or even 100% sequence identity, between the inhibitory RNA and the portion of the target gene. Alternatively, the duplex region of the RNA may be defined functionally as a nucleotide sequence that is capable of hybridizing with a portion of the target gene transcript (e.g., 400 mM NaCi, 40 mM PIPES pH 6.4, 1 mM EDTA, 50° C. or 70° C. hybridization for 12-16 hours; followed by washing). The length of the identical nucleotide sequences may be at least 25, 30, 35, 40, 45, 50, 75, 100, 125, 150, 175, 200, 225, 250, 275, 300, 400, 500, 600, 700, 800, 900, 1000 or more bases. 100% sequence identity between the RNA and the target gene is not required. Thus the invention has the advantage of being able to tolerate sequence variations that might be expected due to genetic mutation, strain polymorphism, or evolutionary divergence.

The RNA may include modifications which are well known in the art to either the phosphate-sugar backbone or the nucleosides. For example, the phosphodiester linkages of natural RNA may be modified to include at least one of a nitrogen or sulfur heteroatom. Modifications in RNA structure may be tailored to allow specific genetic inhibition. Likewise, bases may be modified to block the activity of adenosine deaminase. RNA may be produced enzymatically or by partial/total organic synthesis, any modified ribonucleotide can be introduced by in vitro enzymatic or organic synthesis.

C. Altering AIP Expression Via Transfection

The skilled artisan will readily recognize that the expression level of AIPs can be increased using any of the techniques described above in section IV. Expression Vectors and Transfected Cells. Altering AIP expression via transfection can also be done according to the methods of U.S. Pat. Nos. 4,980,281; 5,266,464; 5,688,655 and 5,877,007.

Such methods involve the insertion of a polynucleotide sequence encoding an AIP into an appropriate vector and the generation of cell lines which contain either (1) the expression vector alone ("control" cell lines) or (2) the expression vector containing the inserted polynucleotide (e.g., cDNA) sequence encoding the AIP. Using the appropriate vector system, recipient cell lines, and growth conditions, test cell lines can thus be generated which stably overproduce the corresponding AIP. Under the appropriate growth conditions, these cell lines will exhibit a "graded cellular response" to activators of the AIP. A graded cellular response is an increase in the phenotypic change exhibited by the cell which becomes greater with increasing expression of the AIP. It is by this specialized response that activators of apoptosis via AIP binding can be distinguished from agents that act upon other cell metabolites to effect a phenotypic change. A screening system can thus be set up whereby the control and test cell lines are propagated in defined growth conditions in tissue culture dishes (or even in experimental animals) and large numbers of compounds (or crude substances which may contain active compounds) can be screened for their ability to bind AIP and activate apoptosis.

Substances which bind to one or more AIPs and activate apoptosis may affect characteristics such as growth rate, tumorigenic potential, anti-tumorigenic potential, anti-metastatic potential, cell morphology, antigen expression, and/or anchorage-independent growth capability. Substances which specifically bind one or more AIPs and activate apoptosis may be distinguished from substances which affect cell morphology or growth by other mechanisms in that they will have a greater effect on the test lines than on the control lines.

D. Altering AIP Expression at the Genomic Level

Another aspect of the present invention involves altering the level of AIP expression at the genomic level. A gene encoding an AIP is one that can be mutated to have aberrant expression, altered expression, modified expression, or misexpression due to gene mutations, or mutations upstream or downstream of the gene. Thus, a misexpressed protein may be one having an amino acid sequence that differs from wild-type (e.g. by amino acid substitution or deletion). These terms also include ectopic expression (e.g. by altering the normal spatial or temporal expression), over-expression (e.g. by multiple gene copies), under expression, and non-expression (e.g. by gene knockout or blocking expression that would otherwise normally occur, for example, by using antisense or RNA interference).

Such methods may involve operably associating an endogenous AIP encoded nucleotide sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of the endogenous AIP encoding nucleotide, flanking the promoter. The targeting sequence will be sufficiently near the 5' end of the AIP encoding nucleotide so the promoter will be operably linked to the endogenous sequence upon homologous recombination. The promoter and the targeting sequences can be amplified using PCR. The amplified promoter may contain distinct restriction enzyme sites on the 5' and 3' ends. The 3' end of the first targeting sequence may contain the same restriction enzyme site as the 5' end of the amplified promoter and the 5' end of the second targeting sequence may contain the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

As in the methods involving transfecting cells with AIP expression vectors, a graded cellular response is used to detect AIP binding agents which activate apoptosis. Specifically, the affect of a test compound on a test cell with a elevated or normal level of AIP expression is determined by comparison to the affect of a test compound on a control cell having respectively a normal or reduced level of AIP expression. As described above, test compounds which bind to an AIP and activate apoptosis may affect characteristics such as growth rate, tumorigenic potential, anti-tumorigenic potential, anti-metastatic potential, cell morphology, antigen expression, cell cycle and/or anchorage-independent growth capability. Substances which specifically bind an AIP and activate apoptosis may be distinguished from substances which affect cell morphology, cell cycle or growth by other mechanisms in that they will have a greater effect on the test lines than on the control lines.

E. Identifying Compounds That Activate the Caspase Cascade

The invention relates to a method for identifying potentially therapeutically effective antineoplastic compounds wherein a test compound is determined to have potential therapeutic efficacy if said caspase cascade activity is enhanced in response to the presence of said test compound, the method comprising (a) obtaining viable cultured eukaryotic cells expressing AIP (and optionally expresses a cancer phenotype) by culturing those cells in a cell growth medium under conditions which result in growth; (b) exposing the viable cultured cells to a test compound for a predetermined period of time at a predetermined temperature; (c) adding a reporter compound having at least one measurable property which is responsive to the caspase cascade; (d) measuring the caspase cascade activity of said exposed viable cultured cells by measuring said at least one measurable property of said reporter compound; and (e) wherein an increase in the measured caspase cascade activity in the presence of the test compound is an indication that the test compound is a potentially therapeutically effective antineoplastic compound.

In one embodiment, two populations of cells are screened in parallel. A first population expresses an elevated level of AIP relative to a second population. Where the first population of cells are cells that up regulate AIP, the second population of cells can be normal cells or cells which down regulate AIP (mediated, for example, by antisense nucleotides, RNAi, or altered genes). Where the first population of cells are normal cells, the second population of cells can be cells which down regulate AIP. The first and second population are separately exposed to the test compound and the reporter molecule which gives rise to a measurable property upon activation of the caspase cascade. Any increase in the reporter compound's measurable property in the first population relative to the second population is an indication that the test compound binds AIP, activates the caspase cascade, and is a potentially therapeutic antineoplastic compound.

The skilled artisan will recognize that cells with up regulated levels of AIP are expected to be more susceptible to apoptosis activated by a composition which binds to these polypeptides than are normal cells or cells which down regulate AIP. Likewise, the skilled artisan will recognize that normal cells are expected to be more susceptible to apoptosis activated by a composition which binds to these polypeptides than are cells with down regulated AIP. Hence, the first population of cells can be normal cells which neither up regulate or down regulate AIP and the second population of cells can be those which down regulate AIP.

In contrast to screening methodology using reporter compounds, the ability of a test compound to activate apoptosis can be monitored by microscopically observing changes in cellular morphology. As described in U.S. Pat. No. 6,274,309, cells can, in conjunction with the screening techniques described above, be assayed for apoptotic morphology using standard techniques well known to those of skill in the art. Among the characteristics of apoptotic morphology are cellular condensation, nuclear condensation, including chromatin condensation, and the apoptotic characteristic plasma membrane ruffling and blebbing referred to as "zeiosis" See Sanderson, C. J., 1982, in Mechanisms of Cell-Mediated Cytotoxicity, Clark, W. R. & Golstein, R., eds., Plenum Press, pp. 3-21; Godman, G. C. et al., 1075, J. Cell Biol. 64:644-667. For example, morphologic changes characteristic of nuclear apoptosis can be assayed and quantified by staining using a DNA-specific fluorochrome such as bis-benzimide (Hoechst-33258; Sigma according to standard methods. See Bose, et al., 1995, Cell 82:405-414.

As described by U. S. Pat. No. 5,932,418, DNA fragmentation is another morphological change indicative of apoptosis. DNA fragmentation may be detected with the terminal transferase assay (TUNEL; Thiry M., 1992, Highly sensitive immunodetection of DNA on sections with exogenous terminal deoxynucleotidyl transferase and non-isotopic nucleotide analogues; J. Histochem. *Cytochem.* 40:419-441; Gavrieli Y, Sherman Y and Ben-Sasson SA; 1992, Identification of programmed cell death in situ-via specific labeling of nuclear DNA fragmentation; *J. Cell Biol.* 119:493-501). The TUNEL assay is used to detect 3' OH termini of nicked or broken DNA strands. These nicks or breaks may be generated directly by activating apoptosis. In vivo, apoptosis can be assayed via, for example, DNA terminal transferase nick-end translation, or TUNEL assay, according to standard techniques. See Fuks, Z. et al., 1995, *Cancer J.* 1: 62-72.

Accordingly, the present invention relates to a screening method for identifying potentially therapeutically effective antineoplastic compounds by determining the ability of test compounds to alter cellular morphology in cultured eukaryotic cells expressing AIP wherein a test compound is determined to have potential therapeutic efficacy if the cellular morphology is altered in response to the presence of said test compound, the method comprising (a) obtaining cultured eukaryotic cells expressing AIP (and optionally expresses a cancer phenotype) by culturing those cells in a cell growth medium under conditions which result in growth; (b) exposing the viable cultured cells to a test compound for a predetermined period of time at a predetermined temperature; (c) microscopically examining the cellular morphology; and (d) wherein morphological changes indicative of apoptosis in the presence of the test compound is an indication that the test compound is a potentially therapeutically effective antineoplastic compound.

In another embodiment, two populations of cells are screened in parallel. A first population expresses an elevated level of AIP relative to a second population. Where the first population of cells are cells that up regulate AIP, the second population of cells can be normal cells or cells which down regulate AIP (mediated, for example, by antisense nucleotides, RNAi, or altered genes). Where the first population of cells are normal cells, the second population of cells can be cells which down regulate AIP. The first and second population are separately exposed to the test compound and the reporter molecule which gives rise to a measurable property upon activation of the caspase cascade. Any increase in the reporter compound's measurable property in the first population relative to the second population is an indication that the test compound binds AIP, activates the caspase cascade, and is a potentially therapeutic antineoplastic compound.

In contrast to screening methodology by microscopically observing changes in cellular morphology, the ability of a test compound to activate apoptosis can be monitored by following cellular culture growth. Such a screening method relates to a method of identifying potentially therapeutically effective antineoplastic compounds by determining the ability of test compounds to inhibit cellular culture growth in eukaryotic cells expressing an AIP wherein a test compound is determined to have potential therapeutic efficacy if the cellular culture growth is inhibited in response to the presence of said test compound, the method comprising (a) obtaining cultured eukaryotic cells expressing the AIP (and optionally expresses a cancer phenotype) by culturing those cells in a cell growth medium under conditions which result in growth; (b) exposing the cultured cells to a test compound for a predetermined period of time at a predetermined temperature; (c) following the rate of culture growth; and (d) wherein a decrease in culture growth rate in the presence of the test compound is an indication that the test compound is a potentially therapeutically effective antineoplastic compound.

In another embodiment, two populations of cells are screened in parallel. A first population expresses an elevated level of an AIP relative to a second population. Where the first population of cells are cells that up regulate the AIP, the second population of cells can be normal cells or cells which down regulate the AIP (mediated, for example, by antisense nucleotides, RNAi, or altered genes). Where the first population of cells are normal cells, the second population of cells can be cells which down regulate the AIP. The first and second population are separately exposed to the test compound and the reporter molecule which gives rise to a measurable property upon activation of the caspase cascade. Any increase in the reporter compound's measurable property in the first population relative to the second population is an indication that the test compound binds the AIP, activates the caspase cascade, and is a potentially therapeutic antineoplastic compound.

Any of the methodologies discussed in this section can be performed side-by-side with control cells. Hence, in respect to the above described method employing reporter compounds, the invention also relates to a method for assaying the potency of a potentially therapeutically effective antineoplastic compound that functions as an activator of the caspase cascade in viable cultured eukaryotic cells having an intact cell membrane and expressing an AIP comprising: (a) obtaining a first and a second population of viable cultured eukaryotic cells, each of which has an intact cell membrane and each of which expresses the AIP (and optionally expresses a cancer phenotype), by culturing said eukaryotic cells in a cell growth medium under conditions which result in growth; (b) exposing the first population to a predetermined amount of a test compound for a predetermined period of time at a predetermined temperature; (c) exposing the second population to an amount of solvent that was used to dissolve the test compound for the predetermined period of time at the predetermined temperature; (d) adding to said test compound-exposed first population and said solvent-exposed second population a reporter compound having at least one measurable property which is responsive to the caspase cascade; (e) measuring said at least one measurable property of said reporter compound in said test compound-exposed first population and thereby measuring the caspase cascade activity of the test compound-exposed first population; (f) measuring said at least one measurable property of said reporter compound in said solvent-exposed second population and thereby measuring the caspase cascade activity of the solvent-exposed second population; and (g) calculating the ratio of caspase cascade activity measured for the test compound-exposed first population of cells to the caspase cascade activity measured for the solvent-exposed second population of cells to determine the relative potency of the test compound as an activator of the caspase cascade. The skilled artisan will recognize that such side-by-side screening can be modified to accommodate the above described screening methodologies which utilize microscopic observations of changes in cellular morphology, cell cycle or observations of cellular culture growth rate. Because these modified assays do not follow caspase cascade activation, they do not require addition of a reporter compound.

The caspase cascade activity measured for test compounds by this method can also be compared to that measured for compounds which are known to affect enzymes involved in the apoptosis cascade to generate a measure of the relative effectiveness of the test substance. Compounds that can be used in comparison include known activators of enzymes involved in the apoptosis cascade. Known activators, either by direct or indirect mechanisms, of enzymes involved in the apoptosis cascade include but are not limited to vinblastine, etoposide (Yoon, H. J., et al., *Biochim. Biophys. Acta.* 1395: 110-120 (1998)) and doxorubicin (Gamen, S., et al., *FEBS Lett.* 417:360-364 (1997)) which are topoisomerase II inhibitors; cisplatin (Maldonado et al., *Mutat. Res.* 381:67-75 (1997)); chlorambucil (Hickman, J. A., *Cancer Metastasis Rev.* 11: 121-139 (1992)) which is an alkylating agent; and fluorouracil, an RNA/DNA anti-metabolite (Hickman, J. A., *Cancer Metastasis Rev.* 11: 121-139 (1992)).

In a preferred embodiment, a plurality of viable cultured cells are exposed separately to a plurality of test compounds, e.g. in separate wells of a microtiter plate. In this embodiment, a large number of test compounds may be screened at the same time.

In another aspect, the invention relates to a method for assaying the potency of a test compound to synergise with other cancer chemotherapeutic agents as an activator of the caspase cascade, comprising (a) obtaining a first and a second population of viable cultured eukaryotic cells, each of which has an intact cell membrane and expresses AIP (and optionally expresses a cancer phenotype), by culturing the cell populations in a cell growth medium under conditions which result in growth; (b) exposing the first population to a combination of a predetermined amount of a test compound and a subinducing amount of a known cancer chemotherapeutic agent for a first predetermined period of time at a first predetermined temperature; (c) exposing the second population to an equal amount of solvent, which was used to dissolve the test compound, and a subinducing amount of a known cancer chemotherapeutic agent for said first predetermined period of time at said first predetermined temperature; (d) adding a reporter compound to the exposed first population and to the exposed second population, the reporter compound having at least one measurable property which is responsive to the caspase cascade; (e) incubating the resulting mixture of the first population, the test compound, the known cancer chemotherapeutic agent and the reporter compound for a second predetermined time period at a second predetermined temperature; (f) incubating the resulting mixture of said second population, said solvent, said known chemotherapeutic agent, and said reporter compound for a second predetermined time period at a second predetermined temperature; (g) measuring said at least one measurable property of said reporter compound in said first resulting mixture and thereby measuring the caspase cascade activity of the first population in the first resulting mixture; (h) measuring said at least one measurable property of the reporter compound in the second resulting mixture and thereby measuring the caspase cascade activity of the second population in the second resulting mixture; and (i) calculating the ratio of the caspase cascade activity of the first resulting mixture to the caspase cascade activity of the second resulting mixture to determine whether said test compound acts synergistically with the known cancer chemotherapeutic agent. The skilled artisan will recognize that such side-by-side screening can be modified to accommodate the above described screening methodologies which utilize microscopic observations of changes in cellular morphology, cell cycle or observations of cellular culture growth rate. Because these modified assays do not follow caspase cascade activation, they do not require addition of a reporter compound.

The assays described in this section can also be used to screen for compositions that are selective for cell or tissue type. Such methodologies comprise side-by-side comparisons screening the affect of a given test compound on one cell or tissue type as compared to other cell or tissue types. In such an embodiment, cultures of each of the compared cell or tissue types comprise cells having elevated levels of expression of one or more AIPs. Hence, the invention also relates to a method for assaying the cell or tissue selectivity of a potentially therapeutically effective antineoplastic compound that functions as an activator of the caspase cascade in viable cultured eukaryotic cells having an intact cell membrane and expressing elevated levels of an AIP comprising: (a) obtaining a first population of viable cultured eukaryotic cells, each of which has an intact cell membrane and each of which expresses elevated levels of the AIP, by culturing said eukaryotic cells in a cell growth medium under conditions which result in growth; (b) obtaining a second population of viable cultured eukaryotic cells, each of which having an intact cell membrane and expressing elevated levels of the AIP by culturing said eukaryotic cells in a cell growth medium under conditions which result in growth; (c) separately exposing the first and second populations to a predetermined amount of a test compound for a predetermined period of time at a predetermined temperature; (d) adding to said first and second populations a reporter compound having at least one measurable property which is responsive to the caspase cascade; (e) measuring said at least one measurable property of said reporter compound in said first and second populations thereby measuring the caspase cascade activity of the first population relative to the second population; (f) calculating the ratio of caspase cascade activity measured for the first population of cells to the caspase cascade activity measured for the second population of cells to determine the relative cell or tissue type selectivity of the test compound as an activator of the caspase cascade, or the relative cell or tissue type selectivity of the test compound as an AIP binder. For example, the first population of cells can express a cancer phenotype that is not expressed in the second population of cells. Accordingly, this method may be used to identify compounds that while specific for cancerous cells, do not affect non-cancerous cells. The skilled artisan will recognize that such side-by-side screening can be modified to accommodate the above described screening methodologies which utilize microscopic observations of changes in cellular morphology, cell cycle or observations of changes in cellular culture growth rate. Because these modified assays do not follow caspase cascade activation, they do not require addition of a reporter compound.

The invention further relates to a method to further determine the specificity of anticancer agents by determining the ability of the agent to arrest the cell cycle during a particular phase prior to apoptosis. In this embodiment, a time course of test compound treatment determines the phase of the cell cycle arrest that precedes apoptosis. The G2M, S/G2M and G1 phases are the major phases in the cell cycle when one cell divides to become two daughter cells. The cycle starts from a resting quiescent cell (G0 phase) which is stimulated by growth factors leading to a decision (G1 phase) to replicate its DNA. Once the decision is made, the cell starts replicating its DNA (S-phase) and then into a G2 phase before finally dividing into two daughter cells. Cells which then undergo apoptosis contain fragmented DNA in amounts that are less that in the G1 phase and hence are called sub-G1. Thus, a compound leading to a G1 or G2M or S phase arrest and no apoptosis at 24 hr treatment, and leading to apoptosis at 48 hr treatment as determined by the presence of a sub-GI peak, indicates that the test compound arrest the cell cycle at the respective stage before inducing apoptosis. See Sherr, C. J., *Cancer Res.* 60:3689-3695 (2000), for a discussion of cancer cell cycles.

In another aspect, the invention relates to determining the specificity of a test compound by determining at what phase the cell cycle is arrested by the test compound prior to apoptosis. Determining the specificity of a test compound to arrest the cell cycle during a particular phase prior to apoptosis comprises (a) obtaining at least one population of viable cultured cancer cells having intact cell membranes which have an elevated level of an AIP from a cell growth medium under conditions conducive to growth; (b) combining the at least one population with a predetermined amount of at least one test compound dissolved in a solvent for a predetermined period of time at a predetermined temperature thereby generating a first volume; and (c) determining at what phase the cell cycle is arrested.

In this embodiment, the cells are incubated with a range of concentrations of test compound (e.g. 0.02 µM to 5 µM) for 6 h under normal growth conditions and control cultures are treated with DMSO vehicle. The cells are then treated e.g. for 20 min with 800 nM Syto 16. Cytospin preparations are then prepared and the samples are viewed by fluorescent microscopy using a fluorescein filter set. For each concentration of test compound, the number of mitotic figures are counted and expressed as a percentage of the total number of cells. Three fields from each condition are evaluated and the mean and SEM is calculated and plotted as a function of drug concentration. Another method is to simply stain the nuclei with Propidium Iodide and analyze the DNA content using a Fluorescence Activated Cell Sorter and Cell Quest Software (Becton Dickinson).

Reporter compounds, as described above, may be used as a means for measuring caspase cascade activity in the whole-cell assays of the present invention. Typical reporter compounds include fluorogenic, chromogenic or chemiluminescent compounds applied to cells or tissues containing cells at a concentration of about 0.01 nanomolar to about 0.1 molar, or an equivalent amount of a salt or prodrug thereof. A concentration of about 10 micromolar may be used.

The test compounds may be presented to the cells or cell lines dissolved in a solvent. Examples of solvents include, DMSO, water and/or buffers. DMSO may be used in an amount below 2%. Alternatively, DMSO may be used in an amount of 1% or below. At this concentration, DMSO functions as a solubilizer for the test compounds and not as a permeabilization agent. The amount of solvent tolerated by the cells must be checked initially by measuring cell viability or caspase induction with the different amounts of solvent alone to ensure that the amount of solvent has no effect on the cellular properties being measured.

Suitable buffers include cellular growth media, for example Iscove's media (Invitrogen Corporation) with or without 10% fetal bovine serum. Other known cellular incubation buffers include phosphate, PIPES or HEPES buffers. One of ordinary skill in the art can identify other suitable buffers with no more than routine experimentation.

The cells can be derived from any organ or organ system for which it is desirable to find a potentially therapeutically effective antineoplastic compound that functions as an activator of the caspase cascade in viable cultured eukaryotic cells having an intact cell membrane. Cellular genotypes for screening of test compounds include, but are not limited to, cells that are P53 negative, Bcl-2 over expressing, Bcl-xL over expressing, ataxia telengiectasia mutated (e.g. ATCC CRL 7201), multi-drug resistance (e.g. P-glycoprotein over expressing, ATCC CRL-1977), DNA mismatch repair deficiency (e.g., defects in hMSH2, hMSH3, hMSH6, hPMS2, or hPMS1), HL-60 cells (ATCC CCL-240), SH-SY5Y cells (ATCC CRL-2266), and Jurkat cells (ATCC TIB-152), surviving over expressing (e.g. ATCC CCL-185), bcr/abl mutated (eg ATCC CCL-243), p16 mutated, Brcal mutated (e.g. ATCC CRL-2336), or Brca2 mutated. These and other cells may be obtained from the American Type Culture Collection, Manassas, Va.

Suitable solubilizers may be used for presenting reporter compounds to cells or cell lines. Solubilizers include aqueous solutions of the test compounds in water-soluble form, for example as water-soluble salts. The test compounds may be dissolved in a buffer solution containing 20% sucrose (Sigma) 20 mM DTT (Sigma), 200 mM NaCl (Sigma), and 40 mM Na PIPES buffer pH 7.2 (Sigma).

Inasmuch as the caspase cascade takes place in the intracellular environment, measures may be undertaken to enhance transfer of the reporter compound across the cell membrane. This can be accomplished with a suitable permeabilization agent. Permeabilization agents include, but are not limited to, NP-40, n-octyl-O-D-glucopyranoside, n-octyl-O-D-thioglucopyranoside, taurocholic acid, digitonin, CHAPS, lysolecithin, dimethyldecylphosphine oxide (APO-10), dimethyldodecylphosphine oxide (APO-12), N,N-bis-(3-D-gluconamidopropyl)cholamide (Big Chap), N,N-bis-(3-D-gluconamidopropyl)deoxycholamide (Big Chap, deoxy), BRIG-35, hexaethyleneglycol (C10E6), C10E8, C12E6, C12E8, C12E9, cyclohexyl-n-ethyl-O-D-maltoside, cyclohexyl-n-hexyl-O-D-maltoside, cyclohexyl-n-methyl-O-D-maltoside, polyethylene glycol lauryl ether (Genapol C-100), polyethylene glycol dodecyl ether (Genapol X-80), polyoxyethylene isotridecyl ether (Genapol X-100), n-decanoylsucrose, n-decyl-O-D-glucopyranoside, n-decyl-O-D-maltopyranoside, n-decyl-O-D-thiomaltoside, n-dodecanoylsucrose, n-dodecyl-O-D-glucopyranoside, n-dodecyl-O-D-maltoside, n-heptyl-O-D-glucopyranoside, n-heptyl-O-D-thioglucopyranoside, n-hexyl-O-D-glucopyranoside, n-nonyl-O-D-glucopyranoside, n-octanoylsucrose, n-octyl-O-D-maltopyranoside, n-undecyl-O-D-maltoside, n-octanoyl-O-D-glucosylamine (NOGA), PLURONIC[7] F-127, and PLURONIC[7] F-68.

The cell lines are exposed to a predetermined amount of test compounds at concentrations in the range from about 1 picomolar to about 1 millimolar, or about 1-10 micromolar. The predetermined period of time may be about 1 minute to less than about 24 hours, or 1-24 hours, or 3, 5, or 24 hours. The predetermined temperature may be about 4° C. to about 50° C., or about 37° C.

F. Measuring the Potency of Caspase Cascade Activation

Using a fluorescent plate reader, an initial reading (T=0) is made immediately after addition of the reporter reagent solution, employing excitation and emission at an appropriate wavelength (preferably excitation at 485 nm and emission at 530 nm) to determine the background absorption and/or fluorescence of the control sample. After the incubation, the absorption and/or fluorescence of the sample is measured as above (e.g., at T=3 hr).

Sample Calculation:

The Relative Fluorescence Unit values (RFU) are used to calculate the potency of the test compounds as follows:

$RFU_{(T=3\ hr)} - RFU_{(T=0)} = \text{Net } RFU$

The potency of caspase cascade activation is determined by the ratio of the Net RFU value for a test compound to that of control samples as follows:

$$\frac{\text{Net } RFU \text{ of test compound}}{\text{Net } RFU \text{ of control sample}} = \text{Ratio}$$

Preferred test compounds are those indicating a ratio of 2 or greater and most preferably with a measured ratio greater than a statistically significant value calculated as (Ave Control $RFU + 4 \times SD_{Control}$)/(Ave Control RFU) for that run.

Examples of high throughput instrumentation which can be used according to the present invention are well known in the art. Non-limiting examples of such instruments include ImageTrak® (Packard BioScience), the FLIPR® system, SPECTRAMAX® Gemini or FMax (Molecular Devices Corporation, Sunnyvale, Calif.), VIPR™ II Reader (Aurora Biosciences Corporation, San Diego, Calif.), Fluoroskan II (GMI, Inc., Albertville, Minn.), FLUOROSKAN ASCENT® (Labsystems, Franklin, Mass.), CYTOFLUOR® or CYTOF-LUOR®4000 (Perkin Elmer Instruments), CYTOFLUOR® 2300 (Millipore, FLx800TBID, FLx800TBIDE, ELx808, ELx800, FL600 (Bio-Tek Instruments), Spectrafluora, Spectrofluora Plus, Ultra or Polarion (Tecan AG), MFX (Dynex Technologies, Chantilly, Va.), Fluoro Count (Packard Instruments Co.), NOVOstar, POLARstar Galaxy or FLUOstar Galaxy (BMG Lab Technologies GmbH), Fluorolite 1000 (Dynex Technologies), 1420 Victor 2 (EG&G Wallac, Inc., also available through PerkinElmer), and Twinkle LB 970 (Berthold Technologies GmbH & Co.).

VII. Diagnosis and Prognosis

It is believed that certain tissues in mammals with certain diseases (e.g. cancer or autoimmune diseases) express significantly altered (enhanced or decreased) levels of one or more AIPs and mRNA encoding AIP when compared to tissues of a corresponding "standard" mammal, i.e., a mammal of the same species not having the disease. Further, it is believed that altered levels of one or more AIP can be detected in certain body fluids (e.g., sera, plasma, urine, and spinal fluid) from mammals with the disease when compared to sera from mammals of the same species not having the disease. Thus, the invention provides a diagnostic method which involves assaying the expression level of a gene encoding a given AIP in mammalian cells or body fluid and comparing the gene expression level with the gene's standard expression level, whereby an increase or decrease in the gene expression level over the standard expression level is indicative of the disease. The gene's standard expression level can be an average level of expression as determined by measuring the expression level in a given population.

Where a diagnosis has already been made according to conventional methods, the present invention is useful as a prognostic indicator, whereby patients exhibiting lowered AIP gene expression will experience a worse clinical outcome in response to administration of an AIP binding compound relative to patients expressing AIP at a normal level.

By "assaying the expression level of a gene encoding a given AIP" is intended qualitatively or quantitatively measuring or estimating the level of AIP or the level of the mRNA encoding a given AIP in a first biological sample either directly (e.g., by determining or estimating absolute protein level or mRNA level) or relatively (e.g., by comparing to the AIP level or mRNA level in a second biological sample). The AIP level or mRNA level in the first biological sample may be measured or estimated and compared to a standard AIP level or mRNA level, the standard being taken from a second biological sample obtained from an individual not having the cancer, or population of individuals not having the cancer. As will be appreciated in the art, once a standard AIP level or mRNA level (for a particular AIP) is known, it can be used repeatedly as a standard for comparison.

By "biological sample" is intended any biological sample obtained from an individual, cell line, tissue culture, or other source which contains AIP or mRNA encoding AIP. Biological samples include mammalian body fluids (such as sera, plasma, urine, synovial fluid and spinal fluid) which contain secreted AIP, and ovarian, prostate, heart, placenta, pancreas liver, spleen, lung, breast and umbilical tissue.

Total cellular RNA can be isolated from a biological sample using the single-step guanidinium-thiocyanate-phenol-chloroform method described in Chomczynski and Sacchi, Anal. Biochem. 162:156-159 (1987). Levels of mRNA encoding AIP are then assayed using any appropriate method. These include Northern blot analysis, (Harada et al., Cell 63:303-312 (1990) S1 nuclease mapping, (Fijita et al., Cell 49:357-367 (1987)) the polymerase chain reaction (PCR), reverse transcription in combination with the polymerase chain reaction (RT-PCR) (Makino et al., Technique 2:295-301 (1990), and reverse transcription in combination with the ligase chain reaction (RT-LCR).

Assaying AIP levels in a biological sample can be done using antibody-based techniques. For example, AIP expression in tissues can be studied with classical immunohistological methods. (Jalkanen, M., et al., J. Cell. Biol. 101:976-985 (1985); Jalkanen, M., et al., J. Cell. Biol. 105:3087-3096 (1987)).

Other antibody-based methods useful for detecting AIP gene expression include immunoassays, such as the enzyme linked immunosorbent assay (ELISA) and the radioimmunoassay (RIA).

Suitable labels are known in the art and include enzyme labels, such as, Glucose oxidase, and radioisotopes, such as iodine ($^{125}I$, $^{121}I$, carbon ($^{14}C$), sulfur ($^{35}S$), tritium ($^3H$), indium ($^{112}In$), and technetium ($^{99}Tc$), and fluorescent labels, such as fluorescein and rhodamine, and biotin.

VIII. Rational Drug Design Using AIP Structure

As described in U.S. Pat. No. 6,150,088, a structure-based approach can be used, along with available computer-based design programs, to identify or design a drug which will fit into, line or bind a cavity or pocket of an AIP. The structures of transferrin receptor are disclosed in Borhani, D. W. and Harrison, S. C., "Crystallization and X-ray diffraction studies of a soluble form of the human transferrin receptor," *J. Mol. Biol.*, 218: 685-9 (1991); and Lawrence, C. M. et al., "Crystal structure of the ectodomain of human transferrin receptor," *Science*, 286: 779-82 (1999). The structures of clathrin heavy chain are disclosed in Kirchhausen T. & Harrison S. C., "Structural domains of clathrin heavy chains," *J. Cell Biol.* 99:1725-1734 (1984); Kirchhausen T. et al., "Clathrin heavy chain: molecular cloning and complete primary structure," Proc Natl Acad Sci U S A 84:8805-8809 (1987); Ybe, J. A. et al., "Clathrin self-assembly is mediated by a tandemly repeated superhelix," *Nature* 399: 371-5 (1999); Schmid, S. L., "Clathrin-coated vesicle formation and protein sorting: an integrated process," *Annu. Rev. Biochem.* 66: 511-548 (1997); Smith C. J. and Pearse, B. M., "Clathrin: anatomy of a coat protein," *Trends Cell Biol.* 9: 335-8 (1999); Ungewickell, E. "Clathrin: a good view of a shapely leg," *Curr. Biol.* 9(1): R32-5 (1999); and ter Haar, E. et al., "Atomic structure of clathrin: a beta propeller terminal domain joins an alpha zigzag linker," *Cell* 95(4): 563-73 (1998). Non-limiting examples of structures for heat shock protein 90 are disclosed in Stebbins C. E. et al., "Crystal structure of an Hsp90-geldanamycin complex: targeting of a protein chaperone by an antitumor agent," *Cell* 89:239-250 (1997); and Obermann W. M. et al., "In vivo function of Hsp90 is dependent on ATP binding and ATP hydrolysis," *J. Cell Biol.* 143:901-910 (1998).

For example, this method can be carried out by comparing the members of the chemical library with the crystal structure of a the AIP using computer programs known to those of skill in the art (e.g., Dock, Kuntz, I. D. et al., *Science*, 257:1078-1082 (1992); Kuntz, I. D. et al., *J. Mol. Biol.*, 161:269 (1982); Meng, E. C., et al., J Comp. Chem., 13: 505-524 (1992) or CAVEAT). In this method, the library of molecules to be searched can be any library, such as a database (i.e., online, offline, internal, external) which comprises crystal structures, coordinates, chemical configurations or structures of molecules, compounds or drugs to be assessed or screened for their ability to bind an AIP. For example, databases for drug design, such as the Cambridge Structural Database (CSD), which includes about 100,000 molecules whose crystal structures have been determined or the Fine Chemical Director (FCD) distributed by Molecular Design Limited (San Leandro, Calif.) can be used. See Allen, F. H., et al., *Acta Crystallogr. Section B*, 35:2331 (1979). In addition, a library, such as a database, biased to include an increased number of members which comprise indole rings, hydrophobic moieties and/ or negatively-charged molecules can be used.

A drug or molecule which binds or fits into a cavity or pocket on the surface of an AIP, can be used alone or in combination with other drugs (as part of a drug cocktail) to prevent, ameliorate or treat conditions responsive to induction of apoptosis. A drug designed or formed by a method described herein is also the subject of this invention.

EXAMPLES

Example 1

N-(2-Gambogylaminoethyl)biotinamide

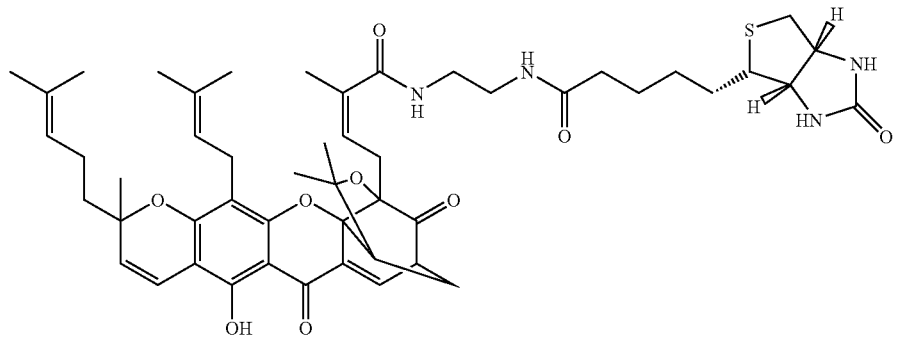

Preparation of
N-(2-Gambogylaminoethyl)biotinamide

A mixture of gambogic acid (85.6 mg, 0.136 mmol), DMAP (19.9 mg, 0.164 mmol), EDC (31.3 mg, 0.164 mmol) and N-(2-aminoethyl)biotinamide (Molecular Probes, 50 mg, 0.14 mmol) in DMF (5 mL) was stirred at room temperature for 72 h. The solution was poured into water (50 mL) and was extracted with ethyl acetate (3×10 mL). The combined organic layer was dried and concentrated to give crude product, which was purified by chromatography ($SiO_2$, EtOAc/ MeOH 4:1) to give the title compound (28 mg, 23%). $^1H$ NMR ($CDCl_3$): 12.92(s, 1H), 7.58 (d, J=6.9 Hz, 1H), 7.05-6.90 (m, 2H), 6.68(d, J=9.9 Hz, 1H), 6.15 (bs, 1H), 5.50 (d, J=10.5 Hz, 1H), 5.28 (m, 2H), 5.05 (m, 2H), 4.49 (m, 1H), 4.32 (m, 1H), 3.58-2.00 (m, 14H), 1.77 (bs, 3H), 1.73 (bs, 3H), 1.69 (bs, 6H), 1.65 (bs, 6H), 1.45 (bs, 3H), 1.29 (bs, 3H). MS: 919 (M+$Na^+$), 897 (M+$H^+$), 895 (M−$H^+$).

Example 2

N-[2-(2-{2-[2-(9,10-Dihydrogambogyl)aminoethoxy]-ethoxy}-ethoxy)-ethyl]-biotinamide

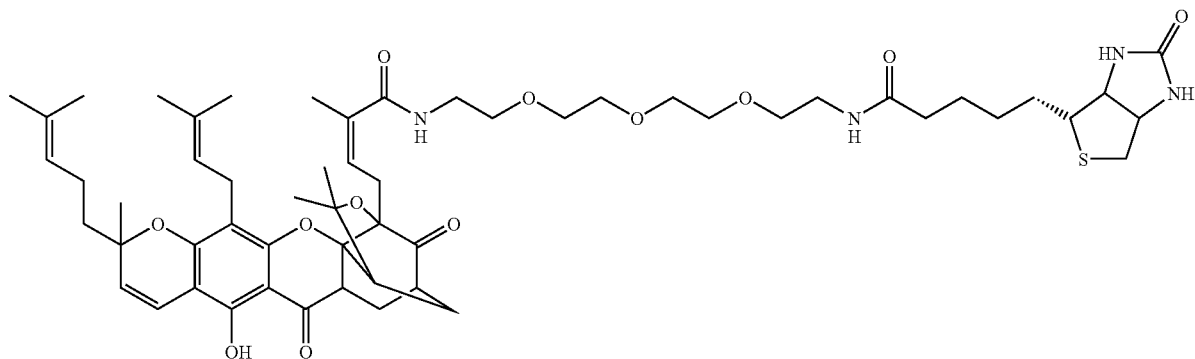

Preparation of N-[2-(2-{2-[2-(9,10-Dihydrogambogyl)aminoethoxy]-ethoxy}-ethoxy)-ethyl]-biotinamide A mixture of N-hydroxysuccinimidyl 9,10-dihydrogambogate (50 mg, 0.068 mmol), N-(2-{2-[2-(2-aminoethoxy)-ethoxy]-ethoxy}-ethyl)-biotinamide (Pierce, 28.8 mg, 0.068 mmol) in dichloromethane (3 mL) was stirred at room temperature for 4 days. The solvent was evaporated and the residue was purified by chromatography (SiO$_2$, CH$_2$Cl$_2$/MeOH 30:1) to give the title compound (11 mg, 16%). $^1$H NMR (CDCl$_3$): 11.94 (s, 1H), 7.15 (bs, 1H), 6.66 (d, J=9.9 Hz, 1H), 6.50 (bs, 1H), 5.86 (t, J=6.90 Hz, 1H), 5.71 (bs, 1H), 5.46 (d, J=9.9 Hz, 1H), 5.18-4.90 (m, 2H), 4.51 (m, 1H), 4.33 (m, 1H), 1.94 (s, 3H), 1.73 (s, 3H), 1.68-1.64 (m, 9H), 1.36 (s, 3H), 1.32 (s, 3H), 1.12 (s, 3H). MS: 1032 (M+H), 1054 (M+Na$^+$), 1030 (M–H), 1065 (M+Cl–1).

Example 3

N-(2-{2-[2-(2-Gambogylaminoethoxy)-ethoxy]-ethoxy}-ethyl)-biotinamide

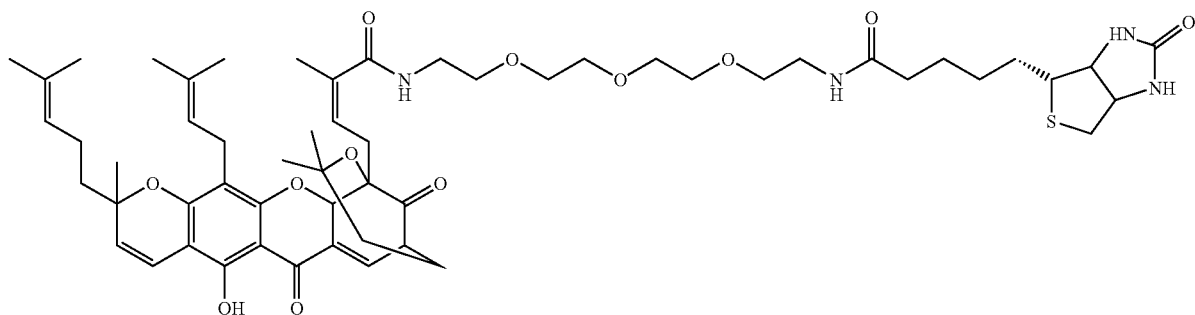

Preparation of N-(2-{2-[2-(2-Gambogylaminoethoxy)-ethoxy]-ethoxy}-ethyl)-biotinamide The title compound was prepared by a procedure similar to that of Example 2 from N-hydroxysuccinimidyl gambogate and N-(2-{2-[2-(2-aminoethoxy)-ethoxy]-ethoxy}-ethyl)-biotinamide (Pierce). Yield: 20%. $^1$H NMR (CDCl$_3$): 13.0 (s, 1H), 7.67 (d, J=6.6 Hz, 1H), 6.80 (m, 1H), 6.78 (d, J=10.2 Hz, 1H), 5.58 (d, J=10.2 Hz, 1H), 5.15-5.10 (m, 2H), 4.30-4.10 (m, 10H), 3.70-3.15 (m, 3H), 3.00-1.20 (m, 56H). MS: 1029 (M+H), 1051(M+Na$^+$).

Example 4

N-{2-[2-(2-Gambogylaminoethoxy)-ethoxy]-ethyl}-biotinamide

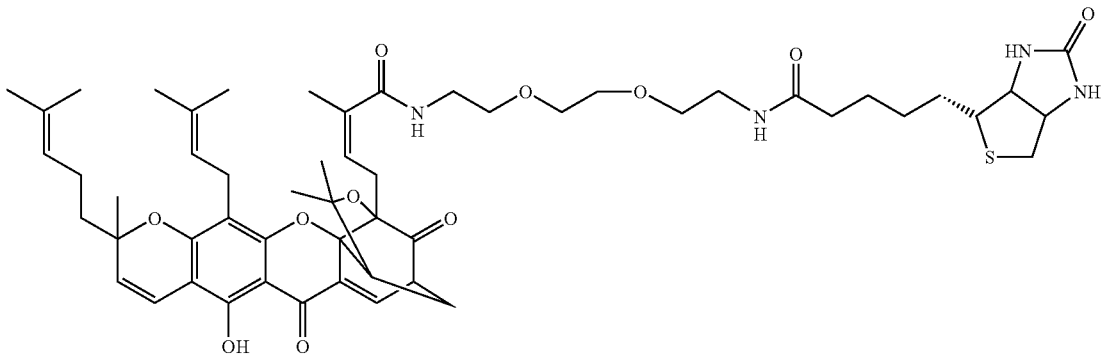

Preparation of N-{2-[2-(2-Gambogylaminoethoxy)-ethoxy]-ethyl}-biotinamide

The title compound was prepared by a procedure similar to that of Example 2 from N-hydroxysuccinimidyl gambogate and N-{2-[2-(2-aminoethoxy)-ethoxy]-ethyl}-biotinamide (Pierce). Yield: 29%. $^1$H NMR (CDCl$_3$): 12.85 (s) and 12.95 (s, 1H), 7.56 (m, 1H), 6.70 (m, 1H), 6.45 (m, 1H), 5.90 (bs, 1H), 5.60-5.30 (m, 2H), 5.20 (bs, 1H), 5.00 (bs, H), 4.60 (bs, 1H), 4.45 (m, 1H), 4.30 (m, 1H), 3.70-3,10 (m, 15H), 3.00-1.20 (m, 45H). MS: 985 (M+H), 983 (M+Na$^+$).

Example 5

N-[2-(2-{2-[2-(2-Gambogylaminoethoxy)-ethoxy]-ethylcarbamoyl}-ethyldisulfanyl)-ethyl]-biotinamide Preparation of N-[2-(2-{2-[2-(2-Gambogylaminoethoxy)-ethoxy]-ethylcarbamoyl}-ethyldisulfanyl)-ethyl]-biotinamide To a solution of N-hydroxysuccinimidyl gambogate (120 mg, 0.164 mmol), 2,2'-(ethylenedioxy)bisethylamine (24.1 μL, 0.164 mmol) in dichloromethane (1.64 mL) was added a few drops of triethylamine and it was stirred at rt for 2 h, then a solution of sulfo-NHS—SS-biotin (Pierce, 50 mg, 0.0824 mmol) in DMF (1.5 mL) was added and stirred at room temperature for 2 days. The solution was diluted with ethyl acetate (30 ml) and was washed with water (3×20 mL), the organic layer was dried over Na$_2$SO$_4$ and concentrated to give crude residue, which was purified by chromatography (SiO$_2$, CH$_2$Cl$_2$/MeOH 10:1) to give the title compound (59.2 mg, 31%). $^1$H NMR (CDCl$_3$): 12.85 (s, 1H), 7.56 (d, J=6.9 Hz, 1H), 7.05 (t, J=7.5 hz, 1H), 6.92 (t, J=7.5 hz, 1H), 6.68 (bs, 1H), 6.67 (d, J=9.9 Hz, 1H), 5.64 (bs, 1H), 5.46 (d, J=10.5 Hz, 1H), 5.37 (t, J=6.9 Hz, 1H), 5.05 (m, 2H), 4.93 (bs, 1H), 4.50 (t, J=7.5 Hz, 1H), 4.32 (t, J=7.5 Hz, 1H), 1.78 (s, 3H), 1.74 (s, 3H), 1.69 (s, 3H), 1.68-1.60 (m, 9H), 1.55 (s, 3H), 1.44 (s, 3H), 1.28 (s, 3H). MS: 1170 (M+Na$^+$), 1148 (M+H$^+$), 1182 (M+Cl−1), 1147 (M−H$^+$).

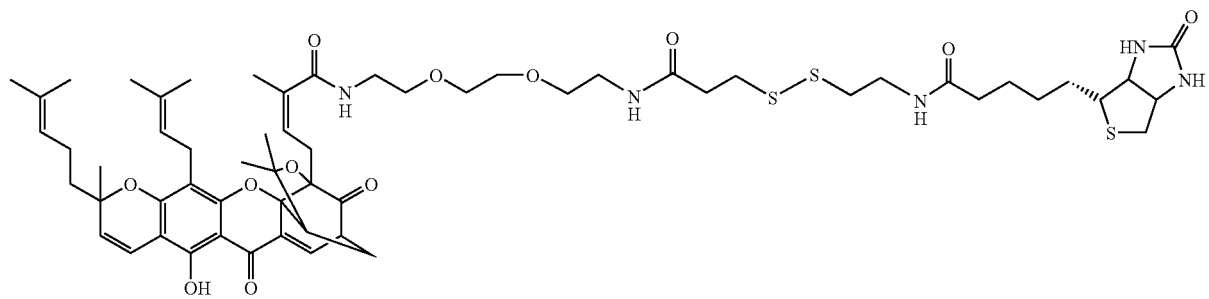

Example 6

N-[2-(2-{2-[2-(9,10-Dihydro-10-methyl-gambogyl) aminoethoxy]-ethoxy}-ethoxy)-ethyl]-biotinamide

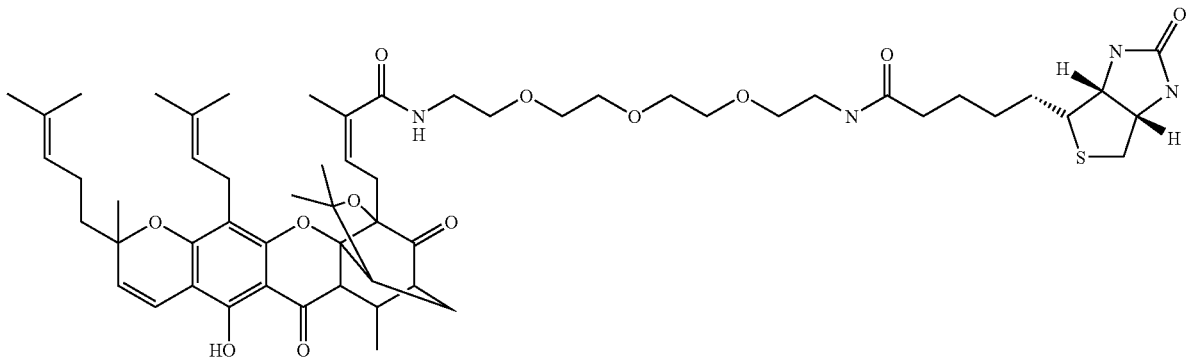

Preparation of N-[2-(2-{2-[2-(9,10-Dihydro-10-methyl-gambogyl) aminoethoxy]-ethoxy}-ethoxy)-ethyl]-biotinamide To a solution of N-hydroxysuccinimidyl 9,10-dihydro-10-methyl-gambogate (57 mg, 0.077 mmol) and N-(2-{2-[2-(2-aminoethoxy)-ethoxy]-ethoxy}-ethyl)-biotinamide (Pierce, 32 mg, 0.077 mmol) in CH$_2$Cl$_2$ (3 mL) was added Et$_3$N (50 µL). The reaction was stirred at rt for 20 hr. The solvent was evaporated and the residue was purified by column chromatography (SiO$_2$, EtOAc:hexanes/10-30% gradient) to give the product (17 mg, 21%): H NMR (300 MHz, CD$_3$Cl) 12.00 (s, 1H), 7.23 (m, 1H), 6.78 (m, 1H), 6.66 (d, J=9.9 Hz, 1H), 6.13 (s, 1H), 5.97 (m, 1H), 4.46 (d, J=10.2 Hz, 1H), 5.20 (s, 1H), 5.12-5.00 (m, 2H), 4.50 (m, 1H), 4.32 (m, 1H), 3.66-3.52 (m, 10H), 3.56 (t, J=4.8 Hz, 3H), 3.50-3.38 (m, 3H), 3.33 (m, 1H), 3.16 (m, 2H), 2.99 (m, 1H), 2.91 (dd, J=4.5, 12.6 Hz, 1H), 2.81 (d, J=3.3 Hz, 1H), 2.78-2.65 (m, 3H), 2.53 (d, J=8.7 Hz, 1H), 2.30 (dd, J=3.6, 5.1 Hz, 1H), 2.24 (t, J=7.2 Hz, 2H), 2.14-2.20 (m, 3H), 1.95 (s, 3H), 1.87 (s, 6H), 1.72 (s, 3H), 1.66 (s, 3H), 1.64 (s, 3H), 1.57 (s, 3H), 1.50-1.40 (m, 3H), 1.38 (m, 1H), 1.35 (s, 3H), 1.34 (s, 3H), 1.38 (s, 3H), 0.98 (d, J=7.2 Hz, 2H); MS (M+1): 1046.

Example 7

5-(Gambogylaminoacetamido)fluorescein

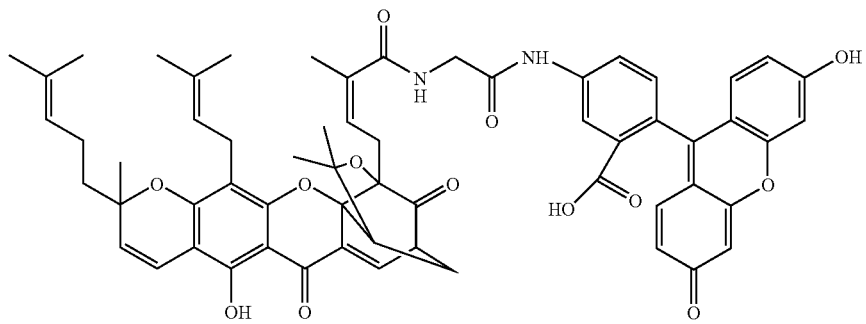

Preparation of 5-(Gambogylaminoacetamido)fluorescein

The title compound was prepared by a procedure similar to that of Example 2 from N-hydroxysuccinimidyl gambogate and 5-(aminoacetamido)fluorescein (Molecular Probes). Yield: 22%. $^1$H NMR (CDCl$_3$): 8.20-7.60 (m, 10H), 7.20 (m, 1H), 6.80-6.60 (m, 3H), 5.90 (bs, 1H), 5.30-5.00 (m, 2H), 4.20 (m, 2H), 3.80-0.90 (m, 39H). MS: 1015 (M+H), 1013 (M−H).

Example 8

N-(5-{2-[2-(2-Gambogylaminoethoxy)-ethoxy]-ethylcarbamoyl}-pentyl)-fluorescein-5-carboxamide mmol) and the mixture was stirred for 3 h. A solution of 6-(fluorescein-5-carboxamido) hexanoic acid succinimidyl ester (Molecular Probes, 30 mg, 0.051 mmol) was added in 900 μL of DMF and the mixture was stirred for 6 h. The reaction mixture was diluted with ethyl acetate (30 mL), washed with water (2×20 mL) and brine (2×30 mL), dried over MgSO$_4$ and concentrated to give the crude product, which was purified by column chromatography (15% methanol/chloroform) to yield the title compound (13.2 mg, 0.011 mmol, 21%). $^1$H NMR (CDCl$_3$): 8.46 (m, 1H), 8.14 (m, 1H), 7.72 (m, 1H), 7.54 (dd, J=6.6 Hz, 1H), 7.13 (m, 1H), 6.89 (m, 1H), 6.63-6.68 (m, 4H), 6.47 (m, 2H), 5.42-5.47 (m, 2H), 5.03

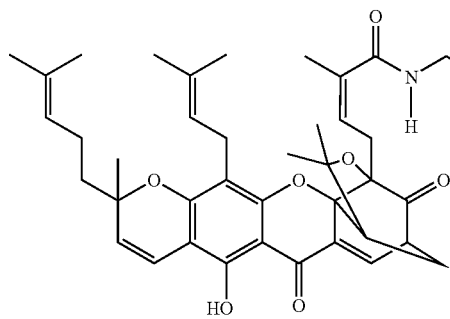
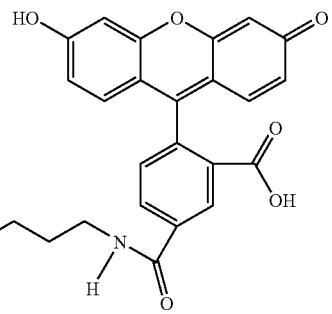

Preparation of N-(5-{2-[2-(2-Gambogylaminoethoxy)-ethoxy]-ethylcarbamoyl}-pentyl)-fluorescein-5-carboxamide To a solution of N-hydroxysuccinimidyl gambogate (43 mg, 0.059 mmol) in 600 μL of dichloromethane was added 2-[2-(2-aminoethoxy)-ethoxy]-ethylamine (8 μL, 0.055

(m, 2H), 3.20-3.54 (m, 17H), 2.80 (m, 1H), 2.45-2.59 (m, 4H), 2.28 (m, 1H), 1.95-2.13 (m, 5H), 1.24-1.75 (m, 35H). MS, [M+H]$^+$=1231.

Example 9

N-{5-[2-(2-Gambogylamino-ethyldisulfanyl)-ethylcarbamoyl]-pentyl}-fluorescein-5-carboxamide

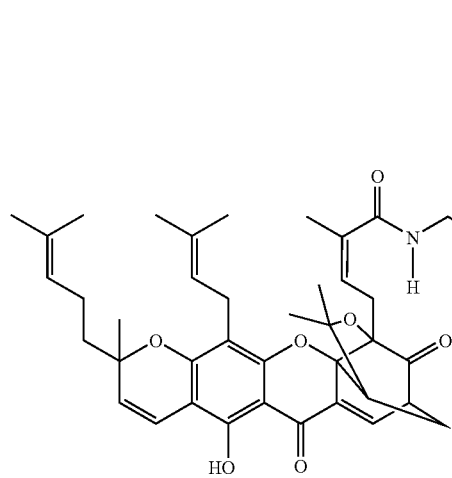
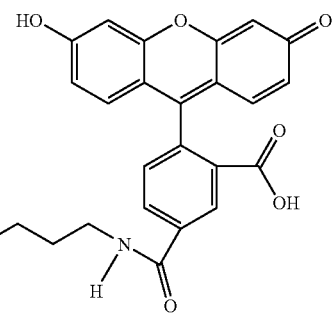

Preparation of N-{5-[2-(2-Gambogylamino-ethyldisulfanyl)-ethylcarbamoyl]pentyl}-fluorescein-5-carboxamide To a solution of N-hydroxysuccinimidyl gambogate (31 mg, 0.044 mmol) and cistein dihydrochloride (9.5 mg, 0.042 mmol) in 500 μL of dichloromethane was added 3 drops of triethylamine and stirred for 2 h. A solution of 6-(fluorescein-5-carboxamido) hexanoic acid succinimidyl ester (Molecular Probes, 25 mg, 0.043 mmol) in 800 μL of DMF was added and the mixture was stirred for 6 h. The reaction mixture was diluted with ethyl acetate (30 mL), washed with water (2×20 mL) and brine (2×30 mL), dried over $MgSO_4$, filtered and concentrated to give the crude product, which was purified by column chromatography (10-15% methanol/dichloromethane) to yield the title compound (5.1 mg, 0.0041 mmol, 10%). $^1$H NMR ($CDCl_3$): 8.32 (m, 1H), 8.10 (m, 1H), 7.73 (m, 1H), 7.58 (m, 2H), 7.23 (m, 2H), 7.04 (m, 1H), 6.81 (m, 1H), 6.62 (m, 2H), 5.21 (m, 1H), 5.02 (m, 3H), 3.21-3.61 (m, 4H), 2.21-2.45 (m, 8H), 2.10 (m, 2H), 0.68-1.73 (m, 48H). MS, $[M-H]^-=1233$.

Preparation of 5-[(5-Gambogylaminopentyl)-thioureidyl]-fluorescein

To a solution of N-hydroxysuccinimidyl gambogate (75 mg, 0.103 mmol) in 1 mL of DMF was added a solution of 5-[(5-aminopentyl)-thioureidyl]-fluorescein dihydrobromide (50 mg, 0.077 mmol) in 1 mL of DMF, followed by 4 drops of triethylamine. The reaction mixture was stirred for 4 h and DMF was removed under high vacuum and the residue was purified by column chromatography (20% methanol/ chloroform) to obtain the title compound (79 mg, 0.072 mmol, 94%). $^1$H NMR ($CDCl_3$/MeOH-$d_4$): 8.24 (m, 1H), 8.18 (m, 1H), 7.95 (m, 1H), 7.58 (m, 1H), 7.14 (m, 3H), 6.81 (m, 2H), 6.62 (m, 2H), 6.51 (m, 1H), 5.43 (m, 1H), 5.26 (m, 1H), 5.11 (m, 2H), 4.21-4.30 (m, 4H), 3.21-3.62 (m, 4H), 2.61-2.73 (m, 2H), 2.34-2.43 (m, 1H), 2.13-0.89 (m, 35H). MS, $[M+H]^+=1103$.

Example 10

5-[(5-Gambogylaminopentyl)-thioureidyl]-fluorescein

Example 11

N-{2-[2-(2-Gambogylaminoethoxy)-ethoxy]-ethyl}-fluorescein-5-carboxamide

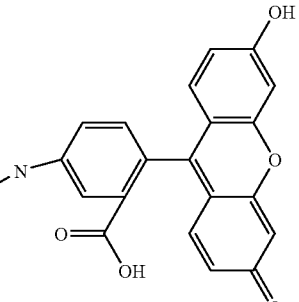

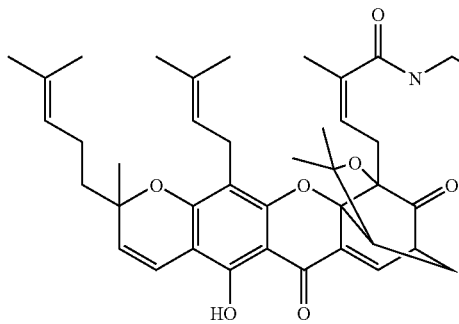

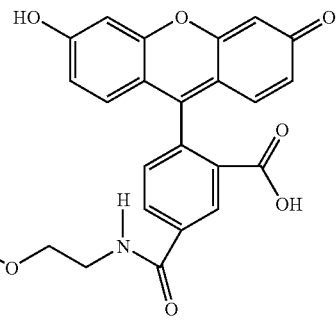

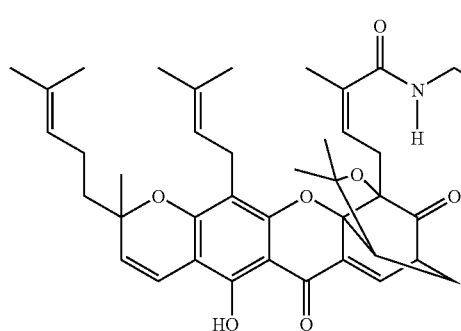

Preparation of N-{2-[2-(2-Gambogylaminoethoxy)-ethoxy]-ethyl}-fluorescein-5-carboxamide To a solution of N-hydroxysuccinimidyl gambogate (32 mg, 0.045 mmol) in 300 μL of dichloromethane was added 2-[2-(2-amino-ethoxy)-ethoxy]-ethylamine (6 mg, 0.040 mmol) and the mixture was stirred for 3 h. To the solution was added 5-Carboxyfluorescein succinimidyl ester (Molecular Probes, 20 mg, 0.042 mmol) in 500 μL of DMF and the mixture was stirred for 6 h. The solvents were removed under vacuum and the residue was purified by column chromatography (5-10% methanol/chloroform) to obtain the title compound (9.0 mg, 0.008 mmol, 20%). $^1$H NMR (DMSO-d$_6$): 8.98 (m, 1H), 8.58 (m, 1H), 8.23 (m, 1H), 7.81 (m, 1H), 7.21 (m, 1H), 6.41-6.67 (m, 5H), 5.98 (m, 1H), 5.81 (s, 1H), 5.18 (m, 3H), 3.52-3.81 (m, 8H), 3.23 (m, 2H), 2.20-2.81 (m, 6H), 0.83-2.15 (m, 32H). MS, [M+H]$^+$=1118, [M−H]$^−$=1116.

Example 12

Preparation of Gambogyl-agarose

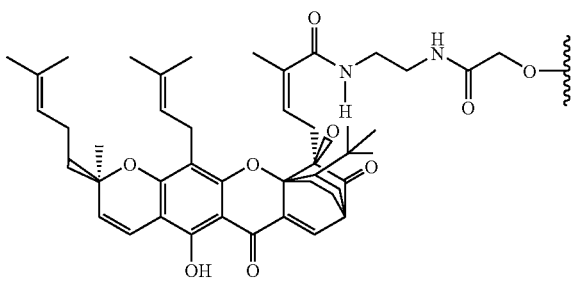

Preparation of Gambogyl-agarose

The affi-gel 102 (Amino-agarose, Bio-Rad laboratories, 100 mL, in aqueous) was transferred to a fritted column and washed with DMSO/H$_2$O gradient (from 20%, 40%, 60%, 80% DMSO, 250 mL each to 100% DMSO, 500 mL).

To the slurry of above agarose (24 mL) in DMSO (20 mL) in the column was added N-hydroxysuccinimidyl gambogate (436 mg, 0.60 mmol). The mixture was shaken gently on a shaker for 9 hr at rt. The DMSO was drained and the agarose in the column was washed with DMSO until the washings is colorless (160 mL), then it was washed with 30% aqueous ethanol (200 mL).

Example 13

Gambogyl-R—SS—R'-agarose

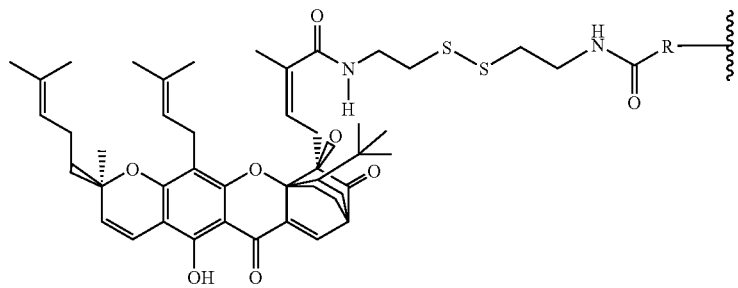

Preparation of Gambogyl-R—SS—R'-agarose

The affi-gel 10 (N-hydroxysuccinimidyl carboxyl-agarose, Bio-Rad laboratories, in isopropanol) was transferred to a fritted column. The isopropanol was drained and the gel was washed with DMSO (100 mL).

To a flask containing cystamine dihydrochloride solution in anhydrous DMSO (20 mL, sonication required) was added Et$_3$N (1.04 mL, 7.5 mmol). The solution was added to the above agarose gel column. The flask was washed with anhydrous DMSO (10 mL) and the washing was added the column. The agarose column was mounted on a shaker and shaken gently for 18 hr at rt. The solvent was drained from the column and the column was washed with anhydrous DMSO (150 mL). This converted the N-hydroxysuccinimidyl carboxyl-agarose into an amino-R—SS—R'-agarose.

A solution of N-hydroxysuccinimidyl gambogate (212 mg, 0.292 mmol) in anhydrous DMSO (28 mL) was added to the above amino-R—SS—R'-agarose column. The column was mounted on a shaker and shaken gently for 3 days. The solvent was drained from the column and the gel was washed with anhydrous DMSO until the washings are colorless (80 mL). The agarose gel column was further washed with 30% aqueous ethanol (200 mL).

Example 14

T$_3$-methyl gambogate

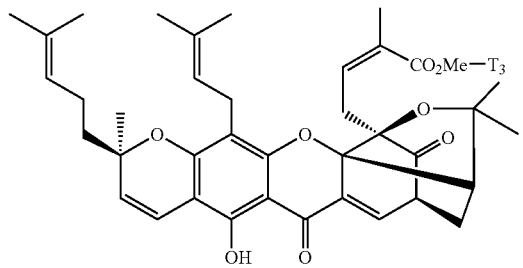

Preparation of methyl gambogate

A solution of methyl iodide (29 µL, 0.477 mmol) in 1.0 mL of N,N-dimethylformamide was added to a solution of gambogic acid (0.200 g, 0.318 mmol) and 1,8-diazabicyclo[5.4.0] undec-7-ene (47.6 µL, 0.318 mmol) in 0.2 mL of N,N-dimethylformamide and the mixture was stirred at room temperature for 3 h. The reaction mixture was poured into brine (30 mL) and was extracted with methylene chloride. The organic layer was wash with brine (2×30 mL) and the combined organic extracts were dried over $MgSO_4$ and concentrated in vacuo to give the crude product. It was purified by column chromatography (18×2 cm column, $SiO_2$, EtOAc/Hexane 1:5) to afford the methyl gambogate as an orange solid (0.14 g, 69 %). $^1$H NMR ($CDCl_3$): 12.85 (s, 1H), 7.54 (d, J=6.9 Hz, 1H), 6.67 (d, J=10.5 Hz, 1H), 5.94 (t, J=6 Hz, 1H), 5.43 (d, J=10.2 Hz, 1H), 5.05 (m, 2H), 3.49 (m, 1H), 3.43 (s, 3H), 3.35-3.10 (s, 2H), 3.00 (t, J=7.2 Hz, 1H), 2.52 (d, J=10.2 Hz, 1H), 2.32 (quar, J=4.8 Hz, 1H), 2.02 (m, 1H), 1.74 (s, 3H), 1.69 (s, 3H), 1.67-1.64 (m, 9H), 1.55 (s, 3H), 1.44 (s, 3H), 1.29 (s, 3H).

Preparation of $T_3$-methyl gambogate

The $T_3$-methyl gambogate was prepared similar to methyl gambogate by using radioactive $T_3$-MeI instead of MeI. The compound was purified by HPLC. Specific activity: 85 Ci/mmol. Radiochemical purity: 96.8% by HPLC.

Example 15

3,4-dihydroxyxanthen-9-one

To a stirring solution of 2-fluorobenzoic acid (5.09 g, 36.3 mmol) and dichloromethane (110 mL) in an ice bath under argon was added dropwise a solution of oxalyl chloride (2.0 M in dichloromethane, 21 mL, 42 mmol), followed by dimethylformamide (6 drops). The ice bath was removed and the solution was stirred at room temperature for 1.5 h. The solution was then concentrated by rotary evaporation. The product was dissolved in hexane (3×50 mL) and the mixture was filtered. The filtrate was rotary evaporated to yield 5.42 g of colorless oil. The oil was added dropwise to a mixture of pyrogallol (6.48 g, 51.3 mmol), aluminum chloride (14.6 g, 110 mmol), chloroform (250 mL) and dichloromethane (700 mL), and the solution was stirred for 17 h at room temperature. The solution was then refluxed for 3 h and cooled to room temperature. The solution was washed with 1 N HCl (3×500 mL). The organic layer was filtered, dried over sodium sulfate, and evaporated to yield an oil. The oil was added to dimethylformamide (120 mL) with sodium carbonate (8.11 g, 76.5 mmol) and it was refluxed for 3.5 h. The solution was concentrated by rotary evaporation with heating, and the residue was purified by column chromatography (95:5 chloroform/methanol) to give a solid. The solid was washed with hexane (2×35 mL), filtered and dried to yield 2.10 g (25 %) of the title compound as an off-white solid. $^1$H NMR (DMSO-$d_6$, 300 MHz): δ 8.16 (d, J=7.42 Hz, 1H), 7.84 (t, J=7.69 Hz, 1H), 7.64 (d, J=8.52 Hz, 1H), 7.57 (d, J=8.79 Hz, 1H), 7.44 (t, J=7.41 Hz, 1H), 6.94 (d, J=8.52 Hz, 1H).

Example 16

3,4-bis-allyloxyxanthen-9-one

A stirred solution of 3,4-dihydroxyxanthen-9-one (290 mg, 1.27 mmol), allyl bromide (800 µL, 9.20 mmol), potassium carbonate hydrate (1.28 g, 7.77 mmol) and acetone (15.0 mL) was refluxed for 2.5 h. The solution was cooled to room temperature and dichloromethane was added. The mixture was filtered and the filtrate was rotary evaporated to yield 372 mg (95%) of the title compound as a white solid. $^1$H NMR (DMSO-$d_6$, 300 MHz): δ 8.33 (dd, $J_1$=7.84 Hz, $J_2$=1.79, 1H), 8.07 (d, J=8.79 Hz, 1H), 7.72 (ddd, $J_1$=8.10 Hz, $J_2$=7.01, $J_3$=1.65, 1H), 7.56 (dd, $J_1$=8.51 Hz, $J_2$=0.55, 1H), 7.38 (ddd, $J_1$=7.76 Hz, $J_2$=7.07, $J_3$=1.03, 1H), 7.00 (d, J=9.06 Hz, 1H), 6.15 (m, 2H), 5.48 (m, 1H), 5.38 (m, 2H), 5.25 (m, 1H), 4.74 (m, 4H).

Example 17

1-Allyl-1,3,3a,4,5,12a-hexahydro-7,13-dioxo-1,5-methano-furo[3,4-d]xanthene

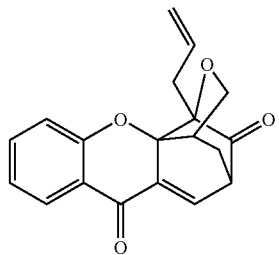

A stirred solution of 3,4-bis-allyloxy-xanthen-9-one (236.4 mg, 0.767 mmol) and diphenyl ether (3.0 mL) was refluxed in an oil bath at 190° C. for 11 h. The solution was cooled to room temperature and product was purified twice by flash column chromatography (dichloromethane) to yield 28.0 mg (12%) of the title compound as a white solid. $^1$H NMR ($CDCl_3$, 300 MHz): δ 7.95 (dd, $J_1$=7.69 Hz, $J_2$=1.65, 1H), 7.56 (ddd, $J_1$=8.17 Hz, $J_2$=7.07, $J_3$=1.58, 1H), 7.34 (d, J=7.14Hz, 1H), 7.08 (m, 1H), 5.22 (m, 1H), 4.69 (m, 1H), 4.53 (m, 1H), 3.91 (d, J=7.97 Hz, 1H), 3.53 (ddd, $J_1$=6.11 Hz, $J_2$=3.43, $J_3$=2.06, 1H), 2.82 (dd, $J_1$=13.33 Hz, $J_2$=5.35, 1H), 2.63 (m, 1H), 2.51 (dd, $J_1$=13.60 Hz, $J_2$=9.48, 1H), 1.90 (m, 1H), 1.78 (ddd, $J_1$=12.22 Hz, $J_2$=10.38, $J_3$=2.39, 1H).

Example 18

1-Allyl-1,3,3a,4,4a,11a-hexahydro-10,12-dioxo-1,4a-methano-furo[3,4-b]xanthene

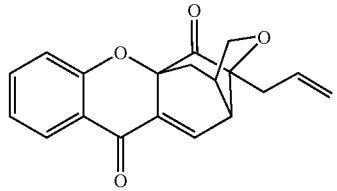

The procedure in example 3 also yielded 44.5 mg (19%) of the title compound as a white solid. $^1$H NMR ($CDCl_3$, 300 MHz): δ 7.93 (dd, $J_1$=7.96 Hz, $J_2$=1.92, 1H), 7.56 (ddd, $J_1$=8.24 Hz, $J_2$=7.01, $J_3$=1.78, 1H), 7.31 (d, J=6.87 Hz, 1H), 7.19 (dd, $J_1$=8.38 Hz, $J_2$=0.96, 1H), 7.08 (m, 1H), 5.60 (m, 1H), 5.15 (s, 1H), 5.11 (m, 1H), 4.09 (dd, $J_1$=8.25 Hz, $J_2$=3.57, 1H), 3.97 (d, J=8.24 Hz, 1H), 3.48 (dd, $J_1$=6.87 Hz, $J_2$=4.39, 1H), 2.63 (dd, $J_1$=14.28 Hz, $J_2$=6.59, 1H), 2.55 (m, 1H), 2.29 (dd, $J_1$=12.50 Hz, $J_2$=5.90, 1H), 2.23 (d, J=5.77 Hz, 1H).

Example 19

1-allyl-1,3,3a,4,5,6,6a,12a-octahydro-7,13-dioxo-1, 5-methano-furo[3,4-d]xanthene

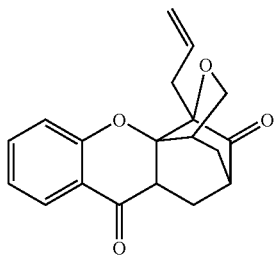

To a stirring solution of 1-allyl-1,3,3a,4,5,12a-hexahydro-7,13-dioxo-1,5-methano-furo[3,4-d]xanthene (29.0 mg, 0.0941 mmol) and tetrahydrofuran (15.0 mL) in a dry ice bath under argon was added dropwise 1.0 M L-Selectride in THF (150 µL, 0.150 mmol) and the solution was stirred for 25 min. The dry ice bath was removed and the solution was stirred for 20 minutes. The solution was concentrated by rotary evaporation and was purified by column chromatography (2:1 hexanes/ethyl acetate) to yield 11.4 mg (39%) of the title compound as a white solid. $^1$H NMR (CDCl$_3$, 300 MHz): δ 7.91 (dd, $J_1$=8.11 Hz, $J_2$=1.79, 1H), 7.54 (ddd, $J_1$=8.17 Hz, $J_2$=6.94, $J_3$=1.45, 1H), 7.08 (m, 2H), 5.86 (m, 1H), 5.27 (m, 1H), 5.12 (dt, $J_1$=10.16 Hz, $J_2$=1.51, 1H), 4.16 (dd, $J_1$=7.97 Hz, $J_2$=4.12, 1H), 3.53 (d, J=7.96 Hz, 1H), 3.40 (dd, $J_1$=11.54 Hz, $J_2$=3.30, 1H), 3.06 (dd, $J_1$=13.46 Hz, $J_2$=6.04, 1H), 2.87 (dd, $J_1$=13.32 Hz, $J_2$=8.93, 1H), 2.82 (dt, $J_1$=14.28 Hz, $J_2$=3.57, 1H), 2.74 (dd, $J_1$=9.89 Hz, $J_2$=4.39, 1H), 2.44 (m, 1H), 2.01 (dd, $J_1$=13.47 Hz, $J_2$=10.44, 1H), 1.78 (ddt, $J_1$=14.15 Hz, $J_2$=11.67 $J_3$=2.68, 1H), 1.67 (dt, $J_1$=14.10 Hz, $J_2$=3.50, 1H).

Example 20

3,4-Bis-(1,1-dimethyl-prop-2-ynyloxy)-xanthen-9-one

A solution of 3,4-dihydroxy-xanthen-9-one (1.25 g, 5.47 mmol), cupric chloride (30.2 mg, 0.225), 3-chloro-3-methyl-1-butyne (3.36 mL, 29.9 mmol), 1,8-diazabicyclo[5.4.0]undec-7-ene (2.00 mL, 13.3 mmol), and acetonitrile (100 mL) was stirred at room temperature for 11 h under argon. The solution was then heated at 75° C. for 2 h and cooled to room temperature. The solution was partitioned between ethyl acetate (100 mL) and water (75 mL). The ethyl acetate layer was dried over sodium sulfate and was concentrated by rotary evaporation. The product was purified by flash column chromatography (10:1 hexanes/ethyl acetate) to yield 496 mg (25%) of the title compound as a light yellow solid. $^1$H NMR (CDCl$_3$, 300 MHz): δ 8.33 (dd, $J_1$=7.97 Hz, $J_2$=1.65, 1H), 8.07 (d, J=9.06 Hz, 1H), 7.71 (ddd, $J_1$=8.18 Hz, $J_2$=7.08, $J_3$=1.58, 1H), 7.65 (d, J=9.06 Hz, 1H), 7.52 (dd, $J_1$=8.52 Hz, $J_2$=0.55, 1H), 7.38 (m, 1H), 2.66 (s, 1H), 2.30 (s, 1H), 1.84 (s, 6H), 1.77 (s, 6H).

Example 21

3,4-Bis-(1,1-dimethyl-allyloxy)-xanthen-9-one

To a solution of 3,4-bis-(1,1-dimethyl-prop-2-ynyloxy)-xanthen-9-one (318 mg, 0.882 mmol) in methanol (25 mL) was added Lindlar's catalsyt (Pd, 5 wt % on calcium carbonate, 75 mg) under hydrogen (1 atm). The mixture was stirred at room temperature for 1 h, then the mixture was filtered through a syringe filter and the solvent was evaporated. The residue was purified by column chromatography (SiO$_2$, EtOAc:hexanes/10-25%) to give the product as a white solid (249 mg, 77%): $^1$H NMR (CDCl$_3$,300 MHz) δ 8.31 (dd, J=1.8, 8.1 Hz, 1H), 7.93 (d, J=9.0 Hz, 1H), 7.70 (m, 1H), 7.50 (dd, J=0.9, 8.7 Hz, 1H), 7.37 (m, 1H), 7.13 (d, J=9.0 Hz, 1H), 6.30 (dd, J=10.8, 17.7 Hz, 1H), 6.20 (dd, J=11.1, 17.1 Hz, 1H), 5.25-5.16 (m, 3H), 5.03 (dd, J=0.9, 10.5 Hz, 1H), 1.59 (s, 3H), 1.58 (s, 3H).

Example 22

1-(3-Methyl-2-butenyl)-3,3-dimethyl-1,3,3a,4,5,12a-hexahydro-7,13-dioxo-1,5-methano-furo[3,4-d]xanthene

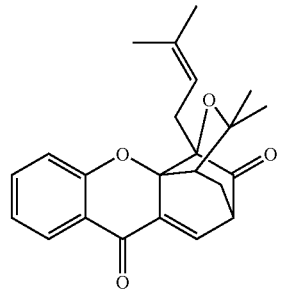

A solution of 3,4-bis-(1,1-dimethyl-allyloxy)-xanthen-9-one (229 mg, 0.587 mmol) in toluene (10 mL) was refluxed under argon for 2 h. The solvent was evaporated and the residue was purified by column chromatography (SiO$_2$, EtOAc:hexanes/10-30%) to give the title compound as white solids (145 mg, 63%): $^1$H NMR (CDCl$_3$, 300 MHz) δ 7.95 (dd, J=1.5, 7.8 Hz, 1H), 7.53 (ddd, J=1.5, 7.2, 8.1 Hz, 1H), 7.44 (dd, J=0.6, 7.2 Hz, 1H), 7.07 (m, 2H), 4.42 (m, 1H), 3.50 (dd, J=4.5, 6.9 Hz, 1H), 2.63 (m, 2H), 2.46 (d, J=9.3 Hz, 1H), 2.35 (dd, J=4.2, 12.6 Hz, 1H), 1.73 (s, 3H), 1.31 (m, 1H), 1.31 (s, 6H), 0.92 (s, 3H); $^{13}$C NMR (CDCl$_3$, 75 MHz) δ 202.8, 176.3, 159.5, 136.1, 134.8, 134.7, 133.6, 126.8, 121.8, 119.0, 118.9, 118.0, 90.3, 84.6, 83.5, 48.8, 46.8, 30.4, 29.2, 25.4, 25.2, 16.8.

Example 23

1-(3-Methyl-2-butenyl)-3,3-dimethyl-1,3,3a,4,4a, 11a-hexahydro-10,12-dioxo-1,4a-methano-furo[3,4-b]xanthene

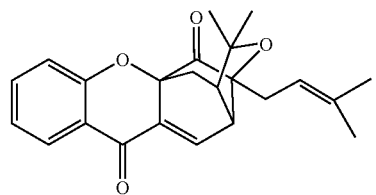

The procedure in example 8 also yielded 18 mg (8%) of the title compound as a white solid. $^1$H NMR (CDCl$_3$, 300 MHz)

δ 7.92 (dd, J=1.8, 8.1 Hz, 1H), 7.55 (ddd, J=1.8, 7.2, 8.7 Hz, 1H), 7.26 (d, J=6.9 Hz, 1H), 7.20 (dd, J=0.6, 8.4 Hz, 1H), 7.07 (dd, J=1.2, 7.2 Hz, 1H), 5.03 (m, 1H), 3.77 (dd, J=4.5, 6.9 Hz, 1H), 2.56 (d, J=13.2 Hz, 1H), 2.50 (dd, J=6.9, 15.3 Hz, 1H), 2.17 (dd, J=4.5, 9.6 Hz, 1H), 2.09 (dd, J=8.4, 14.7 Hz, 1H), 1.88 (dd, J=9.9, 13.2 Hz, 1H), 1.72 (s, 3H), 1.60 (s, 3H), 1.39 (s, 3H), 1.35 (s, 3H); $^{13}$C NMR (CDCl$_3$, 75 MHz) δ 199.7, 175.4, 160.2, 136.5, 136.1, 135.9, 134.9, 127.0, 122.0, 119.2, 118.3, 117.3, 84.1, 83.7, 78.8, 44.8, 42.1, 33.1, 30.2, 29.7, 26.8, 26.0, 18.2.

Example 24

3,4-Bis-allyloxy-benzophenone

To a suspension of 3,4-dihydroxybenzophenone (2.140 g, 10 mmol) and cesium carbonate (7.010 g, 21.6 mmol) in dry acetone (50 mL) was added allylbromide (5.3 mL, 60 mmol). The mixture was stirred at 60° C. for 6 h and additional allybromide (3.0 mL, 34.7 mmol) and cesium carbonate (3.000 g, 9.2 mmol) were added. The mixture was stirred for 3 h, cooled to room temperature, filtered and washed with EtOAc. The filtrate and washing were combined and evaporated under reduced pressure. The crude product was partitioned between EtOAc (50 mL) and H$_2$O (15 mL). The EtOAc phase was separated and evaporated to give a light yellow oil (2.922 g, 99%): $^1$H NMR (CDCl$_3$, 300 MHz) δ 7.77 (m, 1H), 7.74 (m, 1H), 7.57 (m, 1H), 7.50-7.44 (m, 3H), 7.38 (ddd, J=0.9, 2.4, 8.7 Hz, 1H), 6.91 (d, J=8.4 Hz, 1H), 6.08 (m, 2H), 5.47 (m, 1H), 5.41 (m, 1H), 5.32 (m, 2H), 4.68 (m, 4H).

Example 25

(2,5-Diallyl-3,4-dihydroxy)-benzophenone

A solution of 3,4-bis-allyloxy-benzophenone (1.510 g, 5.1 mmol) in diphenyl ether (3 mL) was stirred at 200° C. for 2 h. The reaction mixture was cooled and the mixture was purified by column chromatography (SiO$_2$, 30% EtOAc in hexanes) to give a light yellow oil (0.840 g, 56%): $^1$H NMR (CDCl$_3$, 300 MHz) δ 7.79 (m, 2H), 7.57 (m, 1H), 7.44 (t, J=7.8 Hz, 2H), 6.78 (s, 1H), 6.16-5.86 (m, 3H), 5.60 (brs, 1H), 5.12 (m, 4H), 3.51 (d, J=6.0 Hz, 2H), 3.39 (d, J=6.6 Hz, 2H).

Example 26

(2,5-Diallyl-3,4-bis-allyloxy)-benzophenone

A suspension of (2,5-diallyl-3,4-dihydroxy)-benzophenone (840 mg, 2.85 mmol), cesium carbonate (2.780 g, 8.55 mmol) and allylbromide (1.5 mL, 17.3 mmol) was stirred at 60° C. for 20 h. The mixture was filtered and washed with EtOAc. The filtrate was evaporated and the crude product was purified by column chromatography (SiO$_2$, 10-30% EtOAc: hexanes) to give a light yellow oil (880 mg, 83%): $^1$H NMR (CDCl$_3$, 300 MHz) δ 7.81-7.77 (m, 2H), 7.57 (tt, J=1.5, 7.2 Hz, 1H), 7.47-7.41 (m, 2H), 6.90 (s, 1H), 6.10 (m, 2H), 5.89 (m, 2H), 5.43 (m, 1H), 5.38 (m, 1H), 5.27 (m, 1H), 5.24 (m, 1H), 5.04 (m, 1H), 5.00 (m, 1H), 4.88 (m, 1H), 4.83 (dq, J=10.2, 1.5 Hz, 1H), 4.57-4.51 (m, 4H), 3.50 (dt, J=6.3, 1.5 Hz, 2H), 3.89 (dt, J=6.6, 1.2 Hz, 2H); $^{13}$C NMR (CDCl$_3$, 75 MHz) δ 197.4, 151.6, 150.5, 137.7, 136.9, 136.5, 134.9, 133.8, 133.8, 132.9, 132.1, 131.8, 130.2, 128.2, 125.8, 117.6, 117.4, 115.9, 115.3, 73.7, 73.7, 34.0, 31.0.

Example 27

1,3,7-Triallyl-8-benzoyl-4-oxa-tricyclo[4.3.1.0$^{3,7}$]dec-8-en-2-one

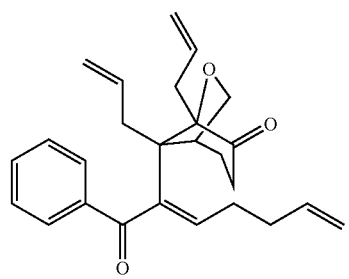

A solution of (2,5-diallyl-3,4-bis-allyloxy)benzophenone (474 mg, 1.27 mmol) in diphenyl ether (3 mL) was stirred at 200° C. for 2 h. The reaction mixture was cooled to room temperature and the product was purified by column chromatography (SiO$_2$, CH$_2$Cl$_2$) to give the title compound (190 mg, 35%). $^1$H NMR (CDCl$_3$, 300 MHz) δ 7.80-7.75 (m, 2H), 7.59 (m, 1H), 7.48-7.43 (m, 2H), 6.23 (s, 1H), 5.85-5.58 (m, 2H), 5.36 (m, 1H), 5.21-5.06 (m, 3H), 5.02-0.591 (m, 3H), 4.14 (dd, J=4.5, 8.7 Hz, 1H), 3.72 (d, J=8.4 Hz, 1H), 3.01 (dd, J=5.7, 13.8 Hz, 1H), 2.93 (dd, J=7.2, 14.4 Hz, 1H), 2.66-2.51 (m, 3H), 2.41-2.29 (m, 2H), 2.08 (dd, J=10.2, 13.2 Hz, 1H), 1.70 (d, J=13.5 Hz, 1H); $^{13}$CNMR (CDCl$_3$, 75 MHz) δ 204.4, 192.8, 141.6, 139.8, 136.5, 133.8, 133.2, 132.5, 132.0, 129.7, 128.3, 119.3, 118.8, 118.5, 83.5, 53.4, 51.1, 50.9, 39.6, 39.3, 34.3, 33.5, 32.7.

Example 28

1,3,7-Triallyl-9-benzoyl-4-oxa-tricyclo[4.3.1.0$^{3,7}$]dec-8-en-2-one

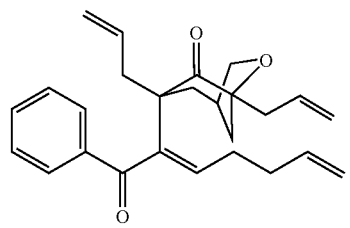

The procedure in example 13 also yielded the title compound (79 mg, 14%). $^1$H NMR (CDCl$_3$, 300 MHz) δ 7.79-7.76 (m, 2H), 7.60 (tt, J=1.5, 6.6 Hz, 1H), 7.50-7.44 (m, 2H), 6.33 (s, 1H), 5.98-5.73 (m, 2H), 5.60 (m, 1H), 5.16-4.95 (m, 6H), 4.18 (dd, J=4.5, 8.4 Hz, 1H), 3.70 (d, J=8.7 Hz, 1H), 3.49 (m, 1H), 2.81 (dd, J=14.4, 8.7 Hz, 1H), 2.67 (dd, J=4.5 Hz, 9.9 Hz, 1H), 2.56-2.50 (m, 2H), 2.45-2.37 (m, 1H), 2.24 (dd, J=9.3, 14.7 Hz, 1H), 2.02 (dd, J=10.2, 12.9 Hz, 1H), 1.69 (d, J=13.8, 1H); $^{13}$C NMR (CDCl$_3$, 75 MHz) δ 205.5, 193.8, 141.2, 141.1, 137.3, 133.7, 133.3, 132.9, 132.0, 129.9, 128.3, 118.9, 118.7, 118.3, 82.7, 74.3, 53.2, 49.5, 39.7, 38.5, 35.3, 34.0, 30.6.

Example 29

7,8-Bis-(1,1-dimethyl-prop-2-ynyloxy)-2-phenyl-chromen-4-one

To a suspension of 7,8-dihydroxy-2-phenyl-chromen-4-one (510 mg, 2 mmol) and $CuCl_2$ (16 mg, 0.12 mmol) in acetonitrile (3 mL) was added 3-chloro-3-methyl-1-butyne (0.5 mL, 4.56 mmol) and 1,8-diazabicyclo[5.4.0]undec-7-ene (0.78 mL, 5.2 mmol) slowly at 0° C. The dark mixture was stirred at 0° C. for 5 h and then at room temperature overnight. The solvent was evaporated and the residue was purified by column chromatography ($SiO_2$, EtOAc:hexanes/10-50%) to give the title compound as a white solid (540 mg, 69%): $^1$H NMR ($CDCl_3$, 300 MHz) δ 8.02 (m, 2H), 7.96 (d, J=9.0 Hz, 1H), 7.69 (d, J=9.0 Hz, 1H), 7.53 (m, 3H), 6.78 (s, 1H), 2.66 (s, 1H), 2.26 (s, 1H), 1.81 (s, 6H), 1.76 (s, 6H).

Example 30

7,8-Bis-(1,1-dimethyl-allyloxy)-2-phenyl-chromen-4-one

To a solution of 7,8-bis-(1,1-dimethyl-prop-2-ynyloxy)-2-phenyl-chromen-4-one (98 mg, 0.254 mmol) in methanol (20 mL) was added Lindlar's catalyst (Pd, 5 wt % on calcium carbonate, 25 mg) under argon. The mixture was stirred at room temperature for 50 min, then it was filtered through a syringe filter and the solvent was evaporated. The residue was purified by column chromatography ($SiO_2$, EtOAc:hexanes/10-25%) to give the product as a white solid (72 mg, 73%): $^1$H NMR ($CDCl_3$, 300 MHz) δ 7.98 (m, 2H), 7.81 (dd, J=0.9, 9.0 Hz, 1H), 7.52 (m, 3H), 7.16 (dd, J=0.6, 9.0 Hz, 1H), 6.75 (d, J=0.6 Hz, 1H), 6.22 (m, 2H), 5.24-5.12 (m, 3H), 4.98 (dd, J=1.2, 10.2 Hz, 1H), 1.56 (s, 6H), 1.55 (s, 6H); $^{13}$C NMR ($CDCl_3$, 75 MHz) δ 178.1, 163.0, 154.9, 152.5, 136.0, 132.0, 131.2, 128.8, 126.6, 120.5, 119.6, 117.5, 107.3, 85.2, 74.9, 74.1, 73.9, 30.7, 29.8.

Example 31

1-(3-Methyl-2-butenyl)-3,3-dimethyl-1,3,3a,4,5,10a-hexahydro-7,11-dioxo-9-phenyl-1,5-methano-furo[3,4-i]chromene

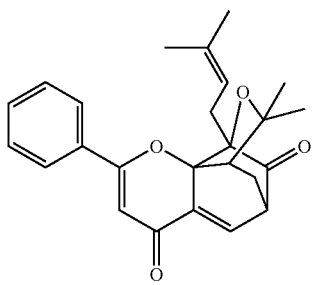

A solution of 7,8-bis-(1,1-dimethyl-allyloxy)-2-phenyl-chromen-4-one in diphenyl ether (2 mL) was stirred at 120° C. under argon for three h. The reaction mixture was cooled to room temperature and the product was purified by column chromatography ($SiO_2$, EtOAc:hexanes/10-30%) to give the title compound (45 mg, 52%): $^1$H NMR ($CDCl_3$, 300 MHz) δ 7.85-7.82 (m, 2H), 7.57-7.46 (m, 3H), 7.30 (d, J=6.9 Hz, 1H), 6.13 (s, 1H), 4.69 (m, 1H), 3.48 (dd, J=4.5, 6.9 Hz, 1H), 2.67-2.56 (m, 2H), 2.52 (d, J=9.3 Hz, 1H), 2.34 (dd, J=4.5 Hz, 13.5 Hz, 1H), 1.69 (s, 3H), 1.40 (s, 3H), 1.31 (s, 3H), 1.36 (m, 1H); $^{13}$C NMR ($CDCl_3$, 75 MHz) δ 203.0, 177.1, 168.4, 134.5, 134.1, 132.9, 131.7, 131.2, 128.8, 126.5, 117.9, 100.8, 92.7, 84.3, 83.2, 49.2, 46.5, 30.4, 29.1, 29.0, 25.7, 25.0, 17.8.

Example 32

1-(3-Methyl-2-butenyl)-3,3-dimethyl-1,3,3 a,4,4a,9a-hexahydro-8,10-dioxo-6-phenyl-1,4a-methano-furo[3,4-g]chromene

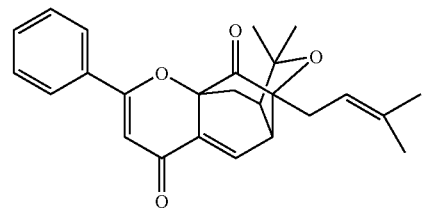

The procedure in example 17 also yielded the title compound (21 mg, 24%): $^1$H NMR ($CDCl_3$, 300 MHz) δ 7.91-7.87 (m, 2H), 7.55-7.43 (m, 3H), 7.06 (d, J=6.6 Hz, 1H), 6.09 (s, 1H), 5.07 (m, 1H), 3.77 (dd, J=4.5, 6.9 Hz, 1H), 2.59 (d, J=13.2 Hz, 1H), 2.53 (dd, J=6.6, 15.3 Hz, 1H), 2.16 (dd, J=4.2, 9.3 Hz, 1H), 2.11 (dd, J=8.7, 15.0 Hz, 1H), 1.91 (dd, J=9.9, 13.2 Hz, 1H), 1.74 (s, 3H), 1.61 (s, 3H), 1.40 (s, 3H), 1.36 (s, 3H); $^{13}$C NMR ($CDCl_3$, 75 MHz) δ 198.7, 175.9, 169.6, 136.1, 135.3, 132.8, 131.8, 131.1, 128.6, 126.8, 117.2, 101.3, 86.0, 83.7, 78.7, 44.5, 41.6, 32.8, 30.2, 29.6, 26.8, 26.0, 18.3.

Example 33

Isolation and Identification of Transferrin Receptor

Isolation of Transferrin Receptor from Intact Cells Using FITC-Tagged Gambogic Acid:

Jurkat cells were grown in RPMI 1640 media containing 25 mM Hepes and L-glutamine (Gibco) supplemented with 10% FCS and penicillin/streptomycin and harvested by centrifugation (200×g, 10 minutes) when they reached a concentration of $1×10^6$ cells/mL. $1×10^9$ Jurkat cells were resuspended in 100 mL RPMI 1640 media with 0.5% FCS. Cells were then treated with either 1% DMSO or 5 µM 5-[(5-gambogylaminopentyl)-thioureidyl]-fluorescein (Example 10) in DMSO for 30 minutes at 37° C. Cells were washed one time with 40 mL phosphate buffered saline (PBS) and lysed in 8 mL RIPA buffer (10×RIPA supplied by Upstate) and 0.1% Protease Inhibitor Cocktail (Sigma). The lysed cells were spun at 20,000×g for 10 minutes and the supernatant collected and referred to as "Jurkat lysate."

Protein Concentration of the Lysate was Determined by DC Assay (BioRad):

30 mg of Jurkat lysate was mixed with 100 µL Protein A SEPHAROSE® beads (Zymed) which had been washed 2 times with 1 mL PBS and incubated at 4° C. for 2 hours. The mix was centrifuged 1 minute at 2,700×g. The supernatant was removed from the Protein A SEPHAROSE® beads and 50 µg of rabbit anti-FITC antibody (Zymed) was added. Lysates and antibody were incubated with gentle rocking at 4° C. for 2 hours. 100 µL pre-washed Protein A SEPHAROSE® beads were added to the mix and further incubated overnight, with gentle rocking at 4° C. The SEPHAROSE®beads were collected by centrifugation (2,700×g, 1 minute) and washed 6 times with 1 mL of PBS+ 0.2% NP-40. 100 µL of 2× SDS sample buffer (Invitrogen Corporation) with 40 mM dithiothreitol (DTT) was added to the beads and the beads were boiled at 100° C. for 5 minutes. Samples were spun down at 20,000×g for 1 minute and the supernatant removed and loaded onto 6 mm wide wells on a 16 cm×20 cm×1 mm 4% SDS polyacrylamide gel in Tris-glycine running buffer (Invitrogen Corporation) and run at 35 mA for 4 hours at room temperature. The gel was removed from the glass plate and stained with 1% coomassie blue in 40% methanol, 7.5% acetic acid overnight at room temperature. The gel was destained in a solution of 40% methanol, 7.5% acetic acid with several changes of solution until protein bands were visible. Stained bands were excised with a clean razor blade and stored in microfuge tubes for tryptic digest.

Trypsin Digestion

The gel slice was further destained in 30% MeOH until the background was nearly clear. The gel slice was incubated for at least an hour in 500 µL of 100 mM ammonium bicarbonate. Then 150 µL of 100 mM ammonium bicarbonate and 10 µL of 45 mM DTT were added and incubated at 60° C. for 30 minutes. Samples were cooled to room temperature and 10 µL of 100 mM iodoacetamide was added and the sample was incubated for 30 minutes in the dark at room temperature. The solution was removed and discarded and 500 µL of 50% acetonitrile and 50% 100 mM ammonium bicarbonate, pH 8.9, was added and the sample was incubated with shaking for 1 hour at room temperature. The gel was removed, cut into 2-3 pieces and transferred to a 200 µL Eppendorf tube. 50µL acetonitrile was added for 10-15 minutes and then removed. The gel slices were dried in a Savant rotatory evaporator. The gel pieces were incubated with 10 µL of 25 mM ammonium bicarbonate containing Promega modified trypsin (sequencing grade) at a concentration such that a substrate to enzyme ratio of 10:1 was achieved (typically 0.1 µg). The protein amounts are estimated from the staining intensity of the gel. After 10-15 minutes 10-20 µL 25 mM ammonium bicarbonate was added to cover the gel pieces and incubated overnight at 37° C. The samples were then frozen at −20° C. until analysis by molecular mass sequencing.

LC-MS/MS Peptide Sequencing and Protein Identification:

This was carried out by standard procedures at a mass spectrometry sequencing facilities: Mass Consortium, San Diego, Calif. or Centre Proteomique de l'Est du Quebec, Ste-Foy, Quebec, Canada or equivalent facilities. In short, the samples were run on LC-MS/MS ion trap instruments and the parent and fragments were analyzed for mass to charge ratios. From the degradation fragments, a peptide sequence was deduced which is generally within 1 amu of the predicted mass. These sequences were then compared to peptide sequences in gene sequence or protein sequence databases. Identity of peptide sequence with predicted tryptic fragments from gene sequences indicates the peptide as part of the gene. The size of the peptide matched and/or the number of matched peptides confirmed the identity of the protein.

The following lists the experimentally deduced peptide sequence having the closest fitting calculated molecular weight.

An NCBI Blast search using this peptide revealed that it is a part of SEQ ID NO: 1 or 4.

| Sequence | aa Positions |
|---|---|
| VSASPLLYTLIEK | amino acids 496-508 of SEQ ID NO.: 1 or 4 |

Example 34

Isolation and Identification of Transferrin Receptor

Isolation of Transferrin Receptor from Plasma Membrane Fraction of Jurkat Cells By Gambogyl Affinity Chromatography:

Jurkat cells were grown in RPMI 1640 media containing 25 mM Hepes and L-glutamine (Gibco) supplemented with 10% FCS and penicillin/streptomycin and harvested by centrifugation (200×g, 10 minutes) when they reached a concentration of 1×106 cells/mL. 5×10$^9$ Jurkat cells were resuspended gently in 4 mL of 10 mM Tris, pH 7.5, with 4 µL of Protease Inhibitor Cocktail (P3840, Sigma) and incubated on ice for 10 minutes. Cells were homogenized with a Dounce homogenizer and type A pestle for five minutes on ice. Cell lysates were stored in microfuge tubes and frozen.

For plasma membrane isolation, 2 mL of lysate was placed into an ultracentrifuge tube (Ultraclear, 15 mL tube, for Beckman rotor JS24.15) along with 2 mL of 60% sucrose, 10 mM Tris, pH 7.5, and mixed. 7 mL of 20% sucrose, 10 mM Tris, pH 7.5, solution was carefully layered onto the lysate and the meniscus marked. 4 ml of a 10% sucrose, 10 mM Tris, pH 7.5, solution was carefully layered on. The tubes were spun at 22,000 rpm (93,000×g) for 2 hours at 4° C. The membrane fraction which is seen at the 10% and 20% sucrose interface (indicated by the meniscus mark) was carefully removed (approximately 3 mL) with a syringe and needle by side puncture of the tube. The membrane fraction was put into a new ultracentrifuge tube, 12 mL of 10 mM Tris, pH 7.5, 140 mM NaCl was added, the solution mixed by inverting the covered tube, and centrifuged at 22,000 rpm for 1 hour at 4° C. The supernatant liquid was removed down close to the cloudy white pellet and a Pasteur pipette was used to remove the remaining liquid. Tubes were turned upside down on a paper towel to drain. The membrane pellet was resuspended in 50 µL of PBS with 1% CHAPS, placed in a microfuge tube and frozen. Protein concentration was determined by DC protein assay (BioRad).

50 µg of membrane protein (approximately 100 µL) was brought up to 500 µL with RIPA buffer (InVitrogen) and clarified by centrifugation, 60,000×g, 15 minutes, 4° C. The supernatant was removed and incubated with gambogyl-R—SS—R'-agarose (Example 13), 60 µL, for 45 minutes at room temperature with gently mixing. (Gambogyl-R—SS—R'-agarose was washed 2 times with 1 mL RIPA buffer prior to use). The beads were collected by centrifugation (2,700×g, 1 minute). Beads were washed 2 times with RIPA buffer and then 2 times with RIPA buffer adjusted to 350 mM NaCl. Washes were done at room temperature, 5 minutes each, and the beads were collected by centrifugation (2,700×g 1 minute). 20 µL RIPA buffer and 80 µL 2×SDS sample buffer (In Vitrogen) with 40 mM DTT was added to the beads and boiled for 5 min. The beads were spun down by centrifugation and the supernatant was removed and loaded onto 6 mm wide 6% SDS polyacrylamide gels (16 cm×20 cm×1 mm) in Tris-glycine running buffer (Invitrogen Corporation) at 35 mA for 4 hours at room temperature.

Proteins are resolved by electrophoresis on a 6% polyacrylamide gel. The gel was removed from the glass plate and stained with 1% coomassie blue in 40% methanol, 7.5% acetic acid overnight at room temperature. The gel was destained in a solution of 40% methanol, 7.5% acetic acid with several changes of solution until protein bands are visible. Stained bands were excised with a clean razor blade and stored in a microfuge tube for tryptic digestion.

Trypsin Digestion

The gel slice was further destained in 30% MeOH until the background was nearly clear. The gel slice was incubated for at least an hour in 500 µL of 100 mM ammonium bicarbonate. Then 150 µL of 100 mM ammonium bicarbonate and 10 µL of 45 mM DTT was added and incubated at 60° C. for 30 minutes. Samples were cooled to room temperature and 10 µL of 100 mM iodoacetamide was added and the sample incubated for 30 minutes in the dark at room temperature. The solution was removed and discarded and 500 µL of 50% acetonitrile and 50% 100 mM ammonium bicarbonate, pH 8.9, was added and the sample was incubated with shaking for 1 hour at room temperature. The gel was removed, cut into 2-3 pieces and transferred to a 200 µL Eppendorf tube. 50µL acetonitrile was added for 10-15 minutes and then removed. The gel slices were dried in a Savant rotatory evaporator. The gel pieces were incubated with 10 µL of 25mM ammonium bicarbonate containing Promega modified trypsin (sequencing grade) at a concentration such that a substrate to enzyme ratio of 10:1 had been achieved (typically 0.1 µg). The protein amounts are estimated from the staining intensity of the gel. After 10-15 minutes, 10-20 µL 25 mM ammonium bicarbonate was added to cover the gel pieces and incubated overnight at 37° C. The samples were then frozen at −20° C. until analysis by molecular mass sequencing.

LC-MS/MS Peptide Sequencing and Protein Identification:

This was carried out by standard procedures at mass spectrometry sequencing facilities: Mass Consortium, San Diego, Calif. or Centre Proteomique de l'Est du Quebec, Ste-Foy, Quebec, Canada or equivalent facilities. In short, the samples were run on LC-MS/MS ion trap instruments and the parent and fragments are analyzed for mass to charge ratios. From the degradation fragments, a peptide sequence was deduced which is generally within 1 amu of the predicted mass. These sequences were then compared to peptide sequences in the gene sequence or protein sequence databases. Identity of peptide sequence with predicted tryptic fragments from gene sequences indicates the peptide as part of the gene. The size of the peptide matched and/or the number of matched peptides confirm the identity of the protein.

The following lists the experimentally deduced peptide sequences having the closest fitting calculated molecular weights. An NCBI Blast search using these peptides revealed that they are a part of SEQ ID NO: 1 or 4.

| Sequence: | aa positions |
|---|---|
| AVLGTSNFK | amino acids 487-495 of SEQ ID NO.: 1 or 4 |
| GFVEPDHYVVVGAQR | amino acids 395-409 of SEQ ID NO.: 1 or 4 |
| ILNIFGVIK | amino acids 386-394 of SEQ ID NO.: 1 or 4 |
| LAVDEEENADNNTK | amino acids 40-53 of SEQ ID NO.: 1 or 4 |
| LLNENSYVPR | amino acids 146-155 of SEQ ID NO.: 1 or 4 |
| LTTDFGNAEK | amino acids 656-665 of SEQ ID NO.: 1 or 4 |
| LVYLVENPGGYVAYSK | amino acids 209-224 of SEQ ID NO.: 1 or 4 |
| SAFSNLFGGEPLSYTR | amino acids 7-22 of SEQ ID NO.: 1 or 4 |
| SSGLPNIPVQTISR | amino acids 326-339 of SEQ ID NO.: 1 or 4 |
| VSASPLLYTLIEK | amino acids 496-508 of SEQ ID NO.: 1 or 4 |

Example 35

Immunofluorescence, Immunohistochemistry, and Electron Microscopy

For detecting internalization of fluorescent transferrin receptor, T47D cells were plated on glass cover slips in a 6-well plate at a density of 3×10⁵ cells per well on the day before the experiment. Cells were pretreated with 2 µM GA for 10 min at 37° C. washed with PBS, and then labeled for 30 min with 1 µg/ml FITC-labeled mouse anti-human transferrin receptor (RDI, Flanders, N.J.) at 37° C. The cells were then fixed with methanol at −20° C. for 5 min, washed with PBS and mounted with Vectashield mounting medium (Hard set with DAPI, Vector Laboratories, Inc., Burlingame, Calif.).

FACS Analysis: For cell surface staining of transferrin receptor, cells were washed with PBS+1% BSA and stained with FITC-conjugated anti-transferrin receptor antibody (RDI, Flanders, N.J.) for 30 minutes at 4° C. After washing, cells were analyzed on a FACS Calibur (BD Biosciences, San Jose, Calif.) using Cellquest software.

For the immunohistochemistry of tumor sections, tumors were fixed in 10% formaldehyde before sectioning. The sections were blocked with Dako peroxidase block (Dako, Glostrup, Denmark) for 30 min and incubated overnight at 4° C. with a 1:50 dilution of cleaved caspase-3 antibody (Cell Signalling Technologies, Beverly, Mass.). Then sections reacted for 30 min with EnVision+TM-rabbit conjugated with peroxidase (Dako, Glostrup, Denmark).

The cleaved caspase-3 immunoreactivity was visualized by developing the sections in 3-3'-diaminobenzidine (DAB). Finally the sections were counterstained with hematoxylin.

For electron microscopy, samples were fixed in Kamovsky's fixative (4% paraformaldehyde, 2.5% glutaraldehyde, 5 mM $CaCl_2$ in 0.1 M Na Cacodylate buffer, pH 7.4) overnight at 4° C. followed by 1% $OSO_4$ in 0.1 M Na Cacodylate buffer, pH 7.4, en bloc staining with 4% uranyl acetate in 50% ethanol, and subsequently dehydrated using a graded series of ethanol solutions followed by propylene oxide and infiltration with epoxy resin (Scipoxy 812, Energy Beam Sciences, Agawam, Mass.). After polymerization at 65° C. overnight, thin sections were cut and stained with uranyl acetate (4% uranyl acetate in 50% ethanol) followed by bismuth subnitrate. Sections were examined at an accelerating voltage of 60 kV using a Zeiss EM10C electron microscope.

Example 36 siRNA Transfections, cDNA Synthesis and Real-Time PCR

Human transferrin receptor and caspase 8 siRNA oligos were chemically synthesized by Ambion (Austin, Tex.). The target sequence for the transferrin receptor siRNA was 5' AAC TTC AAG GTT TCT GCC AGC 3' (nucleotides 1480-1497 of SEQ ID NO.: 27) and for caspase 8 was 5' AAG GAA AGT TGG ACA TCC TGA 3' (SEQ ID NO.: 40). The control siRNA oligos, human cyclophilin and negative control scrambled siRNA were also from Ambion. 293T cells were grown to 50% confluence and allowed to attach overnight. siRNAs were transfected into the cells using Lipofectamine 2000 (Invitrogen, Carlsbad, Calif.) according to the manufacturer's instructions. Briefly, siRNA (at a final concentration of 50 nM) and lipid were individually diluted in low serum media, OPTI-MEM® (Invitrogen, Carlsbad, Calif.) and allowed to incubate for 10-30 min after which they were combined and allowed to form lipid complexes for 20 min. The lipid complexes were added onto the cells and allowed to incubate for 48 h. The cells were then harvested for RNA, protein, FACS analysis, or DAPI staining.

For cDNA synthesis and quantitative PCR, total RNA was extracted using the TRIzol®reagent (Invitrogen, Carlsbad, Calif.) according to the manufacturer's instructions. Total RNA was quantitated, denatured, and electrophoresed in an agarose-formaldehyde gel to determine integrity of total RNA. 2 µg of total RNA was then used to make cDNA by reverse transcription using the RETROSCRIPT® cDNA synthesis kit (Ambion Austin, Tex.) according to the manufacturer's instructions. Both oligo dT and random primers were used to make the cDNA which was used as a template for PCR analysis. Quantitative PCR was done by Sybrgreen incorporation using the Quantitect kit (Qiagen, Valencia, Calif.) on the LIGHTCYCLER® (Roche Molecular Biochemicals, Mannheim, Germany) using standard conditions. Data was normalized against the housekeeping gene, cyclophyllin. The cells transfected with cyclophilin as a control was normalized against glyceraldehyde phosphate dehydrogenase (GAPD).

Example 37

Immunoblotting and Immunoprecipitation

Jurkat cells were cultured at $5 \times 10^6$/ml after which DMSO or 2060 (5 µM) was added for the time as indicated. Cells were lysed in RIPA buffer (Upstate Biotechnologies, Lake Placid, N.Y.) and were subject to SDS PAGE then blotted onto PVDF membrane. Membranes were probed with anti-caspase 3 (BD Biosciences, San Jose, Calif.), Caspase 8 (Biosource, Camarillo, Calif.), Bid (Upstate Biotechnologies, Lake Placid, N.Y.) or Cytochrome c (BD Biosciences, San Jose, Calif.) at µg/ml. For cells treated with the biotinylated caspase inhibitor, fluoromethyl ketone (FK19) (ICN, Costa Mesa, Calif.), Jurkat cells were also cultured at $5 \times 10^6$/ml, FK19 was added at a final concentration of 10 µM for 30 min then cells were treated with DMSO or GA (5 µM) for 1 hr. Cells were then lysed cell in RIPA buffer (Upstate Biotechnologies, Lake Placid, N.Y.). Lysates were mixed with 100 µl of streptavidin-agarose beads (Molecular Probes, Eugene, Oreg.) for 2 hr and were subsequently washed and eluted. Samples were subject to SDS/PAGE analysis and blotted onto nitrocellulose membrane. Membranes were probed with anti-caspase 3 (BD Biosciences, San Jose, Calif.), caspase 9 (Upstate Biotechnologies, Lake Placid, N.Y.) or Caspase 8 (Biosource, Camarillo, Calif.) and detected using ECL (enhanced chemiluminescence) reagent (Amersham Biosciences, Piscataway, N.J.).

For anti-FITC GA immunoprecipitation, Jurkat cells were treated with either DMSO or 5 µM Fluorescein-GA in RPMI and 0.5% FBS for 30 minutes at 37°. Cells were washed two times with PBS and lysed in RIPA buffer plus a protease inhibitor cocktail. Nuclei were spun out.

For the immunoprecipitation, 1 mg of Jurkat lysate was pre-cleared with 50 µl Protein A SEPHAROSE® (Zymed Laboratories, San Francisco, Calif.). Lysates were then incubated with 2.5 µg of rabbit anti-FITC antibody (Zymed Laboratories, San Francisco, Calif.) for 2 h at 4° C. Lysates and antibody were then added to 100 µl pre-washed Protein A SEPHAROSE® and incubated overnight at 4° C. SEPHAROSE® was washed six times with RIPA. 20% of the above immunoprecipitation was subjected to SDS-PAGE and transferred to PVDF. Membranes were blocked in 3% milk, 1% BSA and probed with anti-transferrin receptor antibody (Zymed) as decribed above.

Example 38

Binding Assays

Saturable and temperature dependent receptor binding on cells. Jurkat cells were grown to medium to late log phase and incubated with tritium-GA at 1 µM in growth medium at 37° C. with or without 20 µM of unlabeled GA. At indicated time points cells were washed with ice-cold PBS at 4° C. and the amount of bound tritium-GA was determined by liquid scintillation counting.

96-well plates were coated with soluble human transferrin receptor (shTR) (Merck Biosciences, Schwalbach, Germany) at 375 ng/well and blocked with Bovine Serum Albumin (BSA). Wells were incubated with increasing concentrations of biotin-GA in binding/washing buffer containing 0.5% BSA, 0.1% Tween®-20, 150 mM NaCl and 10 mM Tris-HCl (pH 7.4) for 1 hour at room temperature. Wells were washed 4 times, incubated with Eu-Streptavidin (Perkin-Elmer, Wellesey, Mass.) and washed again. Amounts of bound Eu-Streptavidin were quantified after incubation with Enhancement Solution (Perkin-Elmer, Wellesey, Mass.) by measuring time-delayed fluorescence on a Wallac Victor plate reader (Perkin-Elmer, Wellesey, Mass.) according to manufacturer's protocol. Uncoated wells were used to determine background binding. Biotinylated inactive GA (biotin-α,β saturated GA) was used as a control and produced only low background signal in both coated and uncoated wells. In competition experiments biotin-GA at 1 µM was pre-mixed with increasing amounts of GA or inactive-GA. $K_d$ and competition $EC_{50}$ values were calculated using PRIZM software. ShTR-coated wells were incubated with GA-biotin as described above, washed and incubated with non-tagged analogs or binding/washing buffer as a wash off control. Separate control wells were probed with biotinylated holo-transferrin (bio-Trn) to control for TR retention and possible denaturation over long incubation times.

Example 39

Transferrin Receptor Binding Assay of Small Molecules

The assay was run similar as described in Example 38. Wells of a 96-well assay plate were coated with 500 ng of HTR in 100 µl of PBS per well overnight at 4° C. These were washed twice with 200 µl of PBS and incubated with 200 µl of 1% BSA solution in PBS and washed twice with 200 µl of PBS. 100 µl of 1 µM biotin-GA solution in binding buffer (PBS/0.1% BSA/0.1% Tween-20) was added per well and incubated for 45 minutes at room temperature. For competition of binding assays biotin-GA was pre-mixed with indicated compounds at various concentrations. Final concentration of DMSO in binding mixtures was adjusted to 1% v/v. Wells were washed 4 times with 200 µl of binding buffer. 100 µl of 100 ng/ml Eu-labeled streptavidin solution in binding buffer were added per well and incubated for 45 minutes at room temperature. Wells were washed twice with 200 µl of binding buffer and twice with 200 µl of PBS. 100 µl of DELFIA Enhancement Solution were added per well and incubated for 10 minutes at room temperature. Plates were read on a Wallac Victor plate reader (Wallac-PerkinElmer Life Sciences) using delayed fluorescence Eu protocol at default manufacturer's settings.

Coated wells with no competing agent added were used to determine total binding (T). Non-coated wells were used to determine background binding (B). Background binding was consistently lower than 20%. Inhibition of binding was calculated as I=(T−BC)/(T−B)*100%, where BC was a reading corresponding to a well with a competing compound C added.

Other controls included assays of Biotin-GA binding to the wells coated with 500 µg/well of BSA or mouse Immunoglobulin G, the secondary reagent (Eu-labeled streptavidin) alone binding to the wells coated with 500 µg/well of HTR. Non-specific binding in these assays was not significantly higher than background binding to non-coated wells. The results are summarized in Table I.

TABLE I

Binding of Small Molecules to Transferrin Receptors by Inhibition of Biotin-GA Binding to Transferrin Receptors

| Example # | % Inhibition |
| --- | --- |
| Example 17 | 52 |
| Example 18 | 42 |
| Example 19 | 0 |
| Example 22 | 51 |
| Example 23 | 59 |
| Example 27 | 11 |
| Example 28 | 8 |
| Example 31 | 47 |
| Example 32 | 61 |

Compounds were tested at 20 µM. Concentration of biotin-GA was kept at 1 µM.

Table I showed that several small molecules, including the compounds of Examples 17-18, 22-23 and 31-32, have good binding to Transferrin Receptors by inhibiting efficiently the binding of biotin-GA to Transferrin Receptors. Therefore the binding assay can be used to identify compounds that bind to the Transferrin Receptors.

Example 40

Identification of Small Molecules as Caspase Cascade Activators and Inducers of Apoptosis in Solid Tumor Cells Human breast cancer cell lines T-47D and DLD-1 were grown according to media component mixtures designated by American Type Culture Collection +10% FCS (Invitrogen Corporation), in a 5% $CO_2$-95% humidity incubator at 37° C. T-47D and DLD-1 cells were maintained at a cell density between 50 and 80% confluency at a cell density of 0.1 to $0.6 \times 10^6$ cells/mL. Cells were harvested at 600×g and resuspended at $0.65 \times 10^6$ cells/mL into appropriate media +10% FCS. An aliquot of 22.5 µL of cells was added to a well of a 384-well microtiter plate containing 2.5 µL of a 10% DMSO in RPMI-1640 media solution containing 0.16 to 100 µM of test compound (0.016 to 10 µM final). An aliquot of 22.5 µL of cells was added to a well of a 384-well microtiter plate containing 2.5 µL of a 10% DMSO in RPMI-1640 media solution without test compound as the control sample. The samples were mixed by agitation and then incubated at 37° C. for 48 h in a 5% $CO_2$-95% humidity incubator. After incubation, the samples were removed from the incubator and 25 µL of a solution containing 14 µM of N-(Ac-DEVD)-N'-ethoxycarbonyl-R110 (SEQ ID NO.: 41) fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SPECTRAfluor Plus, Tecan), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:

The Relative Fluorescence Unit values (RFU) were used to calculate the sample readings as follows:

$RFU_{(T=3h)}$−Control $RFU_{(T=0)}$=Net $RFU_{(T=3h)}$

The activity of caspase cascade activation was determined by the ratio of the net RFU value for test compound to that of control samples. The $EC_{50}$ (nM) was determined by a sigmoidal dose-response calculation (Prism 3.0, GraphPad Software Inc.).

The caspase activity (Ratio) and potency ($EC_{50}$) are summarized in Table II:

TABLE II

Caspase Activity and Potency of Small Molecules

| | T-47D | |
| --- | --- | --- |
| Example # | Ratio | $EC_{50}$ (nM) |
| Example 17 | 9.8 | 8383 |
| Example 18 | 2.9 | 6603 |
| Example 19 | 1.0 | Inactive |
| Example 22 | 9.9 | 4017 |
| Example 23 | 14.1 | 3735 |
| Example 27 | 1.5 | Inactive |
| Example 28 | 1.3 | Inactive |

TABLE II-continued

Caspase Activity and Potency of Small Molecules

| | T-47D | |
|---|---|---|
| Example # | Ratio | EC$_{50}$ (nM) |
| Example 31 | 11.4 | 3854 |
| Example 32 | 10.6 | 3092 |

Table II shows that several small molecules, including compounds of Example 17-18, 22-23 and 31-32, activate caspases and induce apoptosis in tumor cells. These compounds also have good binding to Transferrin Receptors as shown in Table I in Example 39 Therefore the binding assay can be used to identify compounds that bind to the Transferrin Receptors and are activator of caspases and inducers of apoptosis.

Example 41

Isolation and Identification of Clathrin Heavy Chain

Isolation of Clathrin Heavy Chain from Intact Cells Using FITC-Tagged Gambogic Acid:

Jurkat cells were grown in RPMI 1640 media containing 25 mM Hepes and L-glutamine (Gibco) supplemented with 10% FCS and penicillin/streptomycin and harvested by centrifugation (200×g, 10 min) when they reached a concentration of 1×10$^6$ cells/ml. 1×10$^9$ Jurkat cells were resuspended in 100 mL RPMI 1640 media with 0.5% FCS. Cells were then treated with either 1% DMSO or 5 uM 5-[(5-gambogylaminopentyl)-thioureidyl]-fluorescein (Example 10) in DMSO for 30 minutes at 37° C. Cells were washed one time with 40 mls phosphate buffered saline (PBS) and lysed in 8 mls RIPA buffer (10×RIPA supplied by Upstate) and 0.1% Protease Inhibitor Cocktail (Sigma). The lysed cells were spun at 20,000×g for 10 min and the supernatant collected and are referred to as "Jurkat lysate."

Protein concentration of the lysate was determined by DC Assay (BioRad). 30 mgs of Jurkat lysate was mixed with 100 μL Protein A SEPHAROSE® beads (Zymed) which had been washed 2 times with 1 ml PBS and incubated at 4° C. for 2 hours. The mix was centrifuged 1 minute at 2,700×g. The supernatant was removed from the Protein A SEPHAROSE® beads and 50 μg of rabbit anti-FITC antibody (Zymed) was added. Lysates and antibody were incubated with gentle rocking at 4° C. for 2 hours. 100 μL pre-washed Protein A SEPHAROSE® beads were added to the mix and further incubated overnight, with gentle rocking at 4° C. The SEPHAROSE® beads were collected by centrifugation (2,700×g, 1 minute) and washed 6 times with 1 ml of PBS+ 0.2% NP-40. 100 μL of 2×SDS sample buffer (Invitrogen Corporation) with 40 mM dithiothreitol (DTT) was added to the beads and the beads were boiled at 100° C. for 5 minutes. Samples were spun down at 20,000×g for 1 min and the supernatant removed and loaded onto 6 mm wide well on a 16 cm×20 cm×1 mm 4% SDS polyacrylamide gel in Tris-glycine running buffer (Invitrogen Corporation) and run at 35 mA for 4 hours at room temperature. The gel was removed from the glass plate and stained with 1% coomassie blue in 40% methanol, 7.5% acetic acid overnight at room temperature. The gel was destained in a solution of 40% methanol, 7.5% acetic acid with several changes of solution until protein bands were visible. Stained bands were excised with a clean razor blade and stored in microfuge tubes for tryptic digest.

Trypsin Digestion:

The gel slice was further destained in 30% MeOH until the background was nearly clear. The gel slice was incubated for at least an hour in 500 μL of 100 mM ammonium bicarbonate. Then 150 μL of 100 mM ammonium bicarbonate and 10 μL of 45 mM DTT were added and incubated at 60° C. for 30 minutes. Samples were cooled to room temperature and 10 μL of 100 mM iodoacetamide was added and the sample incubated for 30 min in the dark at room temperature. The solution was removed and discarded and 500 μL of 50% acetonitrile and 50% 100 mM ammonium bicarbonate, pH 8.9, were added and the sample incubated with shaking for 1 hour at room temperature. The gel was removed, cut into 2-3 pieces and transferred to a 200 μL Eppendorf tube. 50 μL acetonitrile was added for 10-15 minutes and then removed. The gel slices were dried in a Savant rotatory evaporator. The gel pieces were incubated with 10 μL of 25 mM ammonium bicarbonate containing Promega modified trypsin (sequencing grade) at a concentration such that a substrate to enzyme ratio of 10:1 was achieved (typically 0.1 ug). The protein amounts were estimated from the staining intensity of the gel. After 10-15 minutes 10-20 μL 25 mM ammonium bicarbonate was added to cover the gel pieces and incubated overnight at 37° C. The samples were then frozen at −20° C. until analysis by molecular mass sequencing.

LC-MS/MS Peptide Sequencing and Protein Identification:

This was carried out by standard procedures at mass spectrometry sequencing facilities: Mass Consortium, San Diego, Calif. or Centre Proteomique de l'Est du Quebec, Ste-Foy, Quebec, Canada or equivalent facilities. The samples were run on LC-MS/MS ion trap instruments and the parent and fragments are analyzed for mass to charge ratios. From the degradation fragments, a peptide sequence is deduced which is generally within 1 amu (atomic mass unit) of the predicted mass. These sequences are then compared to peptide sequences in gene sequence or protein sequence databases. Identity of peptide sequence with predicted tryptic fragments from gene sequences indicates the peptide as part of the gene. The size of the peptide matched and/or the number of matched peptides confirm the identity of the protein.

The following table lists the experimentally determined molecular weights, Mr(expt), of the column fractions, and peptides having the closest fitting calculated molecular weight, Mr(calc). The difference between Mr(expt) and Mr(calc) is indicated as "Delta." An NCBI Blast search using these peptides revealed that they are a part of SEQ ID NO: 34. Query refers to the sample number, Observed is the m/z ratio, Mr(expt) is the experimental mass adjusted for charge, Mr(calc) is the predicted peptide mass, Delta is the difference between the experimental and calculated mass, and Peptide is the amino acid sequence.

```
Query  Observed Mr(expt) Mr(calc) Delta  Peptide 232    443.20   884.38   884.40  -0.02  AYEFAER (amino acids
                                         1095-1101 of SEQ ID
                                         NO. 34)
```

-continued

| Query | Observed | Mr(expt) | Mr(calc) | Delta | Peptide |
|---|---|---|---|---|---|
| 242 | 445.28 | 888.54 | 889.45 | -0.91 | LDASESLR (amino acids 1613-1620 of SEQ ID NO. 34) |
| 297 | 470.70 | 939.38 | 939.45 | -0.06 | VMEYINR + Oxidation (M) (amino acids 1040-1046 of SEQ ID NO. 34) |
| 373 | 522.14 | 1042.26 | 1042.44 | -0.17 | ENPYYDSR (amino acids 896-903 of SEQ ID NO. 34) |
| 551 | 652.83 | 1303.64 | 1303.65 | -0.01 | NNLAGAEELFAR (amino acids 355-366 of SEQ ID NO. 34) |
| 563 | 438.49 | 1312.45 | 1312.71 | -0.27 | LEKHELIEFR (amino acids 1499-1508 of SEQ ID NO. 34) |
| 592 | 667.86 | 1333.70 | 1333.63 | 0.08 | IYIDSNNNPER (amino acids 882-892 of SEQ ID NO. 34) |
| 624 | 677.15 | 1352.28 | 1352.68 | -0.39 | VVGAMQLYSVDR + Oxidation (M) (amino acids 177-188 of SEQ ID NO. 34) |
| 642 | 457.00 | 1367.98 | 1367.69 | 0.29 | NNRPSEGPLQTR (amino acids 572-583 of SEQ ID NO. 34) |
| 673 | 702.04 | 1402.06 | 1401.67 | 0.39 | CNEPAVWSQLAK (amino acids 1102-1113 of SEQ ID NO. 34) |
| 686 | 708.14 | 1414.26 | 1414.72 | -0.46 | IVLDNSVFSEHR (amino acids 1011-1022 of SEQ ID NO. 34) |
| 739 | 489.27 | 1464.79 | 1463.73 | 1.06 | ALEHFTDLYDIK (amino acids 626-637 of SEQ ID NO. 34) |
| 837 | 776.21 | 1550.40 | 1550.75 | -0.34 | GQFSTDELVAEVEK (amino acids 838-851 of SEQ ID NO. 34) |
| 882 | 525.34 | 1573.00 | 1572.79 | 0.20 | RPISADSAIMNPASK + Oxidation (M) (amino acids 64-78 of SEQ ID NO. 34) |
| 925 | 806.97 | 1611.92 | 1611.84 | 0.08 | ESYVETELIFALAK (amino acids 1166-1179 of SEQ ID NO. 34) |
| 1195 | 981.65 | 1961.28 | 1962.00 | -0.72 | AFMTADLPNELIELLEK + Oxidation (M) (amino acids 994-1010 of SEQ ID NO. 34) |
| 1250 | 1020.57 | 2039.12 | 2040.08 | -0.96 | LPVVIGGLLDVDCSEDVIK (amino acids 812-830 of SEQ ID NO. 34) |
| 1284 | 707.71 | 2120.11 | 2120.03 | 0.08 | DTELAEELLQWFLQEEK (amino acids 1546-1562 of SEQ ID NO. 34) |
| 1409 | 785.79 | 2354.35 | 2354.14 | 0.21 | SVNESLNNLFITEEDYQALR (amino acids 1462-1481 of SEQ ID NO. 34) |

-continued

| Query | Observed | Mr(expt) | Mr(calc) | Delta | Peptide |
|---|---|---|---|---|---|
| 1570 | 961.42 | 2881.24 | 2880.51 | 0.73 | RPLIDQVVQTALSETQDPEEVS VTVK (amino acids 968- 993 of SEQ ID NO. 34) |

Example 42

Isolation and Identification of IQ Motif Containing GTPase Activating Protein Isolation of IQ Motif Containing GTPase Activating Protein from Intact Cells ITC-Tagged Gambogic Acid:

Jurkat cells were grown in RPMI 1640 media containing 25 mM Hepes and L-glutamine (Gibco) supplemented with 10% FCS and penicilin/streptomycin and harvested by centrifugation (200×g, 10 min) when they reached a concentration of $1×10^6$ cells/ml. $1×10^9$ Jurkat cells were resuspended in 100 mL RPMI 1640 media with 0.5% FCS. Cells were then treated with either 1% DMSO or 5 μM 5-[(5-gambogylaminopentyl)-thioureidyl]-fluorescein (Example 10) in DMSO for 30 minutes at 37° C. Cells were washed one time with 40 mls phosphate buffered saline (PBS) and lysed in 8 mls RIPA buffer (10×RIPA supplied by Upstate) and 0.1% Protease Inhibitor Cocktail (Sigma). The lysed cells were spun at 20,000×g for 10 min and the supernatant collected and are referred to as "Jurkat lysate."

Protein concentration of the lysate was determined by DC Assay (BioRad). 30 mgs of Jurkat lysate was mixed with 100 μL Protein A SEPHAROSE® beads (Zymed) which had been washed 2 times with 1 ml PBS and incubated at 4° C. for 2 hours. The mix was centrifuged 1 minute at 2,700×g. The supernatant was removed from the Protein A SEPHAROSE® beads and 50 μg of rabbit anti-FITC antibody (Zymed) was added. Lysates and antibody were incubated with gentle rocking at 4° C. for 2 hours. 100 μL pre-washed Protein A SEPHAROSE® beads were added to the mix and further incubated overnight, with gentle rocking at 4° C. The SEPHAROSE® beads were collected by centrifugation (2,700×g, 1 minute) and washed 6 times with 1 ml of PBS+ 0.2% NP-40. 100 μL of 2× SDS sample buffer (Invitrogen Corporation) with 40 mM dithiothreitol (DTT) was added to the beads and the beads were boiled at 100° C. for 5 minutes. Samples were spun down at 20,000×g for 1 min and the supernatant removed and loaded onto 6 mm wide well on a 16 cm×20 cm ×1 mm 4% SDS polyacrylamide gel in Tris-glycine running buffer (Invitrogen Corporation) and run at 35 mA for 4 hours at room temperature. The gel was removed from the glass plate and stained with 1% coomassie blue in 40% methanol, 7.5% acetic acid overnight at room temperature. The gel was destained in a solution of 40% methanol, 7.5% acetic acid with several changes of solution until protein bands were visible. Stained bands were excised with a clean razor blade and stored in microfuge tubes for tryptic digest.

Trypsin Digestion:

The gel slice was further destained in 30% MeOH until the background was nearly clear. The gel slice was incubated for at least an hour in 500 μL of 100 mM ammonium bicarbonate. Then 150 μL of 100 mM ammonium bicarbonate and 10 μL of 45mM DTT were added and incubated at 60° C. for 30 minutes. Samples were cooled to room temperature and 10 μL of 100 mM iodoacetamide was added and the sample incubated for 30 min in the dark at room temperature. The solution was removed and discarded and 500 μL of 50% acetonitrile and 50% 100 mM ammonium bicarbonate, pH 8.9, were added and the sample incubated with shaking for 1 hour at room temperature. The gel was removed, cut into 2-3 pieces and transferred to a 200 μL Eppendorf tube. 50μL acetonitrile was added for 10-15 minutes and then removed. The gel slices were dried in a Savant rotatory evaporator. The gel pieces were incubated with 10 μL of 25 mM ammonium bicarbonate containing Promega modified trypsin (sequencing grade) at a concentration such that a substrate to enzyme ratio of 10:1 was achieved (typically 0.1 μg). The protein amounts were estimated from the staining intensity of the gel. After 10-15 minutes 10-20 μL 25 mM ammonium bicarbonate was added to cover the gel pieces and incubated overnight at 37° C. The samples were then frozen at −20° C. until analysis by molecular mass sequencing.

LC-MS/MS peptide sequencing and protein identification:

This was carried out by standard procedures at mass spectrometry sequencing facilities: Mass Consortium, San Diego, Calif. or Centre Proteomique de l'Est du Québec, Ste-Foy, Quebec, Canada or equivalent facilities. The samples were run on LC-MS/MS ion trap instruments and the parent and fragments are analyzed for mass to charge ratios. From the degradation fragments, a peptide sequence is deduced which is generally within 1 amu (atomic mass unit) of the predicted mass. These sequences are then compared to peptide sequences in gene sequence or protein sequence databases. Identity of peptide sequence with predicted tryptic fragments from gene sequences indicates the peptide as part of the gene. The size of the peptide matched and/or the number of matched peptides confirm the identity of the protein.

The following table lists the experimentally determined molecular weights, Mr(expt), of the column fractions, and peptides having the closest fitting calculated molecular weight, Mr(calc). The difference between Mr(expt) and Mr(calc) is indicated as "Delta." An NCBI Blast search using these peptides revealed that they are a part of SEQ ID NO: 36. Query refers to the sample number, Observed is the m/z ratio, Mr(expt) is the experimental mass adjusted for charge, Mr(calc) is the predicted peptide mass, Delta is the difference between the experimental and calculated mass, and Peptide is the amino acid sequence.

| Query | Observed | Mr(expt) | Mr(calc) | Delta | Peptide |
|---|---|---|---|---|---|
| 225 | 465.51 | 929.00 | 930.50 | −1.50 | TALQEEIK (amino acids 1028-1035 of SEQ ID NO.: 36) |

-continued

| Query | Observed | Mr(expt) | Mr(calc) | Delta | Peptide |
|---|---|---|---|---|---|
| 254 | 508.23 | 1014.44 | 1014.49 | -0.05 | MLQHAASNK + Oxidation (M) (amino acids 1231-1239 of SEQ ID NO.: 36) |
| 287 | 547.15 | 1092.28 | 1092.48 | -0.19 | LTAEEMDER (amino acids 26-34 of SEQ ID NO.: 36) |
| 312 | 589.01 | 1176.00 | 1175.57 | 0.44 | EDSNLTLQEK (amino acids 1446-1455 of SEQ ID NO.: 36) |
| 331 | 617.58 | 1233.14 | 1232.59 | 0.55 | FPDAGEDELLK (amino acids 1175-1185 of SEQ ID NO.: 36) |
| 502 | 735.11 | 1468.20 | 1467.66 | 0.55 | VDFTEEEINNMK (amino acids 175-186 of SEQ ID NO.: 36) |
| 508 | 742.83 | 1483.64 | 1483.65 | -0.01 | VDFTEEEINNMK + Oxidation (M) (amino acids 175-186 of SEQ ID NO.: 36) |
| 509 | 745.88 | 1489.74 | 1489.76 | -0.02 | SVKEDSNLTLQEK (amino acids 1443-1455 of SEQ ID NO.: 36) |
| 535 | 783.23 | 1564.44 | 1564.65 | -0.20 | FDVPGDENAEMDAR (amino acids 1369-1382 of SEQ ID NO.: 36) |
| 539 | 791.27 | 1580.52 | 1580.64 | -0.12 | FDVPGDENAEMDAR + Oxidation (M) (amino acids 1369-1382 of SEQ ID NO.: 36) |
| 561 | 544.15 | 1629.43 | 1628.72 | 0.71 | NKEQLSDMMMINK + 3 Oxidation (M) (amino acids 941-953 of SEQ ID NO.: 36) |

Example 43

Isolation and Identification of Heat Shock Protein

Isolation of Heat Shock Protein from Plasma Membrane Fraction of Jurkat Cells By Gambogyl Affinity Chromatography:

Jurkat cells were grown in RPMI 1640 media containing 25 mM Hepes and L-glutamine (Gibco) supplemented with 10% FCS and penicillin/streptomycin and harvested by centrifugation (200×g, 10 minutes) when they reached a concentration of 1×10$^6$ cells/mL. 5×10$^9$ Jurkat cells were resuspended gently in 4 mL of 10 mM Tris, pH 7.5, with 4 µL of Protease Inhibitor Cocktail (P3840, Sigma) and incubated on ice for 10 minutes. Cells were homogenized with a Dounce homogenizer and type A pestle for five minutes on ice. Cell lysates were stored in microfuge tubes and frozen.

For plasma membrane isolation, 2 mL of lysate was placed into an ultracentrifuge tube (Ultraclear, 15 mL tube, for Beckman rotor JS24.15) along with 2 mL of 60% sucrose, 10 mM Tris, pH 7.5, and mixed. 7 mL of 20% sucrose, 10 mM Tris, pH 7.5, solution was carefully layered onto the lysate and the meniscus marked. 4 ml of a 10% sucrose, 10 mM Tris, pH 7.5, solution was carefully layered on. The tubes were spun at 22,000 rpm (93,000×g) for 2 hours at 4° C. The membrane fraction which is seen at the 10% and 20% sucrose interface (indicated by the meniscus mark) was carefully removed (approximately 3 mL) with a syringe and needle by side puncture of the tube. The membrane fraction was put into a new ultracentrifuge tube, 12 mL of 10 mM Tris, pH 7.5, 140 mM NaCl was added, the solution mixed by inverting the covered tube, and centrifuged at 22,000 rpm for 1 hour at 4° C. The supernatant liquid was removed down close to the cloudy white pellet and a Pasteur pipette was used to remove the remaining liquid. Tubes were turned upside down on a paper towel to drain. The membrane pellet was resuspended in 50 µL of PBS with 1% CHAPS, placed in a microfuge tube and frozen. Protein concentration was determined by DC protein assay (BioRad).

50 µg of membrane protein (approximately 100 µL) was brought up to 500 µL with RIPA buffer (Invitrogen Corporation) and clarified by centrifugation, 60,000×g, 15 minutes, 4° C. The supernatant was removed and incubated with gambogyl-R—SS—R'-agarose (Example 13), 60 µL, for 45 minutes at room temperature with gently mixing. (Gambogyl-R—SS—R'-agarose was washed 2 times with 1 mL RIPA buffer prior to use). The beads were collected by centrifugation (2,700×g, 1 minute). Beads were washed 2 times with RIPA buffer and then 2 times with RIPA buffer adjusted to 350 mM NaCl. Washes were done at room temperature, 5 minutes each, and the beads were collected by centrifugation (2,700×g 1 minute). 20 µL RIPA buffer and 80 µL 2×SDS sample buffer (Invitrogen Corporation) with 40 mM DTT was added to the beads and boiled for 5 min. The beads were spun down by centrifugation and the supernatant was removed and loaded onto 6 mm wide 6% SDS polyacrylamide gels (16 cm×20 cm×1 mm) in Tris-glycine running buffer (Invitrogen Corporation) at 35 mA for 4 hours at room temperature.

Proteins are resolved by electrophoresis on a 6% polyacrylamide gel. The gel was removed from the glass plate and stained with 1% coomassie blue in 40% methanol, 7.5% acetic acid overnight at room temperature. The gel was destained in a solution of 40% methanol, 7.5% acetic acid with several changes of solution until protein bands are visible. Stained bands were excised with a clean razor blade and stored in a microfuge tube for tryptic digestion.

Trypsin Digestion:

The gel slice was further destained in 30% MeOH until the background was nearly clear. The gel slice was incubated for at least an hour in 500 µL of 100 mM ammonium bicarbonate.

Then 150 µL of 100 mM ammonium bicarbonate and 10 µL of 45 mM DTT was added and incubated at 60° C. for 30 minutes. Samples were cooled to room temperature and 10 µL of 100 mM iodoacetamide was added and the sample incubated for 30 minutes in the dark at room temperature. The solution was removed and discarded and 500 µL of 50% acetonitrile and 50% 100 mM ammonium bicarbonate, pH 8.9, was added and the sample was incubated with shaking for 1 hour at room temperature. The gel was removed, cut into 2-3 pieces and transferred to a 200 µL Eppendorf tube. 50 µL acetonitrile was added for 10-15 minutes and then removed. The gel slices were dried in a Savant rotatory evaporator. The gel pieces were incubated with 10 µL of 25 mM ammonium bicarbonate containing Promega modified trypsin (sequencing grade) at a concentration such that a substrate to enzyme ratio of 10:1 had been achieved (typically 0.1 µg). The protein amounts are estimated from the staining intensity of the gel. After 10-15 minutes, 10-20 µL 25 mM ammonium bicarbonate was added to cover the gel pieces and incubated overnight at 37° C. The samples were then frozen at −20° C. until analysis by molecular mass sequencing.

LC-MS/MS Peptide Sequencing and Protein Identification

This was carried out by standard procedures at mass spectrometry sequencing facilities: Mass Consortium, San Diego, Calif. or Centre Proteomique de l'Est du Quebec, Ste-Foy, Quebec, Canada or equivalent facilities. In short, the samples were run on LC-MS/MS ion trap instruments and the parent and fragments are analyzed for mass to charge ratios. From the degradation fragments, a peptide sequence was deduced which is generally within 1 amu of the predicted mass. These sequences were then compared to peptide sequences in the gene sequence or protein sequence databases. Identity of peptide sequence with predicted tryptic fragments from gene sequences indicates the peptide as part of the gene. The size of the peptide matched and/or the number of matched peptides confirm the identity of the protein.

The following table lists the experimentally deduced peptide sequences having the closest fitting calculated molecular weights. An NCBI Blast search using these peptides revealed that they are a part of SEQ ID NO: 38.

| Sequence: | aa positions |
| --- | --- |
| ADLINNLGTIAK | amino acids 96-107 of SEQ ID NO.: 38 |
| AKFENLCK | amino acids 558-565 of SEQ ID NO.: 38 |
| ALLFIPR | amino acids 331-337 of SEQ ID NO.: 38 |
| ELISNASDALDK | amino acids 42-53 of SEQ ID NO.: 38 |
| ELISNASDALDKIR | amino acids 42-55 of SEQ ID NO.: 38 |
| ELKIDIIPNPQER | amino acids 70-82 of SEQ ID NO.: 38 |
| EQVANSAFVER | amino acids 492-502 of SEQ ID NO.: 38 |
| FYEAFSK | amino acids 429-435 of SEQ ID NO.: 38 |
| GVVDSEDLPLNISR | amino acids 379-392 of SEQ ID NO.: 38 |
| HLEINPDHPIVETLR | amino acids 625-639 of SEQ ID NO.: 38 |
| HSQFIGYPITLYLEK | amino acids 205-219 of SEQ ID NO.: 38 |
| HSQFIGYPITLYLEKER | amino acids 205-221 of SEQ ID NO.: 38 |
| KHLEINPDHPIVETLR | amino acids 624-639 of SEQ ID NO.: 38 |
| KHSQFIGYPITLYLEK | amino acids 204-219 of SEQ ID NO.: 38 |
| NPDDITQEEYGEFYK | amino acids 292-306 of SEQ ID NO.: 38 |
| RAPFDLFENK | amino acids 338-347 of SEQ ID NO.: 38 |
| SIYYITGESK | amino acids 482-491 of SEQ ID NO.: 38 |
| SIYYITGESKEQVANSAFVER | amino acids 482-502 of SEQ ID NO.: 38 |
| SLTNDWEDHLAVK | amino acids 307-319 of SEQ ID NO.: 38 |
| SLVSVTK | amino acids 532-538 of SEQ ID NO.: 38 |
| TLTLVDTGIGMTK | amino acids 83-95 of SEQ ID NO.: 38 |
| YESLTDPSKLDSGK | amino acids 56-69 of SEQ ID NO.: 38 |
| YIDQEELNK | amino acids 276-284 of SEQ ID NO.: 38 |

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method of identifying potentially therapeutic anticancer compounds comprising:
   (a) forming a complex with a TRRAIP comprising the amino acid sequence of SEQ ID NO: 1 and gambogic acid in vitro;
   (b) contacting the complex with one or more test compounds;
   (c) monitoring the extent to which the one or more test compounds displaces gambogic acid from said complex to identify test compounds that bind as strongly or more strongly than gambogic acid to said TRRAIP comprising the amino acid sequence of SEQ ID NO: 1;
   (d) exposing cultured eukaryotic cancer cells expressing a TRRAIP comprising the amino acid sequence of SEQ ID NO: 1 to a test compound identified in step (c) as binding as strongly or more strongly than gambogic acid to said TRRAIP comprising the amino acid sequence of SEQ ID NO: 1; and
   (e) measuring the caspase cascade activity of said cultured eukaryotic cancer cells,
   wherein an increase in the caspase cascade activity in said cultured eukaryotic cancer cells in the presence of the test compound as compared to the caspase cascade activity in a different culture of said eukaryotic cancer cells which have not been exposed to a test compound is an indication that the test compound is a potentially therapeutic anticancer compound.

2. The method of claim 1, wherein said monitoring of (c) comprises determining whether said one or more test compounds bind to said TRRAIP in a homogeneous assay.

3. The method of claim 2, wherein said homogeneous assay is selected from the group consisting of a fluorescence polarization assay and a radioassay.

4. The method of claim 1, wherein said monitoring of (c) comprises determining whether said one or more test compounds bind to said TRRAIP in a heterogeneous assay.

5. The method of claim 4, wherein said heterogeneous assay is selected from the group consisting of a fluorescence polarization assay and a radioassay.

6. The method of claim 1, wherein said TRRAIP comprises a detectable label.

7. The method of claim 6, wherein said detectable label is selected from the group consisting of a fluorescent label and a radiolabel.

8. The method of claim 1, wherein said gambogic acid compound has a detectable label wherein in (c) said label is detected.

9. The method of claim 8, wherein said detectable label is selected from the group consisting of a fluorescent label and a radiolabel.

* * * * *